United States Patent
Amit et al.

(10) Patent No.: US 11,959,098 B2
(45) Date of Patent: *Apr. 16, 2024

(54) METHODS AND CULTURE MEDIA FOR CULTURING PLURIPOTENT STEM CELLS

(71) Applicant: Technion Research & Development Foundation Limited, Haifa (IL)

(72) Inventors: Michal Amit, Yuvalim (IL); Joseph Itskovitz-Eldor, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 1078 days.

This patent is subject to a terminal disclaimer.

(21) Appl. No.: 16/809,771

(22) Filed: Mar. 5, 2020

(65) Prior Publication Data

US 2020/0224157 A1 Jul. 16, 2020

Related U.S. Application Data

(63) Continuation of application No. 15/403,303, filed on Jan. 11, 2017, now Pat. No. 10,597,635, which is a continuation of application No. 13/821,244, filed as application No. PCT/IL2011/000722 on Sep. 7, 2011, now Pat. No. 10,214,722.

(60) Provisional application No. 61/380,388, filed on Sep. 7, 2010.

(51) Int. Cl.
*C12N 5/074* (2010.01)
*C12N 5/0735* (2010.01)
*C12N 5/077* (2010.01)
*C12N 5/0775* (2010.01)
*C12N 5/079* (2010.01)

(52) U.S. Cl.
CPC ......... *C12N 5/0607* (2013.01); *C12N 5/0606* (2013.01); *C12N 5/0653* (2013.01); *C12N 5/0654* (2013.01); *C12N 5/0655* (2013.01); *C12N 5/0696* (2013.01); *C12N 5/0618* (2013.01); *C12N 5/0662* (2013.01); *C12N 2500/90* (2013.01); *C12N 2500/92* (2013.01); *C12N 2500/98* (2013.01); *C12N 2501/115* (2013.01); *C12N 2501/13* (2013.01); *C12N 2501/23* (2013.01); *C12N 2501/2306* (2013.01); *C12N 2501/2311* (2013.01); *C12N 2501/237* (2013.01); *C12N 2506/02* (2013.01); *C12N 2506/03* (2013.01); *C12N 2506/45* (2013.01); *C12N 2509/10* (2013.01)

(58) Field of Classification Search
CPC .. C12N 5/0607; C12N 5/0606; C12N 5/0653; C12N 5/0654; C12N 5/0655; C12N 5/0696; C12N 5/0618; C12N 5/0662; C12N 2500/90; C12N 2500/92; C12N 2500/98; C12N 2501/115; C12N 2501/13; C12N 2501/23; C12N 2501/2306; C12N 2501/2311; C12N 2501/237; C12N 2506/02; C12N 2506/03; C12N 2506/45; C12N 2509/10

See application file for complete search history.

(56) References Cited

U.S. PATENT DOCUMENTS

| | | | |
|---|---|---|---|
| 9,040,297 B2 | 5/2015 | Amit et al. | |
| 10,214,722 B2 | 2/2019 | Amit et al. | |
| 2004/0235160 A1 | 11/2004 | Nishikawa et al. | |
| 2005/0037492 A1 | 2/2005 | Xu et al. | |
| 2005/0233446 A1 | 10/2005 | Parsons et al. | |
| 2007/0053890 A1 | 3/2007 | Rosic-Kablar et al. | |
| 2007/0155013 A1 | 7/2007 | Akaike et al. | |
| 2007/0264713 A1 | 11/2007 | Terstegge et al. | |
| 2008/0159994 A1 | 7/2008 | Mantalaris et al. | |
| 2008/0241919 A1 | 10/2008 | Parsons et al. | |
| 2009/0029462 A1 | 1/2009 | Beardsley et al. | |
| 2009/0130759 A1 | 5/2009 | Smith et al. | |
| 2010/0304489 A1 | 12/2010 | Geijsen et al. | |
| 2013/0236961 A1 | 9/2013 | Amit et al. | |
| 2017/0183628 A1 | 6/2017 | Amit et al. | |

(Continued)

FOREIGN PATENT DOCUMENTS

| | | |
|---|---|---|
| JP | 2005-501554 | 1/2005 |
| JP | 2006-527995 | 12/2006 |
| WO | WO 03/020920 | 3/2003 |

(Continued)

OTHER PUBLICATIONS

Final Official Action dated Jun. 7, 2021 From the US Patent and Trademark Office Re. U.S. Appl. No. 16/055,110. (8 Pages).

(Continued)

*Primary Examiner* — Titilayo Moloye

(57) ABSTRACT

Provided is an isolated population of human pluripotent stem cells comprising at least 50% human pluripotent stem cells characterized by an OCT4+/TRA1-60-/TRA1-81-/SSEA1+/SSEA4- expression signature, and novel methods of generating and maintaining same in a pluripotent, undifferentiated state a suspension culture devoid of cell clumps. Also provided are novel culture media, cell cultures and methods for culturing pluripotent stem cells in a suspension culture or a two-dimensional culture system while maintaining the cells in a proliferative, pluripotent and undifferentiated state. The novel culture media comprise interleukin 11 (IL11) and Ciliay Neurotrophic Factor (CNTF); bFGF at a concentration of at least 50 ng/ml and an IL6RIL6 chimera; or an animal contaminant-free serum replacement and an IL6RIL6 chimera. Also provided are methods for generating lineage-specific cells from the pluripotent stem cells.

13 Claims, 28 Drawing Sheets
(27 of 28 Drawing Sheet(s) Filed in Color)
Specification includes a Sequence Listing.

(56) References Cited

U.S. PATENT DOCUMENTS

2018/0334650 A1 11/2018 Amit et al.
2022/0056406 A1 2/2022 Amit et al.

FOREIGN PATENT DOCUMENTS

| WO | WO 03/046141 | 6/2003 |
|---|---|---|
| WO | WO 2005/007840 | 1/2005 |
| WO | WO 2006/040763 | 4/2006 |
| WO | WO 2006/084314 | 8/2006 |
| WO | WO 2007/026353 | 3/2007 |
| WO | WO 2008/015682 | 2/2008 |
| WO | WO 2010/108126 | 9/2010 |
| WO | WO 2011/058558 | 5/2011 |
| WO | WO 2012/032521 | 3/2012 |

OTHER PUBLICATIONS

Advisory Action Before the Filing of An Appeal Brief dated Jun. 9, 2017 From the US Patent and Trademark Office Re. U.S. Appl. No. 13/821,244. (5 Pages).
Applicant-Initiated Interview Summary dated Jan. 21, 2015 From the US Patent and Trademark Office Re. U.S. Appl. No. 13/821,244.
Communication Pursuant to Article 94(3) EPC dated Mar. 14, 2016 From the European Patent Office Re. Application No. 11770876.8.
Communication Pursuant to Article 94(3) EPC dated May 28, 2018 From the European Patent Office Re. Application No. 11770876.8. (9 Pages).
Communication Relating to the Results of the Partial International Search dated Jan. 2, 2012 From the International Searching Authority Re. Application No. PCT/IL2011/000722.
European Search Report and the European Search Opinion dated Oct. 24, 2019 From the European Patent Office Re. Application No. 19181517.4. (12 Pages).
Examiner-Initiated Communication Request Form dated Oct. 5, 2017 From the Intellectual Property Office of Singapore, IPOS International Re. Application No. 10201509953V. (15 Pages).
Final Official Action dated May 5, 2020 from the US Patent and Trademark Office Re. U.S. Appl. No. 15/546,377. (23 pages).
International Preliminary Report on Patentability dated Mar. 21, 2013 From the International Bureau of WIPO Re. Application No. PCT/IL2011/000722.
International Search Report and the Written Opinion dated Mar. 28, 2012 From the International Searching Authority Re. Application No. PCT/IL2011/000722.
Notice of Reason for Rejection dated Jun. 3, 2016 From the Japanese Patent Office Re. Application No. 2013-527735 and Its Translation Into English.
Notice of Reason for Rejection dated Nov. 6, 2015 From the Japanese Patent Office Re. Application No. 2013-527735 and Its Translation Into English.
Notice of Reason for Rejection dated dec. 7, 2018 From the Japan Patent Office Re. Application No. 2017-113227 and Its Translation Into English. (8 Pages).
Notice of Reason for Rejection dated Feb. 10, 2017 From the Japanese Patent Office Re. Application No. 2013-527735 and Its Translation Into English. (6 Pages).
Notice of Reason for Rejection dated Jun. 12, 2018 From the Japan Patent Office Re. Application No. 2017-113227 and Its Translation Into English. (12 Pages).
Office Action dated Jul. 14, 2019 From the Israel Patent Office Re. Application No. 265107 and Its Translation Into English. (6 Pages).
Office Action dated Nov. 16, 2015 From the Israel Patent Office Re. Application No. 225070 and Its Translation Into English.
Office Action dated Dec. 18, 2016 From the Israel Patent Office Re. Application No. 225070 and Its Translation Into English. (6 Pages).
Office Action dated Jan. 31, 2018 From the Israel Patent Office Re. Application No. 225070 and Its Translation Into English. (4 Pages).
Official Action dated Nov. 2, 2017 From the US Patent and Trademark Office Re. U.S. Appl. No. 13/821,244. (10 pages).
Official Action dated May 6, 2015 From the US Patent and Trademark Office Re. U.S. Appl. No. 13/821,244.
Official Action dated Sep. 7, 2018 From the US Patent and Trademark Office Re. U.S. Appl. No. 15/403,303. (46 pages).
Official Action dated Feb. 9, 2017 From the US Patent and Trademark Office Re. U.S. Appl. No. 13/821,244. (26 pages).
Official Action dated Apr. 11, 2019 From the US Patent and Trademark Office Re. U.S. Appl. No. 15/403,303. (14 pages).
Official Action dated Aug. 12, 2014 From the US Patent and Trademark Office Re. U.S. Appl. No. 13/821,244.
Official Action dated May 18, 2016 From the US Patent and Trademark Office Re. U.S. Appl. No. 13/821,244.
Official Action dated Oct. 30, 2019 From the US Patent and Trademark Office Re. U.S. Appl. No. 16/055,110. (40 Pages).
Requisition by the Examiner dated Jul. 25, 2018 From the Innovation, Science and Economic Development Canada, Canadian Intellectual Property Office Re. Application No. 2,810,488. (5 Pages).
Requisition by the Examiner dated Jun. 25, 2019 From the Canadian Intellectual Property Office Re. Application No. 2,810,488. (4 Pages).
Restriction Official Action dated Mar. 6, 2014 From the US Patent and Trademark Office Re. U.S. Appl. No. 13/821,244.
Search and Examination Report dated Aug. 18, 2015 From the Intellectual Property Office of Singapore Issued by the Austrian Patent Office Re. Application No. 201301636-5.
Search Report and Written Opinion dated Jan. 7, 2020 From the Intellectual Property Office of Singapore Re. Application No. 10201800628Q. (8 Pages).
Search Report and Written Opinion dated Apr. 9, 2018 From the Intellectual Property Office of Singapore, IPOS Re. Application No. 10201800628Q. (13 Pages).
Search Report and Written Opinion dated Dec. 23, 2013 From the Intellectual Property Office of Singapore Issued by the Austrian Patent Office Re. Application No. 201301636-5.
Search Report and Written Opinion dated Sep. 23, 2016 From the Intellectual Property Office of Singapore Re. Application No. 11201509953V. (15 Pages).
Second Written Opinion dated Dec. 11, 2014 From the Intellectual Property Office of Singapore Issued by the Austrian Patent Office Re. Application No. 201301636-5.
Summons to Attend Oral Proceedings Pursuant to Rule 115(1) EPC Dated Oct. 17, 2017 From the European Patent Office Re. Application No. 11770876.8. (9 Pages).
Amit et al. "Clonally Derived Human Embryonic Stem Cell Lines Maintain Pluripotency and Proliferative Potential for Prolonged Periods of Culture", Developmental Biology, 227(2): 271-278, 2000.
Amit et al. "Feeder-Layer- and Serum-Free Culture of Human Embryonic Stem Cells", Biology of Reproduction, XP002978624, 70: 837-845, Jan. 2004.
Amit et al. "Suspension Culture of Undifferentiated Human Embryonic and Induced Pluripotent Stem Cells", Stem Cell Reviews, XP055015267, 6(2): 248-259, Jun. 2010.
Andaeng et al. "Optimized Mouse ES Cell Culture System by Suspension Growth in A Fully Defined Medium", Nature Protocols, XP055190263, 3(6): 1013-1017, Published Online May 22, 2008.
Aoi et al. "Generation of Pluripotent Stem Cells From Adult Mouse Liver and Stomach Cells", Science, 321(5889): 699-702, Aug. 1, 2008.
Azarin et al. "Development of Scalable Culture Systems for Human Embryonic Stem Cells", Biochemical Engineering Journal, 48(3): 378-384,Feb. 15, 2010.
Bhattacharya et al. "Gene Expression in Human Embryonic Stem Cell Lines: Unique Molecular Signature", Blood, 103(8): 2956-2964, 2004.
Brimble et al. "The Cell Surface Glycosphingolipids SSEA-3 and SSEA-4 Are Not Essential for Human ESC Pluripotency", Stem Cells, 25(1): 54-62, 2007.
Buecker et al. "A Murine ESC-Like State Facilities Transgenesis and Homologous Recombination in Human Pluripotent Stem Cells", Cell Stem Cell, XP055015337, 6(6): 535-546, Jun. 4, 2010. Abstract, p. 536, 541, 542, Figs. 1C, 3A, 4I.

(56) References Cited

OTHER PUBLICATIONS

Catalina et al. "Human ESCs Predisposition to Karyotypic Instability: Is A Matter of Culture Adaptation or Differential Vulnerability Among hESC Lines Due to Inherent Properties?", Molecular Cancer, 7(76): 1-9, Oct. 3, 2008.
Chen et al. "Actin-Myosin Contractility Is Responsible for the Reduced Viability of Dissociated Human Embryonic Stem Cells", Cell Stem Cell, 7(2): 240-248, Aug. 6, 2010.
Chen et al. "Bioreactor Expansion of Human Adult Bone Marrow-Derived Mesenchymal Stem Cells", Stem Cell, 24(9): 2052-2059, Published Online May 25, 2006.
Chin et al. "Defined and Serum-Free Media Support Undifferentiated Human Embryonic Stem Cell Growth", Stem Cells And Development, 19(6): 753-761, 2010.
Conover et al. "Ciliary Neurotrophic Factor Maintains the Pluripotentiality of Embryonic Stem Cells", Development, 119(3): 559-565, Nov. 27, 1993. Fig.2.
Daheron et al. "LIF/STAT3 Signaling Fails to Maintain Self-Renewal of Human Embryonic Stem Cells", Stem Cells 22(5): 770-778, Sep. 2004.
Dani et al. "Paracrine Induction of Stem Cell Renewal by LIF-Deficient Cells: A New ES Cell Regulatory Pathway", Developmental Biology, 203(1): 149-162, Nov. 1, 1998.
Ernst et al. "GP130-Mediated Signal Transduction in Embryonic Stem Cells Involves Activation of Jak and Ras/Mitogen-Activation Protein Kinase Pathways", The Journal of Biological Chemistry, 271(47): 30136-30143, Nov. 22, 1996.
Germanguz et al. "Molecular Characterization and Functional Properties of Cardiomyocytes Derived From Human Inducible Pluripotent Stem Cells", Journal of Cellular and Molecular Medicine, 15(1): 38-51, 2011.
Hanna et al. "Treatment of Sickle Cell Anemia Mouse Model With iPS Cells Generated From Autologous Skin", Science, 318(5858): 1920-1923, Dec. 21, 2007.
Humphrey et al. "Maintenance of Pluripotency in Human Embryonic Stem Cells Is STAT3 Independent", Stem Cells, XP002463152, 22(4): 522-530, Jul. 2004.
Itskovitz-Eldor et al. "Differentiation of Human Embryonic Stem Cells Into Embryoid Bodies Comprising the Three Embryonic Germ Layers", Molecular Medicine, 6(2): 88-95, 2000.
Kehoe et al. "Scalable Stirred-Suspension Bioreactor Culture of Human Pluripotent Stem Cells", Tissue Engineering, Part A, 16(2): 405-421, 2010.
King et al. "The Protein Phosphatase-1/Inhibitor-2 Complex Differentially Regulates GSK-3 Dephosphorylation and Increases Sarcoplasmic/Endoplasmic Reticulum Calcium ATPase 2 Levels", Experimental Cell Research, 312(18): 3693-3700, Nov. 1, 2006.
Lo et al. "Allelic Variation in Gene Expression Is Common in the Human Genome", Genome Research 13(8): 1855-1862, Aug. 2003.
Lowry et al. "Generation of Human Induced Pluripotent Stem Cells From Dermal Fibroblasts", Proc. Natl. Acad. Sci. USA, PNAS, 105(8): 2883-2888, Feb. 26, 2008.
Ludwig et al. "Derivation of Human Embryonic Stem Cells in Defined Conditions", Nature Biotechnology, 24(2): 185-187, Feb. 2006.
Meissner et al. "Direct Reprogramming of Genetically Unmodified Fibroblasts Into Pluripotent Stem Cells", Nature Biotechnology, 25(10): 1177-1181, Oct. 2007.
Nakagawa et al. "Generation of Induced Pluripotent Stem Cells Without Myc From Mouse and Human Fibroblasts", Nature Biotechnology, 26(1): 101-106, Jan. 2008.
Neben et al. "Synergistic Effects of Interleukin-11 With Other Growth Factors on the Expansion of Murine Hematopoietic Progenitors and Maintenance of Stem Cells in Liquid Culture", Experimental Hematology, 22(4): 353-359, Apr. 1994. Abstract. Abstract.
Odabas et al. "Separation of Mesenchymal Stem Cells With Magnetic Nanosorbents Carrying CD105 and CD73 Antibodies in Flow-Through and Batch Systems", Journal of Chromatography B, 861(1): 74-80, Available Online Nov. 23, 2007.
Okada et al. "Retinoic-Acid-Concentration-Dependent Acquisition of Neural Cell Identity During In Vitro Differentiation of Mouse Embryonic Stem Cells", Developmental Biology, 275(1): 124-142, Available Online Sep. 8, 2004.
Okita et al. "Generation of Germline-Competent Induced Pluripotent Stem Cells", Nature, 448: 313-318, Jul. 19, 2007.
Olmer et al. "Long Term Expansion of Undifferentiated Human iPS and ES Cells in Suspension Culture Using A Defined Medium", Stem Cell Research, XP027106371, 5(1): 51-64, Jul. 1, 2010. p. 61-62, Figs.7, 8.
Park et al. "Reprogramming of Human Somatic Cells to Pluripotency With Defined Factors", Nature, 451(7175): 141-146, Jan. 10, 2008.
Pera et al. "Human Embryonic Stem Cells", Journal of Cell Science, 113: 5-10, 2000.
Pera et al. "Regulation of Human Embryonic Stem Cell Differentiation by BMP-2 and Its Antagonist Noggin", Journal of Cell Science, XP009030261, 117(7): 1269-1280, Apr. 1, 2004.
Peterson et al. "Qualitative Modeling Identifies IL-11 as A Novel Regulator in Maintainig Self-Renewal in Human Pluripotent Stem Cells", Frontiers in Physiology, XP055633035, 4(Art.ID 303): 1-13, Published Online Oct. 28, 2013.
Rae "Methods and Mechanisms for Preserving Dissociated Human ESC", retrived from http://www.sens.org/research/research-blog, 2.P., May 2, 2010.
Roeb et al. "Regulation of Tissue Inhibitor of Metalloproteinases-1 Gene Expression by Cytokines and Dexamethasone in Rat Hepatocyte Primary Cultures", Hepatology, 18(6): 1437-1442, Dec. 1993. Abstract.
Samuel et al. "Dying Alone: A Tale of Rho" Cell Stem Cell, 7(2): 135-136, Aug. 6, 2010.
Schulz et al. "Differentiation of Human Embryonic Stem Cells to Dopaminergic Neurons in Serum-Free Suspension Culture", Stem Cells, 22(7): 1218-1238, Dec. 2004.
Singh et al. "Up-Scaling Single Cell-Inoculated Suspension Culture of Human Embryonic Stem Cells", Stem Cell Research, XP027054727, 4(3): 165-179, May 2010.
Stankoff et al. "Ciliary Neurotrophic Factor (CNTF) Enhances Myelin Formation: A Novel Role for CNTF and CNTF-Related Molecules", The Journal of Neuroscience, 22(21): 9221-9227, Nov. 1, 2002.
Steiner et al. "Derivation, Propagation and Controlled Differentiation of Human Embryonic Stem Cells in Suspension", Nature Biotechnology, 28(4): 361-364, Published Online Mar. 28, 2010.
Sulzbacher et al. "Activin A-Induced Differentiation of Embryonic Stem Cells Into Endoderm and Pancreatic Progenitors—The Influence of Differentiation Factors and Culture Conditions", Stem Cell Reviews, 5(2): 159-173, Published Online Mar. 5, 2009.
Takahashi et al. "Induction of Pluripotent Stem Cells From Mouse Embryonic and Adult Fibroblast Cultures by Defined Factors", Cell, 126(4): 663-676, Aug. 25, 2006.
Takahashi et al. "Induction of Pluripotent Stem Cells From Mouse Embryonic and Adult Fibroblast Cultures by Defined Factors", Cell, 131(5): 861-872, Nov. 30, 2007.
Thomson et al. "Embryonic Stem Cell Lines Derived From Human Blastocysts", Science, 282(5391): 1145-1147, Nov. 6, 1998.
Thomson et al. "Isolation of A Primate Embryonic Stem Cell Line", Proc. Natl. Acad. Sci. USA, 92: 7844-7848, Aug. 1995.
Thomson et al. "Pluripotent Cell Lines Derived From Common Marmoset (Callithrix Jacchus) Blastocysts", Biology of Reproduction, 55: 254-259, 1996.
Trivedi et al. "Derivation and Immunological Characterization of Mesenchymal Stromal Cells From Human Embryonic Stem Cells", Experimental Hematology, 36(3): 350-359, Mar. 2008.
Tsuji et al. "Maintenance of Undifferentiated Mouse Embryonic Stem Cells in Suspension by the Serum- and Feeder-Free Defined Culture Condition", Developmental Dynamics, 237(8): 2129-2138, Published Online Jul. 10, 2008.
Verfaillie et al. "Stem Cells: Hype and Reality", American Society of Hematology Education Program Book, 2002(1): 369-391, 2002.
Yu et al. "Human Induced Pluripotent Stem Cells Free of Vector and Transgene Sequences", Science, 324(5928): 797-801, May 8, 2009.
Yu et al. "Induced Pluripotent Stem Cell Lines Derived From Human Somatic Cells", Science, 318: 1917-1920, Dec. 21, 2007.

(56) References Cited

OTHER PUBLICATIONS

Examination Report dated Dec. 2, 2022 From the Intellectual Property Office of Singapore, IPOS Re. Application No. 10201800628Q. (5 pages).
Interview Summary dated Aug. 17, 2020 from the US Patent and Trademark Office Re. U.S. Appl. No. 16/055,110. (3 pages).
Search Report and Written Opinion dated Nov. 29, 2021 From the Intellectual Property Office of Singapore, IPOS Re. Application No. 10202109393R. (9 Pages).
Notice of Eligibility for Grant and Examination Report dated Aug. 21, 2023 From the Intellectual Property Office of Singapore, IPOS Re. Application No. 10202109393R. (8 Pages).
Requisition by the Examiner dated Apr. 14, 2023 From the Innovation, Science and Economic Development Canada, Canadian Intellectual Property Office Re. Application No. 3,150,342. (4 pages).
Lazzari et al. "Long-Term Expansion and Maintenance of Cord Blood Haematopoietic Stem Cells Using Thrombopoietin, Flt3-ligand, Interleukin (IL)-6 and IL-11 in a Serum-Free and Stroma-Free Culture System", British Journal of Haematology, 112(2): 397-404, Dec. 20, 2001.
Notice of Reason for Rejection dated Aug. 18, 2020 From the Japan Patent Office Re. Application No. 2019-149488 and Its Translation Into English.
Rose-John "GP130 Stimulation and the Maintenance of Stem Cells", Trends in Biotechnology, 20(10): 417-419, Oct. 2002.
Requisition by the Examiner dated May 15, 2023 From the Innovation, Science and Economic Development Canada, Canadian Intellectual Property Office Re. Application No. 2,810,488. (3 pages).
Notice of Reason for Rejection dated Dec. 16, 2022 From the Japan Patent Office Re. Application No. 2022-007129 and Its Translation Into English. (8 Pages).
Official Action dated Nov. 4, 2020 From the US Patent and Trademark Office Re. U.S. Appl. No. 16/055,110. (34 Pages).
Berrill et al. "Assessment of Stem Cell Markers During Long-Term Culture of Mouse Embryonic Stem Cells", Cytotechnology, 44(1-2): 77-91, Jan. 2004.
Lee et al. "Tumorigenicity as A Clinical Hurdle for Pluripotent Stem Cell Therapies", Nature Medicine, 19(8): 998-1004, Aug. 2013.

Oct 4

SSEA4

TRA-1-60

TRA-1-81

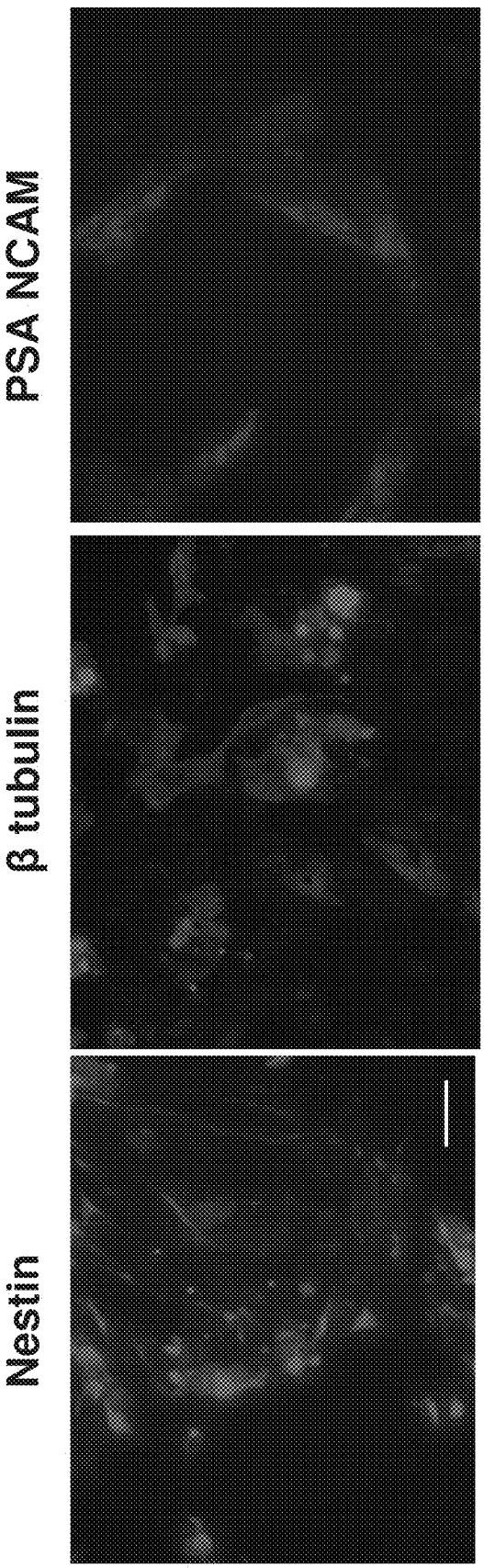

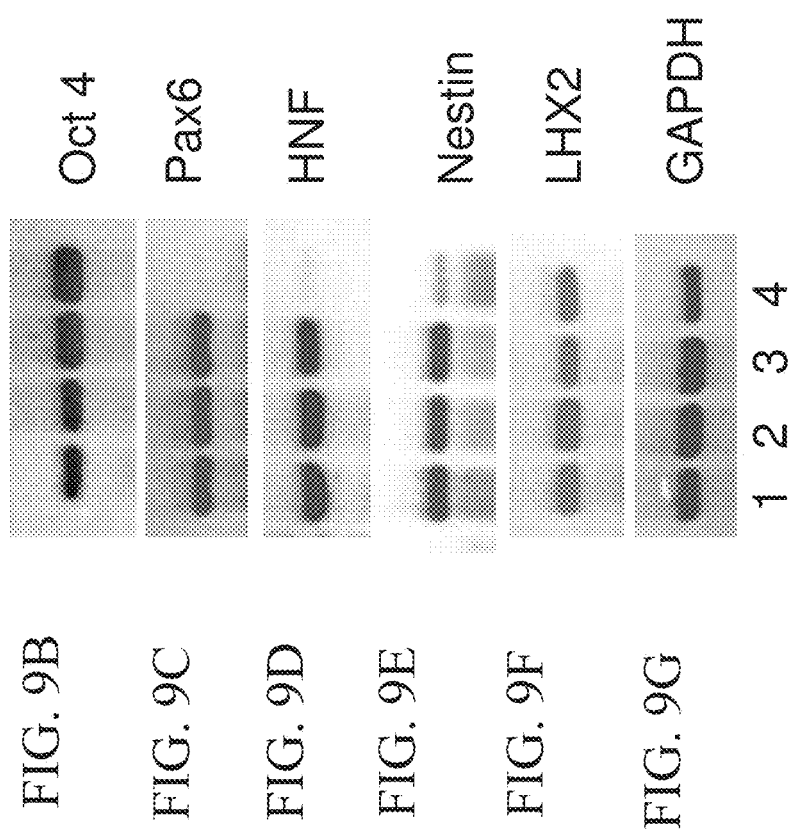

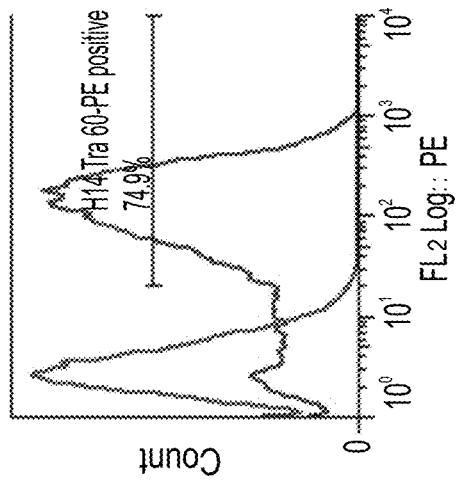
FIG. 12A TRA1-60, 2D
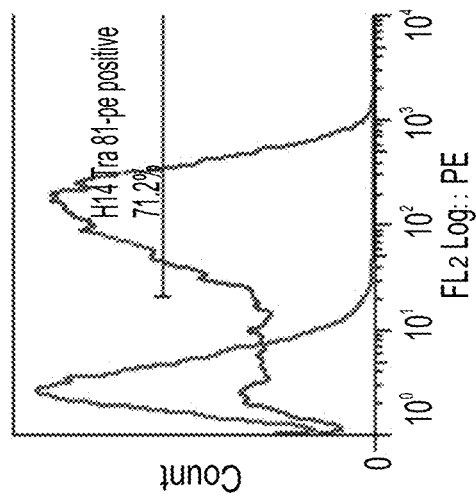
FIG. 12B TRA1-81, 2D

TRA1-60, suspension clumps

TRA1-81, suspension clumps

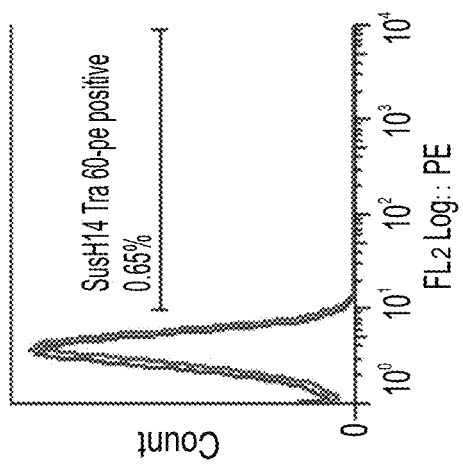
FIG. 12E TRA1-60, suspension single cells
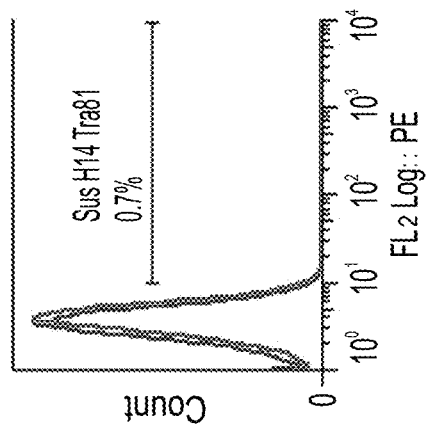
FIG. 12F TRA1-81, suspension single cells

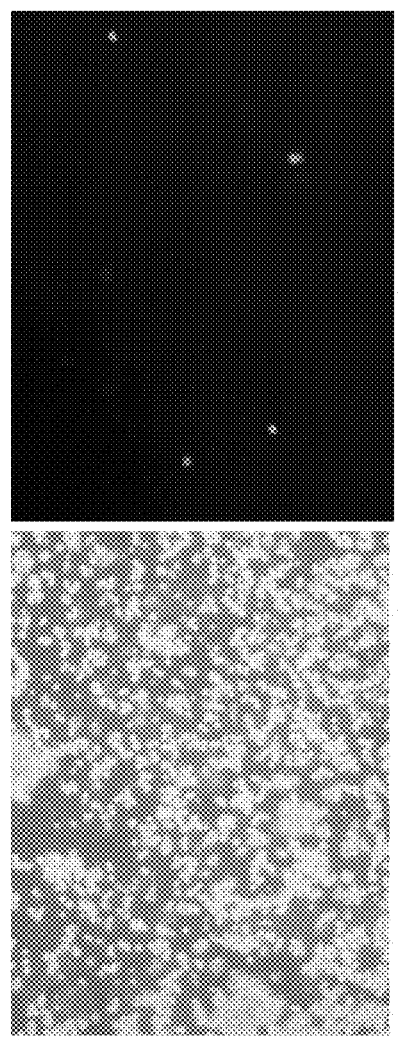

SEQUENCE LISTING

```
<160> NUMBER OF SEQ ID NOS: 51

<210> SEQ ID NO 1
<211> LENGTH: 225
<212> TYPE: DNA
<213> ORGANISM: Homo sapiens

<400> SEQUENCE: 1
gacaacaatg agaaccttca ggagatatgc aaagcagaaa ccctcgtgca ggcccgaaag      60
agaaagcgaa ccagtatcga gaaccgagtg agaggcaacc tggagaattt gttcctgcag     120
tgcccgaaac ccacgctgca gcagatcagc cacatcgccc agcagcttgg gctcgagaag     180
gatgtggtcc gagtggtccg agtgtggttc tgtaaccggc gccag                     225

<210> SEQ ID NO 2
<211> LENGTH: 23
<212> TYPE: DNA
<213> ORGANISM: Artificial sequence
<220> FEATURE:
```

<223> OTHER INFORMATION: Single strand DNA oligonucleotide

<400> SEQUENCE: 2
gagaacaatg agaaccttca gga                                           23

<210> SEQ ID NO 3
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 3
ttctggcgcc ggttacagaa cca                                           23

<210> SEQ ID NO 4
<211> LENGTH: 2098
<212> TYPE: DNA
<213> ORGANISM: Homo sapiens

<400> SEQUENCE: 4

| | |
|---|---|
| attataaatc tagagactcc aggattttaa cgttctgctg gactgagctg gttgcctcat | 60 |
| gttattatgc aggcaactca ctttatccca atttcttgat acttttcctt ctggaggtcc | 120 |
| tatttctcta acatcttcca gaaaagtctt aaagctgcct taaccttttt tccagtccac | 180 |
| ctcttaaatt ttttcctcct cttcctctat actaacatga gtgtggatcc agcttgtccc | 240 |
| caaagcttgc cttgctttga agcatccgac tgtaaagaat cttcacctat gctgtgatt | 300 |
| tgtgggcctg aagaaaacta ccatccttg caaatgtctt ctgctgagat gcctcacacg | 360 |
| gagactgtct ctcctcttcc ttcctccatg gatctgctta ttcaggacag ccctgattct | 420 |
| tccaccagtc ccaaaggcaa acaacccact tctgcagaga gagtgtcgc aaaaaaggaa | 480 |
| gacaaggtcc cggtcaagaa acagaagacc agaactgtgt tctcttccac ccagctgtgt | 540 |
| gtactcaatg atagatttca gagacagaaa tacctcagcc tccagcagat gcaagaactc | 600 |
| tccaacatcc tgaacctcag ctacaaacag gtgaagacct ggttccagaa ccagagaatg | 660 |
| aaatctaaga ggtggcagaa aaacaactgg ccgaagaata gcaatggtgt gacgcagaag | 720 |
| gcctcagcac ctacctaccc cagcctttac tcttcctacc accagggatg cctggtgaac | 780 |
| ccgactggga accttccaat gtggagcaac cagacctgga caattcaac ctggagcaac | 840 |
| cagacccaga catccagtc ctggagcaac cactcctgga cactcagac tggtgcacc | 900 |
| caatcctgga caatcaggc ctggaacagt cccttctata actgtggaga ggaatctctg | 960 |
| cagtcctgca tgcagttcca gccaaattct cctgccagtg acttggaggc tgccttggaa | 1020 |
| gctgctgggg aaggccttaa tgtaatacag cagaccacta ggtatttag tactccacaa | 1080 |
| accatggatt tattcctaaa ctactccatg aacatgcaac ctgaagacgt gtgaagatga | 1140 |
| gtgaaactga tattactcaa tttcagtctg gacactggct gaatccttcc tctcccctcc | 1200 |
| tcccatccct cataggattt ttcttgtttg gaaaccacgt gttctggttt ccatgatgcc | 1260 |
| catccagtca atctcatgga gggtggagta tggttggagc ctaatcagcg aggtttcttt | 1320 |
| tttttttttt ttcctattgg atcttcctgg agaaaatact ttttttttt ttttttttga | 1380 |
| aacggagtct tgctctgtcg cccaggctgg agtgcagtgg cgcggtcttg ctcactgca | 1440 |
| agctccgtct cccgggttca cgccattctc ctgcctcagc ctcccgagca gctgggacta | 1500 |
| caggcgcccg ccacctcgcc cggctaatat tttgtatttt tagtagagac ggggtttcac | 1560 |
| tgtgttagcc aggatggtct cgatctcctg accttgtgat ccacccgcct cggcctccct | 1620 |

| | |
|---|---|
| aacagctggg atttacaggc gtgagccacc gcgccctgcc tagaaaagac attttaataa | 1680 |
| ccttggctgc cgtctctggc tatagataag tagatctaat actagtttgg atatctttag | 1740 |
| ggtttagaat ctaacctcaa gaataagaaa tacaagtaca aattggtgat gaagatgtat | 1800 |
| tcgtattgtt tgggattggg aggctttgct tattttttaa aaactattga ggtaaagggt | 1860 |
| taagctgtaa catacttaat tgatttctta ccgttttggg ctctgttttg ctatatcccc | 1920 |
| taatttgttg gttgtgctaa tctttgtaga aagaggtctc gtatttgctg catcgtaatg | 1980 |
| acatgagtac tgctttagtt ggtttaagtt caaatgaatg aaacaactat ttttccttta | 2040 |
| gttgatttta ccctgatttc accgagtgtt tcaatgagta aatatacagc ttaaacat | 2098 |

<210> SEQ ID NO 5
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 5

| | |
|---|---|
| actaacatga gtgtggatcc | 20 |

<210> SEQ ID NO 6
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 6

| | |
|---|---|
| tcatcttcac acgtcttcag | 20 |

<210> SEQ ID NO 7
<211> LENGTH: 933
<212> TYPE: DNA
<213> ORGANISM: Homo sapiens

<400> SEQUENCE: 7

| | |
|---|---|
| atgagccagc aactgaagaa acgggcaaag acaagacacc agaaaggcct gggtggaaga | 60 |
| gcccccagtg gggctaagcc caggcaaggc aagtcaagcc aagacctgca ggcggaaata | 120 |
| gaacctgtca gcgcggtgtg ggccttatgt gatggctatg tgtgctatga gcctggccct | 180 |
| caggctctcg gagggatga tttctcagac tgttacatag aatgcgtcat aagggggtgag | 240 |
| ttttctcaac ccatcctgga agaggactca ctttttgagt ccttggaata cctaaagaaa | 300 |
| ggatcagaac aacagctttc tcaaaaggtt ttcgaagcaa gctcccttga atgttctttg | 360 |
| gaatacatga aaaaggggt aaagaaagag cttccacaaa agatagttgg agagaattcg | 420 |
| cttgagtatt ctgagtacat gacaggcaag aagcttccgc ctggaggaat acctggcatt | 480 |
| gacctatcag atcctaaaca gctcgcagaa tttgctagaa agaagccccc cataaataaa | 540 |
| gaatatgaca gtctgagcgc aatcgcttgt cctcagagtg gatgcactag gaagttgagg | 600 |
| aatagagctg ccctgagaaa gcatctcctc attcatggtc cccgagacca cgtctgtgcg | 660 |
| gaatgtggga agcgttcgt tgagagctca aaactaaaga acatttcct ggttcatact | 720 |
| ggagagaagc cgtttcggtg cacttttgaa gggtgcggaa agcgcttctc tctggacttt | 780 |
| aatttgcgta cgcacgtgcg catccacacg ggggagaaac gtttcgtgtg tcccttcaa | 840 |
| ggctgcaaca ggaggtttat tcagtcaaat aacctgaaag cccacatcct aacgcatgca | 900 | aatacgaaca agaatgaaca agagggaaag tag                            933

<210> SEQ ID NO 8
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 8
gcgtacgcaa attaaagtcc aga                                       23

<210> SEQ ID NO 9
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 9
cagcatccta aacagctcgc agaat                                     25

<210> SEQ ID NO 10
<211> LENGTH: 1220
<212> TYPE: DNA
<213> ORGANISM: Homo sapiens

<400> SEQUENCE: 10
gggagcgggc gagtaggagg gggcgccggg ctatatatat agcggctcgg cctcgggcgg    60
gcctggcgct cagggaggcg cgcactgctc ctcagagtcc cagctccagc cgcgcgcttt   120
ccgcccggct cgccgctcca tgcagccggg gtagagcccg gcgcccgggg gccccgtcgc   180
ttgcctcccg cacctcctcg gttgcgcact cctgcccgag gtcggccgtg cgctcccgcg   240
ggacgccaca ggcgcagctc tgcccccag cttcccgggc gcactgaccg cctgaccgac    300 gcacggcccct cgggccggga tgtcggggcc cggacggcc gcgtagcgc tgctcccggc   360 ggtcctgctg gccttgctgg cgccctgggc gggccgaggg ggcgccgccg cacccactgc   420
acccaacggc acgctggagg ccgagctgga gcgccgctgg gagagcctgg tggcgctctc   480
gttggcgcgc ctgccggtgg cagcgcagcc caaggaggcg gccgtccaga gcggcgccgg   540
cgactacctg ctgggcatca gcggctgcg gcggctctac tgcaacgtgg gcatcggctt   600
ccacctccag gcgctccccg acggccgcat cggcggcgcg cacgcggaca cccgcgacag   660
cctgctggag ctctcgcccg tggagcgggg cgtggtgagc atcttcggcg tggccagccg   720
gttcttcgtg gccatgagca gcaagggcaa gctctatggc tcgcccttct tcaccgatga   780
gtgcacgttc aaggagattc tccttcccaa caactacaac gcctacgagt cctacaagta   840
ccccggcatg ttcatcgccc tgagcaagaa tgggaagacc aagaagggga accgagtgtc   900
gcccaccatg aaggtcaccc acttcctccc caggctgtga ccctccagag gacccttgcc   960
tcagcctcgg gaagccctgg ggagggcagt gccgagggtc accttggtgc actttcttcg  1020
gatgaagagt ttaatgcaag agtaggtgta agatatttaa attaattatt taaatgtgta  1080
tatattgcca ccaaattatt tatagttctg cgggtgtgtt ttttaattttt ctggggggaa  1140 aaaagacaa aacaaaaaac caactctgac ttttctggtg caacagtgga gaatcttacc  1200
attggatttc tttaacttgt                                             1220

<210> SEQ ID NO 11
<211> LENGTH: 23

```
<212> TYPE: DNA
<213> ORGANISM: Artificial sequence
<220> FEATURE:
<223> OTHER INFORMATION: Single strand DNA oligonucleotide

<400> SEQUENCE: 11
ctacaacgcc tacgagtcct aca                                             23

<210> SEQ ID NO 12
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 12
gttgcaccag aaaagtcaga gttg                                            24

<210> SEQ ID NO 13
<211> LENGTH: 1085
<212> TYPE: DNA
<213> ORGANISM: Homo sapiens

<400> SEQUENCE: 13
cacagcgccc gcatgtacaa catgatggag acggagctga agccgccggg cccgcagcaa      60
acttcggggg gcggcggcgg caactccacc gcggcggcgg ccggcggcaa ccagaaaaac     120
agcccggacc gcgtcaagcg gcccatgaat gccttcatgg tgtggtcccg cgggcagcgg     180
cgcaagatgg cccaggagaa ccccaagatg cacaactcgg agatcagcaa gcgcctgggc     240
gccgagtgga aacttttgtc ggagacggag aagcggccgt tcatcgacga ggctaagcgg     300
ctgcgagcgc tgcacatgaa ggagcacccg gattataaat accggccccg gcggaaaacc     360
aagacgctca tgaagaagga taagtacacg ctgcccggcg ggctgctggc ccccggcggc     420
aatagcatgg cgagcgggt cggggtgggc gccggcctgg gcgcgggcgt gaaccagcgc     480
atggacagtt acgcgcacat gaacggctgg agcaacggca gctacagcat gatgcaggac     540
cagctgggct acccgcagca cccgggcctc aatgcgcacg gcgcagcgca gatgcagccc     600
atgcaccgct acgacgtgag cgccctgcag tacaactcca tgaccagctc gcagacctac     660
atgaacggct cgcccaccta cagcatgtcc tactcgcagc agggcacccc tggcatggct     720
cttggctcca tgggttcggt ggtcaagtcc gaggccagct ccagccccc tgtggttacc     780 tcttcctccc actccagggc gccctgccag gccggggacc tccgggacat gatcagcatg     840
tatctccccg gcgccgaggt gccggaaccc gccgccccca gcagacttca catgtcccag     900
cactaccaga gcggccccgt gcccggcacg gccattaacg gcacactgcc cctctcacac     960
atgtgagggc cggacagcga actggagggg ggagaaattt tcaaagaaaa acgagggaaa    1020
tgggaggggt gcaaaagagg agagtaagaa acagcatgga gaaacccgg tacgctcaaa    1080 aaaaa                                                               1085

<210> SEQ ID NO 14
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 14
cccccggcgg caatagca                                                   18
```

<210> SEQ ID NO 15
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 15
tcggcgccgg ggagatacat                                              20

<210> SEQ ID NO 16
<211> LENGTH: 1310
<212> TYPE: DNA
<213> ORGANISM: Homo sapiens

<400> SEQUENCE: 16
aaattgagcc cgcagcctcc cgcttcgctc tctgctcctc ctgttcgaca gtcagccgca    60
tcttcttttg cgtcgccagc cgagccacat cgctcagaca ccatggggaa ggtgaaggtc   120
ggagtcaacg gatttggtcg tattgggcgc ctggtcacca gggctgcttt taactctggt   180
aaagtggata ttgttgccat caatgacccc ttcattgacc tcaactacat ggtttacatg   240
ttccaatatg attccaccca tggcaaattc catggcaccg tcaaggctga aacgggaag    300 cttgtcatca atggaaatcc catcaccatc ttccaggagc gagatcccctc caaaatcaag   360 tggggcgatg ctggcgctga gtacgtcgtg gagtccactg gcgtcttcac caccatggag   420
aaggctgggg ctcatttgca gggggagcc aaaagggtca tcatctctgc cccctctgct   480
gatgccccca tgttcgtcat gggtgtgaac catgagaagt atgacaacag cctcaagatc   540
atcagcaatg cctcctgcac caccaactgc ttagcacccc tggccaaggt catccatgac   600
aactttggta tcgtggaagg actcatgacc acagtccatg ccatcactgc cacccagaag   660
actgtggatg gcccctccgg gaaactgtgg cgtgatggcc gcgggctct ccagaacatc    720 atccctgcct ctactggcgc tgccaaggct gtgggcaagg tcatccctga gctgaacggg   780
aagctcactg gcatggcctt ccgtgtcccc actgccaacg tgtcagtggt ggacctgacc   840
tgccgtctag aaaaacctgc caaatatgat gacatcaaga aggtggtgaa gcaggcgtcg   900 gagggcccc tcaagggcat cctgggctac actgagcacc aggtggtctc ctctgacttc   960
aacagcgaca cccactcctc cacctttgac gctggggctg gcattgccct caacgaccac  1020
tttgtcaagc tcatttcctg gtatgacaac gaatttggct acagcaacag ggtggtggac  1080
ctcatggccc acatggcctc caaggagtaa gaccccctgga ccaccagccc cagcaagagc  1140
acaagaggaa gagagagacc ctcactgctg gggagtccct gccacactca gtcccccacc  1200
acactgaatc tcccctcctc acagttgcca tgtagacccc ttgaagaggg gaggggccta  1260
gggagccgca ccttgtcatg taccatcaat aaagtaccct gtgctcaacc              1310

<210> SEQ ID NO 17
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 17
aatcccatca ccatcttcca                                              20

<210> SEQ ID NO 18
<211> LENGTH: 19

-continued

```
<212> TYPE: DNA
<213> ORGANISM: Artificial sequence
<220> FEATURE:
<223> OTHER INFORMATION: Single strand DNA oligonucleotide

<400> SEQUENCE: 18
gcctgcttca ccaccttct                                                    19

<210> SEQ ID NO 19
<211> LENGTH: 543
<212> TYPE: PRT
<213> ORGANISM: Artificial sequence
<220> FEATURE:
<223> OTHER INFORMATION: IL6R/IL6 chimeric protein

<400> SEQUENCE: 19
```

Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

```
Pro Pro Ala Glu Asn Glu Val Ser Thr Pro Met Gln Ala Leu Thr Thr
            325                 330                 335

Asn Lys Asp Asp Asp Asn Ile Leu Phe Arg Asp Ser Ala Asn Ala Thr
            340                 345                 350

Ser Leu Pro Val Glu Phe Met Pro Val Pro Pro Gly Glu Asp Ser Lys
            355                 360                 365

Asp Val Ala Ala Pro His Arg Gln Pro Leu Thr Ser Ser Glu Arg Ile
            370                 375                 380

Asp Lys Gln Ile Arg Tyr Ile Leu Asp Gly Ile Ser Ala Leu Arg Lys
385                 390                 395                 400

Glu Thr Cys Asn Lys Ser Asn Met Cys Glu Ser Ser Lys Glu Ala Leu
            405                 410                 415

Ala Glu Asn Asn Leu Asn Leu Pro Lys Met Ala Glu Lys Asp Gly Cys
            420                 425                 430

Phe Gln Ser Gly Phe Asn Glu Glu Thr Cys Leu Val Lys Ile Ile Thr
            435                 440                 445

Gly Leu Leu Glu Phe Glu Val Tyr Leu Glu Tyr Leu Gln Asn Arg Phe
            450                 455                 460

Glu Ser Ser Glu Glu Gln Ala Arg Ala Val Gln Met Ser Thr Lys Val
465                 470                 475                 480

Leu Ile Gln Phe Leu Gln Lys Lys Ala Lys Asn Leu Asp Ala Ile Thr
            485                 490                 495

Thr Pro Asp Pro Thr Thr Asn Ala Ser Leu Leu Thr Lys Leu Gln Ala
            500                 505                 510

Gln Asn Gln Trp Leu Gln Asp Met Thr Thr His Leu Ile Leu Arg Ser
            515                 520                 525

Phe Lys Glu Phe Leu Gln Ser Ser Leu Arg Ala Leu Arg Gln Met
            530                 535                 540

<210> SEQ ID NO 20
<211> LENGTH: 6883
<212> TYPE: DNA
<213> ORGANISM: Homo sapiens

<400> SEQUENCE: 20 accctcttttt cttatcattg acatttaaac tctggggcag gtcctcgcgt agaacgcggc    60
tgtcagatct gccacttccc ctgccgagcg gcggtgagaa gtgtgggaac cggcgctgcc   120
aggctcacct gcctccccgc cctccgctcc caggaatctg agaattgctc tcacacacca   180
acccagcaac atccgtggag aaaactctca ccagcaactc cttaaaaaca ccgtcatttc   240
aaaccattgt ggtcttcaag caacaacagc agcacaaaaa accccaacca acaaaaactc   300
ttgacagaag ctgtgacaac cagaaaggat gcctcataaa gggggaagac tttaactagg   360
ggcgcgcaga tgtgtgaggc cttttattgt gagagtggac agacatccga gatttcagag   420
ccccatattc gagccccgtg gaatcccgcg gcccccagcc agagccagca tgcagaacag   480
tcacagcgga gtgaatcagc tcggtggtgt ctttgtcaac gggcggccac tgccggactc   540
cacccggcag aagattgtag agctagctca gcgggggcc cggccgtgcg acatttcccg   600
aattctgcag gtgtccaacg gatgtgtgag taaaattctg ggcaggtatt acgagactgg   660
ctccatcaga cccagggcaa tcggtggtag taaaccgaga gtagcgactc cagaagttgt   720
aagcaaaata gcccagtata agcgggagtg cccgtccatc tttgcttggg aaatccgaga   780
cagattactg tccgaggggg tctgtaccaa cgataacata ccaagcgtgt catcaataaa   840
cagagttctt cgcaacctgg ctagcgaaaa gcaacagatg ggcgcagacg gcatgtatga   900
```

```
taaactaagg atgttgaacg ggcagaccgg aagctggggc acccgccctg gttggtatcc    960
ggggacttcg gtgccagggc aacctacgca agatggctgc cagcaacagg aaggaggggg   1020
agagaatacc aactccatca gttccaacgg agaagattca gatgaggctc aaatgcgact   1080
tcagctgaag cggaagctgc aaagaaatag aacatccttt acccaagagc aaattgaggc   1140
cctggagaaa gagtttgaga gaacccatta tccagatgtg tttgcccgag aaagactagc   1200
agccaaaata gatctacctg aagcaagaat acaggtatgg ttttctaatc gaagggccaa   1260
atggagaaga gaagaaaaac tgaggaatca gagaagacag gccagcaaca cacctagtca   1320
tattcctatc agcagtagtt tcagcaccag tgtctaccaa ccaattccac aacccaccac   1380
accggtttcc tccttcacat ctggctccat gttgggccga acagacacag ccctcacaaa   1440
cacctacagc gctctgccgc ctatgccag cttcaccatg gcaaataacc tgcctatgca   1500
acccccagtc cccagccaga cctcctcata ctcctgcatg ctgcccacca gcccttcggt   1560
gaatgggcgg agttatgata cctacacccc cccacatatg cagacacaca tgaacagtca   1620
gccaatgggc acctcgggca ccacttcaac aggactcatt tcccctggtg tgtcagttcc   1680
agttcaagtt cccggaagtg aacctgatat gtctcaatac tggccaagat acagtaaaa   1740 aaaaaaaaaa aaaaaaaaag gaaggaaat attgtgttaa ttcagtcagt gactatgggg   1800
acacaacagt tgagctttca ggaaagaaag aaaaatggct gttagagccg cttcagttct   1860
acaattgtgt cctgtattgt accactgggg aaggaatgga cttgaaacaa ggacctttgt   1920
atacagaagg cacgatatca gttggaacaa atcttcattt tggtatccaa acttttattc   1980
attttggtgt attatttgta aatgggcatt tgtatgttat aatgaaaaaa agaacaatgt   2040
agactggatg gatgtttgat ctgtgttggt catgaagttg ttttttttt ttttaaaaag   2100 aaaaccatga tcaacaagct tgccacgaa tttaagagtt ttatcaagat atatcgaata   2160
cttctaccca tctgttcata gtttatggac tgatgttcca agtttgtatc attcctttgc   2220
atataattaa acctggaaca acatgcacta gatttatgtc agaaatatct gttggtttc   2280 caaaggttgt taacagatga agtttatgtg caaaaagg taagatataa attcaaggaa   2340
gaaaaaaagt tgatagctaa aaggtagagt gtgtcttcga tataatccaa tttgttttat   2400
gtcaaaatgt aagtatttgt cttccctaga aatcctcaga atgatttcta taataaagtt   2460
aatttcattt atatttgaca agaatataga tgttttatac acattttcat gcaatcatac   2520 gtttctttt tggccagcaa aagttaattg ttcttagata tagttgtatt actgttcacg   2580
gtccaatcat tttgtgcatc tagagttcat tcctaatcaa ttaaaagtgc ttgcaagagt   2640
tttaaactta agtgtttga agttgttcac aactacatat caaaattaac cattgttgat   2700
tgtaaaaaac catgccaaag cctttgtatt tcctttatta tacagttttc tttttaacct   2760
tatagtgtgg tgttacaaat tttatttcca tgttagatca acattctaaa ccaatggtta   2820
ctttcacaca cactctgttt tacatcctga tgatccttaa aaaataatcc ttatagatac   2880
cataaatcaa aaacgtgtta gaaaaaaatt ccacttacag cagggtgtag atctgtgccc   2940
atttataccc acaacatata tacaaaatgg taacatttcc cagttagcca tttaattcta   3000
aagctcaaag tctagaaata atttaaaaat gcaacaagcg attagctagg aattgttttt   3060
tgaattagga ctggcatttt caatctgggc agatttccat tgtcagccta tttcaacaat   3120
gatttcactg aagtatattc aaaagtagat ttccttaagg agactttctg aaagctgttg   3180
cctttttcaa ataggccctc tccctttct gtctccctcc cctttgcaca agaggcatca   3240
```

```
tttcccattg aaccactaca gctgttccca tttgaatctt gctttctgtg cggttgtgga    3300
tggttggagg gtggagggggg gatgttgcat gtcaaggaat aatgagcaca gacacatcaa    3360
cagacaacaa caaagcagac tgtgactggc cggtgggaat taaaggcctt cagtcattgg    3420
cagcttaagc caaacattcc caaatctatg aagcagggcc cattgttggt cagttgttat    3480
ttgcaatgaa gcacagttct gatcatgttt aaagtggagg cacgcagggc aggagtgctt    3540
gagcccaagc aaaggatgga aaaaaataag cctttgttgg gtaaaaaagg actgtctgag    3600
actttcattt gttctgtgca acatataagt caatacagat aagtcttcct ctgcaaactt    3660
cactaaaaag cctgggggtt ctggcagtct agattaaaat gcttgcacat gcagaaacct    3720
ctggggacaa agacacactt ccactgaatt atactctgct ttaaaaaaat ccccaaaagc    3780
aaatgatcag aaatgtagaa attaatgaaa ggatttaaac atgaccttct cgttcaatat    3840
ctactgtttt ttagttaagg aattacttgt gaacagataa ttgagattca ttgctccggc    3900
atgaaatata ctaataattt tattccacca gagttgctgc acatttggag acaccttcct    3960
aagttgcagt ttttgtatgt gtgcatgtag ttttgttcag tgtcagcctg cactgcacag    4020
cagcacattt ctgcagggga gtgagcacac atacgcactg ttggtacaat gccggtgca    4080 gacatttcta cctcctgaca ttttgcagcc tacattccct gagggctgtg tgctgaggga    4140
actgtcagag aagggctatg tgggagtgca tgccacagct gctggctggc ttacttcttc    4200
cttctcgctg gctgtaattt ccaccacggt caggcagcca gttccggccc acggttctgt    4260
tgtgtagaca gcagagactt tggagacccg gatgtcgcac gccaggtgca agaggtggga    4320
atgggagaaa aggagtgacg tgggagcgga gggtctgtat gtgtgcactt gggcacgtat    4380
atgtgtgctc tgaaggtcag gattgccagg gcaaagtagc acagtctggt atagtctgaa    4440
gaagcggctg ctcagctgca gaagccctct ggtccggcag gatgggaacg gctgccttgc    4500
cttctgccca caccctaggg acatgagctg tccttccaaa cagagctcca ggcactctct    4560
tggggacagc atggcaggct ctgtgtggta gcagtgcctg ggagttggcc ttttactcat    4620
tgttgaaata atttttgttt attatttatt taacgataca tatatttata tatttatcaa    4680
tggggtatct gcaggatgt tttgacacca tcttccagga tggagattat ttgtgaagac    4740
ttcagtagaa tcccaggact aaacgtctaa attttttctc caaacttgac tgacttggga    4800
aaaccaggtg aatagaataa gagctgaatg ttttaagtaa taaacgttca aactgctcta    4860
agtaaaaaaa tgcattttac tgcaatgaat ttctagaata ttttccccc aaagctatgc    4920 ctcctaaccc ttaaatggtg aacaactggt ttcttgctac agctcactgc catttcttct    4980
tactatcatc actaggtttc ctaagattca ctcatacagt attatttgaa gattcagctt    5040
tgttctgtga atgtcatctt aggattgtgt ctatattctt ttgcttattt ctttttactc    5100
tgggcctctc atactagtaa gattttaaaa agccttttct tctctgtatg tttggctcac    5160
caaggcgaaa tatatattct tctctttttc atttctcaag aataaacctc atctgctttt    5220
ttgtttttct gtgttttggc ttggtactga atgactcaac tgctcggttt taaagttcaa    5280
agtgtaagta cttagggtta gtactgctta tttcaataat gttgacggtg actatctttg    5340
gaaagcagta acatgctgtc ttagaaatga cattaataat gggcttaaac aaatgaatag    5400
gggggtcccc ccactctcct tttgtatgcc tatgtgtgtc tgatttgtta aaagatggac    5460
agggaattga ttgcagagtg tcgcttcctt ctaaagtagt tttattttgt ctactgttag    5520
tatttaaaga tcctggaggt ggacataagg aataaatgga agagaaaagt agatattgta    5580
tggtggctac taaaaggaaa ttcaaaaagt cttagaaccc gagcacctga gcaaactgca    5640
```

```
gtagtcaaaa tatttatctc atgttaaaga aaggcaaatc tagtgtaaga aatgagtacc      5700
atatagggtt ttgaagttca tatactagaa acacttaaaa gatatcattt cagatattac      5760
gtttggcatt gttcttaagt atttatatct ttgagtcaag ctgataatta aaaaaaatct      5820
gttaatggag tgtatatttc ataatgtatc aaaatggtgt ctatacctaa ggtagcatta      5880
ttgaagagag atatgtttat gtagtaagtt attaacataa tgagtaacaa ataatgtttc      5940
cagaagaaag gaaaacacat tttcagagtg cgtttttatc agaggaagac aaaaatacac      6000
acccctctcc agtagcttat ttttacaaag ccggcccagt gaattagaaa acaaagcac      6060 ttggatatga ttttttggaaa gcccaggtac acttattatt caaaatgcac ttttactgag      6120
tttgaaaagt ttctttttata tttaaaataa gggttcaaat atgcatattc aatttttata      6180
gtagttatct atttgcaaag catatattaa ctagtaattg gctgttaatt ttatagacat      6240
ggtagccagg gaagtatatc aatgacctat taagtatttt gacaagcaat ttacatatct      6300
gatgacctcg tatctctttt tcagcaagtc aaatgctatg taattgttcc attgtgtgtt      6360
gtataaaatg aatcaacacg gtaagaaaaa ggttagagtt attaaaataa taaactgact      6420
aaaatactca tttgaattta ttcagaatgt tcataatgct ttcaaaggac atagcagagc      6480
ttttgtggag tatccgcaca acattattta ttatctatgg actaaatcaa tttttttgaag      6540 ttgctttaaa atttaaaagc accttttgctt aatataaagc cctttaatttt taactgacag      6600 atcaattctg aaactttatt ttgaaaagaa aatggggaag aatctgtgtc tttagaatta      6660
aaagaaatga aaaaaataaa cccgacattc taaaaaaata gaataagaaa cctgattttt      6720
agtactaatg aaatagcggg tgacaaaata gttgtctttt tgattttgat cacaaaaaat      6780
aaactggtag tgacaggata tgatggagag atttgcatc ctggcaaatc actgtcattg      6840
attcaattat tctaattctg aataaaagct gtatacagta aaa                       6883

<210> SEQ ID NO 21
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 21
aacagacaca gccctcacaa aca                                              23

<210> SEQ ID NO 22
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 22
cgggaacttg aactggaact gac                                              23

<210> SEQ ID NO 23
<211> LENGTH: 5591
<212> TYPE: DNA
<213> ORGANISM: Homo sapiens

<400> SEQUENCE: 23
gctactccca ccccgcccg ccccgtcatt gtcccgtcg gtctcttttc tcttccgtcc         60
taaaagctct gcgagccgct cccttctccc ggtgccccgc gtctgtccat cctcagtggg      120
```

| | |
|---|---|
| tcagacgagc aggatggagg gctgcatggg ggaggagtcg tttcagatgt gggagctcaa | 180 |
| tcggcgcctg gaggcctacc tggcccgggt caaggcgctg gaggagcaga atgagctgct | 240 |
| cagcgcggag ctcgggggc tccgggcaca atccgcggac acctcctggc gggcgcatgc | 300 |
| cgacgacgag ctggcggccc tgcgggccct cgttgaccaa cgctggcggg agaagcacgc | 360 |
| ggccgaggtg gcgcgcgaca acctggctga agagctggag ggcgtggcag gccgatgcca | 420 |
| gcagctgcgg ctggcccggg agcggacgac ggaggaggta gcccgcaacc ggcgcgccgt | 480 |
| cgaggcagag aaatgcgccc gggcctggct gagtagccag gtggcagagc tggagcgcga | 540 |
| gctagaggct ctacgcgtgg cgcacgagga ggagcgcgtc ggcctgaacg cgcaggctgc | 600 |
| ctgtgccccc cgctgccccg cgccgcccg cgggcctccc gcgccggccc cggaggtaga | 660 |
| ggagctggca aggcgactgg gcgaggcgtg gcgcggggca gtgcgcggct accaggagcg | 720 |
| cgtggcacac atggagacgt cgctgggcca ggcccgcgag cggctgggcc gggcggtgca | 780 |
| gggtgcccgc gagggccgcc tggagctgca gcagctccag gctgagcgcg gaggcctcct | 840 |
| ggagcgcagg gcagcgttgg aacagaggtt ggagggccgc tggcaggagc ggctgcgggc | 900 |
| tactgaaaag ttccagctgg ctgtggaggc cctggagcag gagaaacagg gcctacagag | 960 |
| ccagatcgct caggtcctgg aaggtcggca gcagctggcg cacctcaaga tgtccctcag | 1020 |
| cctggaggtg gccacgtaca ggaccctcct ggaggctgag aactcccggc tgcaaacacc | 1080 |
| tggcggtggc tccaagactt ccctcagctt tcaggacccc aagctggagc tgcaattccc | 1140 |
| taggacccca gagggccggc gtcttggatc tttgctccca gtcctgagcc caacttccct | 1200 |
| cccctcaccc ttgcctgcta cccttgagac acctgtgcca gcctttctta agaaccaaga | 1260 |
| attcctccag gcccgtaccc ctaccttggc cagcaccccc atccccccca cacctcaggc | 1320 |
| accctctcct gctgtagatg cagagatcag agcccaggat gctcctctct ctctgctcca | 1380 |
| gacacagggt gggaggaaac aggctccaga gcccctgcgg gctgaagcca gggtggccat | 1440 |
| tcctgccagc gtcctgcctg accagagga gcctgggggc cagcggcaag aggccagtac | 1500 |
| aggccagtcc ccagaggacc atgcctcctt ggcaccaccc ctcagccctg accactccag | 1560 |
| tttagaggct aaggatggag aatccggtgg gtctagagtg ttcagcatat gccgagggga | 1620 |
| aggtgaaggg caaatctggg ggttggtaga gaaagaaaca gccatagagg gcaaagtggt | 1680 |
| aagcagcttg cagcaggaaa tatgggaaga agaggatcta aacaggaagg aaatccagga | 1740 |
| ctcccaggtt cctttggaaa agaaaccct gaagtctctg ggagaggaga ttcaagagtc | 1800 |
| actgaagact ctggaaaacc agagccatga gacactagaa agggagaatc aagaatgtcc | 1860 |
| gaggtcttta gaagaagact tagaaacact aaaaagtcta gaaaaggaaa ataaagagct | 1920 |
| attaaaggat gtgaggtag tgagacctct agaaaaagag gctgtaggcc aacttaagcc | 1980 |
| tacaggaaaa gaggacacac agacattgca atccctgcaa aaggagaatc aagaactaat | 2040 |
| gaaatctctt gaaggtaatc tagagacatt tttatttcca ggaacggaaa atcaagaatt | 2100 |
| agtaagttct ctgcaagaga acttagagtc attgacagct ctggaaaagg agaatcaaga | 2160 |
| gccactgaga tctccagaag taggggatga ggaggcactg agacctctga caaggagaa | 2220 |
| tcaggaaccc ctgaggtctc ttgaagatga gaacaaagag gcctttagat ctctagaaaa | 2280 |
| agagaaccag gagccactga agactctaga agaagaggac cagagtattg tgagacctct | 2340 |
| agaaacagag aatcacaaat cactgaggtc tttagaagaa caggaccaag agacattgag | 2400 |
| aactcttgaa aaagagactc aacagcgacg gaggtctcta ggggaacagg atcagatgac | 2460 |
| attaagaccc ccagaaaaag tggatctaga accactgaag tctcttgacc aggagatagc | 2520 |

-continued

```
tagacctctt gaaaatgaga atcaagagtt cttaaagtca ctcaaagaag agagcgtaga    2580
ggcagtaaaa tctttagaaa cagagatcct agaatcactg aagtctgcgg gacaagagaa    2640
cctggaaaca ctgaaatctc cagaaactca agcaccactg tggactccag aagaaataaa    2700 tcaggggca atgaatcctc tagaaaagga aattcaagaa ccactggagt ctgtggaagt     2760
gaaccaagag acattcagac tcctggaaga ggagaatcag gaatcattga gatctctggg    2820
agcatggaac ctggagaatt tgagatctcc agaggaggta gacaaggaaa gtcaaaggaa    2880
tctggaagag gaagagaacc tgggaaaggg agagtaccaa gagtcactga ggtctctgga    2940
ggaggaggga caggagctgc cgcagtctgc agatgtgcag aggtgggaag atacggtgga    3000
gaaggaccaa gaactggctc aggaaagccc tcctgggatg gctggagtgg aaaatgagga    3060
tgaggcagag ctgaatctga gggagcagga tggcttcact gggaaggagg aggtggtaga    3120
gcagggagag ctgaatgcca cagaggaggt ctggatccca ggcgaggggc acccagagag    3180
ccctgagccc aaagagcaga gaggcctggt tgagggagcc agtgtgaagg aggggctga    3240 gggcctccag accctgaag gcaatcaca acaggtgggg gccccaggcc tccaggctcc     3300
ccaggggctg ccagaggcga tagagccct ggtggaagat gatgtggccc caggggtga    3360 ccaagcctcc ccagaggtca tgttggggtc agagcctgcc atgggtgagt ctgctgcggg    3420
agctgagcca ggccgggc aggggtgggg agggctgggg gacccaggcc atctgaccag     3480
ggaagaggtg atggaaccac ccctggaaga ggagagtttg gaggcaaaga gggttcaggg    3540
cttggaaggg cctagaaagg acctagagga ggcaggtggt ctggggacag agttctccga    3600
gctgcctggg aagagcagag acccttggga gcctcccagg gagggtaggg aggagtcaga    3660
ggctgaggcc ccaggggag cagaggaggc gttccctgct gagaccctgg gccacactgg    3720
aagtgatgcc ccttcacctt ggcctctggg gtcagaggaa gctgaggagg atgtaccacc    3780
agtgctggtc tcccccagcc caacgtacac cccgatcctg gaagatgccc ctgggcctca    3840
gcctcaggct gaagggagtc aggaggctag ctgggggtg caggggaggg ctgaagccct    3900
ggggaaagta gagagcgagc aggaggagtt gggttctggg gagatccccg agggccccca    3960
ggaggaaggg gaggagagca gagaagagag cgaggaggat gagctcgggg agaccttcc    4020 agactccact ccctgggct tctacctcag gtcccccacc tccccaggt gggaccccac     4080 tggagagcag aggccacccc ctcaagggga gactggaaag gagggctggg atcctgctgt    4140
cctggcttcc gagggccttg aggccccacc ctcagaaaag gaggaggggg aggagggaga    4200
agaggagtgt ggccgtgact ctgacctgtc agaagaattt gaggacctgg ggactgaggc    4260 acctttctt cctggggtcc ctggggaggt ggcagaacct ctgggccagg tgccccagct     4320
gctactggat cctgcagcct gggatcgaga tggggagtcc gatgggtttg cagatgagga    4380
agaaagtggg gaggagggag aggaggatca ggaggagggg agggagccag gggctgggcg    4440 gtggggcca gggtcttctg ttggcagcct ccaggccctg agtagctccc agagagggga    4500
attcctggag tctgattctg tgagtgtcag tgtcccctgg gatgacagct gaggggtgc    4560 agtggctggt gcccccaaga ctgccctgga aacggagtcc caggacagtg ctgagccttc    4620
tggctcagag gaagagtctg accctgtttc cttggagagg gaggacaaag tccctggccc    4680
tctagagatc cccagtggga tggaggatgc aggcccaggg gcagacatca ttggtgttaa    4740
tggccagggt cccaacttgg agggggaagtc acagcatgtg aatggggag tgatgaacgg    4800 gctggagcag tctgaggaag tggggcaagg aatgccgcta gtctctgagg gagaccgagg    4860
```

```
gagcccctttt caggaggagg aggggagtgc tctgaagacc tcttgggcag gggctcctgt   4920
tcacctgggc cagggtcagt tcctgaagtt cactcagagg gaaggagata gagagtcctg   4980
gtcctcaggg gaggactagg aaaagaccat ctgcccggca ctggggactt aggggtgcgg   5040
ggaggggaag gacgcctcca agcccgctcc ctgctcagga gcagcactct taacttacga   5100
tctcttgaca tatggtttct ggctgagagg cctggcccgc taaggtgaaa aggggtgtgg   5160
caaaggagcc tactccaaga atggaggctg taggaatata acctcccacc ctgcaaaggg   5220
aatctcttgc ctgctccatc tcataggcta agtcagctga atcccgatag tactaggtcc   5280
ccttccctcc gcatcccgtc agctggaaaa ggcctgtggc ccagaggctt ctccaaaggg   5340
agggtgacat gctggctttt gtgcccaagc tcaccagccc tgcgccacct cactgcagta   5400
gtgcaccatc tcactgcagt agcacgccct cctgggccgt ctggcctgtg gctaatggag   5460
gtgacggcac tcccatgtgc tgactccccc catccctgcc acgctgtggc cctgcctggc   5520
tagtccctgc ctgaataaag taatgcctcc gcttcaaaaa aaaaaaaaaa aaaaaaaaa   5580 aaaaaaaaaa a                                                        5591

<210> SEQ ID NO 24
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 24
cagctggcgc acctcaagat g                                             21

<210> SEQ ID NO 25
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 25
agggaagttg ggctcaggac tgc                                           23

<210> SEQ ID NO 26
<211> LENGTH: 3271
<212> TYPE: DNA
<213> ORGANISM: Homo sapiens

<400> SEQUENCE: 26
gctgtgacag ccacacgccc caaggcctcc aagatgagct acacgttgga ctcgctgggc   60
aacccgtccg cctaccggcg ggtaaccgag accgctcga gcttcagccg cgtcagcggc   120
tccccgtcca gtggcttccg ctcgcagtcg tggtcccgcg gctcgcccag caccgtgtcc   180
tcctcctata gcgcagcat gctcgccccg cgctcgcttt acagtcggc catgctcagc   240 tccgccgaga gcagccttga cttcagccag tcctcgtccc tgctcaacgg cggctccgga   300
cccggcggcg actacaagct gtcccgctcc aacgagaagg agcagctgca ggggctgaac   360
gaccgctttg ccggctacat agagaaggtg cactacctgg agcagcagaa taaggagatt   420
gaggcggaga tccaggcgct gcggcagaag caggcctcgc acgcccagct gggcgacgcg   480
tacgaccagg agatccgcga gctgcgcgcc accctggaga tggtgaacca cgagaaggct   540
caggtgcagc tggactcgga ccacctggag gaagacatcc accggctcaa ggagcgcttt   600
gaggaggagg cgcggttgcg cgacgacact gaggcggcca tccgcgcgct gcgcaaagac   660
```

```
atcgaggagg cgtcgctggt caaggtggag ctggacaaga aggtgcagtc gctgcaggat      720
gaggtggcct tcctgcggag caaccacgag gaggaggtgg ccgaccttct ggcccagatc      780
caggcatcgc acatcacggt ggagcgcaaa gactacctga agacagacat ctcgacggcg      840
ctgaaggaaa tccgctccca gctcgaaagc cactcagacc agaatatgca ccaggccgaa      900
gagtggttca aatgccgcta cgccaagctc accgaggcgg ccgagcagaa caaggaggcc      960
atccgctccg ccaaggaaga gatcgccgag taccggcgcc agctgcagtc caagagcatc     1020
gagctagagt cggtgcgcgg caccaaggag tccctggagc ggcagctcag cgacatcgag     1080
gagcgccaca accacgacct cagcagctac caggacacca tccagcagct ggaaaatgag     1140
cttcggggca caaagtggga atggctcgt catttgcgcg aataccagga cctcctcaac      1200
gtcaagatgg ctctggatat agaaatcgct gcgtacagaa aactcctgga gggtgaagag     1260
actagattta gcacatttgc aggaagcatc actgggccac tgtatacaca ccgaccccca     1320
atcacaatat ccagtaagat tcagaaaccc aaggtggaag ctcccaagct taaggtccaa     1380
cacaaatttg tcgaggagat catagaggaa accaaagtgg aggatgagaa gtcagaaatg     1440
gaagaggccc tgacagccat tacagaggaa ttggccgttt ccatgaagga agagaagaaa     1500
gaagcagcag aagaaaagga agaggaaccc gaagctgaag aagaagaagt agctgccaaa     1560
aagtctccag tgaaagcaac tgcacctgaa gttaaagaag aggaagggga aaaggaggaa     1620
gaagaaggcc aggaagaaga ggaggaagaa gatgagggag ctaagtcaga ccaagccgaa     1680
gagggaggat ccgagaagga aggctctagt gaaaaagagg aaggtgagca ggaagaagga     1740
gaaacagaag ctgaagctga aggagaggaa gccgaagcta aagaggaaaa gaaagtggag     1800
gaaaagagtg aggaagtggc taccaaggag gagctggtgg cagatgccaa ggtggaaaag     1860
ccagaaaaag ccaagtctcc tgtgccaaaa tcaccagtgg aagagaaagg caagtctcct     1920
gtgcccaagt caccagtgga agagaaaggc aagtctcctg tgcccaagtc accagtggaa     1980
gagaaaggca agtctcctgt gccgaaatca ccagtggaag agaaaggcaa gtctcctgtg     2040
tcaaaatcac cagtggaaga gaaagccaaa tctcctgtgc caaaatcacc agtggaagag     2100
gcaaagtcaa agcagaagt ggggaaaggt gaacagaaag aggaagaaga aaaggaagtc      2160
aaggaagctc ccaaggaaga gaaggtagag aaaaaggaag agaaaccaaa ggatgtgcca     2220
gagaagaaga agctgagtc ccctgtaaag gaggaagctg tggcagaggt ggtcaccatc      2280
accaaatcgg taaaggtgca cttggagaaa gagaccaaag aagagggaa gccactgcag      2340 caggagaaag agaaggagaa agcgggagga gaggaggaa gtgaggagga agggagtgat      2400
aaaggtgcca agggatccag gaaggaagac atagctgtca atggggaggt agaaggaaaa     2460
gaggaggtag agcaggagac caaggaaaaa ggcagtggga gggaagagga gaaaggcgtt     2520
gtcaccaatg gcctagactt gagcccagca gatgaaaaga aggggggtga taaaagtgag     2580
gagaaagtgg tggtgaccaa aacgtgaaa aaaatcacca gtgagggggg agatggtgct      2640
accaaataca tcactaaatc tgtaaccgtc actcaaaagg ttgaagagca tgaagagacc     2700
tttgaggaga aactagtgtc tactaaaaag gtagaaaaag tcacttcaca cgccatagta     2760
aaggaagtca cccagagtga ctaagatttg agtccattgc aaaaggttaa gccatatgac     2820
aatttcaaaa tgcatgtgat tggcagcttc aaaacagaac gggttctccc atgggggctc     2880
cagacattgt attttacttt gtgcaatatg aggggactgc atgcaagctc agggtgctcc     2940
ctcctcagtc tttgggggat tcaaatgcat gatattgtat gtacctggga aatttgccga     3000
```

| | |
|---|---|
| tttcctaagc tgttggaagg gggtcactta agggggatg tcttgagatg tattatgcaa | 3060 |
| agtaccaact gagccaaaaa caataaacga aacacagaac tcagccttaa gaaagctata | 3120 |
| tatgaataat tatgtttacc tcactggtgc atttaaaatg acttttgtt catgggagaa | 3180 |
| cctcgttgac atgcacagtt tgcaatctta tgttgatcga tgttaaacgt cacagcagta | 3240 |
| cttgctcaat aaaggtcata ttggaaacat a | 3271 |

<210> SEQ ID NO 27
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 27

| | |
|---|---|
| cagcgatttc tatatccaga gcc | 23 |

<210> SEQ ID NO 28
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 28

| | |
|---|---|
| gagcgcaaag actacctgaa ga | 22 |

<210> SEQ ID NO 29
<211> LENGTH: 2416
<212> TYPE: DNA
<213> ORGANISM: Homo sapiens

<400> SEQUENCE: 29

| | |
|---|---|
| gactgcagag ccggggctgg gctaggcgcg cgcttggaga gcattgcgcg cggctgggcc | 60 |
| cgcggccggc ggctcctcct cccactctgc tcctcctctt ttttctcctc ctccacctcc | 120 |
| tcctccgcct cctcctcctc ctcttcctcc tcctcttcaa ttctcccggt ggctcgactc | 180 |
| ggctcgcagg cttcggagaa accctactc cagtcgccga ctcagcgccc aagagggtcg | 240 |
| ccttgggctg ggggcgcacc ccagggaggg gaggggtcca ggcagctggg ccgccgcgga | 300 |
| cacctagcgg cttcagggtg aaccccgacc gcagccgtcg ccgcctcggg cagagtttgc | 360 |
| gcccttgctt tgcgccccgg gcgctgaagc cgggcgggcg atgcccgcgg cgtgaaagcg | 420 |
| cccgcggcgg gcgccgacct ctgtcctagt ctcctgctcc ccccgccccg cttgtcccgt | 480 |
| gcccttgtga ccctggcttt ggcgccgtcg cccagcgcc ccgcaatgta gctgcccctg | 540 |
| cgcctcggcg ggaggcgtcc tgccccgcga gcgcccgggg cccggagccc ggcctggggg | 600 |
| ctcagccgag ctcgggcggg gccggggccg cggtggcgat gcaccgggcc cgttagcgcc | 660 |
| aggagcgcca ggcagctgag gcgggggca agccctccct cggaggagcc gcgccccgg | 720 |
| ccccgccggt cccgccgcga tgctgttcca cagtctgtcg ggccccgagg tgcacggggt | 780 |
| catcgacgag atggaccgca gggccaagag cgaggctccc gccatcagct ccgccatcga | 840 |
| ccgcggcgac accgagacga ccatgccgtc catcagcagt gaccgcgccg cgctgtgcgc | 900 |
| cggctgcggg ggcaagatct cggaccgcta ctacctgctg gcggtggaca gcagtggca | 960 |
| catgcgctgc ctcaagtgct gcgagtgcaa gctcaacctg gagtcggagc tcacctgttt | 1020 |
| cagcaaggac ggtagcatct actgcaagga agactactac aggcgcttct ctgtgcagcg | 1080 |
| ctgcgcccgc tgccacctgg gcatctcggc ctcggagatg gtgatgcgcg ctcgggactt | 1140 |

```
ggtttatcac ctcaactgct tcacgtgcac cacgtgtaac aagatgctga ccacgggcga   1200
ccacttcggc atgaaggaca gcctggtcta ctgccgcttg cacttcgagg cgctgctgca   1260
gggcgagtac cccgcacact tcaaccatgc cgacgtggca gcggcggccg ctgcagccgc   1320 gcggccaag agcgcggggc tgggcgcagc aggggccaac cctctgggtc ttccctacta    1380
caatggcgtg ggcactgtgc agaaggggcg gccgaggaaa cgtaagagcc gggccccgg    1440 tgcggatctg gcggcctaca acgctgcgct aagctgcaac gaaaacgacg cagagcacct   1500
ggaccgtgac cagccatacc cgagcagcca gaagaccaag cgcatgcgca cgtccttcaa   1560
gcaccaccag cttcggacca tgaagtctta ctttgccatt aaccacaacc ccgacgccaa   1620
ggacttgaag cagctcgcgc aaaagacggg cctcaccaag cgggtcctcc aggtctggtt   1680
ccagaacgcc cgagccaagt tcaggcgcaa cctcttacgg caggaaaaca cgggcgtgga   1740
caagtcgaca gacgcggcgc tgcagacagg gacgccatcg ggcccggcct cggagctctc   1800
caacgcctcg ctcagcccct ccagcacgcc caccaccctg acagacttga ctagccccac   1860
cctgccaact gtgacgtccg tcttaacttc tgtgcctggc aacctggagg gccatgagcc   1920
tcacagcccc tcacaaacga ctcttaccaa ccttttctaa tgactcgcaa ccccctcaccc  1980 cacaatttct ttaaaaaaga aattatcttt agttgaattc caagtgtatt ttaaaataga   2040
ggctttgagc aactaactaa ccacatttta ggatctcgcc tggaaacaga ggtaaaaaaa   2100
agaagtgtgc gcccggctaa tgcagcgtg tggaccgagg aacaacttgg aagatctacc    2160
tgcaacacaa catttgtgtc actgtacagt tttgtggact gagcgaggaa aaacaacaaa   2220
taatttaagt tggctagagc ttctgtattt tcaaagactg ccacgtgcct taggaatact   2280
gttttatctc catactttgg atgacttgtt cattttctc tccctctttt tctctgtata    2340
tttatgacca gagcaaaaat gtaaaaaaca aaaaaaacaa caaaaaaagt ttgttacttt   2400
gaatagtcct aaaaag                                                   2416
```

<210> SEQ ID NO 30
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 30
ccaaggactt gaagcagctc                                               20

<210> SEQ ID NO 31
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 31
tgccaggcac agaagttaag                                               20

<210> SEQ ID NO 32
<211> LENGTH: 199
<212> TYPE: PRT
<213> ORGANISM: Homo sapiens

<400> SEQUENCE: 32

Met Asn Cys Val Cys Arg Leu Val Leu Val Val Leu Ser Leu Trp Pro
1               5                   10                  15

Asp Thr Ala Val Ala Pro Gly Pro Pro Gly Pro Pro Arg Val Ser
            20                  25                  30

Pro Asp Pro Arg Ala Glu Leu Asp Ser Thr Val Leu Thr Arg Ser
        35                  40                  45

Leu Leu Ala Asp Thr Arg Gln Leu Ala Ala Gln Leu Arg Asp Lys Phe
50                  55                  60

Pro Ala Asp Gly Asp His Asn Leu Asp Ser Leu Pro Thr Leu Ala Met
65                  70                  75                  80

Ser Ala Gly Ala Leu Gly Ala Leu Gln Leu Pro Gly Val Leu Thr Arg
                85                  90                  95

Leu Arg Ala Asp Leu Leu Ser Tyr Leu Arg His Val Gln Trp Leu Arg
            100                 105                 110

Arg Ala Gly Gly Ser Ser Leu Lys Thr Leu Glu Pro Glu Leu Gly Thr
        115                 120                 125

Leu Gln Ala Arg Leu Asp Arg Leu Leu Arg Arg Leu Gln Leu Leu Met
130                 135                 140

Ser Arg Leu Ala Leu Pro Gln Pro Pro Asp Pro Pro Ala Pro Pro
145                 150                 155                 160

Leu Ala Pro Pro Ser Ser Ala Trp Gly Gly Ile Arg Ala Ala His Ala
                165                 170                 175

Ile Leu Gly Gly Leu His Leu Thr Leu Asp Trp Ala Val Arg Gly Leu
            180                 185                 190

Leu Leu Leu Lys Thr Arg Leu
            195

<210> SEQ ID NO 33
<211> LENGTH: 2354
<212> TYPE: DNA
<213> ORGANISM: Homo sapiens

<400> SEQUENCE: 33

| | | |
|---|---|---|
| gctcagggca catgcctccc ctccccaggc cgcggcccag ctgaccctcg ggctccccc | 60 |
| ggcagcggac agggaagggt taaaggcccc cggctccctg cccctgccc tggggaaccc | 120 |
| ctggccctgt ggggacatga actgtgtttg ccgcctggtc ctggtcgtgc tgagcctgtg | 180 |
| gccagataca gctgtcgccc ctgggccacc acctggcccc cctcgagttt ccccagaccc | 240 |
| tcgggccgag ctggacagca ccgtgctcct gacccgctct ctcctggcgg acacgcggca | 300 |
| gctggctgca cagctgaggg acaaattccc agctgacggg gaccacaacc tggattccct | 360 |
| gcccacccctg gccatgagtg cgggggcact gggagctcta cagctcccag gtgtgctgac | 420 |
| aaggctgcga gcggacctac tgtcctacct gcggcacgtg cagtggctgc gccgggcagg | 480 |
| tggctcttcc ctgaagaccc tggagcccga gctgggcacc ctgcaggccc gactggaccg | 540 |
| gctgctgcgc cggctgcagc tcctgatgtc ccgcctggcc ctgccccagc caccccgga | 600 |
| cccgccggcg ccccgctgg cgccccctc ctcagcctgg ggggcatca gggccgccca | 660 |
| cgccatcctg gggggctgc acctgacact tgactgggcc gtgaggggac tgctgctgct | 720 |
| gaagactcgg ctgtgacccg ggcccaaag ccaccaccgt ccttccaaag ccagatctta | 780 |
| tttattttatt tatttcagta ctgggggcga aacagccagg tgatccccccc gccattatct | 840 |
| cccccctagtt agagacagtc cttccgtgag gcctggggg catctgtgcc ttatttatac | 900 |
| ttatttatt caggagcagg ggtgggaggc aggtggactc ctgggtcccc gaggaggagg | 960 |
| ggactggggt cccggattct tgggtctcca agaagtctgt ccacagactt ctgccctggc | 1020 |

| | |
|---|---|
| tcttccccat ctaggcctgg gcaggaacat atattattta tttaagcaat tactttcat | 1080 |
| gttggggtgg ggacggaggg gaaagggaag cctgggtttt tgtacaaaaa tgtgagaaac | 1140 |
| ctttgtgaga cagagaacag ggaattaaat gtgtcataca tatccacttg agggcgattt | 1200 |
| gtctgagagc tggggctgga tgcttgggta actggggcag ggcaggtgga ggggagacct | 1260 |
| ccattcaggt ggaggtcccg agtgggcggg gcagcgactg ggagatgggt cggtcaccca | 1320 |
| gacagctctg tggaggcagg gtctgagcct tgcctggggc cccgcactgc atagggcctt | 1380 |
| ttgtttgttt tttgagatgg agtctcgctc tgttgcctag gctggagtgc agtgaggcaa | 1440 |
| tctgaggtca ctgcaacctc cacctcccgg gttcaagcaa ttctcctgcc tcagcctccc | 1500 |
| gattagctgg gatcacaggt gtgcaccacc atgcccagct aattatttat ttcttttgta | 1560 |
| tttttagtag agacagggtt tcaccatgtt ggccaggctg gtttcgaact cctgacctca | 1620 |
| ggtgatcctc ctgcctcggc ctcccaaagt gctgggatta caggtgtgag ccaccacacc | 1680 |
| tgacccatag gtcttcaata aatatttaat ggaaggttcc acaagtcacc ctgtgatcaa | 1740 |
| cagtacccgt atgggacaaa gctgcaaggt caagatggtt cattatggct gtgttcacca | 1800 |
| tagcaaactg gaaacaatct agatatccaa cagtgagggt taagcaacat ggtgcatctg | 1860 |
| tggatagaac gccacccagc cgcccggagc agggactgtc attcagggag gctaaggaga | 1920 |
| gaggcttgct tgggatatag aaagatatcc tgacattggc caggcatggt ggctcacgcc | 1980 |
| tgtaatcctg gcactttggg aggacgaagc gagtggatca ctgaagtcca agagttcgag | 2040 |
| accggcctgc gagacatggc aaaccctgt ctcaaaaaag aaagaatgat gtcctgacat | 2100 |
| gaaacagcag gctacaaaac cactgcatgc tgtgatccca ttttgtgtt ttctttcta | 2160 |
| tatatggatt aaaacaaaaa tcctaagggg aaatacgcca aaatgttgac aatgactgtc | 2220 |
| tccaggtcaa aggagagagg tgggattgtg ggtgactttt aatgtgtatg attgtctgta | 2280 |
| ttttacagaa tttctgccat gactgtgtat tttgcatgac acattttaaa aataataaac | 2340 |
| actatttta gaat | 2354 |

<210> SEQ ID NO 34
<211> LENGTH: 200
<212> TYPE: PRT
<213> ORGANISM: Homo sapiens

<400> SEQUENCE: 34

```
Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
        35                  40                  45

Asn Leu Asp Ser Ala Asp Gly Met Pro Val Ala Ser Thr Asp Gln Trp
    50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
```

```
                    130                 135                 140
Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
        195                 200

<210> SEQ ID NO 35
<211> LENGTH: 1914
<212> TYPE: DNA
<213> ORGANISM: Homo sapiens

<400> SEQUENCE: 35
agagtcacat ctcttatttg gaccagtata gacagaagta aacccagctg acttgtttcc    60
tgggacagtt gagttaaggg atggctttca cagagcattc accgctgacc cctcaccgtc   120
gggacctctg tagccgctct atctggctag caaggaagat tcgttcagac ctgactgctc   180
ttacggaatc ctatgtgaag catcagggcc tgaacaagaa catcaacctg actctgcgg    240
atgggatgcc agtggcaagc actgatcagt ggagtgagct gaccgaggca gagcgactcc   300
aagagaacct tcaagcttat cgtaccttcc atgttttgtt ggccaggctc ttagaagacc   360
agcaggtgca ttttacccca accgaaggtg acttccatca agctatacat acccttcttc   420
tccaagtcgc tgcctttgca taccagatag aggagttaat gatactcctg aatacaaga    480
tcccccgcaa tgaggctgat gggatgccta ttaatgttgg agatggtggt ctctttgaga   540
agaagctgtg gggcctaaag gtgctgcagg agctttcaca gtggacagta aggtccatcc   600
atgaccttcg tttcatttct ctcatcaga ctgggatccc agcacgtggg agccattata    660
ttgctaacaa caagaaaatg tagcagttag tcccttctct cttccttgct ttctcttcta   720
atggaatatg cgtagttccc tggggcctcg ctttcccatc ttaaatttct aaaaacagtt   780
aagacaacag gcattttctt tcttttttct ctgaccacct gcagcctgtt gaaggactac   840
aggtattttc atcaagtagc gttggagaca tacacaaatg gcatacaag tttagcctgg    900
ggggtgtgat ttgtgtgcgt gcttgcatgt gctgcaggtg taagagagtg ggagcaggga   960
caacgtcctt ccacttcagg gttctaacct ttctaaccca ctaagtaacc tctacaggca  1020
tttaactgcc ttacagacag aatatacata tgttaattct agtcctggat gactcggtct  1080
gagaagattc aatttaaaat cagactcttt agttgattta aactcttaga gaataagaat  1140
aataatggct aactttttatt atcttctata ttaaggcagt atgccaaggg tctttatgta  1200
tattatgtac agcgtttaca accttgtgag caaggtggtg ttactcccat taggtagatg  1260
agaaaacagg ctcacagaga tttggttaag ctcacacagc taacaagtag cacactgagt  1320
ttgaacacag atcattctcc ttgtaaaagc ctatgtgcct ttcactttag aggcttgatc  1380
atgaatcact gcacctcttt gtcacagggt gttggaagat gcatccatgt aatctattcc  1440
catcgctgga aaacagctgc tgttagatgt cctcagaagt cagttgcaaa ttttagcgtt  1500
aaagtcagga tttattgttc atacttggcg gtgaggaggg cagctggaga tcttaagatt  1560
ccatttgga aaatgattag gcccgccaaa cttctgaact ttggaagctg gggatgttta   1620
gtaatacagc ctggttttta agtactcact aaaagttctc aaatattggg ttgggcacgg  1680
cttataccag gttacctcac ttttaattag tgatgcaggc agtgtaaccc aagcatttgt  1740
```

-continued

```
ggacaatgag tggaatacta aagttaaaaa gtcaaacttt cacctcagat tttctggact    1800
tagtcatgag gagagggtga ggcccactct gttcctactg gagataccag agactctgaa    1860
actatagaat aaagcctctg tgctgcacaa caaaaaaaaa aaaaaaaaaa aaaa          1914
```

<210> SEQ ID NO 36
<211> LENGTH: 252
<212> TYPE: PRT
<213> ORGANISM: Homo sapiens

<400> SEQUENCE: 36

```
Met Gly Val Leu Leu Thr Gln Arg Thr Leu Leu Ser Leu Val Leu Ala
1               5                   10                  15

Leu Leu Phe Pro Ser Met Ala Ser Met Ala Ala Ile Gly Ser Cys Ser
            20                  25                  30

Lys Glu Tyr Arg Val Leu Leu Gly Gln Leu Gln Lys Gln Thr Asp Leu
        35                  40                  45

Met Gln Asp Thr Ser Arg Leu Leu Asp Pro Tyr Ile Arg Ile Gln Gly
    50                  55                  60

Leu Asp Val Pro Lys Leu Arg Glu His Cys Arg Glu Arg Pro Gly Ala
65                  70                  75                  80

Phe Pro Ser Glu Glu Thr Leu Arg Gly Leu Gly Arg Arg Gly Phe Leu
                85                  90                  95

Gln Thr Leu Asn Ala Thr Leu Gly Cys Val Leu His Arg Leu Ala Asp
            100                 105                 110

Leu Glu Gln Arg Leu Pro Lys Ala Gln Asp Leu Glu Arg Ser Gly Leu
        115                 120                 125

Asn Ile Glu Asp Leu Glu Lys Leu Gln Met Ala Arg Pro Asn Ile Leu
    130                 135                 140

Gly Leu Arg Asn Asn Ile Tyr Cys Met Ala Gln Leu Leu Asp Asn Ser
145                 150                 155                 160

Asp Thr Ala Glu Pro Thr Lys Ala Gly Arg Gly Ala Ser Gln Pro Pro
                165                 170                 175

Thr Pro Thr Pro Ala Ser Asp Ala Phe Gln Arg Lys Leu Glu Gly Cys
            180                 185                 190

Arg Phe Leu His Gly Tyr His Arg Phe Met His Ser Val Gly Arg Val
        195                 200                 205

Phe Ser Lys Trp Gly Glu Ser Pro Asn Arg Ser Arg Arg His Ser Pro
    210                 215                 220

His Gln Ala Leu Arg Lys Gly Val Arg Arg Thr Arg Pro Ser Arg Lys
225                 230                 235                 240

Gly Lys Arg Leu Met Thr Arg Gly Gln Leu Pro Arg
                245                 250
```

<210> SEQ ID NO 37
<211> LENGTH: 252
<212> TYPE: PRT
<213> ORGANISM: Homo sapiens

<400> SEQUENCE: 37

```
Met Gly Val Leu Leu Thr Gln Arg Thr Leu Leu Ser Leu Val Leu Ala
1               5                   10                  15

Leu Leu Phe Pro Ser Met Ala Ser Met Ala Ala Ile Gly Ser Cys Ser
            20                  25                  30

Lys Glu Tyr Arg Val Leu Leu Gly Gln Leu Gln Lys Gln Thr Asp Leu
        35                  40                  45
```

```
Met Gln Asp Thr Ser Arg Leu Leu Asp Pro Tyr Ile Arg Ile Gln Gly
        50                  55                  60

Leu Asp Val Pro Lys Leu Arg Glu His Cys Arg Glu Arg Pro Gly Ala
 65                  70                  75                  80

Phe Pro Ser Glu Glu Thr Leu Arg Gly Leu Gly Arg Arg Gly Phe Leu
                 85                  90                  95

Gln Thr Leu Asn Ala Thr Leu Gly Cys Val Leu His Arg Leu Ala Asp
                100                 105                 110

Leu Glu Gln Arg Leu Pro Lys Ala Gln Asp Leu Glu Arg Ser Gly Leu
            115                 120                 125

Asn Ile Glu Asp Leu Glu Lys Leu Gln Met Ala Arg Pro Asn Ile Leu
        130                 135                 140

Gly Leu Arg Asn Asn Ile Tyr Cys Met Ala Gln Leu Leu Asp Asn Ser
145                 150                 155                 160

Asp Thr Ala Glu Pro Thr Lys Ala Gly Arg Gly Ala Ser Gln Pro Pro
                165                 170                 175

Thr Pro Thr Pro Ala Ser Asp Ala Phe Gln Arg Lys Leu Glu Gly Cys
                180                 185                 190

Arg Phe Leu His Gly Tyr His Arg Phe Met His Ser Val Gly Arg Val
            195                 200                 205

Phe Ser Lys Trp Gly Glu Ser Pro Asn Arg Ser Arg Arg His Ser Pro
        210                 215                 220

His Gln Ala Leu Arg Lys Gly Val Arg Arg Thr Arg Pro Ser Arg Lys
225                 230                 235                 240

Gly Lys Arg Leu Met Thr Arg Gly Gln Leu Pro Arg
                245                 250

<210> SEQ ID NO 38
<211> LENGTH: 1880
<212> TYPE: DNA
<213> ORGANISM: Homo sapiens

<400> SEQUENCE: 38
agccgagagg tgtcaccccc agcgggcgcg ggccggagca cgggcaccca gcatggggt      60 actgctcaca cagaggacgc tgctcagtct ggtccttgca ctcctgtttc caagcatggc     120
gagcatggcg gctataggca gctgctcgaa agagtaccgc gtgctccttg ccagctcca     180 gaagcagaca gatctcatgc aggacaccag cagactcctg gacccctata cgtatcca     240 aggcctggat gttcctaaac tgagagagca ctgcagggag cgccccgggg ccttccccag    300
tgaggagacc ctgaggggc tgggcaggcg ggcttcctg cagaccctca atgccacact      360
gggctgcgtc ctgcacagac tggccgactt agagcagcgc ctcccaagg cccaggattt     420 ggagaggtct gggctgaaca tcgaggactt ggagaagctg cagatggcga ggccgaacat    480
cctcgggctc aggaacaaca tctactgcat ggcccagctg ctggacaact cagacacggc    540
tgagcccacg aaggctggcc ggggggcctc tcagccgccc accccacccc tgcctcgga    600 tgctttcag cgcaagctgg agggctgcag gttcctgcat ggctaccatc gcttcatgca     660
ctcagtgggg cgggtcttca gcaagtgggg ggagagcccg aaccggagcc ggagacacag    720 ccccaccag gccctgagga agggggtgcg caggaccaga ccctccagga aaggcaagag    780
actcatgacc aggggacagc tgccccggta gcctcgagag cacccttgc cggtgaagga    840 tgcggcaggt gctctgtgga tgagaggaac catcgcagga tgcagctcc cgggtcccca    900 aacctgttcc cctctgctac tagccactga gaagtgcact ttaagaggtg ggagctgggc    960
```

```
agacccctct acctcctcca ggctgggaga cagagtcagg ctgttgcgct cccacctcag    1020
ccccaagttc cccaggccca gtggggtggc cgggcgggcc acgcgggacc gactttccat    1080
tgattcaggg gtctgatgac acaggctgac tcatggccgg gctgactgcc cccctgcctt    1140
gctccccgag gcctgccggt ccttccctct catgacttgc agggccgttg cccccagact    1200
tcctcctttc cgtgtttctg aaggggaggt cacagcctga gctggcctcc tatgcctcat    1260
catgtcccaa accagacacc tggatgtctg ggtgacctca ctttaggcag ctgtaacagc    1320
ggcagggtgt cccaggagcc ctgatccggg ggtccaggga atggagctca ggtcccaggc    1380
cagccccgaa gtcgccacgt ggcctgggc aggtcacttt acctctgtgg acctgttttc    1440
tctttgtgaa gctagggagt tagaggctgt acaaggcccc cactgcctgt cggttgcttg    1500
gattccctga cgtaaggtgg atattaaaaa tctgtaaatc aggacaggtg gtgcaaatgg    1560
cgctgggagg tgtacacgga ggtctctgta aaagcagacc cacctcccag cgccgggaag    1620
cccgtcttgg gtcctcgctg ctggctgctc ccctggtgg tggatcctgg aattttctca    1680
cgcaggagcc attgctctcc tagagggggt ctcagaaact gcgaggccag ttccttggag    1740
ggacatgact aatttatcga ttttatcaa ttttatcag tttatattt ataagcctta     1800 tttatgatgt atatttaatg ttaatattgt gcaaacttat atttaaaact tgcctggttt    1860 ctaaaaaaa aaaaaaaaa                                                  1880
```

<210> SEQ ID NO 39
<211> LENGTH: 288
<212> TYPE: PRT
<213> ORGANISM: Homo sapiens

<400> SEQUENCE: 39

```
Met Val Gly Val Gly Gly Asp Val Glu Asp Val Thr Pro Arg Pro
1               5                   10                  15

Gly Gly Cys Gln Ile Ser Gly Arg Ala Arg Gly Cys Asn Gly Ile
            20                  25                  30

Pro Gly Ala Ala Ala Trp Glu Ala Ala Leu Pro Arg Arg Pro Arg
        35                  40                  45

Arg His Pro Ser Val Asn Pro Arg Ser Arg Ala Ala Gly Ser Pro Arg
    50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Gly Arg
                85                  90                  95

Gly Arg Gly Arg Ala Pro Glu Arg Val Gly Gly Arg Gly Arg Gly Arg
            100                 105                 110

Gly Thr Ala Ala Pro Arg Ala Ala Pro Ala Ala Arg Gly Ser Arg Pro
        115                 120                 125

Gly Pro Ala Gly Thr Met Ala Ala Gly Ser Ile Thr Thr Leu Pro Ala
    130                 135                 140

Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
            180                 185                 190

Ile Lys Leu Gln Leu Gln Ala Glu Glu Arg Gly Val Val Ser Ile Lys
        195                 200                 205
```

```
Gly Val Cys Ala Asn Arg Tyr Leu Ala Met Lys Glu Asp Gly Arg Leu
            210                 215                 220

Leu Ala Ser Lys Cys Val Thr Asp Glu Cys Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
            260                 265                 270

Gly Pro Gly Gln Lys Ala Ile Leu Phe Leu Pro Met Ser Ala Lys Ser
        275                 280                 285

<210> SEQ ID NO 40
<211> LENGTH: 6774
<212> TYPE: DNA
<213> ORGANISM: Homo sapiens

<400> SEQUENCE: 40
```

| | | | | | |
|---|---|---|---|---|---|
| cggccccaga | aaacccgagc | gagtagggggg | cggcgcgcag | gagggaggag | aactgggggc | 60 |
| gcgggaggct | ggtgggtgtg | gggggtggag | atgtagaaga | tgtgacgccg | cggcccggcg | 120 |
| ggtgccagat | tagcggacgc | ggtgcccgcg | gttgcaacgg | gatcccgggc | gctgcagctt | 180 |
| gggaggcggc | tctccccagg | cggcgtccgc | ggagacaccc | atccgtgaac | cccaggtccc | 240 |
| gggccgccgg | ctcgccgcgc | accagggcc | ggcggacaga | gagcggccg | agcggctcga | 300 |
| ggctggggga | ccgcgggcgc | ggccgcgcgc | tgccgggcgg | gaggctgggg | ggccggggcc | 360 |
| ggggccgtgc | cccggagcgg | gtcggaggcc | ggggccgggg | ccggggacg | gcggctcccc | 420 |
| gcgcggctcc | agcggctcgg | ggatcccggc | cgggccccgc | agggaccatg | gcagccggga | 480 |
| gcatcaccac | gctgcccgcc | ttgcccgagg | atggcggcag | cggcgccttc | ccgccccggcc | 540 |
| acttcaagga | ccccaagcgg | ctgtactgca | aaaacggggg | cttcttcctg | cgcatccacc | 600 |
| ccgacggccg | agttgacggg | gtccgggaga | gagcgaccc | tcacatcaag | ctacaacttc | 660 |
| aagcagaaga | gagaggagtt | gtgtctatca | aggagtgtg | tgctaaccgt | tacctggcta | 720 |
| tgaaggaaga | tggaagatta | ctggcttcta | aatgtgttac | ggatgagtgt | ttctttttg | 780 |
| aacgattgga | atctaataac | tacaatactt | accggtcaag | gaaatacacc | agttggtatg | 840 |
| tggcactgaa | acgaactggg | cagtataaac | ttggatccaa | aacaggacct | gggcagaaag | 900 |
| ctatactttt | tcttccaatg | tctgctaaga | gctgatttta | atggccacat | ctaatctcat | 960 |
| ttcacatgaa | agaagaagta | tattttagaa | atttgttaat | gagagtaaaa | gaaaataaat | 1020 |
| gtgtatagct | cagtttggat | aattggtcaa | acaattttt | atccagtagt | aaaatatgta | 1080 |
| accattgtcc | cagtaaagaa | aaataacaaa | agttgtaaaa | tgtatattct | ccctttata | 1140 |
| ttgcatctgc | tgttacccag | tgaagcttac | ctagagcaat | gatctttttc | acgcatttgc | 1200 |
| tttattcgaa | aagaggcttt | taaaatgtgc | atgtttagaa | acaaaatttc | ttcatggaaa | 1260 |
| tcatatacat | tagaaaatca | cagtcagatg | tttaatcaat | ccaaaatgtc | cactatttct | 1320 |
| tatgtcattc | gttagtctac | atgtttctaa | acatataaat | gtgaatttaa | tcaattcctt | 1380 |
| tcatagtttt | ataattctct | ggcagttcct | tatgatagag | tttataaaac | agtcctgtgt | 1440 |
| aaactgctgg | aagttcttcc | acagtcaggt | caattttgtc | aaaccttct | ctgtacccat | 1500 |
| acagcagcag | cctagcaact | ctgctggtga | tgggagttgt | attttcagtc | ttcgccaggt | 1560 |
| cattgagatc | catccactca | catcttaagc | attcttcctg | gcaaaatttt | atggtgaatg | 1620 |
| aatatggctt | taggcggcag | atgatataca | tatctgactt | cccaaaagct | ccaggatttg | 1680 |

-continued

```
tgtgctgttg ccgaatactc aggacggacc tgaattctga ttttatacca gtctcttcaa    1740
aaacttctcg aaccgctgtg tctcctacgt aaaaaaagag atgtacaaat caataataat    1800
tacacttttta gaaactgtat catcaaagat tttcagttaa agtagcatta tgtaaaggct    1860
caaaacatta ccctaacaaa gtaaagtttt caatacaaat tctttgcctt gtggatatca    1920
agaaatccca aaatattttc ttaccactgt aaattcaaga agcttttgaa atgctgaata    1980
tttctttggc tgctacttgg aggcttatct acctgtacat ttttggggtc agctctttt     2040
aacttcttgc tgctctttt cccaaaaggt aaaaatatag attgaaaagt taaaacattt     2100
tgcatggctg cagttccttt gtttcttgag ataagattcc aaagaactta gattcatttc    2160
ttcaacaccg aaatgctgga ggtgtttgat cagttttcaa gaaacttgga atataaataa    2220
ttttataatt caacaaaggt tttcacattt tataaggttg atttttcaat taaatgcaaa    2280
tttgtgtggc aggatttta ttgccattaa catattttg tggctgcttt tctacacat      2340
ccagatggtc cctctaactg gctttctct aattttgtga tgttctgtca ttgtctccca     2400
aagtatttag gagaagccct ttaaaaagct gccttcctct accactttgc tggaaagctt    2460
cacaattgtc acagacaaag attttttgttc caatactcgt tttgcctcta tttttcttgt   2520
ttgtcaaata gtaaatgata tttgcccttg cagtaattct actggtgaaa aacatgcaaa    2580
gaagaggaag tcacagaaac atgtctcaat tcccatgtgc tgtgactgta gactgtctta    2640
ccatagactg tcttacccat ccctggata tgctcttgtt ttttccctct aatagctatg     2700
gaaagatgca tagaaagagt ataatgttt aaaacataag gcattcgtct gccattttt     2760
aattacatgc tgacttccct tacaattgag atttgcccat aggttaaaca tggttagaaa    2820
caactgaaag cataaaagaa aaatctaggc cgggtgcagt ggctcatgcc tatattccct   2880
gcactttggg aggccaaagc aggaggatcg cttgagccca ggagttcaag accaacctgg    2940
tgaaaccccg tctctacaaa aaaacacaaa aaatagccag gcatggtggc gtgtacatgt   3000
ggtctcagat acttgggagg ctgaggtggg agggttgatc acttgaggct gagaggtcaa    3060
ggttgcagtg agccataatc gtgccactgc agtccagcct aggcaacaga gtgagacttt    3120
gtctcaaaaa aagagaaatt tccttaata agaaaagtaa ttttactct gatgtgcaat      3180
acatttgtta ttaaatttat tatttaagat ggtagcacta gtcttaaatt gtataaaata    3240
tccccctaaca tgtttaaatg tccattttta ttcattatgc tttgaaaaat aattatgggg   3300
aaatacatgt ttgttattaa atttattatt aaagatagta gcactagtct taaatttgat    3360
ataacatctc ctaacttgtt taaatgtcca tttttattct ttatgtttga aaataaatta    3420
tggggatcct atttagctct tagtaccact aatcaaaagt tcggcatgta gctcatgatc    3480
tatgctgttt ctatgtcgtg gaagcaccgg atggggtag tgagcaaatc tgccctgctc     3540
agcagtcacc atagcagctg actgaaaatc agcactgcct gagtagtttt gatcagttta    3600
acttgaatca ctaactgact gaaaattgaa tgggcaaata agtgcttttg tctccagagt    3660
atgcgggaga cccttccacc tcaagatgga tatttcttcc ccaaggattt caagatgaat    3720
tgaaattttt aatcaagata gtgtgcttta ttctgttgta tttttattta tttaatata    3780
ctgtaagcca aactgaaata acatttgctg tttttataggt ttgaagaaca taggaaaaac   3840
taagaggttt tgttttatt tttgctgatg aagagatatg tttaaatatg ttgtattgtt    3900
ttgtttagtt acaggacaat aatgaaatgg agtttatatt tgttatttct attttgttat   3960
atttaataat agaattagat tgaaataaaa tataatggga aataatctgc agaatgtggg    4020
```

```
ttttcctggt gtttccctct gactctagtg cactgatgat ctctgataag gctcagctgc    4080
tttatagttc tctggctaat gcagcagata ctcttcctgc cagtggtaat acgattttt     4140
aagaaggcag tttgtcaatt ttaatcttgt ggatacc ttt atactcttag ggtattattt    4200
tatacaaaag ccttgaggat tgcattctat tttctatatg accctcttga tatttaaaaa    4260
acactatgga taacaattct tcatttacct agtattatga agaatgaag gagttcaaac     4320
aaatgtgttt cccagttaac tagggtttac tgtttgagcc aatataaatg tttaactgtt    4380
tgtgatggca gtattcctaa agtacattgc atgttttcct aaatacagag tttaaataat    4440
ttcagtaatt cttagatgat tcagcttcat cattaagaat atcttttgtt ttatgttgag    4500
ttagaaatgc cttcatatag acatagtctt tcagacctct actgtcagtt ttcatttcta   4560
gctgctttca gggttttatg aattttcagg caaagcttta atttatacta agcttaggaa    4620
gtatggctaa tgccaacggc agttttttc ttcttaattc cacatgactg aggcatatat     4680
gatctctggg taggtgagtt gttgtgacaa ccacaagcac ttttttttt tttaaagaaa     4740
aaaaggtagt gaattttaa tcatctggac tttaagaagg attctggagt atacttaggc    4800
ctgaaattat atatatttgg cttggaaatg tgttttttctt caattacatc tacaagtaag  4860
tacagctgaa attcagagga cccataagag ttcacatgaa aaaaatcaat ttatttgaaa    4920
aggcaagatg caggagagag gaagccttgc aaacctgcag actgcttttt gcccaatata    4980
gattgggtaa ggctgcaaaa cataagctta attagctcac atgctctgct ctcacgtggc    5040
accagtggat agtgtgagag aattaggctg tagaacaaat ggccttctct ttcagcattc    5100
acaccactac aaaatcatct tttatatcaa cagaagaata agcataaact aagcaaaagg    5160
tcaataagta cctgaaacca agattggcta gagatatatc ttaatgcaat ccatttttctg   5220
atggattgtt acgagttggc tatataatgt atgtatggta ttttgatttg tgtaaaagtt    5280
ttaaaaatca agctttaagt acatggacat ttttaaataa aatatttaaa gacaatttag    5340
aaaattgcct taatatcatt gttggctaaa tagaataggg gacatgcata ttaaggaaaa    5400
ggtcatggag aaataatatt ggtatcaaac aaatacattg atttgtcatg atacacattg    5460
aatttgatcc aatagtttaa ggaataggta ggaaaatttg gtttctattt ttcgatttcc    5520
tgtaaatcag tgacataaat aattcttagc ttatttata tttccttgtc ttaaatactg     5580
agctcagtaa gttgtgttag gggattattt ctcagttgag actttcttat atgcattttt    5640
actatgtttt gacttcctga ctattaaaaa taaatagtag atacaatttt cataaagtga    5700
agaattatat aatcactgct ttataactga ctttattata tttatttcaa agttcattta    5760
aaggctacta ttcatcctct gtgatggaat ggtcaggaat ttgttttctc atagtttaat    5820
tccaacaaca atattagtcg tatccaaaat aaccttttaat gctaaacttt actgatgtat   5880
atccaaagct tctcattttc agacagatta atccagaagc agtcataaac agaagaatag    5940
gtggtatgtt cctaatgata ttatttctac taatggaata aactgtaata ttagaaatta   6000
tgctgctaat tatatcagct ctgaggtaat ttctgaaatg ttcagactca gtcggaacaa    6060
attggaaaat ttaaattttt attcttagct ataaagcaag aaagtaaaca cattaatttc    6120
ctcaacattt ttaagccaat taaaaatata aagatacac accaatatct tcttcaggct     6180
ctgacaggcc tcctggaaac ttccacatat ttttcaactg cagtataaag tcagaaaata    6240
aagttaacat aactttcact aacacacaca tatgtagatt tcacaaaatc cacctataat    6300
tggtcaaagt ggttgagaat atattttta gtaattgcat gcaaaattt tctagcttcc     6360
atcctttctc cctcgtttct ctttttttg ggggagctgg taactgatga aatcttttcc     6420
```

```
cacctttttct cttcaggaaa tataagtggt tttgtttggt taacgtgata cattctgtat    6480
gaatgaaaca ttggagggaa acatctactg aatttctgta atttaaaata ttttgctgct    6540
agttaactat gaacagatag aagaatctta cagatgctgc tataaataag tagaaaatat    6600
aaatttcatc actaaaatat gctatttaa aatctatttc ctatattgta tttctaatca     6660
gatgtattac tcttattatt tctattgtat gtgttaatga ttttatgtaa aaatgtaatt    6720
gcttttcatg agtagtatga ataaaattga ttagtttgtg ttttcttgtc tccc          6774
```

<210> SEQ ID NO 41
<211> LENGTH: 365
<212> TYPE: PRT
<213> ORGANISM: Homo sapiens

<400> SEQUENCE: 41

```
Met Leu Ala Val Gly Cys Ala Leu Leu Ala Leu Leu Ala Leu Leu Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
```

```
                305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
                340                 345                 350

Ser Leu Pro Gly Ser Arg Arg Gly Ser Cys Gly Leu
                355                 360                 365
```

<210> SEQ ID NO 42
<211> LENGTH: 244
<212> TYPE: PRT
<213> ORGANISM: Homo sapiens

<400> SEQUENCE: 42

```
Val Pro Pro Glu Glu Pro Gln Leu Ser Cys Phe Arg Lys Ser Pro Leu
1               5                   10                  15

Ser Asn Val Val Cys Glu Trp Gly Pro Arg Ser Thr Pro Ser Leu Thr
                20                  25                  30

Thr Lys Ala Val Leu Leu Val Arg Lys Phe Gln Asn Ser Pro Ala Glu
                35                  40                  45

Asp Phe Gln Glu Pro Cys Gln Tyr Ser Gln Glu Ser Gln Lys Phe Ser
        50                  55                  60

Cys Gln Leu Ala Val Pro Glu Gly Asp Ser Ser Phe Tyr Ile Val Ser
65                  70                  75                  80

Met Cys Val Ala Ser Ser Val Gly Ser Lys Phe Ser Lys Thr Gln Thr
                85                  90                  95

Phe Gln Gly Cys Gly Ile Leu Gln Pro Asp Pro Pro Ala Asn Ile Thr
                100                 105                 110

Val Thr Ala Val Ala Arg Asn Pro Arg Trp Leu Ser Val Thr Trp Gln
                115                 120                 125

Asp Pro His Ser Trp Asn Ser Ser Phe Tyr Arg Leu Arg Phe Glu Leu
        130                 135                 140

Arg Tyr Arg Ala Glu Arg Ser Lys Thr Phe Thr Thr Trp Met Val Lys
145                 150                 155                 160

Asp Leu Gln His His Cys Val Ile His Asp Ala Trp Ser Gly Leu Arg
                165                 170                 175

His Val Val Gln Leu Arg Ala Gln Glu Glu Phe Gly Gln Gly Glu Trp
                180                 185                 190

Ser Glu Trp Ser Pro Glu Ala Met Gly Thr Pro Trp Thr Glu Ser Arg
                195                 200                 205

Ser Pro Pro Ala Glu Asn Glu Val Ser Thr Pro Met Gln Ala Leu Thr
        210                 215                 220

Thr Asn Lys Asp Asp Asn Ile Leu Phe Arg Asp Ser Ala Asn Ala
225                 230                 235                 240

Thr Ser Leu Pro
```

<210> SEQ ID NO 43
<211> LENGTH: 212
<212> TYPE: PRT
<213> ORGANISM: Homo sapiens

<400> SEQUENCE: 43

```
Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
                20                  25                  30
```

Gly Glu Asp Ser Lys Asp Val Ala Ala Pro His Arg Gln Pro Leu Thr
         35                  40                  45

Ser Ser Glu Arg Ile Asp Lys Gln Ile Arg Tyr Ile Leu Asp Gly Ile
 50                  55                  60

Ser Ala Leu Arg Lys Glu Thr Cys Asn Lys Ser Asn Met Cys Glu Ser
 65                  70                  75                  80

Ser Lys Glu Ala Leu Ala Glu Asn Asn Leu Asn Leu Pro Lys Met Ala
                 85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
            115                 120                 125

Leu Gln Asn Arg Phe Glu Ser Ser Glu Glu Gln Ala Arg Ala Val Gln
        130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
        210

<210> SEQ ID NO 44
<211> LENGTH: 2217
<212> TYPE: DNA
<213> ORGANISM: Homo sapiens

<400> SEQUENCE: 44
ccccgccgcc gccgcccttc gcgccctggg ccatctccct cccacctccc tccgcggagc      60
agccagacag cgagggcccc ggccgggggc agggggacg ccccgtccgg ggcaccccc      120 cggctctgag ccgcccgcgg ggccggcctc ggcccggagc ggaggaagga gtcgccgagg    180
agcagcctga ggccccagag tctgagacga gccgccgccg ccccgccac tgcggggagg      240 aggggggagga ggagcgggag gagggacgag ctggtcggga gaagaggaaa aaacttttg    300 agacttttcc gttgccgctg ggagccggag gcgcggggac ctcttggcgc gacgctgccc    360
cgcgaggagg caggacttgg ggaccccaga ccgcctccct tgccgccgg ggacgcttgc     420 tccctcccctg ccccctacac ggcgtccctc aggcgccccc attccggacc agccctcggg   480
agtcgccgac ccgcctccc gcaaagactt ttccccagac ctcgggcgca ccccctgcac    540
gccgccttca tcccggcct gtctcctgag ccccgcgca tcctagaccc tttctcctcc    600
aggagacgga tctctctccg acctgccaca gatcccctat tcaagaccac ccaccttctg    660
gtaccagatc gcgcccatct aggttatttc cgtgggatac tgagacaccc ccggtccaag    720
cctcccctcc accactgcgc ccttctccct gaggacctca gctttccctc gaggccctcc    780
taccttttgc cgggagaccc ccagccctg caggggcggg gcctcccac cacaccagcc     840 ctgttcgcgc tctcggcagt gccggggggc gccgcctccc ccatgccgcc ctccgggctg    900
cggctgctgc cgctgctgct accgctgctg tggctactgg tgctgacgcc tggccggccg    960
gccgcgggac tatccacctg caagactatc gacatggagc tggtgaagcg gaagcgcatc   1020

-continued

```
gaggccatcc gcggccagat cctgtccaag ctgcggctcg ccagccccccc gagccagggg    1080 gaggtgccgc ccggcccgct gcccgaggcc gtgctcgccc tgtacaacag cacccgcgac    1140
cgggtggccg gggagagtgc agaaccggag cccgagcctg aggccgacta ctacgccaag    1200
gaggtcaccc cgcgtgctaat ggtggaaacc cacaacgaaa tctatgacaa gttcaagcag    1260
agtacacaca gcatatatat gttcttcaac acatcagagc tccgagaagc ggtacctgaa    1320
cccgtgttgc tctcccgggc agagctgcgt ctgctgaggc tcaagttaaa agtggagcag    1380
cacgtggagc tgtaccagaa atacagcaac aattcctggc gatacctcag caaccggctg    1440 ctggcacccca gcgactcgcc agagtggtta tcttttgatg tcaccggagt tgtgcggcag    1500
tggttgagcc gtggagggga aattgagggc tttcgcctta gcgccactg ctcctgtgac     1560 agcagggata acacactgca agtggacatc aacgggttca ctaccggccg ccgaggtgac    1620
ctggccacca ttcatggcat gaaccggcct ttcctgcttc tcatggccac cccgctggag    1680
agggcccagc atctgcaaag ctcccggcac cgccgagccc tggacaccaa ctattgcttc    1740
agctccacgg agaagaactg ctgcgtgcgg cagctgtaca ttgacttccg caaggacctc    1800
ggctggaagt ggatccacga gcccaagggc taccatgcca acttctgcct cgggccctgc    1860
ccctacattt ggagcctgga cacgcagtac agcaaggtcc tggcccctgta caaccagcat    1920 aacccgggcg cctcggcggc gccgtgctgc gtgccgcagg cgctggagcc gctgccatc     1980 gtgtactacg tgggccgcaa gcccaaggtg agcagctgt ccaacatgat cgtgcgctcc     2040
tgcaagtgca gctgaggtcc cgccccgccc cgccccgccc cggcaggccc ggccccaccc    2100
cgccccgccc ccgctgcctt gcccatgggg gctgtattta aggacacccg tgccccaagc    2160
ccacctgggg ccccattaaa gatggagaga ggactgcgga aaaaaaaaaa aaaaaaa       2217
```

<210> SEQ ID NO 45
<211> LENGTH: 390
<212> TYPE: PRT
<213> ORGANISM: Homo sapiens

<400> SEQUENCE: 45

```
Met Pro Pro Ser Gly Leu Arg Leu Leu Pro Leu Leu Pro Leu Leu
1               5                   10                  15

Trp Leu Leu Val Leu Thr Pro Gly Arg Pro Ala Ala Gly Leu Ser Thr
                20                  25                  30

Cys Lys Thr Ile Asp Met Glu Leu Val Lys Arg Lys Arg Ile Glu Ala
            35                  40                  45

Ile Arg Gly Gln Ile Leu Ser Lys Leu Arg Leu Ala Ser Pro Pro Ser
        50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
```

```
                    165                 170                 175
Asn Ser Trp Arg Tyr Leu Ser Asn Arg Leu Leu Ala Pro Ser Asp Ser
                180                 185                 190

Pro Glu Trp Leu Ser Phe Asp Val Thr Gly Val Val Arg Gln Trp Leu
            195                 200                 205

Ser Arg Gly Gly Glu Ile Glu Gly Phe Arg Leu Ser Ala His Cys Ser
        210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390

<210> SEQ ID NO 46
<211> LENGTH: 5966
<212> TYPE: DNA
<213> ORGANISM: Homo sapiens

<400> SEQUENCE: 46
gtgatgttat ctgctggcag cagaaggttc gctccgagcg gagctccaga agctcctgac      60
aagagaaaga cagattgaga tagagataga aagagaaaga gagaaagaga cagcagagcg     120
agagcgcaag tgaaagaggc aggggagggg gatggagaat attagcctga cggtctaggg     180
agtcatccag gaacaaactg aggggctgcc cggctgcaga caggaggaga cagagaggat     240
ctattttagg gtggcaagtg cctacctacc ctaagcgagc aattccacgt tggggagaag     300
ccagcagagg ttgggaaagg gtgggagtcc aagggagccc ctgcgcaacc ccctcaggaa     360
taaaactccc cagccagggt gtcgcaaggg ctgccgttgt gatccgcagg gggtgaacgc     420
aaccgcgacg gctgatcgtc tgtggctggg ttggcgtttg gagcaagaga aggaggagca     480
ggagaaggag ggagctggag gctggaagcg tttgcaagcg gcggcggcag caacgtggag     540
taaccaagcg ggtcagcgcg cgcccgccag ggtgtaggcc acgagcgca gctcccagag      600 caggatccgc gccgcctcag cagcctctgc ggccctgcg gcacccgacc gagtaccgag      660
cgccctgcga agcgcaccct cctccccgcg gtgcgctggg ctcgccccca gcgcgcgcac     720
acgcacacac acacacacac acacacacgc acgcacacac gtgtgcgctt ctctgctccg     780
gagctgctgc tgctcctgct ctcagcgccg cagtggaagg caggaccgaa ccgctccttc     840
```

```
tttaaatata taaatttcag cccaggtcag cctcggcggc ccccctcacc gcgctcccgg    900
cgccccctccc gtcagttcgc cagctgccag ccccgggacc ttttcatctc ttcccttttg    960
gccggaggag ccgagttcag atccgccact ccgcacccga gactgacaca ctgaactcca   1020
cttcctcctc ttaaatttat ttctacttaa tagccactcg tctctttttt tccccatctc   1080
attgctccaa gaattttttt cttcttactc gccaaagtca gggttccctc tgcccgtccc   1140
gtattaatat ttccactttt ggaactactg gccttttctt tttaaaggaa ttcaagcagg   1200
atacgttttt ctgttgggca ttgactagat tgtttgcaaa agtttcgcat caaaaacaac   1260
aacaacaaaa aaccaaacaa ctctccttga tctatacttt gagaattgtt gatttctttt   1320
ttttattctg acttttaaaa acaacttttt tttccacttt tttaaaaaat gcactactgt   1380
gtgctgagcg cttttctgat cctgcatctg gtcacggtcg cgctcagcct gtctacctgc   1440
agcacactcg atatggacca gttcatgcgc aagaggatcg aggcgatccg cgggcagatc   1500
ctgagcaagc tgaagctcac cagtccccca aagactatc ctgagcccga ggaagtcccc   1560
ccggaggtga tttccatcta caacagcacc agggacttgc tccaggagaa ggcgagccgg   1620
agggcggccg cctgcgagcg cgagaggagc gacgaagagt actacgccaa ggaggtttac   1680
aaaatagaca tgccgcccct tcttccctcc gaaactgtct gcccagttgt tacaacaccc   1740
tctggctcag tgggcagctt gtgctccaga cagtcccagg tgctctgtgg gtaccttgat   1800
gccatcccgc ccactttcta cagaccctac ttcagaattg ttcgatttga cgtctcagca   1860
atggagaaga atgcttccaa tttggtgaaa gcagagttca gagtctttcg tttgcagaac   1920
ccaaaagcca gagtgcctga caacggatt gagctatatc agattctcaa gtccaaagat   1980
ttaacatctc caacccagcg ctacatcgac agcaaagttg tgaaaacaag agcagaaggc   2040
gaatggctct ccttcgatgt aactgatgct gttcatgaat ggcttcacca taaagacagg   2100
aacctgggat ttaaaataag cttacactgt ccctgctgca cttttgtacc atctaataat   2160
tacatcatcc caaataaaag tgaagaacta gaagcaagat ttgcaggtat tgatggcacc   2220
tccacatata ccagtggtga tcagaaaact ataaagtcca ctaggaaaaa aaacagtggg   2280
aagacccccac atctcctgct aatgttattg ccctcctaca gacttgagtc acaacagacc   2340
aaccggcgga agaagcgtgc tttggatgcg gcctattgct ttagaaatgt gcaggataat   2400
tgctgcctac gtccacttta cattgatttc aagagggatc tagggtggaa atggatacac   2460
gaacccaaag ggtacaatgc caacttctgt gctggagcat gcccgtattt atggagttca   2520
gacactcagc acagcagggt cctgagctta tataatacca taaatccaga agcatctgct   2580
tctccttgct gcgtgtccca agatttagaa cctctaacca ttctctacta cattggcaaa   2640
acacccaaga ttgaacagct ttctaatatg attgtaaagt cttgcaaatg cagctaaaat   2700
tcttggaaaa gtggcaagac caaaatgaca atgatgatga taatgatgat gacgacgaca   2760
acgatgatgc ttgtaacaag aaaacataag agagccttgg ttcatcagtg ttaaaaaatt   2820
tttgaaaagg cggtactagt tcagacactt tggaagtttg tgttctgttt gttaaaactg   2880
gcatctgaca caaaaaaagt tgaaggcctt attctacatt tcacctactt tgtaagtgag   2940
agagacaaga agcaaatttt ttttaaagaa aaaaataaac actggaagaa tttattagtg   3000
ttaattatgt gaacaacgac aacaacaaca acaacaacaa acaggaaaat cccattaagt   3060
ggagttgctg tacgtaccgt tcctatcccg cgcctcactt gattttttctg tattgctatg   3120
caataggcac ccttcccatt cttactctta gagttaacag tgagttattt attgtgtgtt   3180
```

```
actatataat gaacgtttca ttgcccttgg aaaataaaac aggtgtataa agtggagacc    3240
aaatactttg ccagaaactc atggatggct taaggaactt gaactcaaac gagccagaaa    3300
aaaagaggtc atattaatgg gatgaaaacc caagtgagtt attatatgac cgagaaagtc    3360
tgcattaaga taaagaccct gaaaacacat gttatgtatc agctgcctaa ggaagcttct    3420
tgtaaggtcc aaaaactaaa aagactgtta ataaaagaaa ctttcagtca gaataagtct    3480
gtaagttttt tttttttcttt ttaattgtaa atggttcttt gtcagtttag taaaccagtg    3540
aaatgttgaa atgttttgac atgtactggt caaacttcag accttaaaat attgctgtat    3600
agctatgcta taggttttttt cctttgtttt ggtatatgta accataccta tattattaaa    3660
atagatggat atagaagcca gcataattga aaacacatct gcagatctct tttgcaaact    3720
attaaatcaa aacattaact actttatgtg taatgtgtaa attttttacca tatttttttat    3780 attctgtaat aatgtcaact atgatttaga ttgacttaaa tttgggctct ttttaatgat    3840
cactcacaaa tgtatgtttc ttttagctgg ccagtacttt tgagtaaagc ccctatagtt    3900
tgacttgcac tacaaatgca ttttttttttt aataacattt gccctacttg tgctttgtgt    3960
ttctttcatt attatgacat aagctacctg ggtccacttg tcttttcttt ttttttgtttc    4020 acagaaaaga tgggttcgag ttcagtggtc ttcatcttcc aagcatcatt actaaccaag    4080
tcagacgtta acaaattttt atgttaggaa aaggaggaat gttatagata catgaaaaat    4140
tgaagtaaaa tgttttcatt ttagcaagga tttagggttc taactaaaac tcagaatctt    4200
tattgagtta agaaaagttt ctctaccttg gtttaatcaa tatttttgta aaatcctatt    4260
gttattacaa agaggacact tcataggaaa catctttttc tttagtcagg ttttttaatat    4320 tcaggggaa attgaaagat atatatttta gtcgattttt caaaagggga aaaaagtcca    4380
ggtcagcata agtcattttg tgtatttcac tgaagtttata aggttttttat aaatgttctt    4440 tgaaggggaa aaggcacaag ccaattttttc ctatgatcaa aaaattcttt ctttcctctg    4500
agtgagagtt atctatatct gaggctaaag tttaccttgc tttaataaat aatttgccac    4560
atcattgcag aagaggtatc ctcatgctgg ggttaataga atatgtcagt ttatcacttg    4620
tcgcttattt agctttaaaa taaaaattaa taggcaaagc aatggaatat ttgcagtttc    4680
acctaaagag cagcataagg aggcgggaat ccaaagtgaa gttgtttgat atggtctact    4740
tcttttttgg aatttcctga ccattaatta aagaattgga tttgcaagtt tgaaaactgg    4800
aaaagcaaga gatgggatgc cataatagta aacagccctt gtgttggatg taacccaatc    4860
ccagatttga gtgtgtgttg attatttttt tgtcttccac ttttctatta tgtgtaaatc    4920
acttttattt ctgcagacat tttcctctca gataggatga cattttgttt tgtattattt    4980
tgtctttcct catgaatgca ctgataatat tttaaatgct ctattttaag atctcttgaa    5040
tctgtttttt tttttttttaa tttgggggtt ctgtaaggtc tttatttccc ataagtaaat    5100
attgccatgg gagggggtg gaggtggcaa ggaagggggtg aagtgctagt atgcaagtgg    5160
gcagcaatta ttttgtgtt aatcagcagt acaatttgat cgttggcatg gttaaaaaat    5220
ggaatataag attgctgtt ttgtattttg atgaccaatt acgctgtatt ttaacacgat    5280
gtatgtctgt ttttgtggtg ctctagtggt aaataaatta tttcgatgat atgtggatgt    5340
ctttttccta tcagtaccat catcgagtct agaaaacacc tgtgatgcaa taagactatc    5400
tcaagctgga aaagtcatac cacctttccg attgccctct gtgctttctc ccttaaggac    5460
agtcacttca gaagtcatgc tttaaagcac aagagtcagg ccatatccat caaggataga    5520
agaaatccct gtgccgtctt tttattccct tatttattgc tatttggtaa ttgtttgaga    5580
```

| | |
|---|---|
| tttagtttcc atccagcttg actgccgacc agaaaaaatg cagagagatg tttgcaccat | 5640 |
| gctttggctt tctggttcta tgttctgcca acgccagggc caaaagaact ggtctagaca | 5700 |
| gtatcccctg tagccccata acttggatag ttgctgagcc agccagatat aacaagagcc | 5760 |
| acgtgctttc tggggttggt tgtttgggat cagctacttg cctgtcagtt tcactggtac | 5820 |
| cactgcacca caaacaaaaa aacccaccct atttcctcca attttttttgg ctgctaccta | 5880 |
| caagaccaga ctcctcaaac gagttgccaa tctcttaata aataggatta ataaaaaaag | 5940 |
| taattgtgac tcaaaaaaaa aaaaaa | 5966 |

<210> SEQ ID NO 47
<211> LENGTH: 1900
<212> TYPE: DNA
<213> ORGANISM: Homo sapiens

<400> SEQUENCE: 47

| | |
|---|---|
| cattactaac caagtcagac gttaacaaat ttttatgtta ggaaaaggag gaatgttata | 60 |
| gatacataga aaattgaagt aaaatgtttt cattttagca aggatttagg gttctaacta | 120 |
| aaactcagaa tctttattga gttaagaaaa gtttctctac cttggtttaa tcaatatttt | 180 |
| tgtaaaatcc tattgttatt acaaagagga cacttcatag gaaacatctt tttctttagt | 240 |
| caggtttta atattcaggg ggaaattgaa agatatatat tttagtcgat ttttcaaaag | 300 |
| gggaaaaaag tccaggtcag cataagtcat tttgtgtatt tcactgaagt tataaggttt | 360 |
| ttataaatgt tctttgaagg ggaaaaggca caagccaatt tttcctatga tcaaaaaatt | 420 |
| cttttctttcc tctgagtgag agttatctat atctgaggct aaagtttacc ttgctttaat | 480 |
| aaataatttg ccacatcatt gcagaagagg tatcctcatg ctggggttaa tagaatatgt | 540 |
| cagtttatca cttgtcgctt atttagcttt aaaataaaaa ttaataggca aagcaatgga | 600 |
| atatttgcag tttcacctaa agagcagcat aaggaggcgg gaatccaaag tgaagttgtt | 660 |
| tgatatggtc tacttctttt ttggaatttc ctgaccatta attaaagaat tggatttgca | 720 |
| agtttgaaaa ctggaaaagc aagagatggg atgccataat agtaaacagc ccttgtgttg | 780 |
| gatgtaaccc aatcccagat ttgagtgtgt gttgattatt ttttttgtctt ccacttttct | 840 |
| attatgtgta aatcactttt atttctgcag acatttttcct ctcagatagg atgacatttt | 900 |
| gttttgtatt atttttgtctt tcctcatgaa tgcactgata atattttaaa tgctctatttt | 960 |
| taagatctct tgaatctgtt ttttttttttt ttaatttggg ggttctgtaa ggtctttatt | 1020 |
| tcccataagt aaatattgcc atgggagggg ggtggaggtg gcaaggaagg ggtgaagtgc | 1080 |
| tagtatgcaa gtgggcagca attattttttg tgttaatcag cagtacaatt tgatcgttgg | 1140 |
| catggttaaa aaatggaata taagattagc tgttttgtat tttgatgacc aattacgctg | 1200 |
| tattttaaca cgatgtatgt ctgttttttgt ggtgctctag tggtaaataa attatttcga | 1260 |
| tgatatgtgg atgtcttttt cctatcagta ccatcatcga gtctagaaaa cacctgtgat | 1320 |
| gcaataagac tatctcaagc tggaaaagtc ataccacctt tccgattgcc ctctgtgctt | 1380 |
| tctcccttaa ggacagtcac ttcagaagtc atgctttaaa gcacaagagt caggccatat | 1440 |
| ccatcaagga tagaagaaat ccctgtgccg tcttttttatt ccccttattta ttgctatttg | 1500 |
| gtaattgttt gagatttagt ttccatccag cttgactgcc gaccagaaaa aatgcagaga | 1560 |
| gatgtttgca ccatgctttg gctttctggt tctatgttct gccaacgcca gggcaaaag | 1620 |
| aactggtcta gacagtatcc cctgtagccc cataacttgg atagttgctg agccagccag | 1680 |

```
ataiaacaag agccacgtgc tttctggggt tggttgtttg ggatcagcta cttgcctgtc    1740
agtttcactg gtaccactgc accacaaaca aaaaaaccca ccctatttcc tccaattttt    1800
ttggctgcta cctacaagac cagactcctc aaacgagttg ccaatctctt aataaatagg    1860
attaataaaa aaagtaattg tgactcaaaa aaaaaaaaaa                          1900
```

```
<210> SEQ ID NO 48
<211> LENGTH: 442
<212> TYPE: PRT
<213> ORGANISM: Homo sapiens

<400> SEQUENCE: 48
```

| | | | | | | | | | | | | | | | |
|---|---|---|---|---|---|---|---|---|---|---|---|---|---|---|---|
| Met | His | Tyr | Cys | Val | Leu | Ser | Ala | Phe | Leu | Ile | Leu | His | Leu | Val | Thr |
| 1 | | | | 5 | | | | | 10 | | | | | 15 | |
| Val | Ala | Leu | Ser | Leu | Ser | Thr | Cys | Ser | Thr | Leu | Asp | Met | Asp | Gln | Phe |
| | | | 20 | | | | | 25 | | | | | 30 | | |
| Met | Arg | Lys | Arg | Ile | Glu | Ala | Ile | Arg | Gly | Gln | Ile | Leu | Ser | Lys | Leu |
| | | 35 | | | | | 40 | | | | | 45 | | | |
| Lys | Leu | Thr | Ser | Pro | Pro | Glu | Asp | Tyr | Pro | Glu | Pro | Glu | Glu | Val | Pro |
| 50 | | | | | 55 | | | | | 60 | | | | | |
| Pro | Glu | Val | Ile | Ser | Ile | Tyr | Asn | Ser | Thr | Arg | Asp | Leu | Leu | Gln | Glu |
| 65 | | | | 70 | | | | | 75 | | | | | 80 | |
| Lys | Ala | Ser | Arg | Arg | Ala | Ala | Ala | Cys | Glu | Arg | Glu | Arg | Ser | Asp | Glu |
| | | | | 85 | | | | | 90 | | | | | 95 | |
| Glu | Tyr | Tyr | Ala | Lys | Glu | Val | Tyr | Lys | Ile | Asp | Met | Pro | Pro | Phe | Phe |
| | | | 100 | | | | | 105 | | | | | 110 | | |
| Pro | Ser | Glu | Thr | Val | Cys | Pro | Val | Val | Thr | Thr | Pro | Ser | Gly | Ser | Val |
| | | | 115 | | | | | 120 | | | | | 125 | | |
| Gly | Ser | Leu | Cys | Ser | Arg | Gln | Ser | Gln | Val | Leu | Cys | Gly | Tyr | Leu | Asp |
| | | 130 | | | | | 135 | | | | | 140 | | | |
| Ala | Ile | Pro | Pro | Thr | Phe | Tyr | Arg | Pro | Tyr | Phe | Arg | Ile | Val | Arg | Phe |
| 145 | | | | | 150 | | | | | 155 | | | | | 160 |
| Asp | Val | Ser | Ala | Met | Glu | Lys | Asn | Ala | Ser | Asn | Leu | Val | Lys | Ala | Glu |
| | | | | 165 | | | | | 170 | | | | | 175 | |
| Phe | Arg | Val | Phe | Arg | Leu | Gln | Asn | Pro | Lys | Ala | Arg | Val | Pro | Glu | Gln |
| | | | 180 | | | | | 185 | | | | | 190 | | |
| Arg | Ile | Glu | Leu | Tyr | Gln | Ile | Leu | Lys | Ser | Lys | Asp | Leu | Thr | Ser | Pro |
| | | | 195 | | | | | 200 | | | | | 205 | | |
| Thr | Gln | Arg | Tyr | Ile | Asp | Ser | Lys | Val | Val | Lys | Thr | Arg | Ala | Glu | Gly |
| | | 210 | | | | | 215 | | | | | 220 | | | |
| Glu | Trp | Leu | Ser | Phe | Asp | Val | Thr | Asp | Ala | Val | His | Glu | Trp | Leu | His |
| 225 | | | | | 230 | | | | | 235 | | | | | 240 |
| His | Lys | Asp | Arg | Asn | Leu | Gly | Phe | Lys | Ile | Ser | Leu | His | Cys | Pro | Cys |
| | | | | 245 | | | | | 250 | | | | | 255 | |
| Cys | Thr | Phe | Val | Pro | Ser | Asn | Asn | Tyr | Ile | Ile | Pro | Asn | Lys | Ser | Glu |
| | | | 260 | | | | | 265 | | | | | 270 | | |
| Glu | Leu | Glu | Ala | Arg | Phe | Ala | Gly | Ile | Asp | Gly | Thr | Ser | Thr | Tyr | Thr |
| | | | 275 | | | | | 280 | | | | | 285 | | |
| Ser | Gly | Asp | Gln | Lys | Thr | Ile | Lys | Ser | Thr | Arg | Lys | Lys | Asn | Ser | Gly |
| | | 290 | | | | | 295 | | | | | 300 | | | |
| Lys | Thr | Pro | His | Leu | Leu | Leu | Met | Leu | Leu | Pro | Ser | Tyr | Arg | Leu | Glu |
| 305 | | | | | 310 | | | | | 315 | | | | | 320 |
| Ser | Gln | Gln | Thr | Asn | Arg | Arg | Lys | Lys | Arg | Ala | Leu | Asp | Ala | Ala | Tyr |
| | | | | 325 | | | | | 330 | | | | | 335 | |

```
Cys Phe Arg Asn Val Gln Asp Asn Cys Cys Leu Arg Pro Leu Tyr Ile
                340                 345                 350

Asp Phe Lys Arg Asp Leu Gly Trp Lys Trp Ile His Glu Pro Lys Gly
                355                 360                 365

Tyr Asn Ala Asn Phe Cys Ala Gly Ala Cys Pro Tyr Leu Trp Ser Ser
                370                 375                 380

Asp Thr Gln His Ser Arg Val Leu Ser Leu Tyr Asn Thr Ile Asn Pro
385                 390                 395                 400

Glu Ala Ser Ala Ser Pro Cys Cys Val Ser Gln Asp Leu Glu Pro Leu
                405                 410                 415

Thr Ile Leu Tyr Tyr Ile Gly Lys Thr Pro Lys Ile Glu Gln Leu Ser
                420                 425                 430

Asn Met Ile Val Lys Ser Lys Cys Ser
                435                 440

<210> SEQ ID NO 49
<211> LENGTH: 414
<212> TYPE: PRT
<213> ORGANISM: Homo sapiens

<400> SEQUENCE: 49

Met His Tyr Cys Val Leu Ser Ala Phe Leu Ile Leu His Leu Val Thr
1               5                   10                  15

Val Ala Leu Ser Leu Ser Thr Cys Ser Thr Leu Asp Met Asp Gln Phe
                20                  25                  30

Met Arg Lys Arg Ile Glu Ala Ile Arg Gly Gln Ile Leu Ser Lys Leu
                35                  40                  45

Lys Leu Thr Ser Pro Pro Glu Asp Tyr Pro Glu Pro Glu Glu Val Pro
50                  55                  60

Pro Glu Val Ile Ser Ile Tyr Asn Ser Thr Arg Asp Leu Leu Gln Glu
65                  70                  75                  80

Lys Ala Ser Arg Arg Ala Ala Ala Cys Glu Arg Glu Arg Ser Asp Glu
                85                  90                  95

Glu Tyr Tyr Ala Lys Glu Val Tyr Lys Ile Asp Met Pro Pro Phe Phe
                100                 105                 110

Pro Ser Glu Asn Ala Ile Pro Pro Thr Phe Tyr Arg Pro Tyr Phe Arg
                115                 120                 125

Ile Val Arg Phe Asp Val Ser Ala Met Glu Lys Asn Ala Ser Asn Leu
                130                 135                 140

Val Lys Ala Glu Phe Arg Val Phe Arg Leu Gln Asn Pro Lys Ala Arg
145                 150                 155                 160

Val Pro Glu Gln Arg Ile Glu Leu Tyr Gln Ile Leu Lys Ser Lys Asp
                165                 170                 175

Leu Thr Ser Pro Thr Gln Arg Tyr Ile Asp Ser Lys Val Val Lys Thr
                180                 185                 190

Arg Ala Glu Gly Glu Trp Leu Ser Phe Asp Val Thr Asp Ala Val His
                195                 200                 205

Glu Trp Leu His His Lys Asp Arg Asn Leu Gly Phe Lys Ile Ser Leu
                210                 215                 220

His Cys Pro Cys Cys Thr Phe Val Pro Ser Asn Asn Tyr Ile Ile Pro
225                 230                 235                 240

Asn Lys Ser Glu Glu Leu Glu Ala Arg Phe Ala Gly Ile Asp Gly Thr
                245                 250                 255

Ser Thr Tyr Thr Ser Gly Asp Gln Lys Thr Ile Lys Ser Thr Arg Lys
                260                 265                 270
```

```
Lys Asn Ser Gly Lys Thr Pro His Leu Leu Met Leu Leu Pro Ser
            275                 280                 285

Tyr Arg Leu Glu Ser Gln Gln Thr Asn Arg Arg Lys Arg Ala Leu
    290                 295                 300

Asp Ala Ala Tyr Cys Phe Arg Asn Val Gln Asp Asn Cys Cys Leu Arg
305                 310                 315                 320

Pro Leu Tyr Ile Asp Phe Lys Arg Asp Leu Gly Trp Lys Trp Ile His
                325                 330                 335

Glu Pro Lys Gly Tyr Asn Ala Asn Phe Cys Ala Gly Ala Cys Pro Tyr
                340                 345                 350

Leu Trp Ser Ser Asp Thr Gln His Ser Arg Val Leu Ser Leu Tyr Asn
            355                 360                 365

Thr Ile Asn Pro Glu Ala Ser Ala Ser Pro Cys Cys Val Ser Gln Asp
370                 375                 380

Leu Glu Pro Leu Thr Ile Leu Tyr Tyr Ile Gly Lys Thr Pro Lys Ile
385                 390                 395                 400

Glu Gln Leu Ser Asn Met Ile Val Lys Ser Cys Lys Cys Ser
                405                 410

<210> SEQ ID NO 50
<211> LENGTH: 3183
<212> TYPE: DNA
<213> ORGANISM: Homo sapiens

<400> SEQUENCE: 50
gacagaagca atggccgagg cagaagacaa gccgaggtgc tggtgaccct gggcgtctga      60
gtggatgatt ggggctgctg cgctcagagg cctgcctccc tgccttccaa tgcatataac     120
cccacacccc agccaatgaa gacgagaggc agcgtgaaca agtcattta gaaagccccc      180 gaggaagtgt aaacaaaaga gaaagcatga atggagtgcc tgagagacaa gtgtgtcctg     240
tactgccccc acctttagct gggccagcaa ctgcccggcc ctgcttctcc ccacctactc     300
actggtgatc tttttttttt tacttttttt tccctttttct tttccattct cttttcttat    360 tttcttcaa ggcaaggcaa ggattttgat tttgggaccc agccatggtc cttctgcttc      420
ttctttaaaa tacccacttt ctccccatcg ccaagcggcg tttggcaata tcagatatcc     480
actctattta ttttacctta aggaaaaact ccagctccct tcccactccc agctgccttg    540 ccaccctcc cagccctctg cttgccctcc acctggcctg ctgggagtca gagcccagca     600
aaacctgttt agacacatgg acaagaatcc cagcgctaca aggcacacag tccgcttctt    660
cgtcctcagg gttgccagcg cttcctggaa gtcctgaagc tctcgcagtg cagtgagttc    720
atgcaccttc ttgccaagcc tcagtctttg ggatctgggg aggccgcctg gttttcctcc   780
ctccttctgc acgtctgctg gggtctcttc ctctccaggc cttgccgtcc cctggcctc    840 tcttcccagc tcacacatga agatgcactt gcaaagggct ctggtggtcc tggccctgct    900
gaactttgcc acggtcagcc tctctctgtc cacttgcacc accttggact cggccacat    960 caagaagaag agggtggaag ccattagggg acagatcttg agcaagctca ggctcaccag   1020 ccccctgag ccaacggtga tgacccacgt cccctatcag gtcctggccc tttacaacag    1080
cacccgggag ctgctggagg agatgcatgg ggagagggag aaggctgca cccaggaaaa    1140 caccgagtcg gaatactatg ccaaagaaat ccataaattc gacatgatcc aggggctggc    1200
ggagcacaac gaactggctg tctgccctaa ggaattacc tccaaggttt ccgcttcaa     1260 tgtgtcctca gtggagaaaa atagaaccaa cctattccga gcagaattcc gggtcttgcg   1320
```

```
ggtgcccaac cccagctcta agcggaatga gcagaggatc gagctcttcc agatccttcg   1380
gccagatgag cacattgcca acagcgcta tatcggtggc aagaatctgc ccacacgggg   1440
cactgccgag tggctgtcct ttgatgtcac tgacactgtg cgtgagtggc tgttgagaag   1500
agagtccaac ttaggtctag aaatcagcat tcactgtcca tgtcacacct ttcagcccaa   1560
tggagatatc ctggaaaaca ttcacgaggt gatggaaatc aaattcaaag gcgtggacaa   1620
tgaggatgac catggccgtg agatctggg gcgcctcaag aagcagaagg atcaccacaa   1680
ccctcatcta atcctcatga tgattccccc acaccggctc gacaacccgg gccagggggg   1740
tcagaggaag aagcgggctt tggacaccaa ttactgcttc cgcaacttgg aggagaactg   1800
ctgtgtgcgc cccctctaca ttgacttccg acaggatctg ggctggaagt gggtccatga   1860
acctaagggc tactatgcca acttctgctc aggcccttgc ccatacctcc gcagtgcaga   1920
cacaacccac agcacggtgc tgggactgta caacactctg aaccctgaag catctgcctc   1980
gccttgctgc gtgccccagg acctggagcc cctgaccatc ctgtactatg ttgggaggac   2040
ccccaaagtg gagcagctct ccaacatggt ggtgaagtct tgtaaatgta gctgagaccc   2100
cacgtgcgac agagagaggg gagagagaac caccactgcc tgactgcccg ctcctcggga   2160
aacacacaag caacaaacct cactgagagg cctggagccc acaaccttcg gctccgggca   2220
aatggctgag atggaggttt cctttttggaa catttctttc ttgctggctc tgagaatcac   2280
ggtggtaaag aaagtgtggg tttggttaga ggaaggctga actcttcaga acacacagac   2340
tttctgtgac gcagacagag gggatgggga tagaggaaag ggatggtaag ttgagatgtt   2400
gtgtggcaat gggatttggg ctaccctaaa gggagaagga agggcagaga atggctgggt   2460
cagggccaga ctggaagaca cttcagatct gaggttggat ttgctcattg ctgtaccaca   2520
tctgctctag ggaatctgga ttatgttata caaggcaagc atttttttt tttttttaaa   2580 gacaggttac gaagacaaag tcccagaatt gtatctcata ctgtctggga ttaagggcaa   2640
atctattact tttgcaaact gtcctctaca tcaattaaca tcgtgggtca ctacagggag   2700
aaaatccagg tcatgcagtt cctggcccat caactgtatt gggccttttg gatatgctga   2760
acgcagaaga aagggtggaa atcaaccctc tcctgtctgc cctctgggtc cctcctctca   2820
cctctccctc gatcatattt cccccttggac acttggttag acgccttcca ggtcaggatg   2880
cacatttctg gattgtggtt ccatgcagcc ttggggcatt atgggttctt ccccacttc   2940 ccctccaaga ccctgtgttc atttggtgtt cctggaagca ggtgctacaa catgtgaggc   3000
attcggggaa gctgcacatg tgccacacag tgacttggcc ccagacgcat agactgaggt   3060
ataaagacaa gtatgaatat tactctcaaa atctttgtat aaataaatat ttttggggca   3120
tcctggatga tttcatcttc tggaatattg tttctagaac agtaaaagcc ttattctaag   3180
gtg                                                                 3183
```

<210> SEQ ID NO 51
<211> LENGTH: 412
<212> TYPE: PRT
<213> ORGANISM: Homo sapiens

<400> SEQUENCE: 51

Met Lys Met His Leu Gln Arg Ala Leu Val Val Leu Ala Leu Leu Asn
1               5                   10                  15

Phe Ala Thr Val Ser Leu Ser Leu Ser Thr Cys Thr Thr Leu Asp Phe
            20                  25                  30

-continued

```
Gly His Ile Lys Lys Arg Val Glu Ala Ile Arg Gly Gln Ile Leu
        35              40              45

Ser Lys Leu Arg Leu Thr Ser Pro Pro Glu Pro Thr Val Met Thr His
 50              55                  60

Val Pro Tyr Gln Val Leu Ala Leu Tyr Asn Ser Thr Arg Glu Leu Leu
 65              70              75                       80

Glu Glu Met His Gly Glu Arg Glu Gly Cys Thr Gln Glu Asn Thr
                 85              90              95

Glu Ser Glu Tyr Tyr Ala Lys Glu Ile His Lys Phe Asp Met Ile Gln
            100             105             110

Gly Leu Ala Glu His Asn Glu Leu Ala Val Cys Pro Lys Gly Ile Thr
            115             120             125

Ser Lys Val Phe Arg Phe Asn Val Ser Ser Val Glu Lys Asn Arg Thr
130                 135             140

Asn Leu Phe Arg Ala Glu Phe Arg Val Leu Arg Val Pro Asn Pro Ser
145             150             155             160

Ser Lys Arg Asn Glu Gln Arg Ile Glu Leu Phe Gln Ile Leu Arg Pro
                165             170             175

Asp Glu His Ile Ala Lys Gln Arg Tyr Ile Gly Gly Lys Asn Leu Pro
            180             185             190

Thr Arg Gly Thr Ala Glu Trp Leu Ser Phe Asp Val Thr Asp Thr Val
        195             200             205

Arg Glu Trp Leu Leu Arg Arg Glu Ser Asn Leu Gly Leu Glu Ile Ser
    210             215             220

Ile His Cys Pro Cys His Thr Phe Gln Pro Asn Gly Asp Ile Leu Glu
225             230             235             240

Asn Ile His Glu Val Met Glu Ile Lys Phe Lys Gly Val Asp Asn Glu
            245             250             255

Asp Asp His Gly Arg Gly Asp Leu Gly Arg Leu Lys Lys Gln Lys Asp
            260             265             270

His His Asn Pro His Leu Ile Leu Met Met Ile Pro Pro His Arg Leu
        275             280             285

Asp Asn Pro Gly Gln Gly Gly Gln Arg Lys Lys Arg Ala Leu Asp Thr
290             295             300

Asn Tyr Cys Phe Arg Asn Leu Glu Glu Asn Cys Cys Val Arg Pro Leu
305             310             315             320

Tyr Ile Asp Phe Arg Gln Asp Leu Gly Trp Lys Trp Val His Glu Pro
            325             330             335

Lys Gly Tyr Tyr Ala Asn Phe Cys Ser Gly Pro Cys Pro Tyr Leu Arg
            340             345             350

Ser Ala Asp Thr Thr His Ser Thr Val Leu Gly Leu Tyr Asn Thr Leu
            355             360             365

Asn Pro Glu Ala Ser Ala Ser Pro Cys Cys Val Pro Gln Asp Leu Glu
370             375             380

Pro Leu Thr Ile Leu Tyr Tyr Val Gly Arg Thr Pro Lys Val Glu Gln
385             390             395             400

Leu Ser Asn Met Val Val Lys Ser Cys Lys Cys Ser
            405             410
```

METHODS AND CULTURE MEDIA FOR CULTURING PLURIPOTENT STEM CELLS

RELATED APPLICATIONS

This application is a continuation of U.S. patent application Ser. No. 15/403,303 filed on Jan. 11, 2017, which is a continuation of U.S. patent application Ser. No. 13/821,244 filed on Mar. 7, 2013, now U.S. Pat. No. 10,214,722, which is a National Phase of PCT Patent Application No. PCT/IL2011/000722 having International Filing Date of Sep. 7, 2011, which claims the benefit of priority under 35 USC § 119(e) of U.S. Provisional Patent Application No. 61/380,388 filed on Sep. 7, 2010. The contents of the above applications are all incorporated by reference as if fully set forth herein in their entirety.

SEQUENCE LISTING STATEMENT

The ASCII file, entitled 81543SequenceListing.txt, created on Feb. 27, 2020, comprising 109,805 bytes, submitted concurrently with the filing of this application is incorporated herein by reference.

FIELD AND BACKGROUND OF THE INVENTION

The present invention, in some embodiments thereof, relates to a method of culturing pluripotent stem cells in a suspension culture as single cells devoid of clumps, and to isolated populations of pluripotent stem cells generated thereby, and, more particularly, but not exclusively, to novel culture media which can maintain pluripotent stem cells in an undifferentiated state, and to methods of culturing the pluripotent stem cells in two-dimensional or three-dimensional culture systems while maintaining the cells in a proliferative, pluripotent and undifferentiated state.

The exceptional differentiation potential of human embryonic stem cells (hESCs) underlines them as one of the best models to study early human development, lineage commitment, differentiation processes and to be used for industrial purposes and cell-based therapy.

Induced pluripotent (iPS) cells are somatic cells which are re-programmed to ESC-like cells capable of differentiation into representative tissues of the three embryonic germ layers both in vitro and in vivo. Mouse or human iPS cells were generated by over expression of four transcription factors, c-Myc, Oct4, KLF4 and Sox2 in somatic cells. The iPS cells were shown to form the same colony morphology as ESCs and to express some typical ESCs markers such as Myb, Kit, Gdf3 and Zic3, but less prominently markers such as Dnmt3a, Dnmt3b, Utf1, Tcl1 and the LIF receptor gene, confirming that iPS cells are similar but not identical to ES cells [Takahashi and Yamanaka, 2006; Takahashi et al, 2007; Meissner et al, 2007; Okita et al, 2007]. Yu Junying et al. (Science 318:1917-1920, 2007) found a common gene expression pattern to fibroblasts-derived iPS cells and hESCs.

Further studies revealed that iPS cells could be obtained by transforming somatic cells with Oct4, Sox2, Nanog and Lin28 while omitting the use of the oncogene C-Myc [Yu J., et al, 2007, Science, 318: 1917-1920; Nakagawa et al, 2008]. Improvements of iPS cells derivation methods include the use of plasmids instead of viral vectors or derivation without any integration to the genome, which might simplify the future use of iPS cells for clinical applications [Yu J, et al., Science. 2009, 324: 797-801].

The currently available iPS cells are those derived from embryonic fibroblasts [Takahashi and Yamanaka, 2006; Meissner et al, 2007], fibroblasts formed from hESCs [Park et al, 2008], Fetal fibroblasts [Yu et al, 2007; Park et al, 2008], foreskin fibroblast [Yu et al, 2007; Park et al, 2008], adult dermal and skin tissues [Hanna et al, 2007; Lowry et al, 2008], b-lymphocytes [Hanna et al 2007] and adult liver and stomach cells [Aoi et al, 2008].

Similarly to hESCs, iPS cells are traditionally cultured with a supportive layer in 2D culture, which allows their continuous growth in the undifferentiated state. For example, iPS cells were cultured on feeder-layers consisting of inactivated mouse embryonic fibroblasts (MEF) or foreskin fibroblasts [Takahashi and Yamanaka 2006, Meisnner at al 2007] in the presence of a medium supplemented with fetal bovine serum (FBS). Further improvements of the culturing methods include culturing iPS cells on MEF feeder layers in the presence of a more defined culture medium containing serum replacement and 10 ng/ml of basic fibroblasts growth factor (bFGF) (Park et al., 2008). However, for clinical applications (e.g., cell-based therapy) or industrial purposes, the iPS cells should be cultured in a defined, xeno-free (e.g., animal-free) and a scalable culture system with controlled processes.

PCT Publication No. WO2007/026353 discloses a well-defined, xeno-free culture media which comprise a TGF-beta isoform or the chimera formed between IL6 and the soluble IL6 receptor (IL6RIL6 hereinafter) for maintaining human embryonic stem cells, in an undifferentiated state in a two-dimensional culture system.

U.S. Patent Application No. 20050233446 discloses a defined medium which comprises bFGF, insulin and ascorbic acid for maintaining hESCs when cultured on Matrigel™ in an undifferentiated state.

Ludwig T E., et al., 2006 (Nature Biotechnology, 24: 185-7) discloses the TeSR1 defined medium for culturing hESCs on a matrix composed of Collagen IV, fibronectin, laminin and virtonectin.

U.S. Patent Application No. 20090029462 discloses methods of expanding pluripotent stem cells in suspension using microcarriers or cell encapsulation.

PCT Publication No. WO/2008/015682 discloses a method of expanding and maintaining human embryonic stem cells in a suspension culture under culturing conditions devoid of substrate adherence.

U.S. Patent Application No. 20070155013 discloses a method of growing pluripotent stem cells in suspension using a carrier which adheres to the pluripotent stem cells.

U.S. Patent Application No. 20080241919 (Parsons et al.) discloses a method of culturing pluripotent stem cells in a suspension culture in a medium which comprises bFGF, insulin and ascorbic acid in a cell culture vessel that includes a cell-free matrix.

U.S. Patent Application No. 20080159994 (Mantalaris et al.) discloses a method of culturing pluripotent ES cells encapsulated within alginate beads in a three-dimensional culture in a medium which comprises serum replacement and bFGF.

U.S. Patent Application No. 20070264713 discloses a method of culturing undifferentiated stem cells in suspension on microcarriers in vessels using a conditioned medium.

PCT Publication No. WO2006/040763 discloses isolated primate embryonic cells which are derived from extended blastocysts (e.g., from at least nine days post fertilization) and methods generated and using same.

Additional background art includes U.S. Patent application 20090130759; Stankoff B., et al., J. Neuroscience 22: 9221-9227, 2002; Ernst M., et al., Journal of Biological Chemistry, 271: 30136-30143, 1996; Roeb E, et al., Hepatology, 1993, 18:1437-42; U.S. Patent application 20040235160; Pera M. F., et al. 2000. Journal of Cell Science 113, 5-10. Human embryonic stem cells. Commentary.

SUMMARY OF THE INVENTION

According to an aspect of some embodiments of the present invention there is provided an isolated population of human pluripotent stem cells comprising at least 50% human pluripotent stem cells characterized by an $OCT4^+$/$TRA1-60^-$/$TRA1-81^-$/$SSEA1^+$/$SSEA4^-$ expression signature, wherein the human pluripotent stem cells are capable of differentiating into the endoderm, ectoderm and mesoderm embryonic germ layers.

According to an aspect of some embodiments of the present invention there is provided a method of expanding and maintaining pluripotent stem cells (PSCs) in an undifferentiated state, the method comprising: (a) passaging the PSCs in a suspension culture by mechanical dissociation of PSC clumps to single cells for at least 2 and no more than 10 passages, to thereby obtain a suspension culture of PSCs devoid of clumps, and; (b) passaging the suspension culture of PSCs devoid of the clumps without dissociation of the clumps, thereby expanding and maintaining the PSCs in the undifferentiated state.

According to some embodiments of the invention, the method further comprising culturing the PSCs under conditions which allow expansion of the pluripotent stem cells in the undifferentiated state.

According to an aspect of some embodiments of the present invention there is provided a method of deriving an embryonic stem cell line, the method comprising: (a) obtaining embryonic stem cells (ESCs) from a pre-implantation stage blastocyst, post-implantation stage blastocyst and/or a genital tissue of a fetus; and (b) passaging the ESCs in a suspension culture by mechanical dissociation of ESC clumps to single cells for at least 2 and no more than 10 passages, to thereby obtain a suspension culture of ESCs devoid of clumps, and; (c) passaging the suspension culture of ESCs devoid of the clumps without dissociation of the clumps, thereby deriving the embryonic stem cell line.

According to some embodiments of the invention, the method further comprising culturing the ESCs under conditions which allow expansion of the embryonic single stem cells in the undifferentiated state.

According to some embodiments of the invention, the passaging is performed under conditions devoid of an enzymatic dissociation.

According to an aspect of some embodiments of the present invention there is provided a method of cloning a pluripotent stem cell, comprising: culturing a single pluripotent stem cell obtained according to the method of some embodiments of the invention, or a single embryonic stem cell obtained according to the method of some embodiments of the invention, in a suspension culture under conditions which allow expansion of the single pluripotent stem cell or of the single embryonic stem cell, respectively, in the undifferentiated state, thereby expanding the single pluripotent stem cell or the embryonic stem cell, respectively, into a clonal culture, thereby cloning the pluripotent stem cell.

According to some embodiments of the invention, the culturing is effected without dissociating cell clumps.

According to an aspect of some embodiments of the present invention there is provided a method of generating lineage-specific cells from pluripotent stem cells, the method comprising: (a) culturing the pluripotent stem cells in a suspension culture according to the method of some embodiments of the invention to thereby obtain expanded, undifferentiated pluripotent stem cells devoid of clumps; and (b) subjecting the expanded, undifferentiated pluripotent stem cells devoid of clumps to culturing conditions suitable for differentiating and/or expanding lineage specific cells, thereby generating the lineage-specific cells from the pluripotent stem cells.

According to an aspect of some embodiments of the present invention there is provided a method of generating embryoid bodies from pluripotent stem cells, the method comprising: (a) culturing the pluripotent stem cells in a suspension culture according to the method of some embodiments of the invention to thereby obtain expanded, undifferentiated pluripotent stem cells devoid of clumps; and (b) subjecting the expanded, undifferentiated pluripotent stem cells devoid of clumps to culturing conditions suitable for differentiating the pluripotent stem cells to embryoid bodies; thereby generating the embryoid bodies from the pluripotent single cells.

According to an aspect of some embodiments of the present invention there is provided a method of generating lineage-specific cells from pluripotent stem cells, the method comprising: (a) culturing the pluripotent stem cells in a suspension culture according to the method of some embodiments of the invention, to thereby obtain expanded, undifferentiated pluripotent stem cells devoid of clumps; (b) subjecting the expanded, undifferentiated pluripotent stem cells devoid of clumps to culturing conditions suitable for differentiating the pluripotent stem cells to embryoid bodies; and (c) subjecting cells of the embryoid bodies to culturing conditions suitable for differentiating and/or expanding lineage specific cells; thereby generating the lineage-specific cells from the pluripotent stem cells.

According to some embodiments of the invention, the suspension culture devoid of clumps comprises single cells or small clusters, each of the clusters comprising no more than about 200 pluripotent stem cells.

According to some embodiments of the invention, the culturing is effected under culturing conditions devoid of substrate adherence.

According to some embodiments of the invention, the culturing conditions being devoid of a Rho-associated kinase (ROCK) inhibitor.

According to some embodiments of the invention, the pluripotent stem cells are human pluripotent stem cells.

According to some embodiments of the invention, the human pluripotent stem cells are embryonic stem cells.

According to some embodiments of the invention, the human pluripotent stem cells are induced pluripotent stem cells.

According to an aspect of some embodiments of the present invention there is provided an isolated population of pluripotent stem cells devoid of cell clumps generated according to the method of some embodiments of the invention and being capable of differentiating into the endoderm, ectoderm and mesoderm embryonic germ layers.

According to an aspect of some embodiments of the present invention there is provided a method of generating a mesenchymal stem cell in a suspension culture, comprising culturing the pluripotent stem cells of some embodiments of the invention in a suspension culture under conditions suitable for differentiation of pluripotent stem cells to mesenchymal stem cells, thereby generating the mesenchymal stem cell in the suspension culture.

According to an aspect of some embodiments of the present invention there is provided an isolated population of mesenchymal stem cells (MSCs) in a suspension culture generated by the method of some embodiments of the invention.

According to some embodiments of the invention, at least 40% of the cells are characterized by a CD73+/CD31−/CD105+ expression signature.

According to some embodiments of the invention, the MSCs are capable of differentiation in a suspension culture into a cell lineage selected from the group consisting of an adipogenic lineage, an osteoblastic lineage, and a chrondrogenic lineage.

According to an aspect of some embodiments of the present invention there is provided a method of generating a neuronal progenitor cell in a suspension culture, comprising culturing the pluripotent stem cells of some embodiments of the invention in a suspension culture under conditions suitable for differentiation of neuronal progenitor cell, thereby generating the neuronal progenitor cell in the suspension culture.

According to an aspect of some embodiments of the present invention there is provided an isolated population of neuronal progenitor cells in a suspension culture generated by the method of some embodiments of the invention.

According to an aspect of some embodiments of the invention, there is provided a method of generating an endodermal cell in a suspension culture, comprising culturing the pluripotent stem cells of some embodiments of the invention in a suspension culture under conditions suitable for differentiation of the pluripotent stem cells to endodermal cells, thereby generating the endodermal cell in the suspension culture.

According to an aspect of some embodiments of the invention, there is provided an isolated population of endodermal cells in a suspension culture generated by the method of some embodiments of the invention.

According to an aspect of some embodiments of the present invention there is provided a culture medium comprising interleukin 11 (IL11) and Ciliary Neurotrophic Factor (CNTF).

According to an aspect of some embodiments of the present invention there is provided a culture medium comprising basic fibroblast growth factor (bFGF) at a concentration of at least 50 ng/ml and an IL6RIL6 chimera.

According to an aspect of some embodiments of the present invention there is provided a culture medium comprising an animal contaminant-free serum replacement and an IL6RIL6 chimera.

According to an aspect of some embodiments of the present invention there is provided a cell culture comprising pluripotent stem cells and the culture medium of some embodiments of the invention.

According to an aspect of some embodiments of the present invention there is provided a culture system comprising a matrix and the culture medium of some embodiments of the invention.

According to an aspect of some embodiments of the present invention there is provided a cell culture comprising pluripotent stem cells and a serum-free culture medium, the culture medium comprising a soluble interleukin 6 receptor (sIL6R) and interleukin 6 (IL6), wherein a concentration of the sIL6R is at least 5 ng/ml, and wherein a concentration of the IL6 is at least 3 ng/ml.

According to an aspect of some embodiments of the present invention there is provided a cell culture comprising pluripotent stem cells and a culture medium which comprises interleukin 11 (IL11) and oncostatin.

According to an aspect of some embodiments of the present invention there is provided a method of expanding and maintaining pluripotent stem cells in an undifferentiated state, the method comprising culturing the pluripotent stem cells in the culture medium of some embodiments of the invention, thereby expanding and maintaining the pluripotent stem cells in the undifferentiated state.

According to an aspect of some embodiments of the present invention there is provided a method of generating lineage-specific cells from pluripotent stem cells, the method comprising: (a) culturing the pluripotent stem cells according to the method of some embodiments of the invention, to thereby obtain expanded, undifferentiated stem cells; (b) subjecting the expanded, undifferentiated stem cells to culturing conditions suitable for differentiating and/or expanding lineage specific cells; thereby generating the lineage-specific cells from the pluripotent stem cells.

According to an aspect of some embodiments of the present invention there is provided a cell culture comprising a population of pluripotent stem cells generated according to the method of some embodiments of the invention, the population comprises at least 1000 pluripotent stem cells per milliliter of medium.

According to an aspect of some embodiments of the present invention there is provided a use of the cell culture of some embodiments of the invention for cell based therapy.

According to an aspect of some embodiments of the present invention there is provided a use of the cell culture of some embodiments of the invention for drug screening.

According to an aspect of some embodiments of the present invention there is provided a use of the cell culture of some embodiments of the invention for production of a vaccine.

According to an aspect of some embodiments of the present invention there is provided a use of the cell culture of some embodiments of the invention for production of proteins.

According to some embodiments of the invention, the IL11 is provided at a concentration of at least 0.1 ng/ml.

According to some embodiments of the invention, the CNTF is provided at a concentration of at least 0.1 ng/ml.

According to some embodiments of the invention, the IL11 is provided at a concentration of 1 ng/ml.

According to some embodiments of the invention, the CNTF is provided at a concentration of 1 ng/ml.

According to some embodiments of the invention, the concentration of the bFGF is selected from the range of between 50 ng/ml to 150 ng/ml.

According to some embodiments of the invention, the IL6RIL6 chimera is provided at a concentration of at least 50 ng/ml.

According to some embodiments of the invention, the IL6RIL6 chimera is provided at a concentration of at least 50 ng/ml.

According to some embodiments of the invention, the culture medium further comprising serum replacement.

According to some embodiments of the invention, the serum replacement is provided at a concentration of at least 10%.

According to some embodiments of the invention, the serum replacement is devoid of animal contaminants.

According to some embodiments of the invention, the IL6RIL6 chimera is provided at a concentration of 50-150 ng/ml.

According to some embodiments of the invention, the IL6RIL6 chimera is provided at a concentration of 50-150 pg/ml.

According to some embodiments of the invention, the culture medium further comprising basic fibroblast growth factor (bFGF).

According to some embodiments of the invention, the bFGF is provided at a concentration of at least 4 ng/ml.

According to some embodiments of the invention, the culture medium further comprising ascorbic acid.

According to some embodiments of the invention, the ascorbic acid is provided at a concentration of 25-100 µg/ml.

According to some embodiments of the invention, the bFGF is provided at a concentration of 100 ng/ml and the IL6RIL6 is provided at a concentration of 100 ng/ml.

According to some embodiments of the invention, the bFGF is provided at a concentration of 100 ng/ml and the IL6RIL6 is provided at a concentration of 100 pg/ml.

According to some embodiments of the invention, the culture medium further comprising TGFβ.

According to some embodiments of the invention, the TGFβ comprises TGFβ1.

According to some embodiments of the invention, the TGFβ comprises TGFβ3.

According to some embodiments of the invention, the culture medium is serum-free.

According to some embodiments of the invention, the culture medium is devoid of animal contaminants.

According to some embodiments of the invention, expanding and maintaining the pluripotent stem cells in the undifferentiated state is effected in a suspension culture.

According to some embodiments of the invention, the culturing is effected under conditions comprising a static suspension culture.

According to some embodiments of the invention, the culturing is effected under conditions comprising a dynamic suspension culture.

According to some embodiments of the invention, the culturing is effected under conditions which enable expansion of the pluripotent stem cells as single cells.

According to some embodiments of the invention, the culturing is effected under conditions devoid of enzymatic dissociation of cell clusters.

According to some embodiments of the invention, the expanding and maintaining the pluripotent stem cells in the undifferentiated state is effected in a two-dimensional culture system.

According to some embodiments of the invention, the two-dimensional culture system comprises a matrix and the culture medium.

According to some embodiments of the invention, the pluripotent stem cells comprise embryonic stem cells.

According to some embodiments of the invention, the pluripotent stem cells comprise induced pluripotent stem (iPS) cells.

According to some embodiments of the invention, the embryonic stem cells are human embryonic stem cells.

According to some embodiments of the invention, the induced pluripotent stem cells are human induced pluripotent stem cells.

According to some embodiments of the invention, the culture medium is capable of expanding the pluripotent stem cells in an undifferentiated state.

According to some embodiments of the invention, at least 85% of the pluripotent stem cells are in an undifferentiated state.

According to some embodiments of the invention, the culture conditions comprise a culture medium which comprises interleukin 11 (IL11) and Ciliary Neurotrophic Factor (CNTF).

According to some embodiments of the invention, the culture conditions comprise a culture medium which comprises basic fibroblast growth factor (bFGF) at a concentration of at least 50 ng/ml and an IL6RIL6 chimera.

According to some embodiments of the invention, the culture conditions comprise a culture medium which comprises an animal contaminant-free serum replacement and an IL6RIL6 chimera.

According to some embodiments of the invention, the culture conditions comprise a serum-free culture medium which comprises a soluble interleukin 6 receptor (sIL6R) and interleukin 6 (IL6), wherein a concentration of the sIL6R is at least 5 ng/ml, and wherein a concentration of the IL6 is at least 3 ng/ml.

According to some embodiments of the invention, the culture conditions comprise a culture medium which comprises interleukin 11 (IL11) and oncostatin.

According to an aspect of some embodiments of the present invention there is provided a culture medium comprising serum and serum replacement.

According to some embodiments of the invention, the serum replacement is provided at a concentration of about 10%.

According to some embodiments of the invention, the serum is provided at a concentration of 10%.

According to some embodiments of the invention, the culture medium which comprises serum and serum replacement is devoid of bFGF.

According to some embodiments of the invention, the culture medium which comprises serum and serum replacement is devoid of the IL6RIL6 chimera.

According to some embodiments of the invention, the culture medium which comprises serum and serum replacement further comprises L-glutamine, β-mercaptoethanol, and non-essential amino acid stock.

According to some embodiments of the invention, the culture medium which comprises serum and serum replacement consists of 80% DMEM/F12, 10% knockout serum replacement (SR), 10% FBS, 2 mM L-glutamine, 0.1 mM β-mercaptoethanol, 1% non-essential amino acid stock.

According to some embodiments of the invention, the culture medium which comprises serum and serum replacement is suitable for differentiation in suspension of pluripotent stem cells into mesenchymal stem cells.

According to some embodiments of the invention, the conditions suitable for differentiation of the pluripotent stem cells to the mesenchymal stem cells comprise a culture medium which comprises serum and serum replacement.

According to some embodiments of the invention, the method further comprising shipping the pluripotent stem cells of some embodiments of the invention as non-frozen living cells.

According to some embodiments of the invention, the pluripotent stem cells remain viable, proliferative and undifferentiated following shipping the cells as non-frozen living cells.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
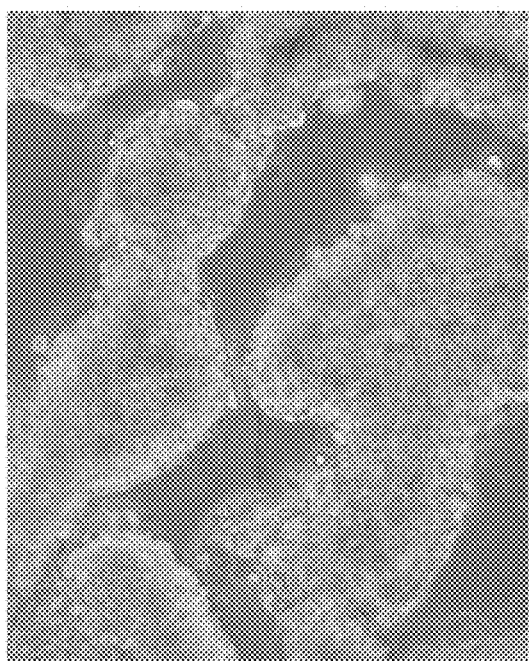
Figure 1C:
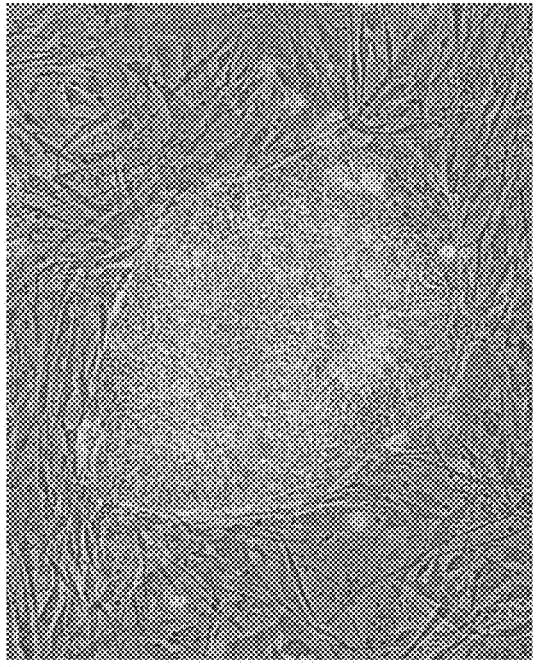
Figure 1B:
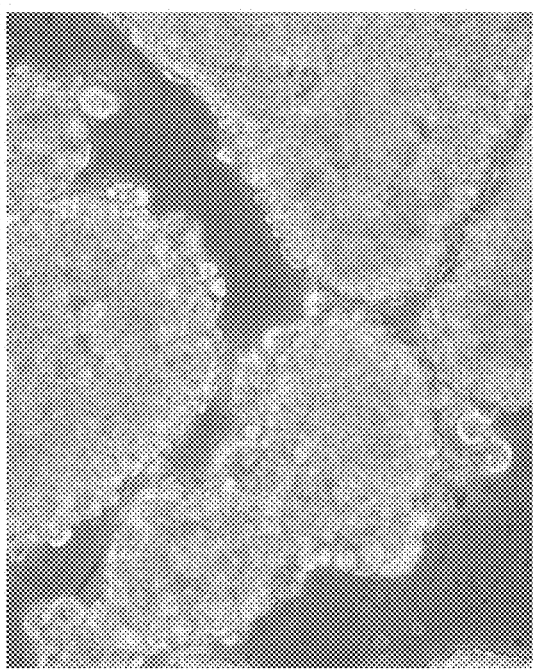

FIGS. 1A-1C are photographs of I3 ESCs, which were grown in a suspension culture according to some embodiments of the invention, following shipment of living cells over the Atlantic Ocean (from Israel to Baltimore USA) which lasted for four days. I3 cells were cultured in suspension for at least 20 passages before they were shipped. FIGS. 1A and 1B—Morphology of I3, 3 days (FIG. 1A) and 1 day (FIG. 1B) after arrival and re-plating in suspension using CM100Fp culture medium. The cells demonstrate typical sphere morphology consisting undifferentiated cells. FIG. 1C—Morphology of I3, 3 days after arrival and re-plating with MEFs. The cells demonstrate ESCs typical colony morphology.

Figure 2A:
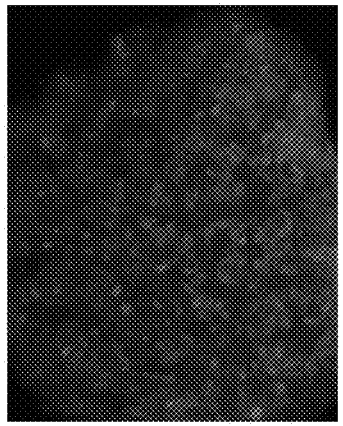
Figure 2B:
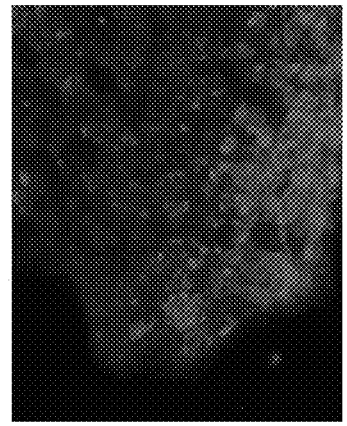
Figure 2C:
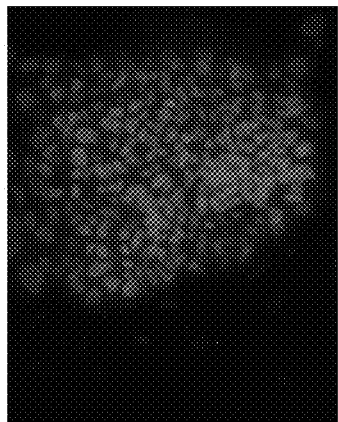
Figure 2D:
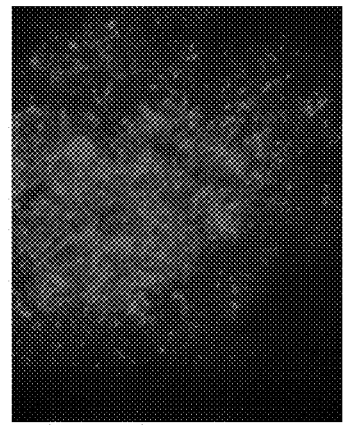

FIGS. 2A-2D are fluorescent images of I3.2 hESCs stained with antibodies to various markers of pluripotency (immunofluorescence staining). Cells cultured in the novel medium of some embodiments of the invention (e.g., the CMTeSR2 medium in this case) were tested for their pluripotency using the typical markers Oct4 (FIG. 2A), SSEA4 (FIG. 2B), Tra-160 (FIG. 2C) and TRA-1-81 (FIG. 2D). In this example I3.2 at passage p19+83 (i.e., the I3.2 clonal cell line was derived from I3 cell line at passage 19, and the cells for analysis were at passage 83 following isolation of the clone) were cultured with CMTESR2 medium for 5 passages in suspension and then re-cultured on MEF. The cells were found positive for all tested markers.

Figure 3A:
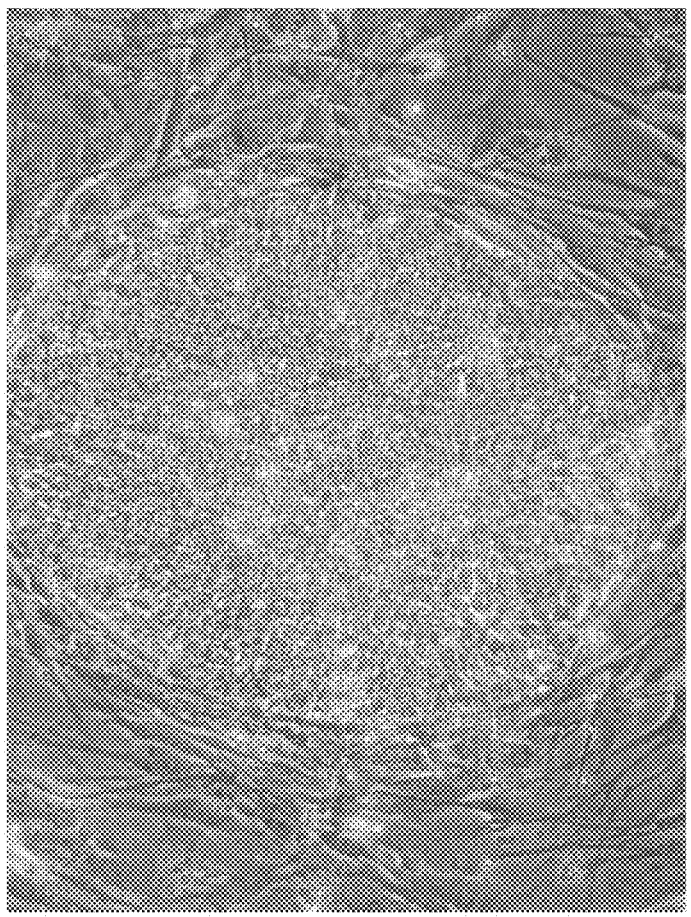
Figure 3B:
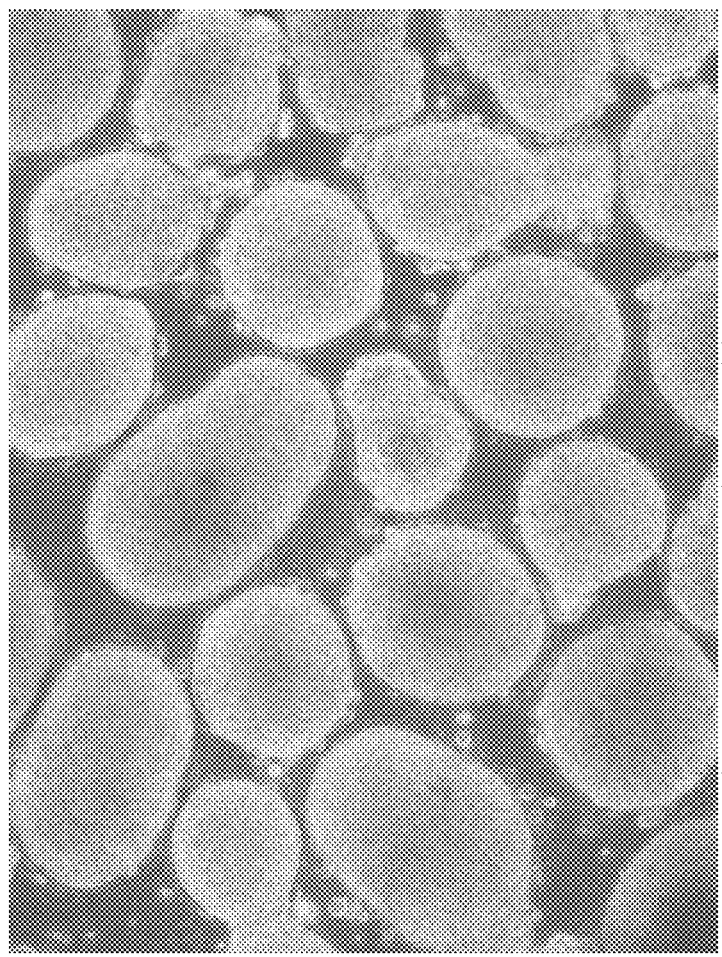
Figure 3C:
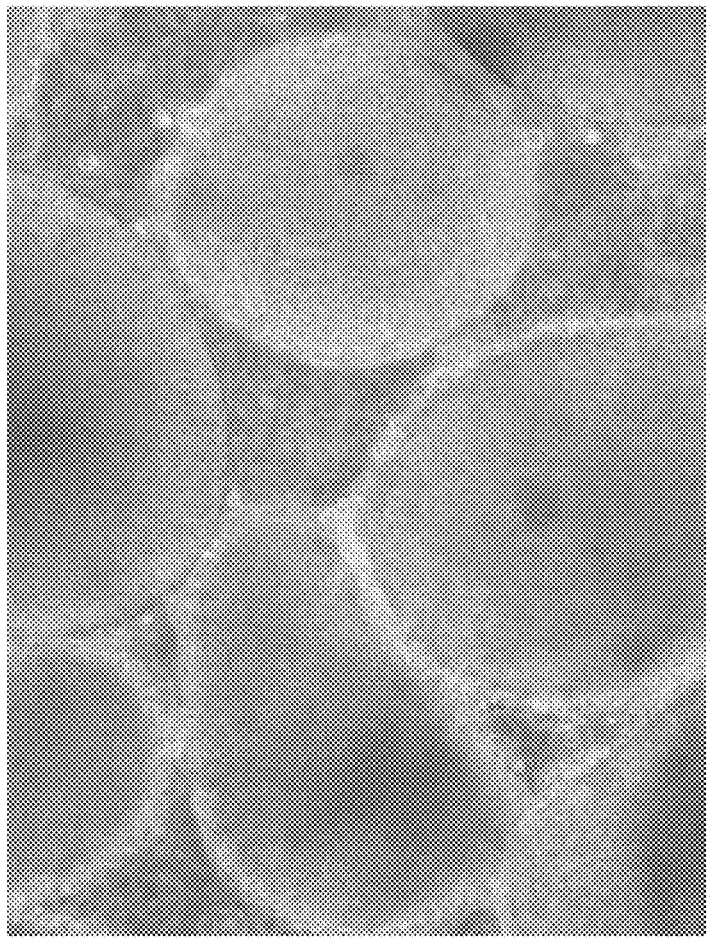

FIGS. 3A-3C are photographs of the I3.2 ESC line depicting morphology of cells cultured in suspension using the novel culture medium of some embodiments of the invention. FIG. 3A—I3.2 at passage p19+87 (i.e., 87 passages following isolation of clone) were cultured in suspension using cmTeSR2 for 26 passages, and then were re-plated with MEFs demonstrating typical ESCs colony morphology. FIG. 3B—J3 cells [delayed (extended) blastocyst cell line] at passage 80 (p80), cultured for 2 passages using NCM100 medium in suspension demonstrating typical sphere morphology of undifferentiated cells. FIG. 3C—H9.2 cells at p29+48 (i.e., H9 cell line at passage 29 was subject to single cell cloning and the resulting clonal hESC line at passage 48 following isolation was used) cultured for 5 passages using ILCNTF medium in suspension demonstrating typical sphere morphology of undifferentiated cells.

Figure 4A:
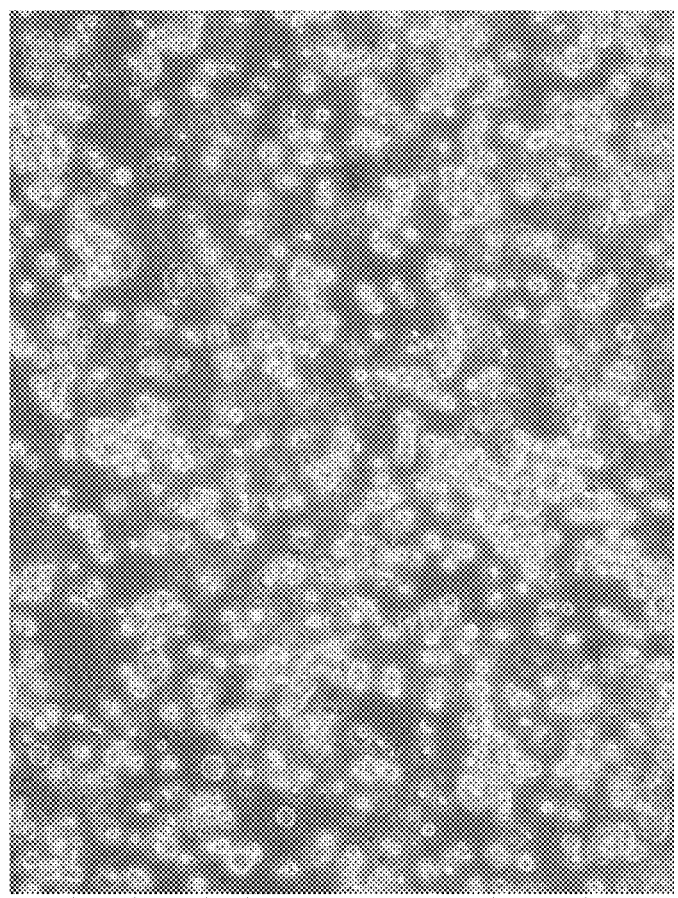
Figure 4B:
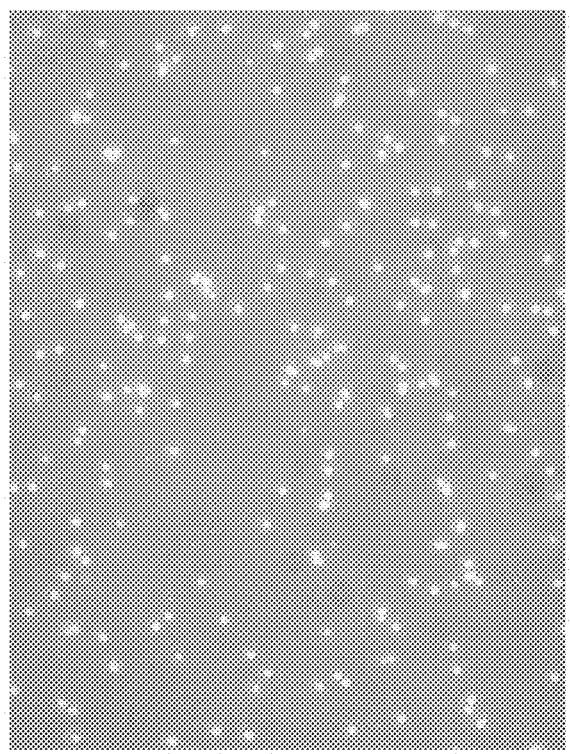

FIGS. 4A-4B are photographs of the H9 hESC line (FIG. 4A) and the human C2 iPS cell line (FIG. 4B) depicting the single cells in the suspension culture. FIG. 4A—H9 at p53 (passage 53) cultured using CMrb100Fp medium for 9 passages in suspension as single cells in a static culture. FIG. 4B—C2 iPS cells cultured for 1.5 months in a spinner flask (a dynamic culture) as single cells using CM100Fp medium. The cells were stained with trepan blue. Dead cells are stained with blue. These results demonstrate that pluripotent stem cells cultured in a suspension culture according to some embodiments of the invention adopt the single cell growth pattern.

Figure 5C:
Figure 5B:
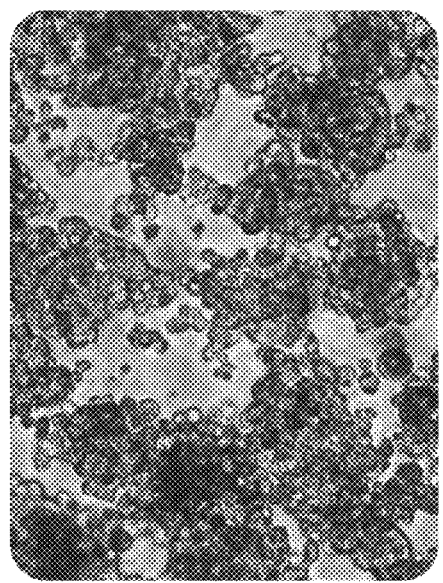
Figure 5A:
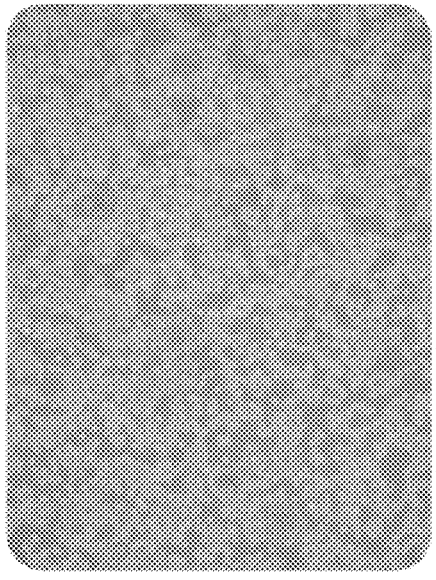

FIGS. 5A-5C are microscopy photographs depicting pluripotent stem cells cultured in suspension under dynamic conditions using a Controlled Wave-bioreactor (Biostat® Cultibag RM, Sartorius North America, Edgewood, New York, USA). Induced pluripotent stem cell line C2 was cultured in controlled wave-bioreactor for five days as single cells (FIG. 5A) or as small spheres of up to 200 μM (FIG. 5B). FIG. 5C—Cells grown in suspension as single cells were re-cultured on MEFs (Oct-4 staining). Living cells numbers increased in 64 folds while maintaining iPS cells features such as Oct4 expression (FIG. 5C).

Figure 6A:
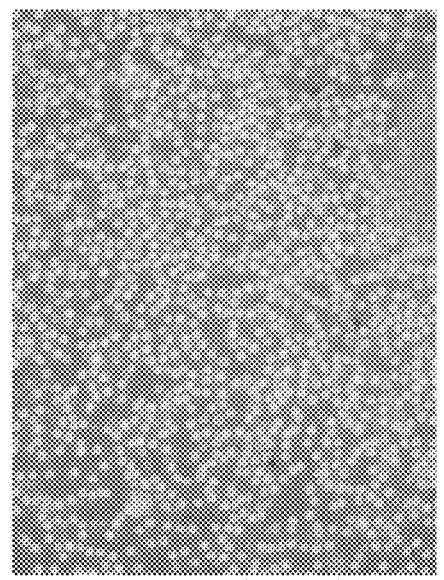
Figure 6B:
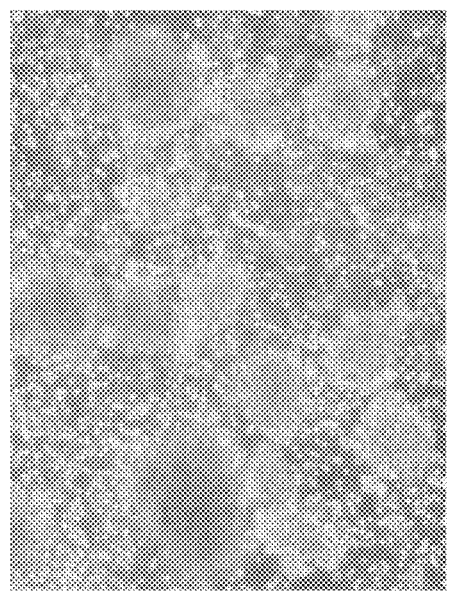
Figure 6C:
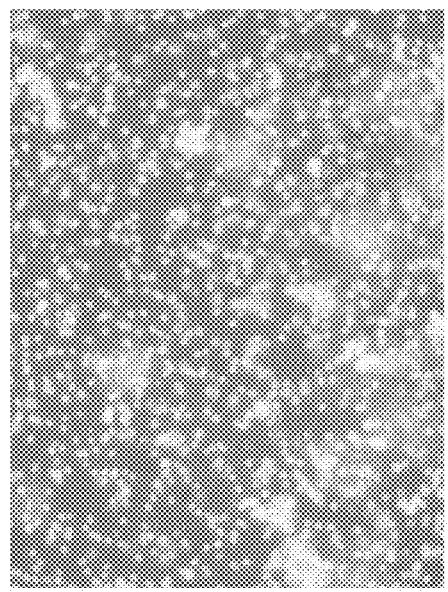

FIGS. 6A-6C are microscopy photographs depicting pluripotent stem cells after freeze/thaw and shears of single cells cultured in suspension. C2 cell line (iPS from foreskin fibroblasts, at passage 89 from derivation, of which the cells were cultured for 48 passages in a suspension culture in the presence of the cmrb100p culture medium) were frozen using the following freezing solutions: 90% serum replacement (SR) and 10% DMSO (FIG. 6A); 20% SR, 20% feral bovine serum (FBS) and 10% DMSO (FIG. 6B); and Serum free freezing solution from Biological Industries (Beit HaEmek, Israel) (FIG. 6C). After being frozen for 5 days in liquid nitrogen the cells were thawed and re-cultured in a suspension culture. Shown are the cells after freeze/thaw and re-culture in a suspension culture. Note that more than 70% of the cells survived the procedure and recovered directly to suspension culture.

FIGS. 7A-7C are images of immunofluorescence staining demonstrating directed differentiation of pluripotent stem cells into cells from the nerve lineage. 16 cultured in suspension for more than 40 passages were induced to differentiation by addition of Retinoic acid and were stained for typical nerve markers: Nestin (FIG. 7A), β-tubulin (FIG. 7B) and Ploysialylated (PSA) Neural Cell Adhesion Molecule (NCAM) (FIG. 7C). The specific markers are stained with red and the blue staining represents DAPI staining.

Figure 8A:
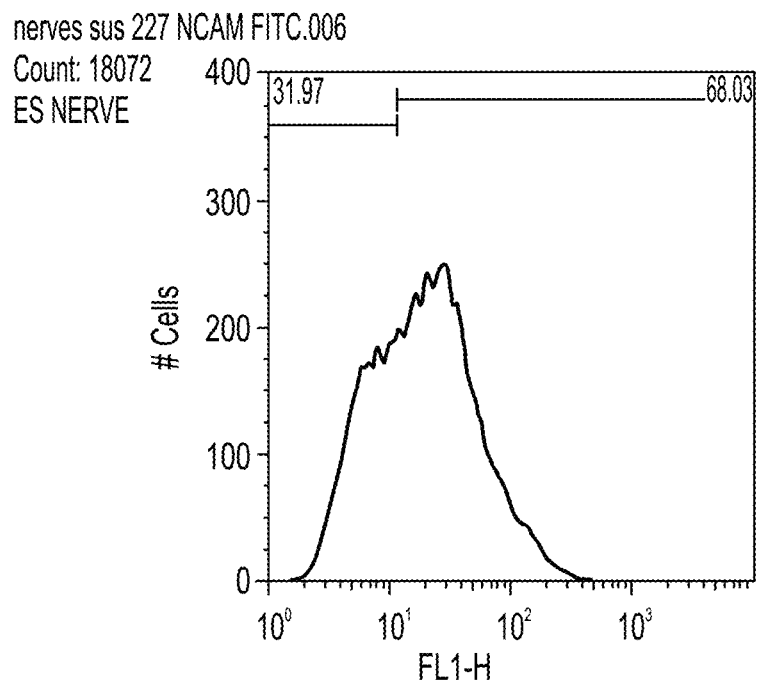
Figure 8B:
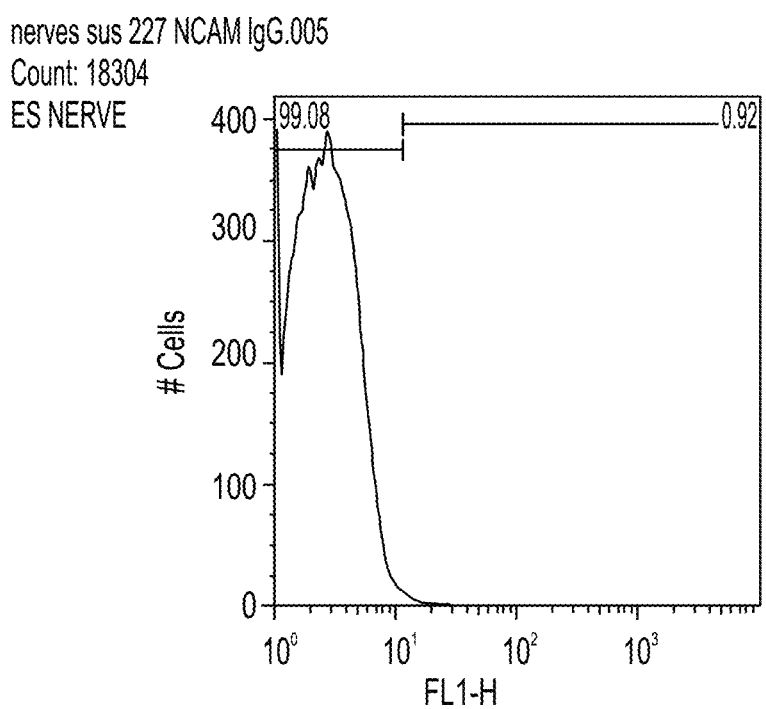
Figure 9A:
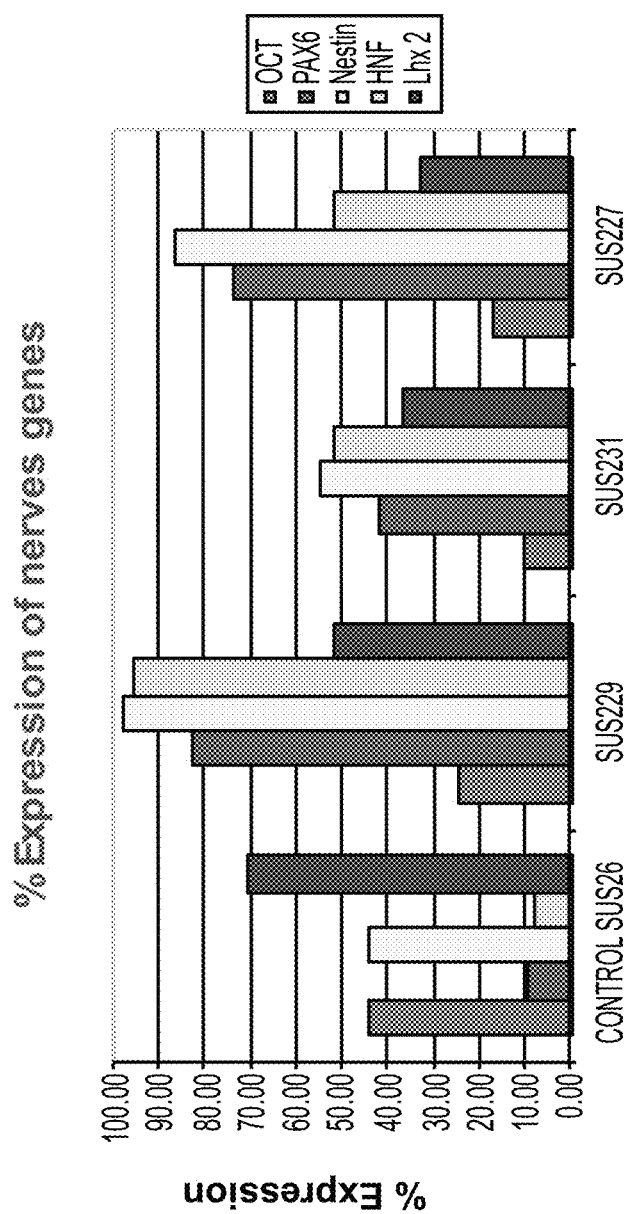

FIGS. 8A-8B are FACS analyses demonstrating differentiation of the pluripotent stem cells into the nerve lineage. FIG. 8A—FACS analysis using the NCM FITC antibody, showing that 68% of the cells are positive for NCAM; FIG. 8B—FACS analysis, isotype control, using NCAM IgG.

FIGS. 9A-9G is a histogram (FIG. 9A) and gel images (FIGS. 9B-9G) depicting the results of a semi quantitated RT-PCR analysis with nerve-specific markers. RT-PCR analysis was performed on cells cultured in suspension and induced to nerve cell lineage by retinoic acid and on cells cultured in suspension as undifferentiated. RT-PCR primers of the OCT-4 (FIG. 9B), PAX6 (FIG. 9C), Heavy chain neural filament (HNF) (FIG. 9D), Nestin (FIG. 9E), and LIM homeobox 2 (LHX2) (FIG. 9F), and GAPDH (control gene, FIG. 9G) genes are described in Table 1 in the Examples section which follows. The results represent average of three independent experiments. Lanes 1-3 are from three different biological repeats, and lane 4 are undifferentiated cells of I6 cultured in suspension for 40 passages.

Figures 10A, 10B:
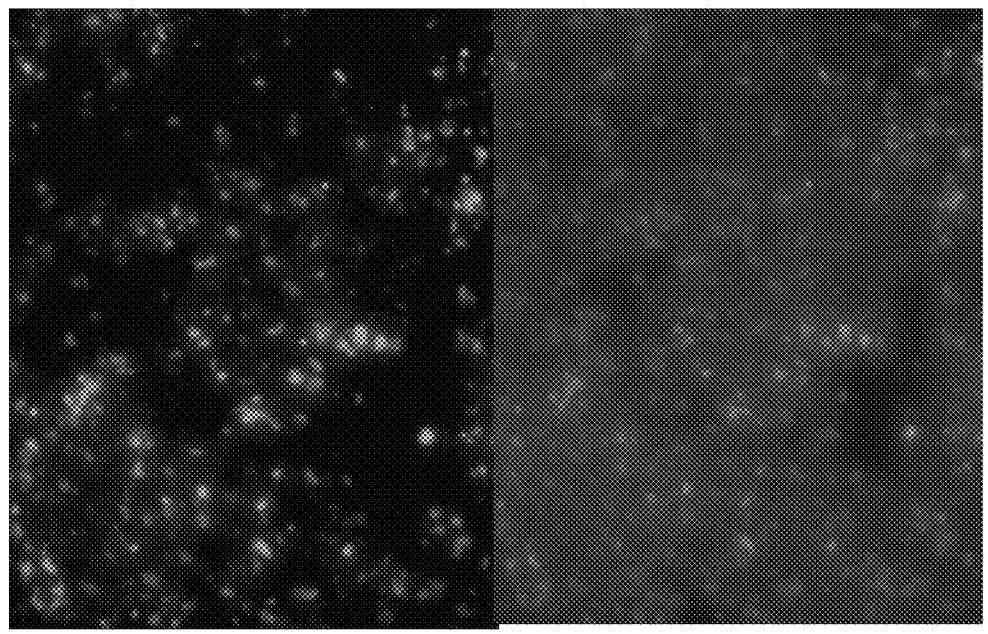

FIGS. 10A-10B are immuno-fluorescence images depicting induction of pluripotent stem cells to cells of the endodermal lineage. Cells from C2 cell line induced to differentiate to endodermal lineage. 10 days post the differentiation induction cells were stained for PDX1 marker (transcription factor related to (β-cells) (FIG. 10A, green) and for DAPI (nucleus staining) (FIG. 10B, blue).

Figure 11A:
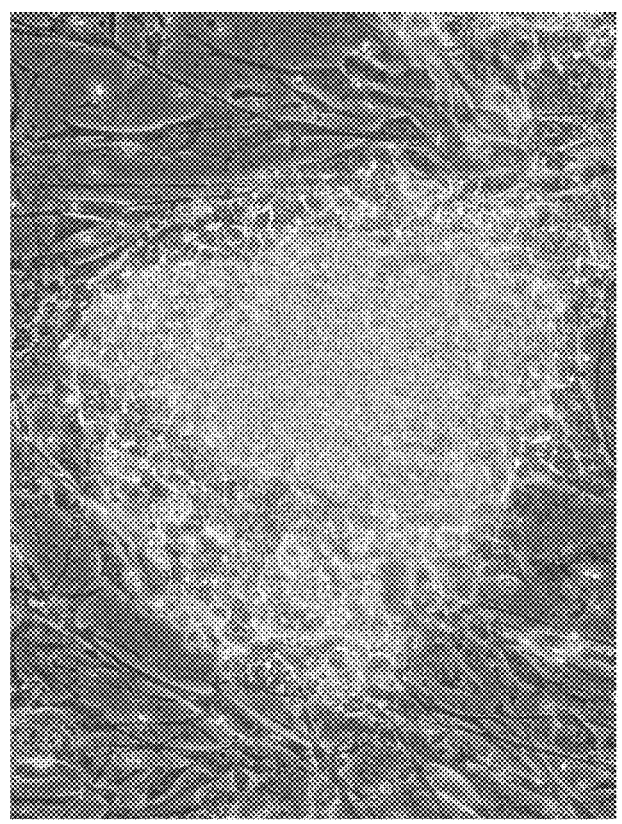
Figure 11B:
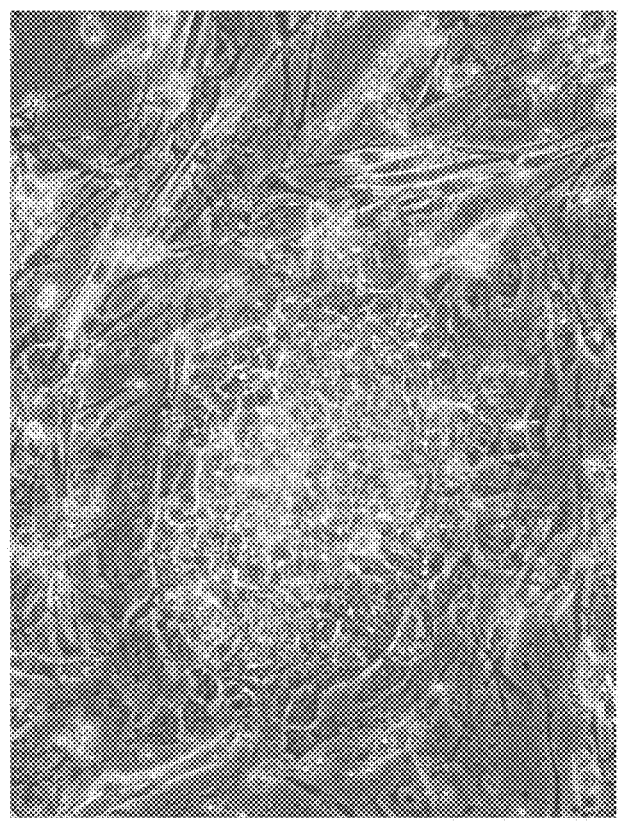

FIGS. 11A-11B are two representative images depicting morphology of hESC colonies after re-plating on MEFs. CL1 (13E1) cells which were cultured for 17 passages in suspension as single cells were re-plated on MEFs and photographed using a phase contrast. Note that when re-plated on feeder cells (MEFs) the cells form colonies characterized by typical morphology of pluripotent cells with spaces between cells, clear borders and high nucleus to cytoplasm ratio.

Figure 12C:
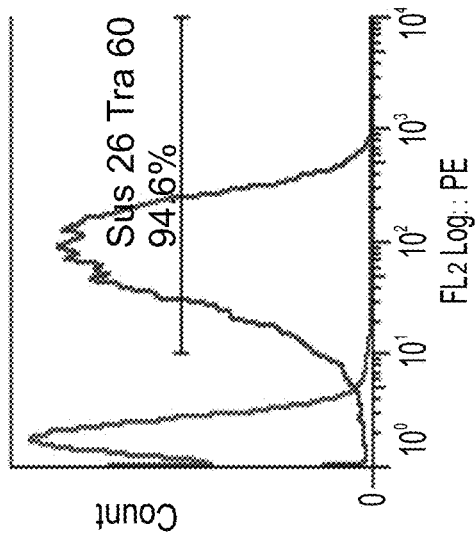
Figure 12D:
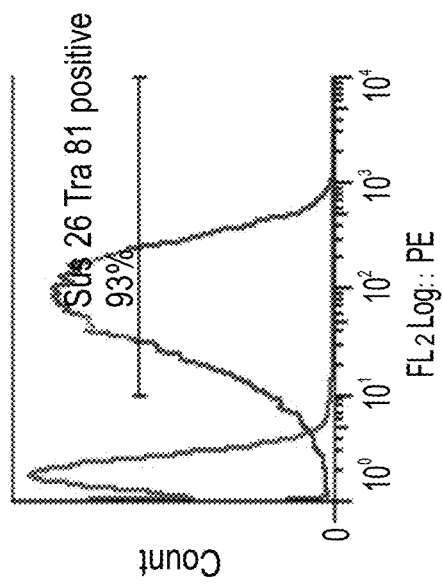
Figure 12G:
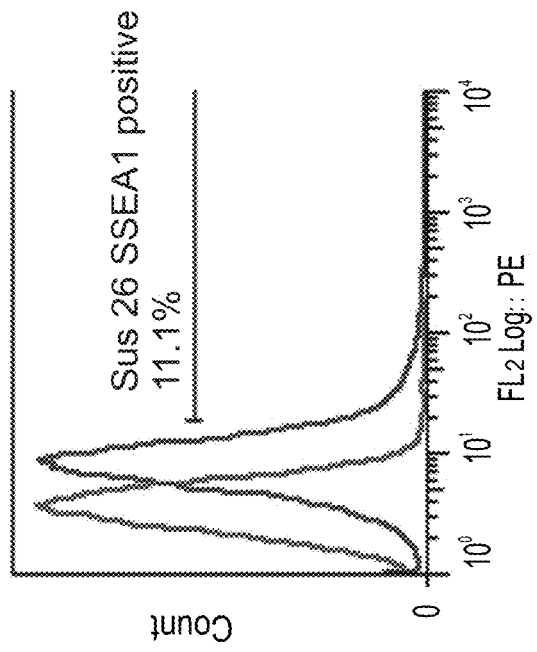
Figure 12H:
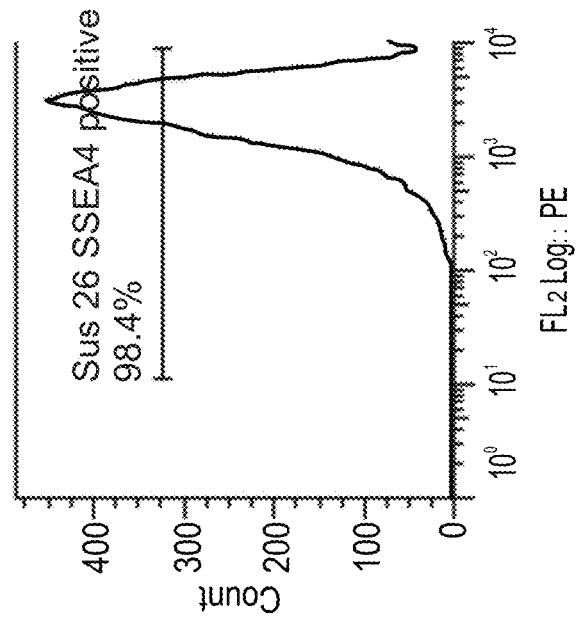
Figure 12I:
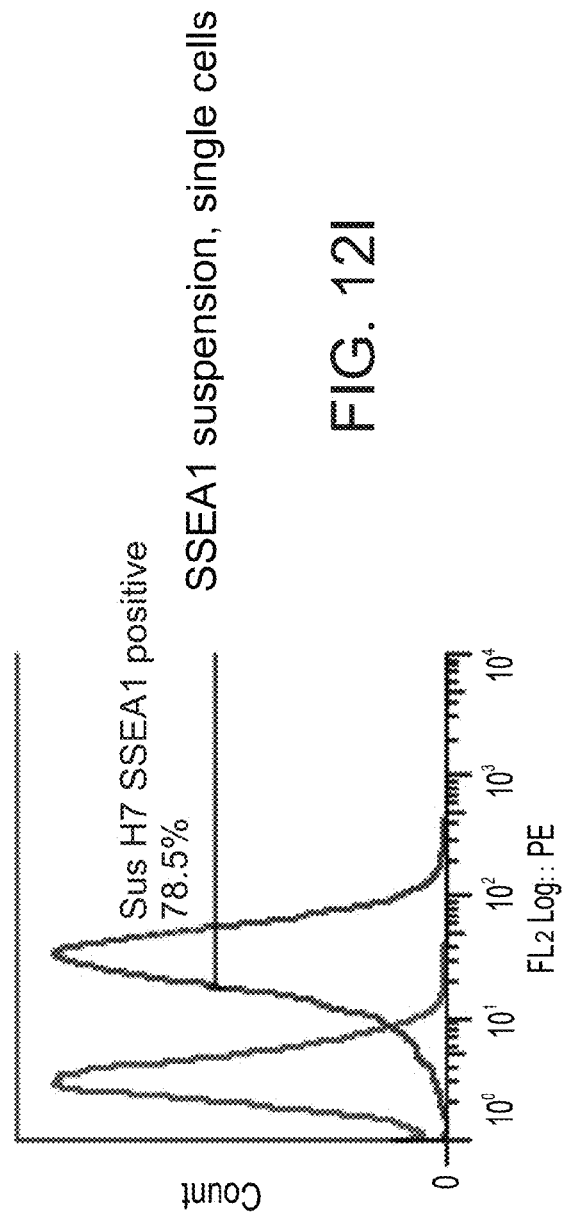
Figure 12J:

FIGS. 12A-12J are histograms depicting FACS analyses of pluripotent markers. Human ESCs were grown on two-dimensional (2-2D) MEFs (FIGS. 12A-12B), in a suspension culture as cell clumps (FIGS. 12C-12D, 12G-12H) or in a suspension culture as single cells devoid of cell clumps (FIGS. 12E-12F, 12I-12J) and the expression of the TRA1-60, TRA1-81, SSEA1 and SSEA4 markers was assayed by FACS. FIG. 12A—H14 cells cultured in 2D, sorted by a TRA1-60 antibody (blue curve). Note that 74.9% of the cells are TRA1-60-positive; FIG. 12B—H14 cells cultured in 2D, sorted by a TRA1-81 antibody (blue curve). Note that 71.2% of the cells are TRA1-81-positive; FIG. 12C—I3 cells cultured in suspension as cell clumps for more than 10 passages, sorted by a TRA1-60 antibody (blue curve). Note that 94.6% of the cells are TRA1-60-positive; FIG. 12D—I3 cells cultured in suspension as cell clumps for more than 10 passages, sorted by a TRA1-81 antibody (blue curve). Note that 93% of the cells are TRA1-81-positive; FIG. 12E—H14 cells cultured in suspension as single cells for more than 10 passages, sorted by a TRA1-60 antibody (blue curve). Note that only 0.65% of the cells are TRA1-60-positive; FIG. 12F—H14 cells cultured in suspension as single cells for more than 10 passages, sorted by a TRA1-81 antibody (blue curve). Note that only 0.7% of the cells are TRA1-81-positive; FIG. 12G—I3 cells cultured in suspension as cell clumps for more than 10 passages, sorted by a SSEA1 antibody (blue curve). Note that 11.1% of the cells are SSEA1-positive; FIG. 12H—I3 cells cultured in suspension as cell clumps for more than 10 passages, sorted by an SSEA4 antibody (grey curve). Note that 98.4% of the cells are SSEA4-positive; FIGS. 12I—H7 cells cultured in suspension as single cells for more than 10 passages, sorted by an SSEA1 antibody (blue curve). Note that 78.5% of the cells are SSEA1-positive; FIG. 12J—H7 cells cultured in suspension as single cells for more than 10 passages, sorted by an SSEA4-antibody (blue curve). Note only 5.43% of the cells are SSEA4-positive. The red curve in each of FIGS. 12A-12G and 12I-12J represents a negative control.

Figure 13A:
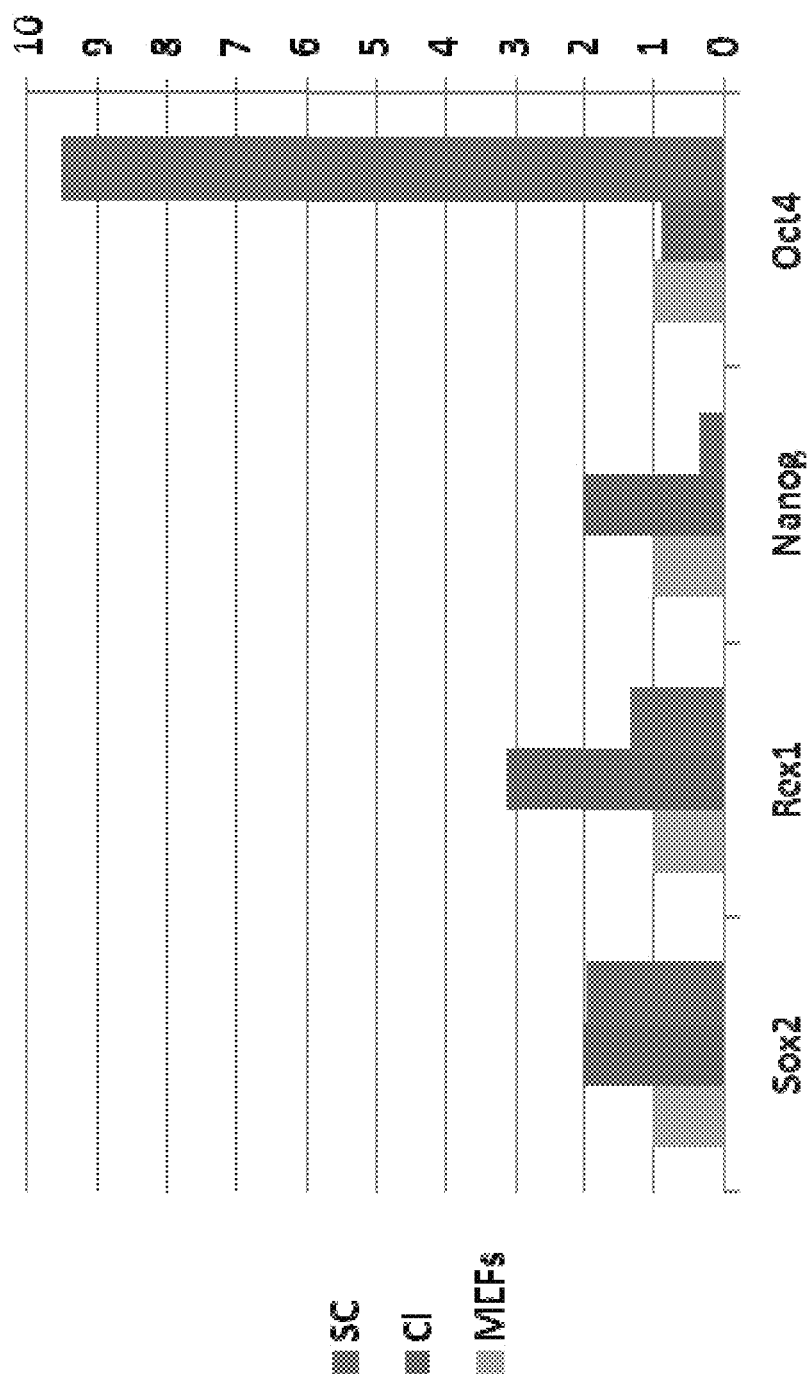
Figure 13B:
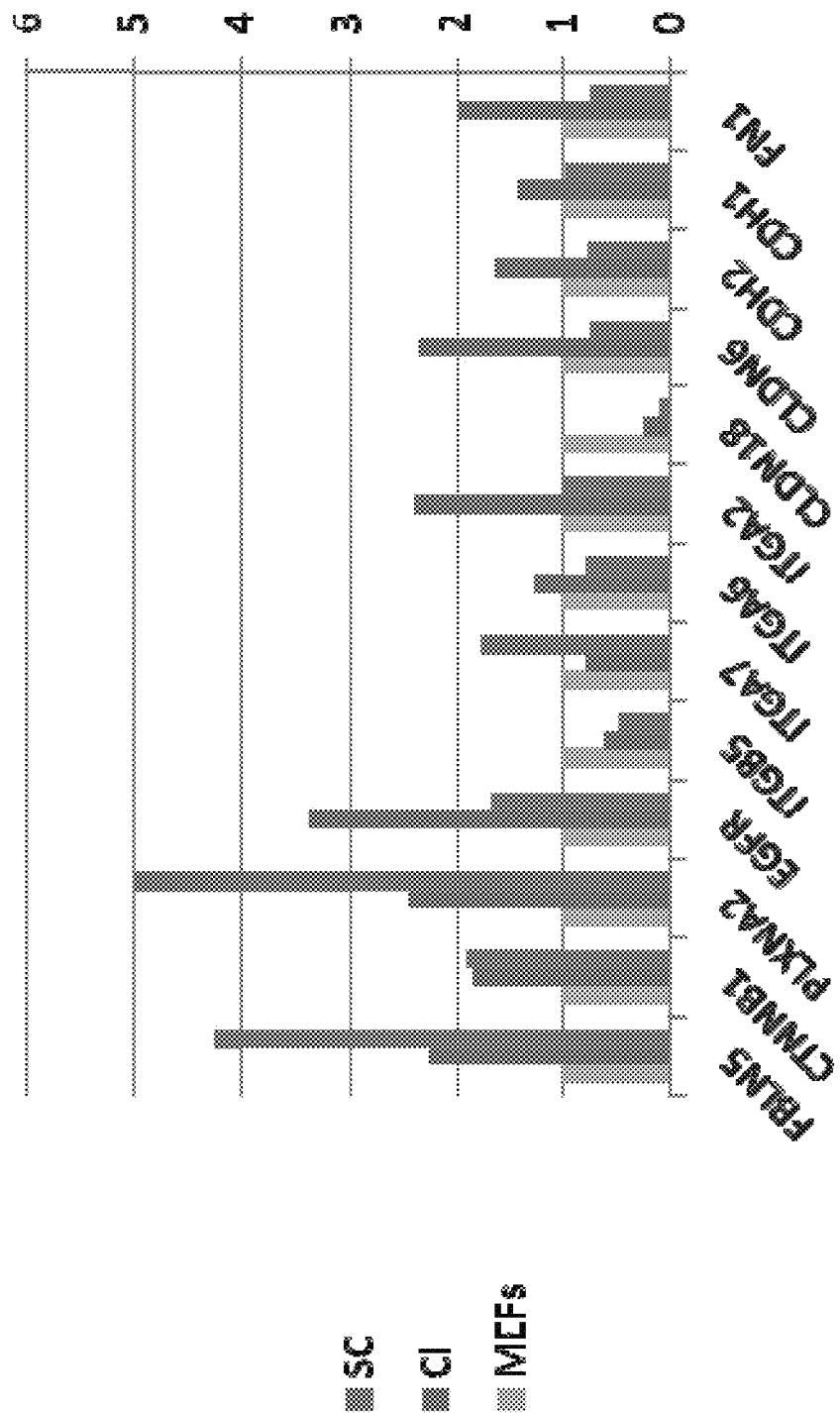

FIGS. 13A-13B are histograms depicting RT-PCR analyses. Shown is the average fold change (three repeats from each) in gene expression by real time PCR for the H7 and CL1 pluripotent stem cells. The average fold change was calculated in comparison to the expression level of the indicated genes in the H7 and CL1 pluripotent stem cells when cultured on MEFs (designated as "1"). FIG. 13A—Shown are the results for Sox2, Rex1, Nanog and Oct4 pluripotency genes; FIG. 13B—Shown are the results for FBLN5, CTNNB1, PLXNA2, EGFR, ITGA7, IGTA6, ITGA2, CLDN18, CLDN6, CDH2, CDH1 and FN1 adhesion molecule genes. Blue bars=single cells (SC) cultured in suspension for more than 10 passages; Red bars=cell clumps (Cl) cultured in suspension for more than 10 passages; Green bars=pluripotent stem cells cultured on mouse embryonic fibroblasts (MEFs) in a standard 2-D culture. Note the slight decrease in Nanog expression in the pluripotent single stem cells as compared to the pluripotent stem cells cultured on MEFs, while the expression of Oct4 was increased in cells cultured as single cells as compared to the same cells when cultured on MEFs or as cell clumps in a suspension culture.

Figure 14:
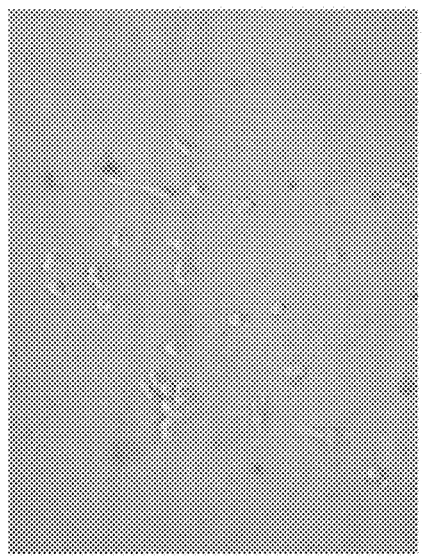

FIG. 14 is an image depicting cloning efficiency of hESCs which were cultured in a suspension culture as single cells. Single cell clones were formed by plating single cells of the H7 hESC line which were cultured in a suspension culture as single cells devoid of cell clumps. Each cell was plated in a single well of a low adhesion 96-well plate and cultured in suspension. Note that the cloning efficiency of the hESCs cultured in a suspension culture as single cells is 95%.

Figure 15:
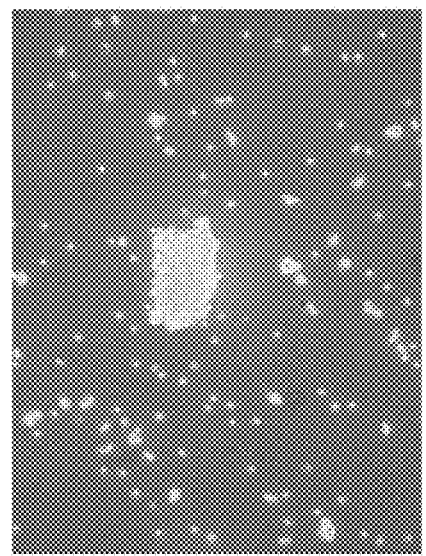

FIG. 15 is an image depicting the thawing efficiency of hESCs cultured in a suspension culture as single cells. Human ESCs cultured as single cells in a suspension culture were frozen using standard freezing solutions, and then were thawed in a suspension culture. The cells recovered well with at least 80% cells surviving.

FIGS. 16A-16B are images depicting genetic manipulation of hESCs cultured in a suspension culture as single cells. Human ESCs cultured in a suspension culture as single cells were subjected to electroporation with a nucleic acid construct including the GFP gene under the CMV promoter. FIG. 16A—a phase contrast image of the cells after genetic manipulation. Note that most of the cells (at least 90%) survived the electroporation procedure; FIG. 16B—a fluorescent microscopy image of the cells after genetic manipulation. The green signals correspond to cells expressing the recombinant construct (GFP under the transcriptional regulation of the CMV promoter).

Figure 17A:
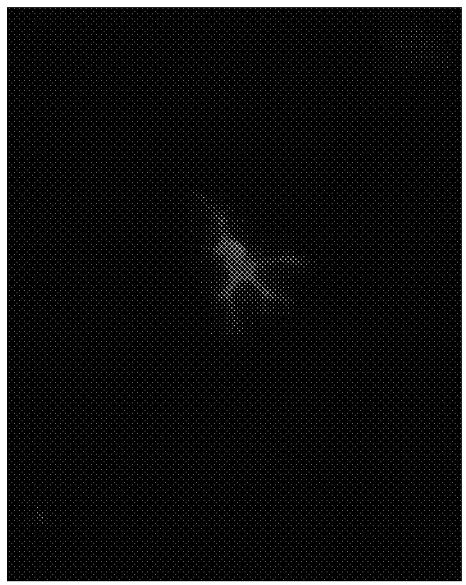
Figure 17B:
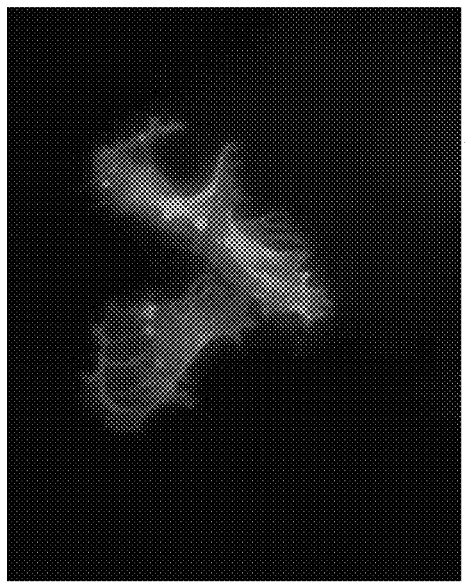
Figure 17C:
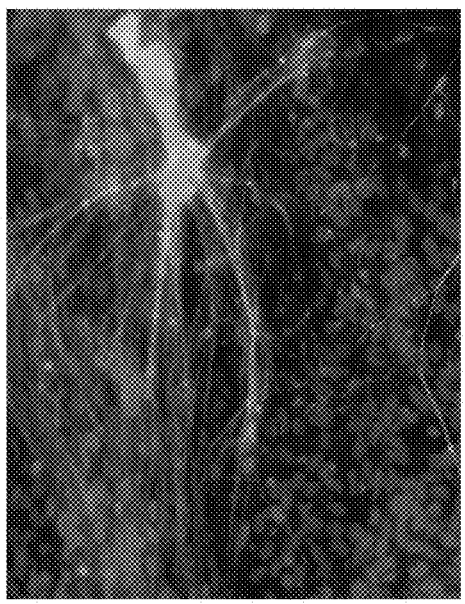

FIGS. 17A-17C are microscopic images depicting the differentiation of human ESCs cultured in a suspension culture as single cells into neural progenitors (NP). Human ESCs cultured in suspension as single cells were induced to differentiate into the neuronal cell lineage. FIG. 17A— astrocytes, GFAP (Red); FIG. 17B—Oligodendrocytes, O4 (green); FIG. 17C—neurons, β-Tubulin (green) and Nestin (red).

Figures 18A, 18B, 18C:
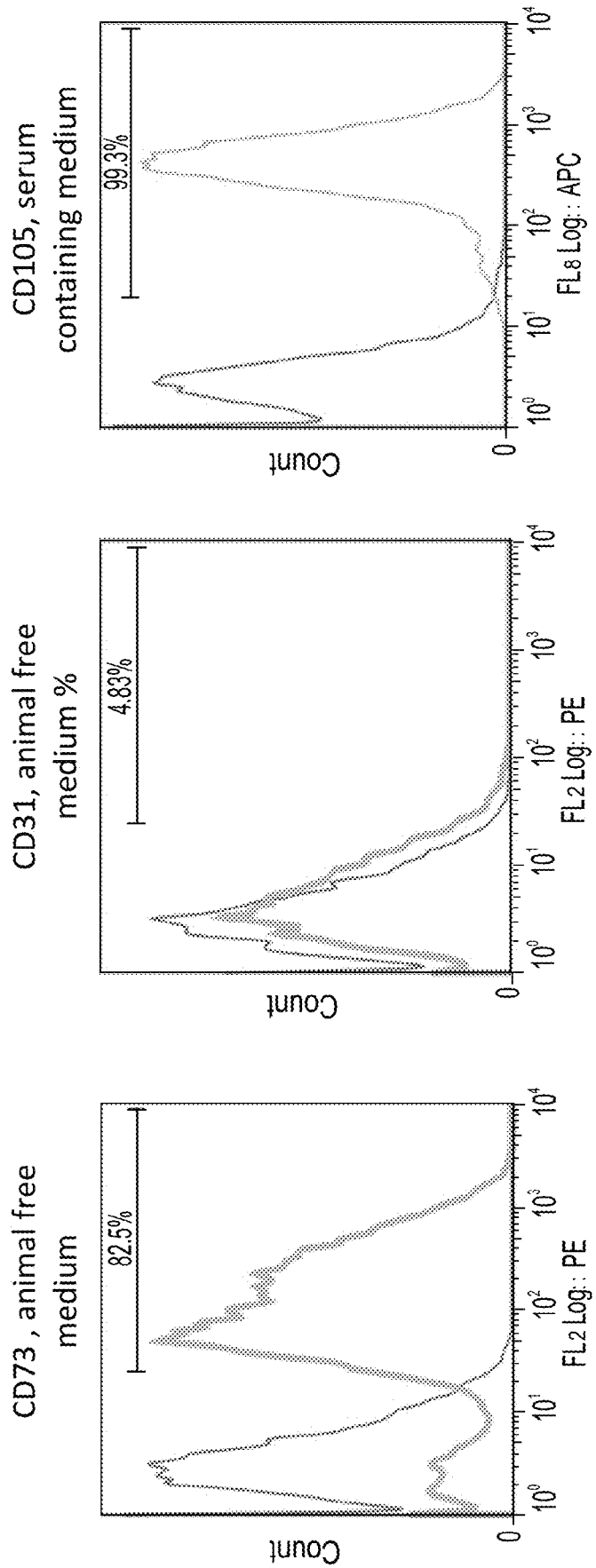

FIGS. 18A-18C are histograms depicting FACS analyses of MSCs which were isolated by differentiation of hESCs grown in suspension culture as single cells. FIG. 18A—MSCs derived from the J3 hESC line grown in animal-free medium, sorted by a CD73 antibody (blue curve). Note that 82.5% are CD73-positive; FIG. 18B—MSCs derived from the J3 hESC line grown in animal-free medium, sorted by a CD31 antibody (blue curve). Note that only 4.83% are CD31-positive; FIG. 18C—MSCs derived from the J3 hESC line grown in a serum-containing medium, sorted by a CD105 antibody (blue curve). Note that 99.3% are CD105-positive.

Figure 19B:
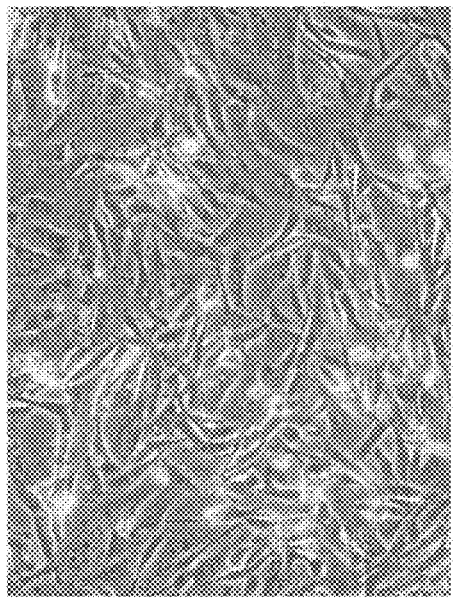
Figure 19D:
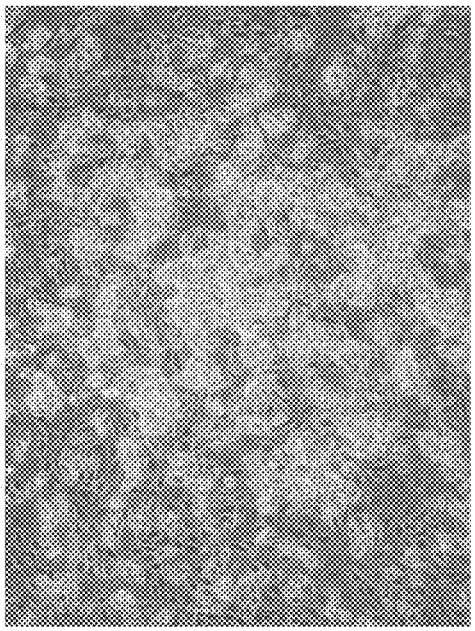
Figure 19A:
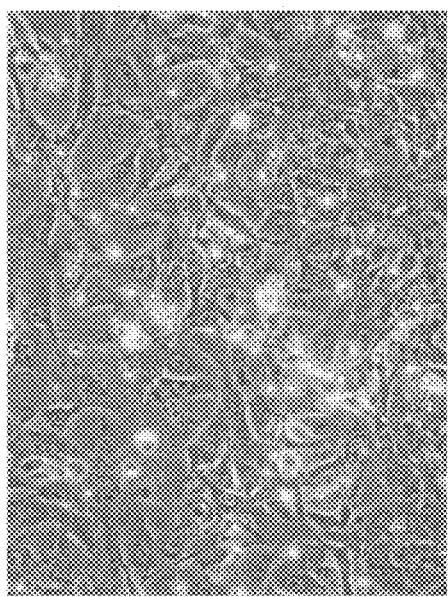
Figure 19C:
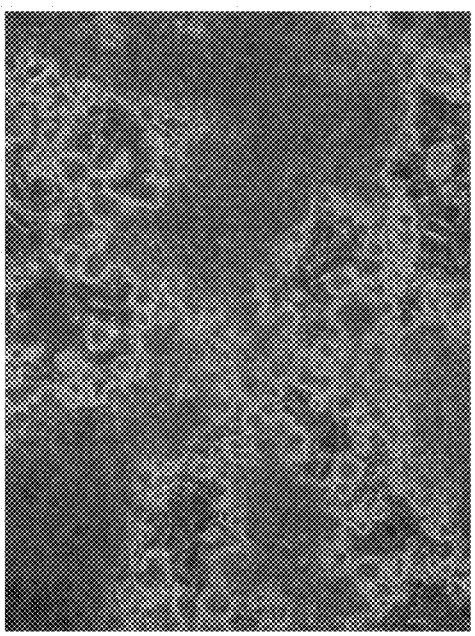

FIGS. 19A-19D are images depicting differentiation of hESCs which are cultured in suspension as single cells into MSCs. Single cells cultured in suspension as single cells can differentiate both in suspension and in 2D to potent MSCs. FIGS. 19A-19B—phase contrast images of MSCs differentiated from human ESCs which were cultured in suspension as single cells. The hESCs were re-plated in a suspension culture and differentiated into MSCs having typical MSCs morphology. FIG. 19A—CL1 cells were differentiated in Fy enriched medium; FIG. 19B—CL1 cells were differentiated in MeSusII medium; FIG. 19C—Alizarin red staining of differentiated MSCs (which were formed by differentiation of the hESCs grown in suspension as single cells) into the bone lineage. FIG. 19D—Oil red staining of differentiated MSCs (which were formed by differentiation of the hESCs grown in suspension as single cells) into adipocytes.

Figure 20B:
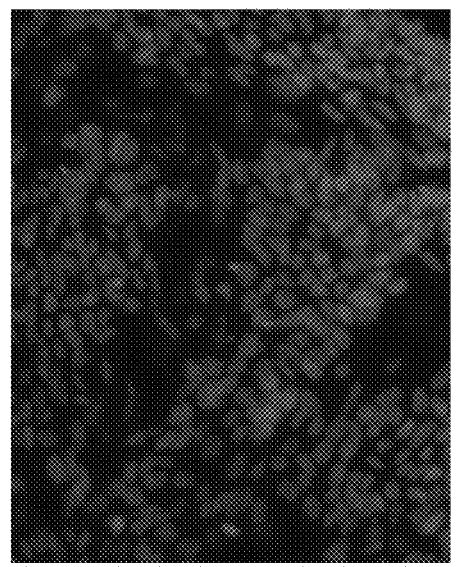
Figure 20A:
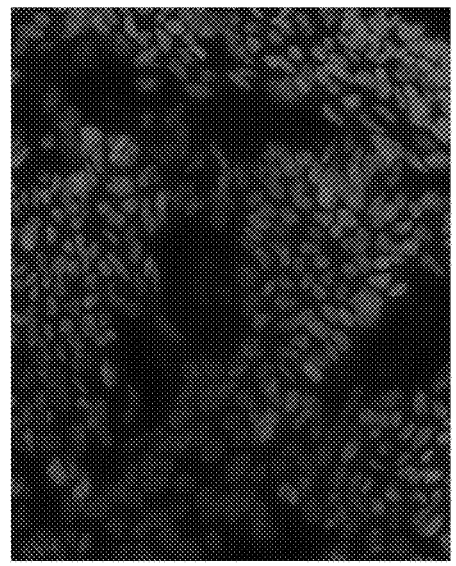

FIGS. 20A-20B are images depicting differentiation of hESCs which are cultured in suspension as single cells into the endoderm germ layer. C2 cells were cultured for more than 10 passages as single cells in suspension. For endoderm differentiation, the bFGF and the IL6RIL6 chimera were removed from the culture medium and activin A in concentration of 10 ng/ml was added for 48 hours in a suspension culture. 10 days after exposure to activin A, the cells were plated on Matrigel or HFF matrix and were stained for PDX1 expression using the anti-PDX1 antibody (R&D Biosystems). FIG. 20A—DAPI staining (nuclear staining) (blue); FIG. 20B—PDX1 (red). Note that all cells which are stained by DAPI (nuclear staining) are also stained with PDX1.

DESCRIPTION OF SPECIFIC EMBODIMENTS OF THE INVENTION

The present invention, in some embodiments thereof, relates to novel methods and culture media which can maintain pluripotent stem cells in an undifferentiated state, novel pluripotent stem cells which are cultured in suspension as single stem cells devoid of cell clumps, and, more particularly, but not exclusively, to methods of culturing the pluripotent stem cells in two-dimensional or three-dimensional culture systems while maintaining the pluripotent stem cells in a proliferative, pluripotent and undifferentiated state.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have uncovered following laborious experimentations defined culture media, which are serum-free and devoid of animal contaminants and which can maintain pluripotent stem cells such as human iPS and ESCs in an undifferentiated state in the absence of feeder cell support while preserving their pluripotent potential to differentiate into all three embryonic germ layers.

Thus, as shown in the Examples section which follows, hESCs and iPS cells (e.g., derived from adult or foreskin fibroblast) were cultured in an undifferentiated state on either two-dimensional or three-dimensional culture systems in the presence of serum-free and defined culture media (e.g., yFIL25, CMrb100F, CMrb100Fp, ILCNTF) as well as in the presence of well-defined culture media which comprise an animal contaminant-free serum replacement (e.g., NCM100F, NCM100Fp, NCMrb100F, NCMrb100Fp, NILCNTF, CmHA13, CmHA13p) which are suitable for use in clinical/therapeutic applications since human pluripotent stem cells cultured therein are completely devoid of animal contaminants. Furthermore, as shown in Example 4 of the Examples section which follows, the pluripotent stem cells cultured in suspension can remain viable, proliferative and pluripotent while being transferred across countries as living cells. While in culture, the pluripotent stem cells exhibit an undifferentiated morphology, and molecular characteristics which is typical to iPS or hESCs including normal karyotype, expression of markers of pluripotency (e.g., Oct4, SSEA4, TRA-1-81, TRA-1-60), and ability to differentiate into all three embryonic germ layers both in vitro (by formation of embryoid bodies after at least 10) and in vivo (by formation of teratomas after at least 20 passages). In addition, as shown in FIGS. 7-10 and described in Example 7 of the Examples section which follows, the pluripotent stem cells were used to generate lineages specific cells of the neuronal, endodermal and mesodermal cell lineages.

In addition, the present inventors have uncovered culturing conditions suitable for maintaining undifferentiated, pluripotent stem cells in a suspension culture as single cells devoid of cell clumps, and isolated a novel population of human pluripotent stem cells which are cultured in a suspension culture as single cells.

Thus, as described in Example 3 of the Examples section which follows, the present inventors cultured pluripotent stem cells (e.g., hESC and human iPS cells) in a suspension culture by mechanically passaging the cells (e.g., using a pipette) without the use of trypsin or ROCK inhibitor. After about 3-7 passages of mechanically separating cell clumps to single cells, the pluripotent stem cells adopted a single cell mode of expansion, which required no further mechanical separation for culture passaging, thus allowing mass production of these cells. When the suspension culture which was cultured as single cells was re-plated on MEFs, the cells formed colonies with typical morphology of pluripotent stem cells (FIGS. 11A-11B). As is further described in Example 8 of the Examples section which follows, the human pluripotent stem cells which were cultured in a suspension culture as single cells exhibit a more naïve pattern of gene expression as compared to human ESCs cultured on MEFs or as compared to hESCs which are cultured in a suspension culture as cell clumps. Thus, the isolated population of pluripotent stem cells which are cultured in suspension as single cells devoid of cell clumps exhibit an SSEA4$^-$/TRA1-60$^-$/TRA1-81$^-$/SSEA1$^+$ expression signature (FIGS. 12E, 12F, 12I and 12J; Table 3), which is different from the typical SSEA4$^+$/TRA1$^-$60$^+$/TRA1-81$^+$/SSEA1$^-$ expression signature of human ESCs cultured on MEFs or in a suspension culture as cell clumps (FIGS. 12A, 12B, 12C, 12D, 12G, 12H; Table 3). In contrast, the pluripotent stem cells, which were cultured in a suspension culture as single cells, exhibit increased levels of OCT-4, a marker of pluripotency, as compared to hESCs cultured on MEFs (2-D) or to hESCs cultured in a suspension culture as cell clumps (Example 8, FIG. 13A). In addition, the pluripotent stem cells which were cultured in suspension as single cells were found to exhibit an increased cloning efficiency (e.g., about 95% efficiency for hESCs) as compared to pluripotent stem cells cultured on 2-D (e.g., between 4-18%, depending on the use of ROCK inhibitor) (Example 9, Table 4), increased survival to freezing and thawing cycles (Example 9, FIG. 15), and higher survival to and efficiency of genetic manipulation (Example 9, FIGS. 16A-16B). The pluripotent stem cells which were cultured in suspension as single cells were shown capable of differentiation to all three embryonic germ layers, i.e., the ectoderm germ layer, by forming neuronal progenitor cells expressing GFAP (Glial fibrillary acidic protein), a marker of astrocytes, O4, a marker of oligodendrocytes, and β-Tubulin and Nestin, markers of neurons (Example 10, FIGS. 17A-17C); the mesoderm germ layer, by forming mesenchymal stem cells expressing CD73 and CD105 (Example 11, FIGS. 18A and 18C) and not-expressing CD31 (Example 11, FIG. 18B); and the endoderm germ layer, by forming endodermal cells which express PDX1 (Example 12, FIGS. 20A-20B). In addition, the present inventors have demonstrated for the first time, the in vitro differentiation in a suspension culture of pluripotent stem cells into mesenchymal stem cells (Example 11). These MSCs were capable of differentiation into an adipogenic cell lineage (Example 11, FIG. 19D), an osteogenic cell lineage (Example 11, FIG. 19C), and a chondrogenic cell lineage (Example 11, and data not shown). Altogether, the novel pluripotent stem cells identified herein can be used as an unlimited source of pluripotent, undifferentiated stem cells for various cell based therapy, drug screening, production of a vaccine and/or production of proteins.

Thus, according to an aspect of some embodiments of the invention there is provided a method of expanding and maintaining pluripotent stem cells (PSCs) in an undifferentiated state, the method comprising: (a) passaging the PSCs in a suspension culture by mechanical dissociation of PSC clumps to single cells for at least 2 and no more than 10 passages, to thereby obtain a suspension culture of PSCs devoid of clumps, and; (b) passaging the suspension culture of PSCs devoid of the clumps without dissociation of the clumps, thereby expanding and maintaining the PSCs in the undifferentiated state.

According to some embodiments of the invention, passaging the PSCs in a suspension culture by mechanical dissociation of PSC clumps to single cells is effected for at least 2 and no more than 9 passages, for at least 2 and no more than 8 passages, for at least 2 and no more than 7 passages, for at least 2 and no more than 6 passages, for at least 2 and no more than 5 passages, for at least 2 and no more than 4 passages, for at least 3 and no more than 9 passages, for at least 3 and no more than 8 passages, for at least 3 and no more than 7 passages, for at least 3 and no more than 6 passages, for at least 3 and no more than 5 passages.

According to some embodiments of the invention, the method further comprising culturing the PSCs under conditions which allow expansion of the pluripotent stem cells in the undifferentiated state.

As used herein the phrase "pluripotent stem cells" refers to cells which are capable of differentiating into cells of all three embryonic germ layers (i.e., endoderm, ectoderm and mesoderm). The phrase "pluripotent stem cells" may read on embryonic stem cells (ESCs) and/or induced pluripotent stem cells (iPS cells).

The phrase "embryonic stem cells" as used herein refers to cells which are obtained from the embryonic tissue formed after gestation (e.g., blastocyst) before implantation (i.e., a pre-implantation blastocyst); extended blastocyst cells (EBCs) which are obtained from a post-implantation/pre-gastrulation stage blastocyst (see WO2006/040763]; and/or embryonic germ (EG) cells which are obtained from the genital tissue of a fetus any time during gestation, preferably before 10 weeks of gestation.

According to some embodiments of the invention, the pluripotent stem cells of the invention are embryonic stem cells, such as from a human or primate (e.g., monkey) origin.

The embryonic stem cells of the invention can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells see Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; and Gardner et al., [Fertil. Steril. 69: 84, 1998].

It will be appreciated that commercially available stem cells can also be used with this aspect of the present invention. Human ES cells can be purchased from the NIH human embryonic stem cells registry (www(dot)//escr(dot)nih(dot)gov). Non-limiting examples of commercially available embryonic stem cell lines are BG01, BG02, BG03, BG04, CY12, CY30, CY92, CY10, TE03, TE04 and TE06.

Extended blastocyst cells (EBCs) can be obtained from a blastocyst of at least nine days post fertilization at a stage prior to gastrulation. Prior to culturing the blastocyst, the zona pellucida is digested [for example by Tyrode's acidic solution (Sigma Aldrich, St Louis, MO, USA)] so as to expose the inner cell mass. The blastocysts are then cultured as whole embryos for at least nine and no more than fourteen days post fertilization (i.e., prior to the gastrulation event) in vitro using standard embryonic stem cell culturing methods.

Embryonic germ (EG) cells are prepared from the primordial germ cells obtained from fetuses of about 8-11 weeks of gestation (in the case of a human fetus) using laboratory techniques known to anyone skilled in the arts. The genital ridges are dissociated and cut into small chunks which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparation human EG cells see Shamblott et al., [Proc. Natl. Acad. Sci. USA 95: 13726, 1998] and U.S. Pat. No. 6,090, 622.

The phrase "induced pluripotent stem (iPS) cell" (or embryonic-like stem cell) as used herein refers to a proliferative and pluripotent stem cell which is obtained by de-differentiation of a somatic cell (e.g., an adult somatic cell).

According to some embodiments of the invention, the iPS cell is characterized by a proliferative capacity which is similar to that of ESCs and thus can be maintained and expanded in culture for an almost unlimited time.

IPS cells can be endowed with pluripotency by genetic manipulation which re-program the cell to acquire embryonic stem cells characteristics. For example, the iPS cells of the invention can be generated from somatic cells by induction of expression of Oct-4, Sox2, Kfl4 and c-Myc in a somatic cell essentially as described in Takahashi and Yamanaka, 2006, Takahashi et al, 2007, Meissner et al, 2007, and Okita K., et al, 2007, Nature 448: 313-318). Additionally or alternatively, the iPS cells of the invention can be generated from somatic cells by induction of expression of Oct4, Sox2, Nanog and Lin28 essentially as described in Yu et al, 2007, and Nakagawa et al, 2008. It should be noted that the genetic manipulation (reprogramming) of the somatic cells can be performed using any known method such as using plasmids or viral vectors, or by derivation without any integration to the genome [Yu J, et al., Science. 2009, 324: 797-801].

The iPS cells of the invention can be obtained by inducing de-differentiation of embryonic fibroblasts [Takahashi and Yamanaka, 2006; Meissner et al, 2007], fibroblasts formed from hESCs [Park et al, 2008], Fetal fibroblasts [Yu et al, 2007; Park et al, 2008], foreskin fibroblast [Yu et al, 2007; Park et al, 2008], adult dermal and skin tissues [Hanna et al, 2007; Lowry et al, 2008], b-lymphocytes [Hanna et al 2007] and adult liver and stomach cells [Aoi et al, 2008].

IPS cell lines are also available via cell banks such as the WiCell bank. Non-limiting examples of commercially available iPS cell lines include the iPS foreskin clone 1 [WiCell Catalogue No. iPS(foreskin)-1-DL-1], the iPSIMR90 clone 1 [WiCell Catalogue No. iPS(IMR90)-1-DL-1], and the iPSIMR90 clone 4 [WiCell Catalogue No. iPS(IMR90)-4-DL-1].

According to some embodiments of the invention, the induced pluripotent stem cells are human induced pluripotent stem cells.

As used herein the term "expanding" refers to increasing the number of pluripotent stem cells over the culturing period (by at least about 5%, 10%, 15%, 20%, 30%, 50%, 100%, 200%, 500%, 1000%, and more). It will be appreciated that the number of pluripotent stem cells, which can be obtained from a single pluripotent stem cell, depends on the proliferation capacity of the pluripotent stem cell. The proliferation capacity of a pluripotent stem cell can be calculated by the doubling time of the cell (i.e., the time needed for a cell to undergo a mitotic division in the culture) and the period the pluripotent stem cell culture can be maintained in the undifferentiated state (which is equivalent to the number of passages multiplied by the days between each passage).

According to some embodiments of the invention, the method of some embodiments of the invention enables the expansion of a single pluripotent stem cell (e.g., hESC or human iPS cell) by at least 8 folds in 5 days, e.g., at least 16 folds in 5 days, e.g., at least 32 folds in 5 days, e.g., at least 64 folds in 5 days.

According to some embodiments of the invention, the method of some embodiments of the invention enables the expansion of a single pluripotent stem cell (e.g., hESC or human iPS cell) or a small cluster of 2-100 cells by at least $2^8$, e.g., $2^{10}$, e.g., $2^{14}$, e.g., $2^{16}$, e.g., $2^{18}$, e.g., $2^{20}$ folds within about one month.

As used herein the term "clump" refers to a cluster of cells which adhere to each other in suspension.

According to some embodiments of the invention, the cell clump remains intact when the medium of the suspension culture is changed (e.g., increased, decreased or replaced) without employing any mechanical or enzymatic dissociation of the clumps.

According to some embodiments of the invention, each of the pluripotent stem cell clumps comprises at least about 200 cells (e.g., about 200), e.g., at least about 500 cells (e.g., about 500), at least about 600 cells (e.g., about 600), at least about 700 cells (e.g., about 700), at least about 800 cells (e.g., about 800), at least about 900 cells (e.g., about 900), at least about 1000 cells (e.g., about 1000), at least about 1100 cells (e.g., about 1100), at least about 1200 cells (e.g., about 1200), at least about 1300 cells (e.g., about 1300), at least about 1400 cells (e.g., about 1400), at least about 1500 cells (e.g., about 1500), at least about $5 \times 10^3$ cells (e.g., about $5 \times 10^3$), at least about $1 \times 10^4$ cells (e.g., about $1 \times 10^4$), at least about $5 \times 10^4$ cells (e.g., about $5 \times 10^4$), at least about $1 \times 10^5$ cells (e.g., about $1 \times 10^5$), or more.

As used herein the term "passaging" as used herein refers to splitting the cells in the culture vessel to 2 or more culture vessels, typically including addition of fresh medium. Passaging is typically done when the cells reach a certain density in culture.

According to some embodiments of the invention, passaging of a cell culture seeded at a concentration of about $1 \times 10^6$ cells per milliliter under static three-dimensional culture system is done when the cells' concentration increases to about 2 or 3 folds (e.g., at a concentration of about $2 \times 10^6$-$3 \times 10^6$ cells/ml), but no more than up to about 4 folds (e.g., at a concentration about $4 \times 10^6$ cells/ml).

According to some embodiments of the invention, passaging of a cell culture seeded at a concentration of about $1 \times 10^6$ cells per milliliter under dynamic three-dimensional culture system is done when the cells' concentration increases about 20-40 folds (e.g., at a concentration of about $20 \times 10^6$-$40 \times 10^6$ cells/ml), but no more than up to about 50 folds (e.g., at a concentration of about $50 \times 10^6$ cells/ml).

According to some embodiments of the invention, the passaging does not necessarily require dissociation of the cell clumps in the cell culture.

As used herein the phrase "mechanical dissociation" refers to separating the pluripotent stem cell clumps to single cells by employing a physical force rather than an enzymatic activity.

As used herein the phrase "single cells" refers to the state in which the pluripotent stem cells do not form cell clusters, each cluster comprising more than about 200 pluripotent stem cells, in the suspension culture.

According to some embodiments of the invention, the pluripotent stem cells do not form cell clusters, each cluster comprising more than about 150, about 100, about 90, about 80, about 70, about 60, about 50, about 40, about 30, about 20, about 19, about 18, about 17, about 16, about 15, about 14, about 13, about 12, about 11, about 10, about 9, about 8, about 7, about 6, about 5, about 3, about 2, or about 1 pluripotent stem cell, in the suspension culture.

According to some embodiments of the invention, each of the plurality of the pluripotent stem cells does not adhere to another pluripotent stem cell while in the suspension culture.

For mechanical dissociation, a pellet of pluripotent stem cells (which may be achieved by centrifugation of the cells) or an isolated pluripotent stem cells clump can be dissociated by pipetting the cells up and down in a small amount of medium (e.g., 0.2-1 ml). For example, pipetting can be performed for several times (e.g., between 3-20 times) using a tip of a 200 μl or 1000 μl pipette.

Additionally or alternatively, mechanical dissociation of large pluripotent stem cells clumps can be performed using a device designed to break the clumps to a predetermined size. Such a device can be obtained from CellArtis Goteborg, Sweden. Additionally or alternatively, mechanical dissociation can be manually performed using a needle such as a 27 g needle (BD Microlance, Drogheda, Ireland) while viewing the clumps under an inverted microscope.

According to some embodiments of the invention, passaging is effected under conditions devoid of enzymatic dissociation.

According to some embodiments of the invention, culturing in suspension is effected under conditions devoid of enzymatic dissociation of cell clusters/clumps.

According to some embodiments of the invention, the culturing conditions are devoid of using an anti-apoptotic agent.

According to some embodiments of the invention, the culturing conditions are devoid of using a Rho-associated kinase (ROCK) inhibitor.

According to some embodiments of the invention, culturing is effected for at least one passage, at least 2, 3, 4, 5, 6, 7, 8, 9, 10, 11, 12, 13, 14, 15, 16, 17, 18, 19, 20 passages in an undifferentiated pluripotent state.

The present inventors have uncovered that when the pluripotent stem cells in a suspension culture are mechanically passaged without enzymatic dissociation of cell clusters for at least about 2 and no more than about 10 passages, the pluripotent stem cells adopt the single cell mode of cell growth (i.e., they are expanded as single cells and not as cell clumps). Thus, as described in Example 3 of the Examples section which follows, cells cultured in suspension while being passaged by only mechanical dissociation of cell clusters for the first 2-10 passages adopted the single cell mode of expansion and grew without the need of further dissociation of cell clusters for at least about 15, 20 or 25 additional passages.

It should be noted that while the cells are cultured as single cells, they still need to be diluted when the concentration of cells exceeds about $1 \times 10^6$ cells per milliliter (e.g., $5 \times 10^6$ cells per 5 ml of Petri dish).

As used herein the phrase "suspension culture" refers to a culture in which the pluripotent stem cells are suspended in a medium rather than adhering to a surface.

It should be noted that some protocols of culturing pluripotent stem cells such as hESCs and iPS cells include microencapsulation of the cells inside a semipermeable hydrogel membrane, which allows the exchange of nutrients, gases, and metabolic products with the bulk medium surrounding the capsule (for details see e.g., U.S. Patent Application No. 20090029462 to Beardsley et al.).

According to some embodiments of the invention, the pluripotent stem cells cultured in the suspension culture are devoid of cell encapsulation.

According to some embodiments of the invention, the conditions for culturing the pluripotent stem cells in suspension are devoid of substrate adherence, e.g., without adherence to an external substrate such as components of extracellular matrix, a glass microcarrier or beads.

According to some embodiments of the invention, the culture medium and/or the conditions for culturing the pluripotent stem cells in suspension are devoid of a protein carrier.

As used herein the phrase "protein carrier" refers to a protein which acts in the transfer of proteins or nutrients (e.g., minerals such as zinc) to the cells in the culture. Such protein carriers can be, for example, albumin (e.g., bovine serum albumin), Albumax (lipid enriched albumin) or plasmanate (human plasma isolated proteins). Since these carriers are derived from either human or animal sources their use in hESCs of human iPS cell cultures is limited by batch-specific variations and/or exposure to pathogens. Thus, a culture medium which is devoid of a protein carrier (e.g., albumin) is highly advantageous since it enables a truly defined medium that can be manufacture from recombinant or synthetic materials.

Culturing in a suspension culture according to the method of some embodiments of the invention is effected by plating the pluripotent stem cells in a culture vessel at a cell density which promotes cell survival and proliferation but limits differentiation. Typically, a plating density (or a seeding density) of between about $1 \times 10^3$ per ml to about $2 \times 10^6$ cells per ml is used. When a bioreactor is used, the concentration of cells seeded in the bioreactor can be from about $1 \times 10^4$ to about $10^6$ cells per ml. It will be appreciated that although single-cell suspensions of stem cells are usually seeded, small clusters such as 10-200 cells may also be used.

In order to provide the pluripotent stem cells with sufficient and constant supply of nutrients and growth factors while in the suspension culture, the culture medium can be replaced on a daily basis, or, at a pre-determined schedule such as every 2-3 days. For example, replacement of the culture medium can be performed by subjecting the pluripotent stem cells suspension culture to centrifugation for about 3 minutes at 80 g, and resuspension of the formed pluripotent stem cells pellet in a fresh medium. Additionally or alternatively, a culture system in which the culture medium is subject to constant filtration or dialysis so as to provide a constant supply of nutrients or growth factors to the pluripotent stem cells may be employed.

The culture vessel used for culturing the pluripotent stem cells in suspension according to the method of some embodiments of the invention can be any tissue culture vessel (e.g., with a purity grade suitable for culturing pluripotent stem cells) having an internal surface designed such that pluripotent stem cells cultured therein are unable to adhere or attach to such a surface (e.g., non-tissue culture treated cells, to prevent attachment or adherence to the surface). Preferably, in order to obtain a scalable culture, culturing according to some embodiments of the invention is effected using a controlled culturing system (preferably a computer-controlled culturing system) in which culture parameters such as temperature, agitation, pH, and $pO_2$ is automatically performed using a suitable device. Once the culture parameters are recorded, the system is set for automatic adjustment of culture parameters as needed for pluripotent stem cells expansion.

According to some embodiments of the invention, culturing is effected under conditions comprising a static (i.e., non-dynamic) suspension culture.

For non-dynamic culturing of pluripotent stem cells, the pluripotent stem cells can be cultured in uncoated 58 mm Petri dishes (Greiner, Frickenhausen, Germany). For example, to initiate a suspension culture on 58 mm Petri dishes the pluripotent stem cells are seeded at a cell density of $1 \times 10^6$-$5 \times 10^6$ cells/dish.

While in the non-dynamic suspension culture, the pluripotent stem cells can be passaged every 5-7 days by dissociating the cell clumps as described above and splitting the culture into additional culture vessels in a ratio of about 1:2-1:4.

According to some embodiments of the invention, culturing is effected under conditions comprising a dynamic suspension culture (e.g., using a Wave reactor or stirred reactor).

For dynamic culturing of pluripotent stem cells, the pluripotent stem cells can be cultured in spinner flasks [e.g., of 200 ml to 1000 ml, for example 250 ml which can be obtained from CellSpin of Integra Biosciences, Fernwald, Germany; of 100 ml which can be obtained from Bellco, Vineland, NJ; or in 125 ml Erlenmeyer (Corning Incorporated, Corning NY, USA)] which can be connected to a control unit and thus present a controlled culturing system. The culture vessel (e.g., a spinner flask, an Erlenmeyer) is shaken continuously. According to some embodiments of the invention the culture vessels are shaken at 40-110 rounds per minute (rpm) using magnetic plate, and placed in the incubator. Additionally or alternatively, the culture vessel can be shaken using a shaker (53.02.10L, ELMI ltd, Riga, Latvia). According to some embodiments of the invention the culture medium is changed every 1-3 days, e.g., every day. Other suitable controlled-bioreactors which stir the medium by an impeller and can be used for dynamic culturing of the pluripotent stem cells in the culture medium according to some embodiments of the invention include the Biostat®Aplus cell culture (Sartorius North America, Edgewood, New York, USA), Cell Optimizer controlled bioreactor (Wheaton Science Products, Millville, NJ, USA) equipped with Cell Lift impeller (Infors HT, Rittergasse, Switzerland), Informs HT Multifors stirred reactor (Informs GA, CH-4103 Bottmingen Switzerland).

Additionally or alternatively, dynamic culturing of pluripotent stem cells can be achieved using a controlled bioreactor in which the dynamics of the cells is achieved by a wave-like motion, such as the Biostat® Cultibag RM (Sartorius North America, Edgewood, New York, USA) (2 litter bag with 1 litter). The reactor parameters may include a speed of tilting: 10-16 rounds per minute (rpm); angle 7°; Temperature: 37° C., PH: 7-7.4, $O_2$ concentration: 50%. Another suitable bioreactor is the WavePod system 20/50 EH5 Wave Bioreactor (GE Healthcare, USA), which while using the same parameters enables increase in 70 folds during 12 days. Additional suitable bioreactor is the 55 ml RWV/STLV bioreactor which allows minimum shear forces within the reactor (Synthecon Incorporated, Houston, TX, USA).

For example, to initiate a suspension culture under dynamic conditions, the pluripotent stem cells are seeded at a concentration of about $10^4$-$10^6$ cells/ml.

While in the dynamic suspension culture, the pluripotent stem cells can be passaged every 5-7 days by dissociating the cell clumps as described above. Since the bioreactors have a large capacity, the cell culture needs no further splitting into additional culture vessels and only addition and/or replacement of medium with a fresh medium can be performed every 3-10 days.

The teachings of the invention can be used for deriving a pluripotent stem cell line.

The term "deriving" as used herein refers to generating an embryonic stem cell line or an induced pluripotent stem cell line from at least one embryonic stem or induced pluripotent cell.

As used herein the phrase "embryonic stem cell line" refers to embryonic stem cells which are derived from a single or a group of embryonic stem cells of a single organism (e.g., a single human blastocyst), and which are characterized by the ability to proliferate in culture while maintaining the undifferentiated state and the pluripotent capacity.

As used herein the phrase "induced pluripotent stem cell line" refers to induced pluripotent stem cells which are derived from a single or a group of induced pluripotent stem cells of a single organism), and which are characterized by the ability to proliferate in culture while maintaining the undifferentiated state and the pluripotent capacity.

According to an aspect of some embodiments of the invention there is provided a method of deriving an embryonic stem cell line, the method comprising: (a) obtaining embryonic stem cells (ESCs) from a pre-implantation stage blastocyst, post-implantation stage blastocyst and/or a genital tissue of a fetus; and (b) passaging the ESCs in a suspension culture by mechanical dissociation of ESC clumps to single cells for at least 2 and no more than 10 passages, to thereby obtain a suspension culture of ESCs devoid of clumps, and; (c) passaging the suspension culture of ESCs devoid of the clumps without dissociation of the clumps, thereby deriving the embryonic stem cell line.

Obtaining an embryonic stem cell from a pre-implantation stage blastocyst, post-implantation stage blastocyst and/or a genital tissue of a fetus can be performed using methods known in the art and as described hereinabove.

According to an aspect of some embodiments of the invention, the method of deriving the embryonic stem cell line further comprising culturing the ESCs under conditions which allow expansion of the embryonic single stem cells in the undifferentiated state.

According to an aspect of some embodiments of the invention there is provided a method of deriving an induced pluripotent stem cell (iPS cell) line, the method comprising: inducing a somatic cell to a pluripotent stem cell; and expanding and maintaining the induced pluripotent stem cells in an undifferentiated state according to the method of some embodiments of the invention (e.g., as described hereinabove and in the Examples section which follows), thereby deriving the induced pluripotent stem cell (iPS cell) line.

As mentioned above and described in Table 4 and Example 9 of the Examples section which follows, the cloning efficiency of the pluripotent stem cells which are cultured in suspension as single cells is significantly higher than that of the same cells when cultured on a 2-dimensional culture system (e.g., on MEFs), without the use of an anti-apoptotic agent such as the ROCK inhibitor.

According to an aspect of some embodiments of the invention there is provided a method of cloning pluripotent stem cells. The method is effected by culturing a single pluripotent stem cell (i.e., one cell) obtained according to the method of some embodiments of the invention, or a single embryonic stem cell (i.e., one cell) obtained according to the method of some embodiments of the invention, in a suspension culture under conditions which allow expansion of the single pluripotent stem cell or of the single embryonic stem cell in the undifferentiated state, thereby expanding the single pluripotent stem cell or the embryonic stem cell into a clonal culture, thereby cloning the pluripotent stem cells.

According to some embodiments of the invention, culturing the single cell suspension culture is performed without dissociating the clumps.

As described in Example 9 of the Examples section which follows, pluripotent stem cells which are cultured as single cells in a suspension culture have a higher tolerance to a freezing-thawing cycle (e.g., about 80% survival) as compared to when the same cells are cultured on 2-D (e.g., on MEFs, up to 50%) under identical assay conditions.

According to some embodiments of the invention, the pluripotent stem cells, which are cultured as single cells in a suspension culture, can be subject to at least one, at least two, at least three, at least four, at least five, at least six, at least seven, at least eight, at least nine, at least ten cycles (e.g., up to 10 cycles) of freeze/thaw without hampering the proliferative capacity of the cells in the undifferentiated state while preserving their pluripotent capacity.

As described in Example 8 of the Examples section which follows, pluripotent stem cells which are cultured according to the method of some embodiments of the invention as single cells in a suspension culture exhibit a unique expression pattern, which is slightly different from that of hESCs, but which is similar to the expression pattern of mouse ESCs (TRA1-60$^-$/TRA1-81$^-$/SSEA1$^+$/SSEA4$^-$; see Pera M. F., et al. 2000. Journal of Cell Science 113, 5-10. Human embryonic stem cells. Commentary). Thus, as shown in Table 3 and in FIG. 13A, pluripotent stem cells which are cultured in a suspension culture as single cells (devoid of cell clumps) express OCT4, a marker of pluripotency, at a significantly higher level (e.g., about 8 folds higher RNA levels) as compared to the level of OCT4 RNA in pluripotent stem cells cultured on MEFs, or as compared to the level of OCT4 RNA in pluripotent stem cells which are cultured in a suspension culture as cell clumps (e.g., with clumps having more than about 200-1×10$^5$ cells per clump).

Cells cultured according to the method of some embodiments of the invention can be further isolated.

Thus, according to an aspect of some embodiments of the invention there is provided an isolated population of pluripotent stem cells generated according to the method of some embodiments of the invention and being capable of differentiating into the endoderm, ectoderm and mesoderm embryonic germ layers.

As shown in FIGS. 12A-12J and described in Example 8 of the Examples section which follows, the pluripotent stem cells which were cultured in suspension as single cells do not express TRA1-60, TRA1-81 or SSEA-4, but do express SSEA1.

Thus, according to an aspect of some embodiments of the invention there is provided an isolated population of human pluripotent stem cells comprising at least about 20%, at least about 30%, at least about 40%, at least about 50%, at least about 60%, at least about 65%, at least about 70% (e.g., 70%), at least about 75% (e.g., 75%), at least about 80% (e.g., 80%), at least about 81% (e.g., 81%), at least about 82% (e.g., 82%), at least about 83% (e.g., 83%), at least about 84% (e.g., 84%), at least about 85% (e.g., 85%), at least about 86% (e.g., 86%), at least about 87% (e.g., 87%), at least about 88% (e.g., 88%), at least about 89% (e.g., 89%), at least about 90% (e.g., 90%), at least about 91% (e.g., 91%), at least about 92% (e.g., 92%), at least about 93% (e.g., 93%), at least about 94% (e.g., 94%), at least about 95% (e.g., 95%), at least about 96% (e.g., 96%), at least about 97% (e.g., 97%), at least about 98% (e.g., 98%), at least about 99% (e.g., 99%), e.g., 100% of human pluripotent stem cells characterized by an OCT4$^+$/TRA1-60$^-$/TRA1-81$^-$/SSEA1$^+$/SSEA4$^-$ expression signature, wherein the human pluripotent stem cells are capable of differentiating into the endoderm, ectoderm and mesoderm embryonic germ layers.

According to some embodiments of the invention, the isolated cell population comprises cells expressing Rex1, Sox2, EGFR, TGA7, TGA6, ITGA2, CTNNB1, CDH1 at a comparable level (within the same order of magnitude) as hESCs cultured on MEFs; and cells expressing significantly higher levels of FBLN5 and PLXNA2 as compared to hESCs cultured on MEFs under identical assay conditions.

As described in Examples 1 and 2 of the Examples section which follows, the present inventors have uncovered novel culture media which can be used to maintain and expand pluripotent stem cells in a proliferative and undifferentiated state.

According to an aspect of some embodiments of the invention, there is provided a defined culture medium suitable for maintaining and expanding pluripotent stem cells in a proliferative, pluripotent and undifferentiated state in the absence of feeder-cell support, under two-dimensional or three-dimensional culture systems.

As used herein the phrase "culture medium" refers to a liquid substance used to support the growth of pluripotent stem cells and maintain them in an undifferentiated state. The culture medium used by the invention according to some embodiments can be a water-based medium which includes a combination of substances such as salts, nutrients, minerals, vitamins, amino acids, nucleic acids, proteins such as cytokines, growth factors and hormones, all of which are needed for cell proliferation and are capable of maintaining the pluripotent stem cells in an undifferentiated state. For example, a culture medium according to an aspect of some embodiments of the invention can be a synthetic tissue culture medium such as the Ko-DMEM (Gibco-Invitrogen Corporation products, Grand Island, NY, USA), DMEM/F12 (Biological Industries, Biet HaEmek, Israel), Mab ADCB medium (HyClone, Utah, USA), Nutristem™ (Biological Industries, Beit HaEmek, Israel; also known as Stemedia™ NutriStem™ XF/FF Culture Medium, STEMGENT, USA), TeSR™ (StemCell Technologies) and TeSR2™ (StemCell Technologies) supplemented with the necessary additives as is further described hereinunder.

According to some embodiments of the invention, the culture medium comprising DMEM/F12 at a concentration range of 80-90%, e.g., about 85%.

According to some embodiments of the invention, the culture medium is serum free.

As used herein the phrase "serum-free" refers to being devoid of a human or an animal serum.

It should be noted that the function of serum in culturing protocols is to provide the cultured cells with an environment similar to that present in vivo (i.e., within the organism from which the cells are derived, e.g., a blastocyst of an embryo). However, the use of serum, which is derived from either an animal source (e.g., bovine serum) or a human source (human serum), is limited by the significant variations in serum components between the donor individuals (from which the serum is obtained) and the risk of having xeno contaminants (in case of an animal serum is used).

According to some embodiments of the invention, the serum-free culture medium does not comprise serum or portions thereof.

According to some embodiments of the invention, the serum-free culture medium of the invention is devoid of serum albumin (e.g., albumin which is purified from human serum or animal serum).

According to some embodiments of the invention the culture medium comprises serum replacement.

As used herein the phrase "serum replacement" refers to a defined formulation, which substitutes the function of serum by providing pluripotent stem cells with components needed for growth and viability.

Various serum replacement formulations are known in the art and are commercially available.

For example, GIBCO™ Knockout™ Serum Replacement (Gibco-Invitrogen Corporation, Grand Island, NY USA, Catalogue No. 10828028) is a defined serum-free formulation optimized to grow and maintain undifferentiated ES cells in culture. It should be noted that the formulation of GIBCO™ Knockout™ Serum Replacement includes Albumax (Bovine serum albumin enriched with lipids) which is from an animal source (International Patent Publication No. WO 98/30679 to Price, P. J. et al). However, a recent publication by Crook et al., 2007 (Crook J M., et al., 2007, Cell Stem Cell, 1: 490-494) describes six clinical-grade hESC lines generated using FDA-approved clinical grade foreskin fibroblasts in cGMP-manufactured Knockout™ Serum Replacement (Invitrogen Corporation, USA, Catalogue No. 04-0095).

Another commercially available serum replacement is the B27 supplement without vitamin A which is available from Gibco-Invitrogen, Corporation, Grand Island, NY USA, Catalogue No. 12587-010. The B27 supplement is a serum-free formulation which includes d-biotin, fatty acid free fraction V bovine serum albumin (BSA), catalase, L-carnitine HCl, corticosterone, ethanolamine HCl, D-galactose (Anhyd.), glutathione (reduced), recombinant human insulin, linoleic acid, linolenic acid, progesterone, putrescine-2-HCl, sodium selenite, superoxide dismutase, T-3/albumin complex, DL alpha-tocopherol and DL alpha tocopherol acetate. However, the use of B27 supplement is limited since it includes albumin from an animal source.

According to some embodiments of the invention, the serum replacement is devoid of (completely free of) animal contaminants. Such contaminants can be pathogens which can infect human cells, cellular components or a-cellular components (e.g., fluid) of animals.

It should be noted that when an animal-contaminant-free serum replacement is used to culture human cells, then the serum replacement is referred to as being "xeno-free".

The term "xeno" is a prefix based on the Greek word "Xenos", i.e., a stranger. As used herein the phrase "xeno-free" refers to being devoid of any components/contaminants which are derived from a xenos (i.e., not the same, a foreigner) species.

For example, a xeno-free serum replacement for use with human cells (i.e., an animal contaminant-free serum replacement) can include a combination of insulin, transferrin and selenium. Additionally or alternatively, a xeno-free serum replacement can include human or recombinantly produced albumin, transferrin and insulin.

Non-limiting examples of commercially available xeno-free serum replacement compositions include the premix of ITS (Insulin, Transferrin and Selenium) available from Invitrogen corporation (ITS, Invitrogen, Catalogue No. 51500-056); Serum replacement 3 (SR3; Sigma, Catalogue No. 52640) which includes human serum albumin, human transferring and human recombinant insulin and does not contain growth factors, steroid hormones, glucocorticoids, cell adhesion factors, detectable Ig and mitogens; Knock-Out™ SR XenoFree [Catalogue numbers A10992-01, A10992-02, part Nos. 12618-012 or 12618-013, Invitrogen GIBCO] which contains only human-derived or human recombinant proteins.

According to some embodiments of the invention, the ITS (Invitrogen corporation) or SR3 (Sigma) xeno-free serum replacement formulations are diluted in a 1 to 100 ratio in order to reach a ×1 working concentration.

According to some embodiments of the invention, the concentration of the serum replacement [e.g., KnockOut™ SR XenoFree (Invitrogen)] in the culture medium is in the range of from about 1% [volume/volume (v/v)] to about 50% (v/v), e.g., from about 5% (v/v) to about 40% (v/v), e.g., from about 5% (v/v) to about 30% (v/v), e.g., from about 10% (v/v) to about 30% (v/v), e.g., from about 10% (v/v) to about 25% (v/v), e.g., from about 10% (v/v) to about 20% (v/v), e.g., about 10% (v/v), e.g., about 15% (v/v), e.g., about 20% (v/v), e.g., about 30% (v/v).

According to some embodiments of the invention the culture medium is capable of maintaining the pluripotent stem cell in a proliferative, pluripotent and undifferentiated state for at least 5 passages, at least 10 passages, at least 15 passages, at least 20 passages, at least 25 passages, at least 30 passages, at least 35 passages, at least 40 passages, at least 45 passages, at least 50 passages (e.g., at least 25, 50, 75, 100, or 250 days in culture).

According to some embodiments of the invention the culture medium is capable of expanding the pluripotent stem cells in an undifferentiated state.

For example, as described in Example 1 of the Examples section which follows, the hESCs or human iPS cells could be maintained in the undifferentiated state for at least 20 passages on a two-dimensional culture system, or for at least 50 passages on a three-dimensional culture system when cultured in suspension. Given that each passage occurs every 5-7 days (e.g., 144 hours), and an observed doubling time of about 25-36 hours, a single hESC or human iPS cell cultured under these conditions could be expanded to give rise to $2^4$-$2^5$ cells (within 6 days). It should be noted that when cultured in a controlled bioreactor, the expansion capacity of the pluripotent stem cells increases to about 64 fold within 5 days. Thus, within a month of culturing (i.e., 720 hours), a single pluripotent stem cells can be expanded up to $2^{20}$ ($1 \times 10^6$) hESCs or human iPS cells.

The present inventors have uncovered that the combination of growth factors interleukin 11 (IL11) and Ciliary Neurotrophic Factor (CNTF); or interleukin 11 (IL11) and oncostatin can be used to support the growth and expansion of pluripotent stem cells in a proliferative, undifferentiated, pluripotent state.

According to an aspect of some embodiments of the invention, there is provided a culture medium comprising interleukin 11 (IL11) and Ciliary Neurotrophic Factor (CNTF); or interleukin 11 and oncostatin.

As used herein the term "interleukin 11" refers to a protein member of the gp130 family of cytokines, also known as AGIF and IL-11. Interleukin 11 [e.g., the human IL-11 polypeptide GenBank Accession No. NP_000632.1 (SEQ ID NO:32); human IL-11 polynucleotide GenBank Accession No. NM_000641.2 (SEQ ID NO:33)] can be obtained from various commercial sources such as R&D Systems or PeproTech.

As used herein the term "Ciliary Neurotrophic Factor" (also known as HCNTF; CNTF) refers to a polypeptide hormone whose actions appear to be restricted to the nervous system where it promotes neurotransmitter synthesis and neurite outgrowth in certain neuronal populations. The protein is a potent survival factor for neurons and oligodendrocytes and may be relevant in reducing tissue destruction during inflammatory attacks. CNTF [e.g., the human CNTF polypeptide GenBank Accession No. NP_000605.1 (SEQ ID NO:34); human CNTF polynucleotide GenBank Accession No. NM_000614 (SEQ ID NO:35)] can be obtained from various commercial sources such as R&D Systems or PeproTech.

As used herein the term "oncostatin" (also known as OSM oncostatin M, OSM) refers to a polypeptide member of a cytokine family that includes leukemia-inhibitory factor, granulocyte colony-stimulating factor, and interleukin 6. Oncostatin [e.g., the human oncostatin polypeptide GenBank Accession NO. NP_065391.1 (SEQ ID NO:36, or P13725 (SEQ ID NO:37); human polynucleotide GenBank Accession No. NM_020530.3 (SEQ ID NO:38)] can be obtained from various commercial sources such as R&D Systems (e.g., R&D Systems Catalogue Number 295-OM-010).

According to some embodiments of the invention, the culture medium is devoid of a Glycogen Synthase Kinase 3 (GSK3) inhibitor.

Non-limiting examples of GSK3 inhibitors include inhibitors of GSK-alpha or GSK-beta such as CHIR 98014, CHIR 99021, AR-AO144-18, SB216763 and SB415286. Examples of GSK3 inhibitors are described in Bennett C, et al, J. Biological Chemistry, vol. 277, no. 34, Aug. 23, 2002, pp 30998-31004; and in Ring D B, et al, Diabetes, vol. 52, March 2003, pp 588-595, each of which is fully incorporated herein by reference.

According to some embodiments of the invention, the IL11 is provided at a concentration of at least about 0.1 ng/ml and no more than about 10 ng/ml, e.g., at a concentration of at least about 0.2 ng/ml, e.g., at least about 0.3 ng/ml, e.g., at least about 0.4 ng/ml, e.g., at least about 0.5 ng/ml, e.g., at least about 0.6 ng/ml, e.g., at least about 0.7 ng/ml, e.g., at least about 0.8 ng/ml, e.g., at least about 0.9 ng/ml, e.g., at least about 1 ng/ml, e.g., about 1 ng/ml.

According to some embodiments of the invention, the IL11 is provided at a concentration of between about 0.5 ng/ml to about 5 ng/ml.

According to some embodiments of the invention, the CNTF is provided at a concentration of at least 0.1 ng/ml and no more than about 10 ng/ml, e.g., at a concentration of at least about 0.2 ng/ml, e.g., at least about 0.3 ng/ml, e.g., at least about 0.4 ng/ml, e.g., at least about 0.5 ng/ml, e.g., at least about 0.6 ng/ml, e.g., at least about 0.7 ng/ml, e.g., at least about 0.8 ng/ml, e.g., at least about 0.9 ng/ml, e.g., at least about 1 ng/ml, e.g., about 1 ng/ml.

According to some embodiments of the invention, the CNTF is provided at a concentration of between about 0.5 ng/ml to about 5 ng/ml.

According to some embodiments of the invention, the oncostatin is provided at a concentration of at least 0.1 ng/ml and no more than about 10 ng/ml, e.g., at a concentration of at least about 0.2 ng/ml, e.g., at least about 0.3 ng/ml, e.g., at least about 0.4 ng/ml, e.g., at least about 0.5 ng/ml, e.g., at least about 0.6 ng/ml, e.g., at least about 0.7 ng/ml, e.g., at least about 0.8 ng/ml, e.g., at least about 0.9 ng/ml, e.g., at least about 1 ng/ml, e.g., about 1 ng/ml.

According to some embodiments of the invention, the oncostatin is provided at a concentration of between about 0.5 ng/ml to about 5 ng/ml.

According to some embodiments of the invention, the medium which comprises IL11 and CNTF; or IL11 and oncostatin further comprises serum replacement (e.g., an animal contaminant-free serum replacement) at a concentration between about 10% to about 20%, e.g., about 15%.

According to some embodiments of the invention, the culture medium which comprises IL11 and CNTF; or IL11 and oncostatin further comprises basic fibroblast growth factor (bFGF).

Basic fibroblast growth factor (also known as bFGF, FGF2 or FGF-β) is a member of the fibroblast growth factor family. BFGF [(e.g., human bFGF polypeptide GenBank Accession No. NP_001997.5 (SEQ ID NO:39); human bFGF polynucleotide GenBank Accession No. NM_002006.4 (SEQ ID NO:40) can be obtained from various commercial sources such as Cell Sciences®, Canton, MA, USA (e.g., Catalogue numbers CRF001A and CRF001B), Invitrogen Corporation products, Grand Island NY, USA (e.g., Catalogue numbers: PHG0261, PHG0263, PHG0266 and PHG0264), ProSpec-Tany TechnoGene Ltd. Rehovot, Israel (e.g., Catalogue number: CYT-218), and Sigma, St Louis, MO, USA (e.g., catalogue number: F0291).

The concentration of bFGF in the culture medium which comprises IL11 and CNTF; or IL11 and oncostatin can be at least about 4 ng/ml and no more than 100 ng/ml, e.g., at least about 5 ng/ml, e.g., at least about 6 ng/ml, e.g., at least about 7 ng/ml, e.g., at least about 8 ng/ml, e.g., at least about 9 ng/ml, e.g., at least about 10 ng/ml.

Non-limiting examples of culture media which comprise the IL11 and CNTF include the ILCNTF, NILCNTF media described in the Examples section which follows, which were shown capable of supporting the growth of hESCs and iPS cells in a proliferative, pluripotent and undifferentiated state for at least 12 passages in a two-dimensional culture system and for at least 10 in a suspension culture.

The present inventors have uncovered that the IL6RIL6 chimera can be used in culture media which are completely devoid of animal contaminants in order to support the growth of human pluripotent stem cells in an undifferentiated state.

Thus, according to an aspect of some embodiments of the invention there is provided a culture medium comprising an animal contaminant-free serum replacement and an IL6RIL6 chimera.

As used herein the phrase "IL6RIL6 chimera" refers to a chimeric polypeptide which comprises the soluble portion of interleukin-6 receptor [IL-6-R, e.g., the human IL-6-R as set forth by GenBank Accession No. AAH89410; SEQ ID NO:41; e.g., a portion of the soluble IL6 receptors as set forth by amino acids 112-355 (SEQ ID NO:42) of GenBank Accession No. AAH89410] and the interleukin-6 (IL6; e.g., human IL-6 as set forth by GenBank Accession No. CAG29292; SEQ ID NO:43) or a biologically active fraction thereof (e.g., a receptor binding domain).

It should be noted that when constructing the IL6RIL6 chimera the two functional portions (i.e., the IL6 and its receptor) can be directly fused (e.g., attached or translationally fused, i.e., encoded by a single open reading frame) to each other or conjugated (attached or translationally fused) via a suitable linker (e.g., a polypeptide linker). According to some embodiments of the invention, the IL6RIL6 chimeric polypeptide exhibits a similar amount and pattern of glycosylation as the naturally occurring IL6 and IL6 receptor. For example, a suitable IL6RIL6 chimera is as set forth in SEQ ID NO:19 and in FIG. 11 of WO 99/02552 to Revel M., et al., which is fully incorporated herein by reference.

It should be noted that once the serum replacement is completely devoid of animal contaminants, the additional culture medium ingredients can be also selected devoid of animal contaminants (e.g., synthetic, recombinant or purified from human sources) such that the entire culture medium is devoid of animal contaminant and can be used as a xeno-free medium for culturing human pluripotent stem cells, suitable for clinical/therapeutic purposes.

The present inventors have uncovered that the IL6RIL6 chimera can be provided at either a high concentration, i.e., between 50-150 ng/ml or at a low concentration, i.e., between 50-150 pg/ml while still maintaining the ability of the medium to support the growth of pluripotent stem cells in an undifferentiated state.

According to some embodiments of the invention, the concentration of the IL6RIL6 chimera is at least about 50 ng/ml and no more than about 350 ng/ml, e.g., between about 50-200 ng/ml, e.g., is in the range from about 55 ng/ml to about 195 ng/ml, e.g., from about 60 ng/ml to about 190 ng/ml, e.g., from about 65 ng/ml to about 185 ng/ml, e.g., from about 70 ng/ml to about 180 ng/ml, e.g., from about 75 ng/ml to about 175 ng/ml, e.g., from about 80 ng/ml to about 170 ng/ml, e.g., from about 85 ng/ml to about 165 ng/ml, e.g., from about 90 ng/ml to about 150 ng/ml, e.g., from about 90 ng/ml to about 140 ng/ml, e.g., from about 90 ng/ml to about 130 ng/ml, e.g., from about 90 ng/ml to about 120 ng/ml, e.g., from about 90 ng/ml to about 110 ng/ml, e.g., from about 95 ng/ml to about 105 ng/ml, e.g., from about 98 ng/ml to about 102 ng/ml, e.g., about 100 ng/ml of the IL6RIL6 chimera.

Non-limiting examples of animal contaminant-free culture media which comprise between about 50-200 ng/ml of the IL6RIL6 chimera include the cmTeSR2, NCMrb100F, NCM100F, cmV5b, and cmHA13.

According to some embodiments of the invention, the concentration of the IL6RIL6 chimera is at least 50 pg/ml and no more than about 150 pg/ml, e.g., between about 50-200 pg/ml, e.g., in the range from about 55 pg/ml to about 195 pg/ml, e.g., from about 60 pg/ml to about 190 pg/ml, e.g., from about 65 pg/ml to about 185 pg/ml, e.g., from about 70 pg/ml to about 180 pg/ml, e.g., from about 75 pg/ml to about 175 pg/ml, e.g., from about 80 pg/ml to about 170 pg/ml, e.g., from about 85 pg/ml to about 165 pg/ml, e.g., from about 90 pg/ml to about 150 pg/ml, e.g., from about 90 pg/ml to about 140 pg/ml, e.g., from about 90 pg/ml to about 130 pg/ml, e.g., from about 90 pg/ml to about 120 pg/ml, e.g., from about 90 pg/ml to about 110 pg/ml, e.g., from about 95 pg/ml to about 105 pg/ml, e.g., from about 98 pg/ml to about 102 pg/ml, e.g., about 100 pg/ml of the IL6RIL6 chimera.

Non-limiting examples of xeno-free culture media which comprise between about 50-200 pg/ml of the IL6RIL6 chimera include the cmTeSR2p, NCMrb100Fp, NCM100Fp, cmV5bp, and cmHA13p.

For example the IL6RIL6 chimera can be added to the TeSR™2 Animal Protein-Free Medium (StemCell Technologies, Catalog #05860/05880) culture medium. The TeSR™2 medium is a complete, animal protein-free, serum-free, defined formulation which contains recombinant human basic fibroblast growth factor (rhbFGF) and recombinant human transforming growth factor β (rhTGFβ).

According to some embodiments of the invention, the animal contaminant-free culture medium which comprises the IL6RIL6 chimera further comprises bFGF.

BFGF can be provided at either a low concentration (e.g., between about 4-20 ng/ml) or at a high concentration (e.g., between 50-150 ng/ml).

According to some embodiments of the invention, the culture medium which comprises an animal contaminant-free serum replacement and the IL6RIL6 chimera, further comprises bFGF at a concentration of at least about 4 ng/ml, e.g., at least about 5 ng/ml, e.g., at least about 6 ng/ml, e.g., at least about 7 ng/ml, e.g., at least about 8 ng/ml, e.g., at least about 9 ng/ml, e.g., at least about 10 ng/ml, e.g., at least about 15 ng/ml, e.g., at least about 20 ng/ml. Non-limiting examples of such culture media include the cmV5b, NCM100Fp, NCM100F and cmV5bp.

According to some embodiments of the invention, the culture medium which comprises an animal contaminant-free serum replacement and the IL6RIL6 chimera, further comprises bFGF at a concentration of at least about 50 ng/ml to about 1 μg, e.g., from about 60 ng/ml to about 1 μg/ml, e.g., from about 70 ng/ml to about 500 ng/ml, e.g., from about 80 ng/ml to about 500 ng/ml, e.g., from about 90 ng/ml to about 250 ng/ml, e.g., from about 50 ng/ml to about 200 ng/ml, e.g., from about 50 ng/ml to about 150 ng/ml, e.g., about 60 ng/ml, e.g., about 70 ng/ml, e.g., about 80 ng/ml, e.g., about 90 ng/ml, e.g., about 50 ng/ml, e.g., about 60 ng/ml, e.g., about 70 ng/ml, e.g., about 80 ng/ml, e.g., about 100 ng/ml, e.g., about 110 ng/ml, e.g., about 120 ng/ml, e.g., about 130 ng/ml, e.g., about 140 ng/ml, e.g., about 150 ng/ml. Non-limiting examples of such culture media include the NCMrb100F and NCMrb100Fp, cmTeSR2, and cmTeSR2p.

According to some embodiments of the invention, the animal contaminant-free culture medium which comprises the IL6RIL6 chimera further comprising ascorbic acid.

Ascorbic acid (also known as vitamin C) is a sugar acid ($C_6H_8O_6$; molecular weight 176.12 grams/mole) with anti-oxidant properties. The ascorbic acid used by the culture medium of some embodiments of the invention can be a natural ascorbic acid, a synthetic ascorbic acid, an ascorbic acid salt (e.g., sodium ascorbate, calcium ascorbate, potassium ascorbate), an ester form of ascorbic acid (e.g., ascorbyl palmitate, ascorbyl stearate), a functional derivative thereof (a molecule derived from ascorbic acid which exhibits the same activity/function when used in the culture medium of the invention), or an analogue thereof (e.g., a functional equivalent of ascorbic acid which exhibits an activity analogous to that observed for ascorbic acid when used in the culture medium of the invention). Non-limiting examples of ascorbic acid formulations which can be used in the culture medium of some embodiments of the invention include L-ascorbic acid and ascorbic acid 3-phosphate.

Ascorbic acid can be obtained from various manufacturers such as Sigma, St Louis, MO, USA (e.g., Catalogue numbers: A2218, A5960, A7506, A0278, A4403, A4544, A2174, A2343, 95209, 33034, 05878, 95210, 95212, 47863, 01-6730, 01-6739, 255564, A92902, W210901).

According to some embodiments of the invention, the concentration of ascorbic acid in the animal contaminant-free culture medium which comprises the IL6RIL6 chimera is between about 25-200 μg/ml, e.g., between 25-150 μg/ml, e.g., between 30-150 μg/ml, e.g., between about 40-120 μg/ml, e.g., between about 40-100 μg/ml, e.g., between about 40-80 μg/ml, e.g., between about 40-60 μg/ml, e.g., about 50 μg/ml. Non-limiting examples of such culture media include the cmHA13p and cmHA13 media described in the Examples section which follows.

According to some embodiments of the invention, the animal contaminant-free culture medium which comprises the IL6RIL6 chimera further comprises a transforming growth factor beta (TGFβ) isoform.

As used herein the phrase "transforming growth factor beta (TGFβ)" refers to any isoform of the transforming growth factor beta (β), which functions through the same receptor signaling system in the control of proliferation, differentiation, and other functions in many cell types. TGFβ acts in inducing transformation and also acts as a negative autocrine growth factor.

According to some embodiments of the invention the term TGFβ refers to TGFβ₁ [Human TGFβ1 mRNA sequence GenBank Accession NO. NM_000660.4 (SEQ ID NO:44), polypeptide sequence GenBank Accession No. NP_000651.3 (SEQ ID NO:45)], TGFβ₂ [human TGFβ2 mRNA sequence GenBank Accession NO. NM_001135599.1 isoform 1 (SEQ ID NO:46), or GenBank Accession NO. NM_003238.2 isoform 2 (SEQ ID NO:47); polypeptide sequence GenBank Accession No. NP_001129071.1 isoform 2 (SEQ ID NO:48) or GenBank Accession NO. NP_003229.1 isoform 2 (SEQ ID NO:49) or TGFβ₃ [human TGFβ3 mRNA sequence GenBank Accession NO. NM_003239.2 (SEQ ID NO:50), polypeptide sequence GenBank Accession No. NP_003230.1 (SEQ ID NO:51)]. The TGFβ isoforms can be obtained from various commercial sources such as R&D Systems Minneapolis MN, USA, and Sigma, St Louis, MO, USA.

According to some embodiments of the invention, the TGFβ which is included in the culture medium is TGFβ1.

According to some embodiments of the invention, the concentration of TGFβ₁ in the culture medium is in the range of about 0.05 ng/ml to about 1 µg/ml, e.g., from 0.1 ng/ml to about 1 µg/ml, e.g., from about of about 0.5 ng/ml to about 100 ng/ml.

According to some embodiments of the invention, the concentration of TGFβ1 in the culture medium is at least about 0.5 ng/ml, e.g., at least about 0.6 ng/ml, e.g., at least about 0.8 ng/ml, e.g., at least about 0.9 ng/ml, e.g., at least about 1 ng/ml, e.g., at least about 1.2 ng/ml, e.g., at least about 1.4 ng/ml, e.g., at least about 1.6 ng/ml, e.g., at least about 1.8 ng/ml, e.g., about 2 ng/ml.

Non-limiting examples of an animal contaminant-free culture medium which comprises the IL6RIL6 chimera, bFGF and TGFβ1 is the cmV5b, cmV5bp, cmTeSR2 and cmTeSR2p which are described in the Examples section which follows.

According to some embodiments of the invention, the TGFβ which is included in the culture medium is TGFβ3.

According to some embodiments of the invention, the concentration of TGFβ₃ in the culture medium is in the range of about 0.05 ng/ml to about 1 µg/ml, e.g., from 0.1 ng/ml to about 1 µg/ml, e.g., from about of about 0.5 ng/ml to about 100 ng/ml.

According to some embodiments of the invention, the concentration of TGFβ₃ in the culture medium is at least about 0.5 ng/ml, e.g., at least about 0.6 ng/ml, e.g., at least about 0.8 ng/ml, e.g., at least about 0.9 ng/ml, e.g., at least about 1 ng/ml, e.g., at least about 1.2 ng/ml, e.g., at least about 1.4 ng/ml, e.g., at least about 1.6 ng/ml, e.g., at least about 1.8 ng/ml, e.g., about 2 ng/ml.

According to an aspect of some embodiments of the invention, there is provided culture medium comprises bFGF at a concentration of at least about 50 ng/ml (e.g., between 50-200 ng/ml) and an IL6RIL6 chimera at either a high concentration (e.g., between 50-200 ng/ml) or low concentration (e.g., between 50-200 pg/ml). Non-limiting examples of such culture media include the CMrb100F, CMrb100Fp, NCMrb100F and NCMrb100Fp culture media which were shown capable of maintaining hESCs and iPS cells in a proliferative, pluripotent and undifferentiated state for at least 5 passages in a two-dimensional culture system, and for at least 15 passages in a three-dimensional culture system.

The present inventors have uncovered that a culture medium which comprises high concentrations of a soluble interleukin 6 receptor (sIL6R) and interleukin 6 (IL6) can be used to support the growth of pluripotent stem cells in a proliferative, undifferentiated and pluripotent state.

Thus, according to an aspect of some embodiments of the invention there is provided a culture medium which comprises sIL6R and IL6, wherein a concentration of the sIL6R is at least about 5 ng/ml, and wherein a concentration of the IL6 is at least about 3 ng/ml.

According to some embodiments of the invention, the concentration of sIL6 is at least about 5 ng/ml, e.g., at least about 6 ng/ml, at least about 7 ng/ml, at least about 8 ng/ml, at least about 9 ng/ml, at least about 10 ng/ml, at least about 15 ng/ml, at least about 20 ng/ml, at least about 25 ng/ml, e.g., in the range of between 10 ng/ml to between 50 ng/ml, e.g., between 20-40 ng/ml, e.g., about 25 ng/ml.

According to some embodiments of the invention, the concentration of IL6 is at least about 3 ng/ml, e.g., at least about 4 ng/ml, at least about 5 ng/ml, at least about 6 ng/ml, at least about 7 ng/ml, at least about 8 ng/ml, at least about 9 ng/ml, at least about 10 ng/ml, at least about 15 ng/ml, at least about 20 ng/ml, at least about 25 ng/ml, e.g., in the range of between 10 ng/ml to between 50 ng/ml, e.g., between 20-40 ng/ml, e.g., about 25 ng/ml.

According to some embodiments of the invention, the medium which comprises sIL6 and IL6 further includes bFGF at a concentration of at least about 4 ng/ml and no more than 100 ng/ml, e.g., at least about 5 ng/ml, e.g., at least about 6 ng/ml, e.g., at least about 7 ng/ml, e.g., at least about 8 ng/ml, e.g., at least about 9 ng/ml, e.g., at least about 10 ng/ml.

According to some embodiments of the invention, the medium which comprises sIL6 and IL6 further includes serum replacement at a concentration of between 10-30%, e.g., about 15%. It should be noted that the concentration of serum replacement can vary depending on the type of serum replacement used.

Non-limiting examples of culture media which comprise sIL6 and IL6 include the yFIL25 medium described in the Examples section which follows.

According to some embodiments of the invention, the culture medium further comprises insulin. Insulin can be obtained from Invitrogen Carlsbad CA, Sigma, St Louis, MO, USA.

The concentration of insulin in the culture medium can be between 0.0001-1 grams/litter (e.g., between about 0.001 µg/µl to about 0.1 µg/µl, e.g., between about 0.005 µg/µl to about 0.05 µg/µl, e.g., about 0.01 µg/µl).

According to some embodiments of the invention, the culture medium further comprises albumin. Albumin can be obtained from Sigma, St Louis, MO, USA.

The concentration of albumin in the culture medium can be between about 0.1% to about 5%.

According to some embodiments of the invention, the culture medium further comprises transferrin. Transferrin can be obtained from Invitrogen Carlsbad CA, Sigma, St Louis, MO, USA.

According to some embodiments of the invention, the culture medium further comprises a lipid mixture.

As used herein the phrase "lipid mixture" refers to a defined (e.g., chemically defined) lipid composition needed for culturing the pluripotent stem cells. It should be noted that the lipid mixture is usually added to a culture medium which is devoid of serum or serum replacement and thus substitutes the lipids which are usually added to formulations of serum or serum replacement.

A non-limiting example of a commercially available lipid mixture, which can be used in the culture medium of some embodiments of the invention, include the Chemically Define Lipid Concentrate available from Invitrogen (Catalogue No. 11905-031).

According to some embodiments of the invention, the concentration of the lipid mixture in the culture medium is from about 0.5% [volume/volume (v/v)] to about 3% v/v, e.g., from about 0.5% v/v to about 2% v/v, e.g., from about 0.5% v/v to about 1% v/v, e.g., about 1% v/v.

According to some embodiments of the invention, the culture medium further comprises sodium bicarbonate. Sodium bicarbonate can be obtained from Biological Industries, Beit HaEmek, Israel.

According to some embodiments of the invention, the concentration of sodium bicarbonate in the culture medium is from about 5% to about 10%, e.g., from about 6% to about 9%, e.g., from about 7% to about 8%, e.g., about 7.5%.

According to some embodiments of the invention, the culture medium further comprising L-glutamine. The concentration of L-glutamine in the culture medium can be from about 0.5 millimolar (mM) to about 10 mM, e.g., about 1-5 mM, e.g., 2 mM.

According to some embodiments of the invention, the culture medium further comprising non-essential amino acid. Non-essential amino acids can be obtained as a stock of 10 mM from various suppliers such as Invitrogen Corporation products, Grand Island NY, USA. The concentration of the non-essential amino acid in the culture medium can be from about 0.1-10%, e.g., about 0.2-5%, e.g., about 0.5-2%, e.g., about 1%.

According to some embodiments of the invention, the culture medium further comprising a reducing agent such as beta-mercaptoethanol (β-mercaptoethanol), at a concentration range between about 0.01-1 mM, e.g., 0.1 mM.

As mentioned, any of the proteinaceous factors used in the culture medium of the present invention (e.g., the interleukin 11, CNTF, oncostatin, bFGF, IL6RIL6 chimera, TGFβ1, TGFβ3, insulin, albumin, transferrin) can be recombinantly expressed or biochemically synthesized. In addition, naturally occurring proteinaceous factors such as bFGF and TGFβ can be purified from biological samples (e.g., from human serum, cell cultures) using methods well known in the art. It should be noted that for the preparation of an animal contaminant-free culture medium the proteinaceous factor is preferably purified from a human source or is recombinantly expressed.

Biochemical synthesis of the proteinaceous factors of the present invention (e.g., the IL6RIL6 chimera) can be performed using standard solid phase techniques. These methods include exclusive solid phase synthesis, partial solid phase synthesis methods, fragment condensation and classical solution synthesis.

Recombinant expression of the proteinaceous factors of the present invention can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680, Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463. Specifically, the IL6RIL6 chimera can be generated as described in PCT publication WO 99/02552 to Revel M., et al. and Chebath J, et al., 1997, which are fully incorporated herein by reference.

Thus, according to an aspect of some embodiments of the invention there is provided a cell culture which comprises the pluripotent stem cells of some embodiments of the invention (e.g., the hESCs or iPSCs which are cultured in suspension as single cells devoid of cell clumps; the hESCs or iPSCs which are cultured in suspension as cell clumps; the pluripotent stem cells cultured on 2-dimensional culture systems; and the like) and the culture medium of some embodiments of the invention.

According to some embodiments of the invention cell culture is feeder cells free (devoid of feeder cell support).

The phrase "feeder cell support" as used herein refers to the ability of a feeder cell (e.g., fibroblasts) to maintain pluripotent stem cells in a proliferative and undifferentiated state when the pluripotent stem cells are co-cultured on the feeder cells or when the pluripotent stem cells are cultured on a matrix (e.g., an extracellular matrix, a synthetic matrix) in the presence of a conditioned medium generated by the feeder cells. The support of the feeder cells depends on the structure of the feeder cells while in culture (e.g., the three dimensional matrix formed by culturing the feeder cells in a tissue culture plate), function of the feeder cells (e.g., the secretion of growth factors, nutrients and hormones by the feeder cells, the growth rate of the feeder cells, the expansion ability of the feeder cells before senescence) and/or the attachment of the pluripotent stem cells to the feeder cell layer(s).

The phrase "absence of feeder cell support" as used herein refers to a culture medium and/or a cell culture being devoid of feeder cells and/or a conditioned medium generated thereby.

According to some embodiments of the invention the pluripotent stem cells which are included in the cell culture of some embodiments of the invention exhibit a stable karyotype (chromosomal stability) during the culturing period, e.g., for at least 2 passages, e.g., at least 4 passages, e.g., at least 8 passages, e.g., at least 15 passages, e.g., at least 20 passages, e.g., at least 25 passages, e.g., at least 30 passages, e.g., at least 35 passages, e.g., at least 40 passages, e.g., at least 45 passages, e.g., at least 50 passages.

According to some embodiments of the invention, the cell culture of the invention exhibits a doubling time of at least 20 hours, e.g., a doubling time which is between 20 to 40 hours (e.g., about 36 hours), thus representing a non-tumorigenic, genetically stable pluripotent stem cells (e.g., hESCs and iPS cells).

According to some embodiments of the invention, the cell culture of the invention is characterized by at least 40%, at least 50%, at least 60%, e.g., at least 70%, e.g., at least 80%, e.g., at least 85%, e.g., at least 90%, e.g., at least 95% of undifferentiated pluripotent stem cells.

The cell culture of some embodiments of the invention comprises at least 1000 pluripotent and undifferentiated stem cells per milliliter (ml) of culture medium. It should be noted that for several applications such as for single cell cloning of the pluripotent stem cells, the concentration of cells can be about 1 cell per 100-200 μl of medium, each cell is placed (seeded) in a separate dish, preferably a dish which is not coated (e.g., a non-culture treated dish), to prevent adhesion of the cell to the dish.

The differentiation or undifferentiation state of the pluripotent stem cells cultured on 2-D, or in suspension as cell clumps can be determined using known methods (e.g., as described in Thomson et al, 1998). For example, the differentiation state can be determined using various approaches including, for example, morphological evaluation (e.g., as shown in FIGS. 1A-1C and 3A-3C) and/or detection of the expression pattern of typical markers of the undifferentiated state using immunological techniques such as flow cytometry for membrane-bound markers, immunohistochemistry or immunofluorescence for extracellular and intracellular markers and enzymatic immunoassay, for secreted molecular markers. For example, immunofluorescence employed on hESCs or human iPS cells cultured in the culture medium according to some embodiments of the invention revealed the expression of Oct4, stage-specific embryonic antigen (SSEA) 4, the tumor-rejecting antigen (TRA)-1-60 and TRA-1-81 (e.g., FIGS. 2A-2D). Additionally, the level of transcripts of specific undifferentiation markers (e.g., Oct 4, Nanog, Sox2, Rex1, Cx43, FGF4) or differentiation markers (e.g., albumin, glucagons, α-cardiac actin, β-globulin, Flk1, AC133 and neurofilament) can be detected using RNA-based techniques such as RT-PCR analysis and/or cDNA microarray analysis.

Determination of ES cell differentiation can also be effected via measurements of alkaline phosphatase activity. Undifferentiated human ES cells have alkaline phosphatase activity which can be detected by fixing the cells with 4% paraformaldehyde and developing with the Vector Red substrate kit according to manufacturer's instructions (Vector Laboratories, Burlingame, California, USA).

According to some embodiments of the invention, the cell culture comprises pluripotent stem cells and a xeno-free medium, thus the medium does not contain any contaminants from a species other than that of the pluripotent stem cells. For example, when the cell culture comprises human pluripotent stem cells then the medium is devoid of animal contaminants. Similarly, when the cell culture comprises primate pluripotent stem cells (e.g., monkey) the culture medium is devoid of other animals or human contaminants.

According to an aspect of some embodiments of the invention, there is provided a method of expanding and maintaining pluripotent stem cells in a pluripotent and undifferentiated state.

According to some embodiments of the invention, the method of expanding and maintaining pluripotent stem cells in an undifferentiated state is effected by culturing the pluripotent stem cells in any of the novel culture media of the invention (described herein).

According to some embodiments of the invention, expanding and maintaining the pluripotent stem cells in the undifferentiated state is effected in a suspension culture.

According to some embodiments of the invention, culturing of the pluripotent stem cells in a suspension culture is effected in a serum-free, and feeder cell-free culture medium.

Since large clusters of pluripotent stem cells may cause cell differentiation, measures are taken to avoid large pluripotent stem cells aggregates. According to some embodiments of the invention, the formed pluripotent stem cells clumps are dissociated every 5-7 days and the single cells or small clumps of cells are either split into additional culture vessels (i.e., passaged) or remained in the same culture vessel yet with additional culture medium.

According to some embodiments of the invention, culturing is effected under conditions which enable expansion of the pluripotent stem cells as single cells.

As described hereinabove, passaging of the pluripotent stem cells can be effected using mechanical dissociation of cell clumps.

Additionally and/or alternatively, passaging of pluripotent stem cells in a suspension culture can be performed using an enzymatic digestion with or without a subsequent mechanical dissociation.

Enzymatic digestion of pluripotent stem cells clump(s) can be performed by subjecting the clump(s) to an enzyme such as type IV Collagenase (Worthington biochemical corporation, Lakewood, NJ, USA) and/or Dispase (Invitrogen Corporation products, Grand Island NY, USA). The time of incubation with the enzyme depends on the size of cell clumps present in the suspension culture. Typically, when pluripotent stem cells cell clumps are dissociated every 5-7 days while in the suspension culture, incubation of 20-60 minutes with 1.5 mg/ml type IV Collagenase results in small cell clumps which can be further cultured in the undifferentiated state. Alternatively, pluripotent stem cells clumps can be subjected to incubation of about 25 minutes with 1.5 mg/ml type IV Collagenase followed by five minutes incubation with 1 mg/ml Dispase. It should be noted that passaging of human ESCs with trypsin may result in chromosomal instability and abnormalities (see for example, Mitalipova M M., et al., Nature Biotechnology, 23: 19-20, 2005 and Cowan C A et al., N. Engl. J. of Med. 350: 1353-1356, 2004). According to some embodiments of the invention, passaging hESC or iPS cell with trypsin should be avoided.

According to some embodiments of the invention, following enzymatic or mechanical dissociation of the large cell clumps, the dissociated pluripotent stem cells clumps are further broken to small clumps using 200 µl Gilson pipette tips (e.g., by pipetting up and down the cells).

According to some embodiments of the invention, the method of expanding and maintaining the pluripotent stem cells in the undifferentiated state is effected in a two-dimensional culture system.

The two-dimensional culture system may comprise a matrix or feeder-cell layer.

For example, culturing on a two-dimensional culture system can be performed by plating the pluripotent stem cells onto a matrix or a feeder cell layer in a cell density which promotes cell survival and proliferation but limits differentiation. Typically, a plating density of between about 15,000 cells/cm$^2$ and about 3,000,000 cells/cm$^2$ is used.

It will be appreciated that although single-cell suspensions of pluripotent stem cells are usually seeded, small clusters may also be used. To this end, enzymatic digestion (such as with type IV collagenase) utilized for cluster disruption (see "General Materials and Experimental Methods" in the Examples section which follows) is terminated before stem cells become completely dispersed and the cells are triturated with a pipette such that clumps (i.e., 10-200 cells) are formed. However, measures are taken to avoid large clusters which may cause cell differentiation.

According to some embodiments of the invention, the culture system comprises a matrix and the culture medium of some embodiments of the invention.

As used herein, the term "matrix" refers to any substance to which the pluripotent stem cells can adhere and which therefore can substitute the cell attachment function of feeder cells. Such a matrix typically contains extracellular components to which the pluripotent stem cells can attach and thus it provides a suitable culture substrate.

According to some embodiments of the invention the matrix comprises an extracellular matrix.

The extracellular matrix can be composed of components derived from basement membrane or extracellular matrix components that form part of adhesion molecule receptor-ligand couplings. MATRIGEL® (Becton Dickinson, USA) is one example of a commercially available matrix which is suitable for use with the present invention. MATRIGEL® is a soluble preparation from Engelbreth-Holm-Swarm tumor cells that gels at room temperature to form a reconstituted basement membrane; MATRIGEL® is also available as a growth factor reduced preparation. Other extracellular matrix components and component mixtures which are suitable for use with the present invention include foreskin matrix, laminin matrix, fibronectin matrix, proteoglycan matrix, entactin matrix, heparan sulfate matrix, collagen matrix and the like, alone or in various combinations thereof.

According to some embodiments of the invention the matrix is devoid of animal contaminant (a xeno-free matrix for culturing human pluripotent stem cells).

In cases where complete animal-free culturing conditions are desired, the matrix is preferably derived from a human source or synthesized using recombinant techniques such as described hereinabove. Such matrices include, for example, human-derived fibronectin, recombinant fibronectin, human-derived laminin, foreskin fibroblast matrix or a synthetic fibronectin matrix. Human derived fibronectin can be from plasma fibronectin or cellular fibronectin, both of which can be obtained from Sigma, St. Louis, MO, USA. Human derived laminin and foreskin fibroblast matrix can be obtained from Sigma, St. Louis, MO, USA. A synthetic fibronectin matrix can be obtained from Sigma, St. Louis, MO, USA.

In case a feeder cell layer is desired, human pluripotent stem cells can be cultured on a human foreskin fibroblasts feeder cell layer.

The present inventors have uncovered that pluripotent stem cells can be shipped as living, non-frozen cells and still remain viable, undifferentiated and pluripotent.

According to some embodiments of the invention, the cells remain viable, undifferentiated and pluripotent following shipment (via air or over-sea) which lasts at least 4 days.

The present inventors have uncovered that the novel culture media of the invention can be used to derive new pluripotent stem cell lines.

According to some embodiments of the invention, the pluripotent stem cell line is an embryonic stem cell line, and the method of deriving the embryonic stem cell line is effected by: (a) obtaining an embryonic stem cell from a pre-implantation stage blastocyst, post-implantation stage blastocyst and/or a genital tissue of a fetus; and (b) culturing the embryonic stem cell in the culture medium of some embodiments of the invention, thereby deriving the embryonic stem cell line.

According to some embodiments of the invention, the pluripotent stem cell line is an induced pluripotent stem cell (iPS cell) line, and the method of deriving the iPS cell line is effected by: (a) inducing a somatic cell to a pluripotent stem cell; and (b) culturing the pluripotent stem cell in the culture medium of some embodiments of the invention, thereby deriving the induced pluripotent stem cell line.

Once obtained the ESCs of iPS cells are further cultured in any of the culture media described hereinabove which allow expansion of the pluripotent stem cells in the undifferentiated state, essentially as described hereinabove.

It will be appreciated that an established pluripotent stem cell line (e.g., embryonic stem cell line or induced pluripotent stem cell line) can be subject to freeze/thaw cycles without hampering the proliferative capacity of the cells in the undifferentiated state while preserving their pluripotent capacity. For example, as is shown in FIGS. 6A-6C and described in Example 6 of the Examples section which follows, using serum replacement (from 10% to 95%) and dimethyl sulfoxide (DMSO; from 5% to 10%) hESCs or human iPS cells were successfully frozen and thawed and more than 70% of the cells survived and directly recovered to the suspension culture.

It should be noted that any of the novel culture media described hereinabove can be used to culture, maintain and expand pluripotent, undifferentiated stem cells in a suspension culture as single cells devoid of cell clumps.

According to some embodiments of the invention, the culture conditions for expanding and maintaining pluripotent stem cells in an undifferentiated state in a suspension culture as single cells devoid of cell clumps comprise the culture medium which comprises interleukin 11 (IL11) and Ciliary Neurotrophic Factor (CNTF).

According to some embodiments of the invention, the culture conditions for expanding and maintaining pluripotent stem cells in an undifferentiated state in a suspension culture as single cells devoid of cell clumps comprise the culture medium which comprises basic fibroblast growth factor (bFGF) at a concentration of at least 50 ng/ml and an IL6RIL6 chimera.

According to some embodiments of the invention, the culture conditions for expanding and maintaining pluripotent stem cells in an undifferentiated state in a suspension culture as single cells devoid of cell clumps comprise the culture medium which comprises an animal contaminant-free serum replacement and an IL6RIL6 chimera.

According to some embodiments of the invention, the culture conditions for expanding and maintaining pluripotent stem cells in an undifferentiated state in a suspension culture as single cells devoid of cell clumps comprise the serum-free culture medium which comprises a soluble interleukin 6 receptor (sIL6R) and interleukin 6 (IL6), wherein a concentration of the sIL6R is at least 5 ng/ml, and wherein a concentration of the IL6 is at least 3 ng/ml.

According to some embodiments of the invention, the culture conditions for expanding and maintaining pluripotent stem cells in an undifferentiated state in a suspension culture as single cells devoid of cell clumps comprise the culture medium which comprises interleukin 11 (IL11) and oncostatin.

Following is a non-limiting description of methods for production of differentiated cell lineages from the pluripotent stem cells of some embodiments of the invention.

As described in Example 2 of the Examples section which follows, hESCs and human iPS cells which were expanded and maintained in any of the culture media described hereinabove are pluripotent (i.e., capable of differentiating into all cell types of the three embryonic germ layers, the ectoderm, the endoderm and the mesoderm) as evidenced in vitro (by the formation of EBs) and in vivo (by the formation of teratomas) after a prolonged culture period (e.g., of at least 10 or 30 passages) in the two-dimensional (e.g., feeder-free matrices) or three-dimensional (e.g., static or dynamic suspension cultures) culture systems.

Thus, hESCs or human iPS cells cultured according to the teachings of the present invention can be used as a source for generating differentiated, lineage-specific cells. Such cells can be obtained directly from the pluripotent stem cells by subjecting the ESCs to various differentiation signals (e.g., cytokines, hormones, growth factors) or indirectly, via the formation of embryoid bodies and the subsequent differentiation of cells of the EBs to lineage-specific cells.

Thus, according to an aspect of the some embodiments of the invention there is provided a method of generating embryoid bodies from pluripotent stem cells. The method is effected by (a) culturing the pluripotent stem cells of some embodiments of the invention according to the method of some embodiment of the invention to thereby obtain expanded, undifferentiated pluripotent stem cells; and (b) subjecting the expanded, undifferentiated pluripotent stem cells to culturing conditions suitable for differentiating the stem cells to embryoid bodies, thereby generating the embryoid bodies from the pluripotent stem cells.

As used herein the phrase "embryoid bodies" refers to morphological structures comprised of a population of ESCs, extended blastocyst cells (EBCs), embryonic germ cells (EGCs) and/or induced pluripotent stem cells which have undergone differentiation. EBs formation initiates following the removal of differentiation blocking factors from the pluripotent stem cell cultures. In the first step of EBs formation, the pluripotent stem cells proliferate into small masses of cells which then proceed with differentiation. In the first phase of differentiation, following 1-4 days in culture for either human ESCs or human iPS cells, a layer of endodermal cells is formed on the outer layer of the small mass, resulting in "simple EBs". In the second phase, following 3-20 days post-differentiation, "complex EBs" are formed. Complex EBs are characterized by extensive differentiation of ectodermal and mesodermal cells and derivative tissues.

Thus, the method according to some embodiments of the invention involves the culturing of the pluripotent stem cells of some embodiments of the invention in any of the culture media described hereinabove (e.g., in suspension as cell clumps or as single cells devoid of cell clumps, or in a 2-dimensional culture system) in order to obtain expanded, undifferentiated pluripotent stem cells and then subjecting the expanded, undifferentiated pluripotent stem cells (e.g., ESCs or iPS cells) to culturing conditions suitable for differentiating the pluripotent stem cells to embryoid bodies. Such differentiation-promoting culturing conditions are substantially devoid of differentiation inhibitory factors which are employed when pluripotent stem cells are to be expanded in an undifferentiated state, such as TGFβ1, TGFβ3, ascorbic acid, IL-11, CNTF, oncostatin, bFGF and/or the IL6RIL6 chimera.

For EBs formation, the pluripotent stem cells (ESCs or iPS cells) are removed from their feeder-free-culturing systems or suspension cultures and are transferred to a suspension culture in the presence of a culture medium containing serum or serum replacement and being devoid of differentiation-inhibitory factors. For example, a culture medium suitable for EBs formation may include a basic culture medium (e.g., Ko-DMEM or DMEM/F12) supplemented with 20% FBSd (HyClone, Utah, USA), 1 mM L-glutamine, 0.1 mM β-mercaptoethanol, and 1% non-essential amino acid stock.

Monitoring the formation of EBs is within the capabilities of those skilled in the art and can be effected by morphological evaluations (e.g., histological staining) and determination of expression of differentiation-specific markers [e.g., using immunological techniques or RNA-based analysis (e.g., RT-PCR, cDNA microarray)].

It will be appreciated that in order to obtain lineage-specific cells from the EBs, cells of the EBs can be further subjected to culturing conditions suitable for lineage-specific cells.

According to some embodiments of the invention, for generating lineage-specific cells from the pluripotent stem cells, the method the method further includes step (c) of subjecting cells of the embryoid bodies to culturing conditions suitable for differentiating and/or expanding lineage specific cells; thereby generating the lineage-specific cells from the embryonic stem cells.

As used herein the phrase "culturing conditions suitable for differentiating and/or expanding lineage specific cells" refers to a combination of culture system, e.g., feeder-free matrix or a suspension culture and a culture medium which are suitable for the differentiation and/or expansion of specific cell lineages derived from cells of the EBs. Non-limiting examples of such culturing conditions are further described hereinunder.

According to some embodiments of the invention, the method of this aspect of the invention further includes isolating lineage specific cells following step (b).

As used herein, the phrase "isolating lineage specific cells" refers to the enrichment of a mixed population of cells in a culture with cells predominantly displaying at least one characteristic associated with a specific lineage phenotype. It will be appreciated that all cell lineages are derived from the three embryonic germ layers. Thus, for example, hepatocytes and pancreatic cells are derived from the embryonic endoderm, osseous, cartilaginous, elastic, fibrous connective tissues, myocytes, myocardial cells, bone marrow cells, vascular cells (namely endothelial and smooth muscle cells), and hematopoietic cells are differentiated from embryonic mesoderm and neural, retina and epidermal cells are derived from the embryonic ectoderm.

According to some preferred embodiments of the invention, isolating lineage specific cells is effected by sorting of cells of the EBs via fluorescence activated cell sorter (FACS).

Methods of isolating EB-derived-differentiated cells via FACS analysis are known in the art. According to one method, EBs are disaggregated using a solution of Trypsin and EDTA (0.025% and 0.01%, respectively), washed with 5% fetal bovine serum (FBS) in phosphate buffered saline (PBS) and incubated for 30 min on ice with fluorescently-labeled antibodies directed against cell surface antigens characteristics to a specific cell lineage. For example, endothelial cells are isolated by attaching an antibody directed against the platelet endothelial cell adhesion molecule-1 (PECAM1) such as the fluorescently-labeled PECAM1 antibodies (30884X) available from PharMingen (PharMingen, Becton Dickinson Bio Sciences, San Jose, CA, USA) as described in Levenberg, S. et al., (Endothelial cells derived from human embryonic stem cells. Proc. Natl. Acad. Sci. USA. 2002. 99: 4391-4396). Hematopoietic cells are isolated using fluorescently-labeled antibodies such as CD34-FITC, CD45-PE, CD31-PE, CD38-PE, CD90-FITC, CD117-PE, CD15-FITC, class I-FITC, all of which IgG1 are available from PharMingen, CD133/1-PE (IgG1) (available from Miltenyi Biotec, Auburn, CA), and glycophorin A-PE (IgG1), available from Immunotech (Miami, FL). Live cells (i.e., without fixation) are analyzed on a FACScan (Becton Dickinson Bio Sciences) by using propidium iodide to exclude dead cells with either the PC-LYSIS or the CELL-QUEST software. It will be appreciated that isolated cells can be further enriched using magnetically-labeled second antibodies and magnetic separation columns (MACS, Miltenyi) as described by Kaufman, D. S. et al., (Hematopoietic colony-forming cells derived from human embryonic stem cells. Proc. Natl. Acad. Sci. USA. 2001, 98: 10716-10721).

According to some embodiments of the invention, isolating lineage specific cells is effected by a mechanical separation of cells, tissues and/or tissue-like structures contained within the EBs.

For example, beating cardiomyocytes can be isolated from EBs as disclosed in U.S. Pat. Appl. No. 20030022367 to Xu et al. Four-day-old EBs of the present invention are transferred to gelatin-coated plates or chamber slides and are allowed to attach and differentiate. Spontaneously contracting cells, which are observed from day 8 of differentiation, are mechanically separated and collected into a 15-mL tube containing low-calcium medium or PBS. Cells are dissociated using Collagenase B digestion for 60-120 minutes at 37° C., depending on the Collagenase activity. Dissociated cells are then resuspended in a differentiation KB medium (85 mM KCl, 30 mM $K_2HPO_4$, 5 mM $MgSO_4$, 1 mM EGTA, 5 mM creatine, 20 mM glucose, 2 mM $Na_2ATP$, 5 mM pyruvate, and 20 mM taurine, buffered to pH 7.2, Maltsev et al., Circ. Res. 75:233, 1994) and incubated at 37° C. for 15-30 min. Following dissociation cells are seeded into chamber slides and cultured in the differentiation medium to generate single cardiomyocytes capable of beating.

According to some embodiments of the invention, isolating lineage specific cells is effected by subjecting the EBs to differentiation factors to thereby induce differentiation of the EBs into lineage specific differentiated cells.

Following is a non-limiting description of procedures and approaches for inducing differentiation of EBs to lineage specific cells.

To differentiate the EBs of some embodiments of the invention into neural precursors, four-day-old EBs are cultured for 5-12 days in tissue culture dishes including DMEM/F-12 medium with 5 mg/ml insulin, 50 mg/ml transferrin, 30 nM selenium chloride, and 5 mg/ml fibronectin (ITSFn medium, Okabe, S. et al., 1996, Mech. Dev. 59: 89-102). The resultant neural precursors can be further transplanted to generate neural cells in vivo (Brüstle, O. et al., 1997. In vitro-generated neural precursors participate in mammalian brain development. Proc. Natl. Acad. Sci. USA. 94: 14809-14814). It will be appreciated that prior to their transplantation, the neural precursors are trypsinized and triturated to single-cell suspensions in the presence of 0.1% DNase.

EBs of some embodiments of the invention can differentiate to oligodendrocytes and myelinate cells by culturing the cells in modified SATO medium, i.e., DMEM with bovine serum albumin (BSA), pyruvate, progesterone, putrescine, thyroxine, triiodothryonine, insulin, transferrin, sodium selenite, amino acids, neurotrophin 3, ciliary neurotrophic factor and Hepes (Bottenstein, J. E. & Sato, G. H., 1979, Proc. Natl. Acad. Sci. USA 76, 514-517; Raff, M. C., Miller, R. H., & Noble, M., 1983, Nature 303: 390-396]. Briefly, EBs are dissociated using 0.25% Trypsin/EDTA (5 min at 37° C.) and triturated to single cell suspensions. Suspended cells are plated in flasks containing SATO medium supplemented with 5% equine serum and 5% fetal calf serum (FCS). Following 4 days in culture, the flasks are gently shaken to suspend loosely adhering cells (primarily oligodendrocytes), while astrocytes are remained adhering to the flasks and further producing conditioned medium. Primary oligodendrocytes are transferred to new flasks containing SATO medium for additional two days. Following a total of 6 days in culture, oligospheres are either partially dissociated and resuspended in SATO medium for cell transplantation, or completely dissociated and a plated in an oligosphere-conditioned medium which is derived from the previous shaking step [Liu, S. et al., (2000). Embryonic stem cells differentiate into oligodendrocytes and myelinate in culture and after spinal cord transplantation. Proc. Natl. Acad. Sci. USA. 97: 6126-6131].

For mast cell differentiation, two-week-old EBs of some embodiments of the invention are transferred to tissue culture dishes including DMEM medium supplemented with 10% FCS, 2 mM L-glutamine, 100 units/ml penicillin, 100 mg/ml streptomycin, 20% (v/v) WEHI-3 cell-conditioned medium and 50 ng/ml recombinant rat stem cell factor (rrSCF, Tsai, M. et al., 2000. In vivo immunological function of mast cells derived from embryonic stem cells: An approach for the rapid analysis of even embryonic lethal mutations in adult mice in vivo. Proc Natl Acad Sci USA. 97: 9186-9190). Cultures are expanded weekly by transferring the cells to new flasks and replacing half of the culture medium.

To generate hemato-lymphoid cells from the EBs of some embodiments of the invention, 2-3 days-old EBs are transferred to gas-permeable culture dishes in the presence of 7.5% $CO_2$ and 5% $O_2$ using an incubator with adjustable oxygen content. Following 15 days of differentiation, cells are harvested and dissociated by gentle digestion with Collagenase (0.1 unit/mg) and Dispase (0.8 unit/mg), both are available from F. Hoffman-La Roche Ltd, Basel, Switzerland. CD45-positive cells are isolated using anti-CD45 monoclonal antibody (mAb) M1/9.3.4.HL.2 and paramagnetic microbeads (Miltenyi) conjugated to goat anti-rat immunoglobulin as described in Potocnik, A. J. et al., (Immunology Hemato-lymphoid in vivo reconstitution potential of subpopulations derived from in vitro differentiated embryonic stem cells. Proc. Natl. Acad. Sci. USA. 1997, 94: 10295-10300). The isolated CD45-positive cells can be further enriched using a single passage over a MACS column (Miltenyi).

It will be appreciated that the culturing conditions suitable for the differentiation and expansion of the isolated lineage specific cells include various tissue culture media, growth factors, antibiotic, amino acids and the like and it is within the capability of one skilled in the art to determine which conditions should be applied in order to expand and differentiate particular cell types and/or cell lineages.

As mentioned above, lineage specific cells can be obtained by directly inducing the expanded, undifferentiated pluripotent stem cells such as ESCs or iPS cells to culturing conditions suitable for the differentiation of specific cell lineage.

For example, as described in Examples 10, 11 and 12 of the Examples section which follows, pluripotent stem cells which were expanded and maintained in a suspension culture as single cells devoid of cell clumps are pluripotent as is evidenced in vitro by direct differentiation of the pluripotent stem cells to neuronal progenitors of the ectoderm cell lineage (FIGS. 17A-17C, Example 10), mesenchymal stem cells (of the mesoderm lineage (FIGS. 18A-18C, Example 11) and PDX1-expressing cells of the endoderm cell lineage (FIGS. 20A-20B, Example 12).

According to an aspect of some embodiments of the invention there is provided a method of generating lineage-specific cells from pluripotent stem cells. The method is effected by (a) culturing the pluripotent stem cells according to the method of some embodiments of the invention, to thereby obtain expanded, undifferentiated stem cells; and (b) subjecting the expanded, undifferentiated stem cells to culturing conditions suitable for differentiating and/or expanding lineage specific cells, thereby generating the lineage-specific cells from the pluripotent stem cells.

Following are non-limiting examples of culturing conditions which are suitable for differentiating and/or expanding lineage specific cells from pluripotent stem cells (e.g., ESCs and iPS cells).

Mesenchymal stromal cells which are CD73-positive and SSEA-4-negative can be generated from hESCs by mechanically increasing the fraction of fibroblast-like differentiated cells formed in cultures of hESCs, essentially as described in Trivedi P and Hematti P. Exp Hematol. 2008, 36(3):350-9. Briefly, to induce differentiation of hESC the intervals between medium changes are increased to 3-5 days, and the cells at the periphery of the ESC colonies become spindle-shaped fibroblast-looking cells. After 9-10 days under these conditions when about 40-50% of the cells in the culture acquire the fibroblast-looking appearance, the undifferentiated portions of ESC colonies are physically removed and the remaining differentiated cells are passaged to new culture plates under the same conditions.

To induce differentiation of hESCs into dopaminergic (DA) neurons, the cells can be co-cultured with the mouse stromal cell lines PA6 or MS5, or can be cultured with a combination of stromal cell-derived factor 1 (SDF-1/CXCL12), pleiotrophin (PTN), insulin-like growth factor 2 (IGF2) and ephrin B1 (EFNB1) essentially as described in Vazin T, et al., PLoS One. 2009 Aug. 12; 4(8):e6606; and in Elkabetz Y., et al., Genes Dev. 2008 Jan. 15; 22: 152-165.

To generate mesencephalic dopamine (mesDA) neurons, hESCs can be genetically modified to express the transcription factor Lmx1a (e.g., using a lentiviral vector with the PGK promoter and Lmx1a) essentially as described in Friling S., et al., Proc Natl Acad Sci USA. 2009, 106: 7613-7618.

To generate lung epithelium (type II pneumocytes) from hESCs, the ESCs can be cultured in the presence of a commercially available cell culture medium (Small Airway Growth Medium; Cambrex, College Park, MD), or alternatively, in the presence of a conditioned medium collected from a pneumocyte cell line (e.g., the A549 human lung adenocarcinoma cell line) as described in Rippon H J., et al., Proc Am Thorac Soc. 2008; 5: 717-722.

To induce differentiation of hESCs or human iPS cells into neural cells, the pluripotent stem cells can be cultured for about 5 days in the presence of a serum replacement medium supplemented with TGF-b inhibitor (SB431542, Tocris; e.g., 10 nM) and Noggin (R&D; e.g., 500 ng/ml), following which the cells are cultured with increasing amounts (e.g., 25%, 50%, 75%, changed every two days) of N2 medium (Li X J., et al., Nat Biotechnol. 2005, 23:215-21) in the presence of 500 ng/mL Noggin, essentially as described in Chambers S M., et al., Nat Biotechnol. 2009, 27: 275-280.

To induce differentiation of hESCs or human iPS cells into neural progenitors, the cells are cultured in suspension, following which the differentiation inhibition factors are removed from the culture medium and $5 \times 10^{-5}$ M Retinoic acid is added for 21 Days. The cells are then transferred to fibronectin coated plates and cultured for additional 5 days before harvesting the cells for analysis. Q-PCR and immunostainings confirm the presence of neuronal progenitor cells (see Example 7 of the Examples section which follows).

To induce differentiation of hESCs or human iPS cells into endoderm cells (including insulin producing cells) the differentiation inhibition factors are removed from the culture medium of the pluripotent stem cells and the cells are exposed to 10 ng/ml Activin for 48 hours, in medium containing cAMP increasers such as forskolin, 8-bromo-cAMP, GABA, IBMX and DBC. Ten days later the cells are analyzed for endodermal markers. Q-PCR for Sox17 demonstrate significant increase in Sox17 expression in treated cells in compare to none treated controls (see Example 7 of the Examples section which follows).

To induce differentiation of hESCs or human iPS cells into mesenchymal stem cells (MSCs) the pluripotent stem cells are transferred to serum containing medium for 14 days and then plated on either gelatin or Matrigel. 7-14 days later the cells are differentiated into MSCs, which can be either frozen or passaged while using trypsin.

In addition to the lineage-specific primary cultures, EBs of the invention can be used to generate lineage-specific cell lines which are capable of unlimited expansion in culture.

Cell lines of the present invention can be produced by immortalizing the EB-derived cells by methods known in the art, including, for example, expressing a telomerase gene in the cells (Wei, W. et al., 2003. Mol Cell Biol. 23: 2859-2870) or co-culturing the cells with NIH 3T3 hph-HOX11 retroviral producer cells (Hawley, R. G. et al., 1994. Oncogene 9: 1-12).

As described in Example 11 of the Examples section which follows, the pluripotent stem cells which are cultured in suspension as single cells devoid of cell clumps can further differentiate into cells of the mesodermal lineage in a suspension culture (3-D) or in a 2-dimensional culture system.

As described in Example 11 of the Examples section which follows, the present inventors have uncovered a novel method of differentiating pluripotent stem cells to mesenchymal stem cells in suspension.

According to an aspect of some embodiments of the invention there is provided a method of generating a mesenchymal stem cell in a suspension culture. The method is effected by culturing the pluripotent stem cells of some embodiments of the invention (e.g., the PSCs which are cultured in suspension as single cells devoid of clumps, or the PSCs which are cultured in suspension as cell clumps) in a suspension culture under conditions suitable for differentiation of pluripotent stem cells to mesenchymal stem cells, thereby generating the mesenchymal stem cell in the suspension culture.

Any known culture medium suitable for differentiating pluripotent stem cells to MSCs can be used.

The present inventors have uncovered that the following culture media are suitable for differentiation of pluripotent stem cells to mesenchymal stem cells:

(1) Fy enriched medium; consisting of 80% DMEM/F12 (Biological Industries, Beit Haemek, Israel), containing 10% knockout serum replacement, 10% fetal bovine serum (FBS; HyClone or Biological Industries) 2 mM L-glutamine, 0.1 mM β-mercaptoethanol, 1% non-essential amino acid stock (all from Invitrogen Corporation products, Grand Island NY, USA, unless otherwise indicated);

(2) MeSus I medium: consisting of 80% DMEM (Biological Industries, Beit Haemek, Israel), containing 20% FBS (HyClone or Biological Industries) 2 mM L-glutamine, (all from Invitrogen Corporation products, Grand Island NY, USA, unless otherwise indicated);

(3) MeSus II medium: consisting of 80% αMEM (Biological Industries, Beit Haemek, Israel), containing 20% FBS (HyClone or Biological Industries) 2 mM L-glutamine, (all from Invitrogen Corporation products, Grand Island NY, USA, unless otherwise indicated);

(4) MeSus III medium: consisting of DMEM/F12 (Biological Industries, Beit Haemek, Israel), 1% ITS (Invitrogen) 2 mM L-glutamine, (all from Invitrogen Corporation products, Grand Island NY, USA, unless otherwise indicated).

The present inventors have uncovered that the culture conditions should include a gradual transfer of the pluripotent stem cells from the suspension culture with undifferentiating medium to a suspension culture with the MSC differentiating medium. Following are non-limiting methods for transferring the pluripotent stem cells to the differentiating medium:

I. (i) 25% differentiation medium 75% pCM100F for one passage; (ii) 50% differentiation medium 50% pCM100F for one passage; (iii) 75% differentiation medium 25% pCM100F for one passage; (iv) 100% differentiation medium.

II. (i) 50% differentiation medium 50% pCM100F for one passage; (ii) 75% differentiation medium 25% pCM100F for one passage; (iii) 100% differentiation medium.

III. (i) 50% differentiation medium 50% pCM100F for one passage; (ii) 100% differentiation medium.

According to an aspect of some embodiments of the invention there is provided an isolated population of mesenchymal stem cells (MSCs) in a suspension culture generated by the method of some embodiments of the invention.

According to some embodiments of the invention, at least about 30% (e.g., 30%), at least about 35% (e.g., 35%), at least about 40% (e.g., 40%), at least about 45% (e.g., 45%), at least about 50% (e.g., 50%), at least about 55% (e.g., 55%), at least about 60% (e.g., 60%), at least about 65% (e.g., 65%), at least about 70% (e.g., 70%), at least about 75% (e.g., 75%), at least about 80% (e.g., 80%), at least about 81% (e.g., 81%), at least about 82% (e.g., 82%), at least about 83% (e.g., 83%), at least about 84% (e.g., 84%), at least about 85% (e.g., 85%), at least about 86% (e.g., 86%), at least about 87% (e.g., 87%), at least about 88% (e.g., 88%), at least about 89% (e.g., 89%), at least about 90% (e.g., 90%), at least about 91% (e.g., 91%), at least about 92% (e.g., 92%), at least about 93% (e.g., 93%), at least about 94% (e.g., 94%), at least about 95% (e.g., 95%), at least about 96% (e.g., 96%), at least about 97% (e.g., 97%), at least about 98% (e.g., 98%), at least about 99% (e.g., 99%), e.g., 100% of the MSCs generated by the method of some embodiments of the invention are characterized by a CD73+/CD31−/CD105+ expression signature.

According to some embodiments of the invention, the MSCs are capable of differentiation in a suspension culture into a cell lineage selected from the group consisting of an adipogenic lineage, an osteoblastic lineage, and a chrondrogenic lineage.

As described in Example 10 of the Examples section which follows, the pluripotent stem cells which are cultured in suspension as single cells devoid of cell clumps can further differentiate into cells of the ectodermal lineage in a suspension culture (3-D) or in a 2-dimensional culture system.

According to an aspect of some embodiments of the invention, there is provided a method of generating a neuronal progenitor cell in a suspension culture, comprising culturing the pluripotent stem cells of some embodiments of the invention (e.g., the pluripotent stem cells which were cultured in a suspension culture as single cells devoid of cell clumps) in a suspension culture under conditions suitable for differentiation of neuronal progenitor cell, thereby generating the neuronal progenitor cell in the suspension culture.

Any known culture medium suitable for differentiating pluripotent stem cells to neuronal progenitor cells can be used. Non-limiting examples include a medium containing retinoic acid ($10^{-3}$ M) or Noggin (10 ngr/ml), essentially as described under "General Materials and Experimental Methods".

According to an aspect of some embodiments of the invention, there is provided an isolated population of neuronal progenitor cells in a suspension culture generated by the method of some embodiments of the invention.

As described in Example 12 of the Examples section which follows, the pluripotent stem cells which are cultured in suspension as single cells devoid of cell clumps can further differentiate into cells of the endodermal lineage in a suspension culture (3-D) or in a 2-dimensional culture system.

According to an aspect of some embodiments of the invention, there is provided a method of generating an endodermal cell in a suspension culture, comprising culturing the pluripotent stem cells of some embodiments of the invention (e.g., the pluripotent stem cells which were cultured in a suspension culture as single cells devoid of cell clumps) in a suspension culture under conditions suitable for differentiation of the pluripotent stem cells to endodermal cells, thereby generating the endodermal cell in the suspension culture.

Any known culture medium suitable for differentiating pluripotent stem cells to endodermal cells can be used. Non-limiting examples include a medium containing activin A (e.g., at concentration of 10 ng/ml), for 24-48 hours, essentially as described under "General Materials and Experimental Methods".

According to an aspect of some embodiments of the invention, there is provided an isolated population of endodermal cells in a suspension culture generated by the method of some embodiments of the invention.

It will be appreciated that since the lineage-specific cells or cell lines obtained according to the teachings of the invention are developed by differentiation processes similar to those naturally occurring in the human embryo they can be further used for human cell-based therapy and tissue regeneration.

Thus, the invention envisages the use of the expanded and/or differentiated lineage-specific cells or cell lines of some embodiments of the invention for treating a disorder requiring cell replacement therapy (cell based therapy).

For example, oligodendrocyte precursors can be used to treat myelin disorders (Repair of myelin disease: Strategies and progress in animal models. Molecular Medicine Today. 1997. pp. 554-561), chondrocytes or mesenchymal cells can be used in treatment of bone and cartilage defects (U.S. Pat. No. 4,642,120) and cells of the epithelial lineage can be used in skin regeneration of a wound or burn (U.S. Pat. No. 5,716,411).

For certain disorders, such as genetic disorders in which a specific gene product is missing [e.g., lack of the CFTR gene-product in cystic fibrosis patients (Davies J C, 2002. New therapeutic approaches for cystic fibrosis lung disease. J. R. Soc. Med. 95 Suppl 41:58-67)], ESC-derived cells or iPS cells-derived cells are preferably manipulated to over-express the mutated gene prior to their administration to the individual. It will be appreciated that for other disorders, the ESC-derived cells or iPS-derived cells should be manipulated to exclude certain genes.

Over-expression or exclusion of genes can be effected using knock-in and/or knock-out constructs [see for example, Fukushige, S. and Ikeda, J. E.: Trapping of mammalian promoters by Cre-lox site-specific recombination. DNA Res 3 (1996) 73-50; Bedell, M. A., Jerkins, N. A. and Copeland, N. G.: Mouse models of human disease. Part I: Techniques and resources for genetic analysis in mice. Genes and Development 11 (1997) 1-11; Bermingham, J. J., Scherer, S. S., O'Connell, S., Arroyo, E., Kalla, K. A., Powell, F. L. and Rosenfeld, M. G.: Tst-1/Oct-6/SCIP regulates a unique step in peripheral myelination and is required for normal respiration. Genes Dev 10 (1996) 1751-62].

The lineage specific cells of some embodiments of the invention can be utilized to produce high amounts (massive production) of proteins such as hormones, cytokines, growth factors and drugs. For example, to produce the proteins the cells should be induced to over-express the protein by transfection for example, and after expansion the protein could be isolated from the culture medium.

The lineage specific cells of some embodiments of the invention can be utilized to prepare a cDNA library. mRNA is prepared by standard techniques from the lineage specific cells and is further reverse transcribed to form cDNA. The cDNA preparation can be subtracted with nucleotides from embryonic fibroblasts and other cells of undesired specificity, to produce a subtracted cDNA library by techniques known in the art.

The lineage specific cells of some embodiments of the invention can be used to screen for factors (such as small molecule drugs, peptides, polynucleotides, and the like) or conditions (such as culture conditions or manipulation) that affect the differentiation of lineage precursor to terminally differentiated cells (e.g., for drug screening). For example, growth affecting substances, toxins or potential differentiation factors can be tested by their addition to the culture medium.

The lineage specific cells of some embodiments of the invention can be used to prepare a vaccine. For example, the pluripotent stem cells, or cells differentiated therefrom, can be inoculated with viral particles and further cultured in a suitable medium until cell lysis occurs and newly produced viral particles are released in the medium. The cells can be used for production of attenuated virus belonging to the family of poxvirus, in particular canarypoxvirus, fowlpoxvirus and vaccinia virus such as native or recombinant vaccinia virus [for example, Modified Vaccinia virus Ankara such as MVA available under ATCC Number VR-1508) or other orthopoxviruses]. For additional description see U.S. Patent Application No. 20040058441 which is fully incorporated herein by reference.

The cell culture of some embodiments of the invention, or the lineage-specific cells generated therefrom can be subject to genetic manipulation by using either infection or transfection of a polynucleotide of interest. The polynucleotide may be included in a nucleic acid construct under the regulation of a promoter.

Methods of introducing the polynucleotide into cells are described in Sambrook et al., [Molecular Cloning: A Laboratory Manual, Cold Springs Harbor Laboratory, New York (1989, 1992)]; Ausubel et al., [Current Protocols in Molecular Biology, John Wiley and Sons, Baltimore, Maryland (1989)]; Chang et al., [Somatic Gene Therapy, CRC Press, Ann Arbor, MI (1995)]; Vega et al., [Gene Targeting, CRC Press, Ann Arbor MI (1995)]; Vectors [A Survey of Molecular Cloning Vectors and Their Uses, Butterworths, Boston MA (1988)] and Gilboa et al. [Biotechniques 4 (6): 504-512 (1986)] and include, for example, stable or transient transfection, lipofection, electroporation and infection with recombinant viral vectors [e.g., using retrovirus, adenovirus (e.g., adenovirus-derived vector Ad-TK, Sandmair et al., 2000. Hum Gene Ther. 11:2197-2205), a chimeric adenovirus/retrovirus vector which combines retroviral and adenoviral components (Pan et al., Cancer Letters 184: 179-188, 2002). See also U.S. Pat. No. 4,866,042 for vectors involving the central nervous system and also U.S. Pat. Nos. 5,464,764 and 5,487,992 for positive-negative selection methods for inducing homologous recombination.

According to some embodiments, the numbers described herein are preceded by about.

The term "ng" refers to nanogram. The term "pg" refers to picogram. The term "ml" refers to milliliter. The term "mM" refers to millimolar. The term "µM" refers to micromolar.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Induced pluripotent stem (iPS) cell lines—iPS cell lines J1.2-3 (from foreskin fibroblasts; Park et al, Nature 451: P141-147, 2008); C2 and C3 (from foreskin fibroblasts, Germanguz et al, JCMM, 2009); iF4 (from adult skin fibroblast) [Park et al, 2008, Germanguz et al, 2009]; KTN7 and KTN3 (from Kartenocytes, Novac-Petraro Cellular Reprogramming, In Press); and KTR13 and KTR13.4 (from Kartenocytes; Novac-Petraro Cellular Reprogramming, In Press) were cultured with inactivated MEF as previously described [Park et al, 2008].

Human embryonic stem cell (hESC) lines—Human ESC lines H9.2, 13, 13.2 and 16.2 (described in Amit et al, J. Anatomy 2002); and human ESC lines H14, H7, H9 (Wisconsin cell lines) were cultured as previously described [Amit et al, 2000].

Human extended blastocyst cell (hEBC) lines—Human extended blastocyst cell lines (described in WO2006/040763) J3 and J6 were cultured as described in Amit et al, Dev Biol, 2000.

Culture media—The following culture medium combinations were tested for their ability to support the growth of iPS, hESC and hEBC lines in attached (2D) cultures or in suspension cultures (three-dimensional, 3D):

yF10—Basic culture medium consisting of 85% DMEM/F12 (Biological Industries, Beit Haemek, Israel), containing 15% knockout serum replacement (SR), 2 mM L-glutamine, 0.1 mM β-mercaptoethanol, 1% non-essential amino acid stock, and 10 ng/ml basic fibroblast growth factor (bFGF) (all from Invitrogen Corporation products, Grand Island NY, USA, unless otherwise indicated). This basic culture medium was used as control and for the routine growth of iPS cells and hESCs with inactivated MEF or foreskin fibroblasts as feeder layers in 2D cultures.

yFIL25—basic medium (yF10) with the addition of 25 ng/ml interleukin 6 (IL6) and IL6 soluble receptor (R&D Biosystems, Minneapolis, MN, USA). It should be mentioned that any gp130 agonist such as Oncostatin, IL11 can be used instead of IL6.

NCM100F—basic medium (yF10) in which instead of knockout serum replacement the serum replacement is the animal free serum replacement (Invitrogen corporation, Knockout SR zeno-free, Catalogue number 12618). In addition the NCM100F medium included 100 ng/ml of the IL6RIL6 [IL6-IL6-receptor chimera (SEQ ID NO:19; which was described in Chebath J, et al., 1997 and WO 99/02552 to Revel M., et al.]. The 85-Kda IL6RIL6 was produced and purified (Serono International SA, Geneva, Switzerland) and was donated by Merck-Serono group (Nes-Ziona, Israel and Geneva, Switzerland).

NCM100Fp—basic medium (yF10) in which instead of knockout serum replacement the serum replacement is the animal free serum replacement (Invitrogen corporation, Knockout SR xeno-free Catalogue Number 12618). In addition the NCM100Fp medium included 100 pg/ml of the IL6RIL6.

ILCNTF—basic medium (yF10) supplemented with 1 ng/ml interleukin 11 (IL11; R&D Biosystems, Catalogue number 18-IL) and Ciliary Neurotrophic Factor (CNTF; R&D Biosystems, Catalogue number 257-NT).

NILCNTF—basic medium (yF10) in which instead of knockout serum replacement the serum replacement is the animal free serum replacement (Invitrogen corporation, Knockout SR xeno-free Catalogue number 12618), and supplemented with 1 ng/ml IL11 and CNTF (R&D Biosystems).

cmV5b—10 ng/ml bFGF (Invitrogen corporation), 100 ng/ml IL6IL6-receptor chimera in Nutristem medium (Biological Industries).

cmV5bp—10 ng/ml bFGF (Invitrogen corporation), 100 pg/ml IL6IL6-receptor chimera in Nutristem (Biological Industries).

cmTeSR—100 ng/ml IL6IL6-receptor chimera in mTeSR medium (StemCell Technologies).

cmTeSRp—100 pg/ml IL6IL6-receptor chimera in mTeSR (StemCell Technologies).

cmTeSR2—100 ng/ml IL6IL6-receptor chimera in TeSR2 (StemCell Technologies).

cmTeSR2p 100 pg/ml IL6IL6-receptor chimera in TeSR2 (StemCell Technologies).

cmHA13 85% DMEM/F12 (Biological Industries, Beit Haemek, Israel), containing 1% SR3 serum replacement (Sigma), 2 mM L-glutamine, ascorbic acid 50 μg/ml, 1% lipid mixture and 10 ng/ml bFGF and the IL6IL6-receptor chimera at 100 ng/ml. The 85-Kda IL6RIL6 was produced and purified as described and was donated by Merck-Serono group. (all from Invitrogen Corporation products, Grand Island NY, USA, unless otherwise indicated).

cmHA13p 85% DMEM/F12 (Biological Industries, Beit Haemek, Israel), containing 1% SR3 serum replacement (Sigma), 2 mM L-glutamine, ascorbic acid 50 μg/ml, 1% lipid mixture and 10 ng/ml bFGF and the IL6IL6-receptor chimera at 100 pg/ml. The 85-Kda IL6RIL6 was produced and purified as described and was donated by Merck-Serono group. (all from Invitrogen Corporation products, Grand Island NY, USA, unless otherwise indicated).

CMrb100F—basic medium (yF10) including; the bFGF concentration was increased to 100 ng/ml, 100 ng/ml of the IL6RIL6 (IL6-IL6-receptor chimera; which was described in Chebath J, et al., 1997 and WO 99/02552 to Revel M., et al). The 85-Kda IL6RIL6 was produced and purified (Serono International SA, Geneva, Switzerland) and was donated by Merck-Serono group (Nes-Ziona, Israel and Geneva, Switzerland).

CMrb100Fp—basic medium (yF10) including; the bFGF concentration was increased to 100 ng/ml, 100 pg/ml of the IL6RIL6 (IL6-IL6-receptor chimera; which was described in Chebath J, et al., 1997 and WO 99/02552 to Revel M., et al). The 85-Kda IL6RIL6 was produced and purified (Serono International SA, Geneva, Switzerland) and was donated by Merck-Serono group (Nes-Ziona, Israel and Geneva, Switzerland).

NCMrb100F—basic medium (yF10) in which instead of knockout serum replacement the serum replacement is the animal free serum replacement (Invitrogen corporation, Knockout SR xeno-free Catalogue Number 12618) and the bFGF concentration was increased to 100 ng/ml. In addition, 100 ng/ml of the IL6RIL6 (IL6-IL6-receptor chimera; which was described in Chebath J, et al., 1997 and WO 99/02552 to Revel M., et al). The 85-Kda IL6RIL6 was produced and purified (Serono International SA, Geneva, Switzerland) and was donated by Merck-Serono group (Nes-Ziona, Israel and Geneva, Switzerland).

NCMrb100Fp—basic medium (yF10) in which instead of knockout serum replacement the serum replacement is the animal free serum replacement (Invitrogen corporation, Knockout SR xeno-free Catalogue Number 12618) and the bFGF concentration was increased to 100 ng/ml. In addition the NCM100F medium included 100 pg/ml of the IL6RIL6 (IL6-IL6-receptor chimera; which was described in Chebath J, et al., 1997 and WO 99/02552 to Revel M., et al. The 85-Kda IL6RIL6 was produced and purified (Serono International SA, Geneva, Switzerland) and was donated by Merck-Serono group (Nes-Ziona, Israel and Geneva, Switzerland).

Culture in 2-dimensional culture systems—For feeder layer free culture system the extracellular matrices Matrigel (BD Biosciences) or human fibronectin (Millipore, Billerica, MA) were used.

Initiation of suspension culture—To initiate suspension cultures, the iPS or ES cells were removed from their culture dish using 1.5 mg/ml type IV collagenase (Worthington biochemical corporation, Lakewood, NJ, USA), or using scrapper, further broken into small clumps using 200-1000 μl Gilson pipette tips, and cultured in suspension in 58 mm Petri dishes (Greiner, Frickenhausen, Germany) at a cell density of $1 \times 10^6$-$5 \times 10^6$ cells/dish. The Petri dishes were kept static in an incubator at 37° C. in 5% $CO_2$. The medium in the suspension culture was changed daily, and the cells were passaged every 5-7 days either by manual cutting of clumps using 27 g needles (only at passages 1-3) or by gentle pipetting using 200-1000 μl Gilson pipette tips. Alternatively, the cells were passaged using trypsin EDTA (0.25%, Biological Industries, Beit Haemek, Israel) combined with one hour treatment with 10 M ROCK inhibitor (EMD Biosciences, Inc. La Jolla, CA, USA) before the incubation with trypsin.

Culture in Spinner flasks—Cell clumps cultured in Petri dish for at least one passage were transferred to a 250 ml spinner flask in the tested medium, shaken continuously at 40-110 rounds per minute (rpm) using magnetic plate, and placed in the incubator. Medium was changed every 1-3 days. Every 5-7 days the clumps were split in a ratio of 1:2-1:4.

Culture in a controlled bioreactor—The cells were cultured in a controlled bioreactor Biostat® Cultibag RM (Sartorius North America, Edgewood, New York, USA) (2 litter bag with 1 litter). The reactor parameters included speed of tilting: 16 rounds per minute (rpm); angle 7°; Temperature: 37° C., PH: 7-7.4, $O_2$ concentration: 50%;

Immunohistochemistry—For fluorescent immunostaining undifferentiated hESCs grown in suspension or re-cultured on MEFs were fixed with 4% paraformaldehyde and exposed to the primary antibodies overnight at 4° C. Cys 3 conjugated antibodies (Chemicon International, Temecula CA, USA) were used as secondary antibodies (1:200 dilution). The primary antibodies (1:50 dilution) include SSEA 1, 3 and 4 (Hybridoma Bank, Iowa, USA), TRA1-60 and TRA1-81 (Chemicon International, Temecula CA, USA), Oct4 (Santa Cruz Biotechnology, Santa Cruz, CA, USA), Oligodendrocyte marker (04; from R&D Biosystems), Glial fibrillary acidic protein (GFAP; from Millipore, Billerica, MA, USA), β-tubulin (Covance, Princeton, New Jersey, USA), nestin (Chemicon, Intnl, Inc. Temecula, CA, USA), PDX1 (the primary antibody is Goat anti human PDX1; two secondary antibodies were used: Rabitt anti goat IgG conjugated to FLUOR (green) or Donkey anti goat NL557 (Red), all from R&D Biosystems).

Flow cytometry analysis—Spheres of hPSCs cultured in suspension were dissociated to single cells using trypLE (Invitrogen Corporation products, Grand Island, NY, USA). The single cells were pipetted up and down with 200 μl pipette tip. The cells were stained with anti-h/mSSEA4, anti-h/mSSEA1, h/mTRA-160, h/mTRA1-81 Ab conjugated to Phycoerythrin, Phycoerythrin conjugated Rat IgG2B were used as isotype control (unless otherwise stated, all antibodies were purchased from R&D systems, Minneapolis, MN, USA). The stained cells were then analyzed with FACS calibur flow cytometer (Becton Dickinson, San Jose, CA, USA) using CellQuest software according to the manufacturer's instructions. The anti-CD73 (BD Pharmingen), CD146 (BD Pharmingen), CD105 (BioScince), CD44 (BioScince), CD45 and CD31 (BD Pharmingen) antibodies.

Karyotype analysis—Karyotype analysis (G-banding) was performed on at least 10 cells from each sample, two samples per test, as previously described [Amit et al, 2003].

Karyotypes were analyzed and reported according to the "International System for Human Cytogenetic Nomenclature" (ISCN).

Embryoid Bodies (EBs) formation—For the formation of EBs, hESCs and iPS cells were passaged as described and transferred to 58 mm Petri dishes (Greiner, Frickenhausen, Germany). EBs were grown in medium consisting of 80% DMEM/F12 (Biological Industries, Beit Haemek, Israel), supplemented with 10% fetal bovine serum (FBS) (HyClone, Utah, USA), 10% serum replacement (SR), 2 mM L-glutamine, 0.1 mM μ-mercaptoethanol, and 1% non-essential amino acid stock (Invitrogen Corporation, Grand Island NY, USA). 10-14 day-old EBs were harvested for RNA isolation and histological examination. For histological analysis EBs were fixed in 10% neutral-buffered formalin, dehydrated in graduated alcohol (70%-100%) and embedded in paraffin. 1-5 □μm sections were deparaffinized and stained with hematoxylin/eosin (H&E).

Reverse transcription polymerase chain reaction (RT PCR)—Total RNA was isolated from hESCs and iPS cells grown for at least 5 passages in suspension (three-dimension, 3D) or at 2-dimension (2D) in the tested medium, and from 10-21 day-old EBs (formed from cells grown in suspension or cells cultured in 2D) using TriReagent (Sigma, St. Louis MO, USA), according to the manufacturer's instructions. Complementary DNA (cDNA) was synthesized from 1 μg total RNA using MMLV reverse transcriptase RNase H minus (Promega, Madison WI, USA). PCR reactions included denaturation for 5 minutes at 94° C. followed by repeated cycles (the number of cycles is indicated in Table 1 below) of: denaturation at 94° C. for 30 seconds, annealing at a specific annealing temperature (as indicated in Table 1 below) and in the presence of a specific $MgCl_2$ concentration (as indicated in Table 1, below) for 30 seconds; and extension at 72° C. for 30 seconds. PCR primers and reaction conditions used are described in Table 1. PCR products were size-fractionated using 2% agarose gel electrophoresis. DNA markers were used to confirm the size of the resultant fragments.

TABLE 1

RT-PCR primers and conditions

| Gene product (GenBank Accession number); SEQ ID NO: | Forward (F) and reverse (R) primers (5'→3') | Reaction Conditions | PCR product size [(base pairs (bp)] |
|---|---|---|---|
| Oct-4 (S81255); SEQ ID NO: 1 | F: GAGAACAATGAGAACCTTC AGGA (SEQ ID NO: 2) R: TTCTGGCGCCGGTTACAGA ACCA (SEQ ID NO: 3) | 30 cycles; annealing temperature: 60° C.; concentration of $MgCl_2$: 1.5 mM | 219 |
| Nanog (NM_024865.2); SEQ ID NO: 4 | F: ACTAACATGAGTGTGGATC C (SEQ ID NO: 5) R: TCATCTTCACACGTCTTCA G (SEQ ID NO: 6) | 30 cycles; annealing temperature: 61° C.; concentration of $MgCl_2$: 1.5 mM | 929 |
| Rex1 (AF450454); SEQ ID NO: 7 | F: GCGTACGCAAATTAAAGTC CAGA (SEQ ID NO: 8) R: CAGCATCCTAAACAGCTCG CAGAAT (SEQ ID NO: 9) | 30 cycles; annealing temperature: 56° C.; concentration of $MgCl_2$: 1.5 mM | 306 |
| FGF4 (NM_002007); SEQ ID NO: 10 | F: CTACAACGCCTACGAGTCC TACA (SEQ ID NO: 11) R: GTTGCACCAGAAAAGTCAG AGTTG (SEQ ID NO: 12) | 30 cycles; annealing temperature: 52° C. concentration of $MgCl_2$: 1.5 mM | 370 |
| Sox2 (Z31560); SEQ ID NO: 13 | F: CCCCCGGCGGCAATAGCA (SEQ ID NO: 14) R: TCGGCGCCGGGGAGATAC AT (SEQ ID NO: 15) | 30 cycles; annealing temperature: 60° C. concentration of $MgCl_2$: 1.5 mM | 448 |
| GAPDH (NM_002046); SEQ ID NO: 16 | F: AATCCCATCACCATCTTC CA (SEQ ID NO: 17) R: GCCTGCTTCACCACCTTC T (SEQ ID NO: 18) | 23 cycles; annealing temperature: 60° C. concentration of $MgCl_2$: 1.5 mM | 581 |

TABLE 1-continued

RT-PCR primers and conditions

| Gene product (GenBank Accession number); SEQ ID NO: | Forward (F) and reverse (R) primers (5'→3') | Reaction Conditions | PCR product size [(base pairs (bp)] |
|---|---|---|---|
| PAX6 (NM_001127612); SEQ ID NO: 20 | F: AACAGACACAGCCCTCACA AACA (SEQ ID NO: 21); R: CGGGAACTTGAACTGGAAC TGAC (SEQ ID NO: 22) | 35 cycles; annealing temperature: 65° C. concentration of $MgCl_2$: 1.5 mM | 274 |
| Nestin (NM_006617.1); SEQ ID NO: 23 | F: CAGCTGGCGCACCTCAAGA TG (SEQ ID NO: 24); R: AGGGAAGTTGGGCTCAGG ACTGC (SEQ ID NO: 25) | 35 cycles; annealing temperature: 65° C. concentration of $MgCl_2$: 1.5 mM | 210 |
| HNF (NM_005382); SEQ ID NO: 26 | F: GAGCGCAAAGACTACCTG AAGA (SEQ ID NO: 28); R: CAGCGATTTCTATATCCAG AGCC (SEQ ID NO: 27); | 35 cycles; annealing temperature: 65° C. concentration of $MgCl_2$: 1.5 mM | 430 |
| Lhx2 (NM_004789.3); SEQ ID NO: 29 | F: CCAAGGACTTGAAGCAGCT C (SEQ ID NO: 30); R: TGCCAGGCACAGAAGTT AAG (SEQ ID NO: 31) | 35 cycles; annealing temperature: 64° C. concentration of $MgCl_2$: 1.5 mM | 285 |

Table 1. Provided are the genes names (identified by GenBank Accession numbers and sequence identifiers) along with the primers (sequences and sequence identifiers) used to detect the expression level of the genes' transcripts. Also provided are the PCR conditions and the resulting PCR products.

Real time RT-PCR—RNA was extracted using TriReagent (Talron) from cells which were cultured in 2-D, in a suspension culture as cell clumps, or in a suspension culture as single cells. The RNA was then subjected to real time RT-PCR using the RT mix (Applied Biosystems) and the primers provided in Table 2, hereinbelow (Applied Biosystems), according to manufacturer's instructions.

TABLE 2

Real time RT-PCR primers

| Gene symbols | Gene ID number | Gene full name | Catalog number |
|---|---|---|---|
| Oct4 | ID: 5460 | POU5F1 | 00999632 |
| NANOG | ID: 79923 | Nanog | 02387400 |
| Rex1 | ID: 132625 | ZFP42 | 00381890 |
| Sox2 | ID: 6657 | Sox2 | 01053049 |
| FN1 | ID: 2335 | Fibronectin 1 | 01549976 |
| THBS4 | ID: 7060 | Thopombospondin | 00170261 |
| CTNNB1 | ID: 1499 | Beta catenin | 00355049 |
| CDH2 | ID: 1000 | N-cadherin | 00983062 |
| CDH1 | ID: 999 | E-cedherin | 00170423 |
| CLDN18 | ID: 51208 | Claudin18 | 00212584 |
| CLDN6 | ID: 9074 | Claudin6 | 00607528 |
| ITGA2 | ID: 3673 | Integrin alpha 2 | 01041011 |
| ITGB5 | ID: 3693 | Integrin beta 5 | 00174435 |
| EGFR | ID: 1956 | Epidermal growth factor receptor | 01076091 |
| FBLN5 | ID: 10516 | Fibulin 5 | 00197064 |

TABLE 2-continued

Real time RT-PCR primers

| Gene symbols | Gene ID number | Gene full name | Catalog number |
|---|---|---|---|
| PLXNA2 | ID: 5362 | Plexin A2 | 00300697 |
| ITGA7 | ID: 3679 | Integrin alpha 7 | 01056475 |
| ITGA6 | ID: 3655 | Integrin, alpha 6 | 01041011 |

Table 2. Provided are the gene symbols, their Gene ID number (Hypertext Transfer Protocol://World Wide Web (dot) ncbi (dot) nlm (dot) nih (dot) gov/gene/), the full gene name, and the Applied Biosystems Catalogue Number of the primers used for real time RT-PCR.

Teratoma formation—Cells from four to six 58 mm dishes, 3-6 wells in 6 wells plate, or 20 ml of a suspension culture were harvested and injected into the hindlimb muscles of four week-old male of severe combined immunodeficiency (SCID)-beige mice. Ten weeks after the injection the resultant teratomas were harvested and prepared for histological analysis using the same method mentioned for EBs.

Testing cloning efficiency of the pluripotent stem cells (PSCs)—PSCs were cultured in 2-D, in a suspension culture as cell clumps or in a suspension culture as single cells were tested for their cloning capacity as follows, wherein for each treatment group, 6 repeats of 96 cells was conducted.

Cloning from 2D cultures with MEFs: H7 cells were trypsinized with 0.05% trypsin 0.53 mM EDTA (Invitrogen) to single cells. Each individual cell was plated in separate well in 96 well plate (Nunc) covered with mitotically inactivated MEFs. 96 cells in each biological repeat were cloned while adding 10 μM/ml Rock inhibitor. 10 days after plating, the number of resulting colonies was calculated. Three colonies were picked up by passage using 1 mg/ml collagenase type IV and 10 mg/ml dispase (both from GibcoBRL). The cloned cultures were grown in pCM100F medium [containing 85% DMEM/F12 (Biological Industries, Beit Haemek, Israel), containing 15% knockout serum replacement (SR), 2 mM L-glutamine, 0.1 mM b-mercaptoethanol, 1% non-essential amino acid stock, and 4 ng/ml bFGF (all from Invitrogen Corporation products, Grand Island NY, USA, unless otherwise indicated) supplemented with 100 pg/ml IL6RIL6 chimera] and were routinely passaged every 5-7 days with 1 mg/ml collagenase type IV. After expansion in culture, the resulting 3 clones were examined for ESCs characteristic.

Cloning from 3D cultures as single cells: H7 cells cultured as single cells in suspension were used. Each individual cell was plated in separate low attachment well in 96-well plate (Nunc) or on plates covered with MEFs. 96 cells in each biological repeat were cloned with or without the addition of 10 μM/ml Rock inhibitor as described in Table 4 in Example 9 of the Examples section which follows. 10 days after plating the number of resulting colonies was calculated. Three colonies were picked up by 200 μL tip. Cloned cultures were grown in pCM100F medium containing Serum replacement, IL6IL6 receptor chimera and 4 ng/ml bFGF, and were routinely passage every 5-7 days by pipette. After expansion in culture the resulting 3 clones were examined for ESCs characteristic.

Freezing and thawing efficiency—Cells were frozen using one of the following freezing solutions:
1. Serum and animal freezing solution (Biological Industries).
2. DMEM supplemented by 10% DMSO and 20% FBS.
3. DMEM supplemented by 10% DMSO and 30% SR.

After 1-7 days at −80° C. refrigerator (using freezing box) the vials were transferred to liquid nitrogen. Cells were thawed and the viability was tested by tripan blue staining. Three separate experiments were conducted.

Genetic manipulation—Cells were transfected using the following vector: CMV promoter-GFP (based on N1 plasmid). The following methods were used:
1. Electroporation using BTX ECM 2001 electroporator with the following parameters: 40 μgr DNA, $10^7$ cells, 3-6 mSc, 220V.
2. Transfection reagent Fugene 6 (Roche) or Lipofectamine (Invitrogen) according to manufacturer instructions (40 μgr DNA for $10^6$ cells).

Neural differentiation—To induce neural differentiation single cells cultured in suspension were transferred to a medium without bFGF and the IL6RIL6 chimera. Either retinoic acid ($10^{-3}$ M) or Noggin (10 ngr/ml) were added for three to seven days. Three weeks after differentiation induction, the cells were plated for staining with fibronectin. The cells were stained for O4 (oligodendrocytes marker), GFAP (Glial fibrillary acidic protein), nestin and β-tubulin.

Media Used for Differentiation of Suspension MSCs to Adipogenic, Osteogenic, and Chondrogenic Cell Lineages:

Adipogenic medium—DMEM F-12 supplemented with 10% FBS, 1 mM L-glutamine, 0.5 mM IBMX, 10 μg/ml Insulin, $10^{-6}$ M Dexamethasone, 0.1 mM Indomethacin.

Osteogenic medium—GMEM BHK-21 supplemented with 10% FBS, 1% Sodium pyruvate, 1% Nonessential amino acids, 50 μg/ml L-ascorbic acid, 0.1 mM β-mercaptoethanol, 10 mM β-glycerol-phosphate, and 0.1 μM Dexamethasone.

Chondrogenic medium—DMEM supplemented with $10^{-7}$ M Dexamethasone, 1% ITS, 50 μg/ml L-ascorbic acid, 1 mM Sodium pyruvate, 4 mM L-proline, and 10 ng/ml TGFβ3.

Differentiation Protocols of Suspension MSCs to Adipogenic, Osteogenic, and Chondrogenic Cell Lineages:

Differentiation procedure for adipogenic differentiation and Oil Red O staining—MSC were seeded in density of 20,000 cell/cm² in 6 well plates and grown in adipogenic medium for 4 weeks with medium changes twice a week.

Adipogenic differentiation was assessed by observation of the accumulation of lipid-rich vacuoles within the cells after Oil Red O staining.

Oil Red O staining—cells were rinsed once with PBS, fixed with 4% Paraformaldehyde (PFA) for 20 minutes, rinsed again and stained with Oil Red O solution for 10 minutes in room temperature. Staining solution was removed and the cells were washed 5 times with water.

Differentiation procedure for osteogenic differentiation and Alizarin red staining—MSC were seeded in density of 2000-3000 cell/cm² in 6 well plate, and grown in osteogenic medium for 4 weeks with medium changes twice a week. Cells cultures were assayed for mineral content by Alizarin red staining.

Alizarin red staining—cells were rinsed once with PBS, fixed with 4% Paraformaldehyde (PFA) for 20 minutes, rinsed again and stained with 2% Alizarin red solution for 15 minutes in room temperature. Staining solution was removed and the cells were washed a few times with water.

Differentiation procedure for chondrogenic differentiation, hematoxylin and eosin and Alcian blue staining—For chondrogenic differentiation, $2 \times 10^5$ MSC were centrifuged at 300 g for 5 minutes in 15 ml polypropylene falcon tubes to form a cell pellet. The cells were grown in chondrogenic medium for 9 weeks with medium changes twice a week without disturbing the cell mass. Cell sections were made after fixing the cell pellets with 4% PFA and embedding it in low melting agarose (1.5%).

Hematoxylin and eosin (H&E) and Alcian blue stainings—were performed by the pathologic laboratory at Rambam Medical Center.

Differentiation protocols of MSCs in suspension—The same adipogenic, osteogenic, and chondrogenic media (described hereinabove) were used to differentiate the MSCs in suspension, without seeding the MSCs on a 2-D culture system.

Example 1

Suspension Culture of Pluripotent Stem Cells in the Novel Culture Media of Some Embodiments of the Invention Culture of pluripotent cells in suspension holds significant advantages over conventional cultures, particularly when aiming to obtain large amounts of cells for cell and tissue transplantation. To initiate suspension cultures from pluripotent cells grown with MEF or in feeder layer-free conditions [Amit et al, 2004], a number of growth factors and cytokines were employed. Pluripotent cells from different sources were used: iPS cells from newborn (foreskin fibroblasts), iPS cells from adults (fibroblasts) and hESCs.

Experimental Results

Suspension cultures—At 24 hours after being placed in a suspension culture in the presence of the following culture media: yFIL25, NCM100F, NCM100Fp, ILCNTF, NILCNTF, cmV5b, cmV5bp, cmTeSR, cmTeSRp, cmTeSR2, cmTeSR2p, cmHA13, CMrb100F, CMrb100Fp, NCMrb100F, or NCMrb100Fp, the pluripotent cells created spheroid clumps or disc-like structures which upon histological examination revealed a homogenous population of small cells with large nuclei. The spheroids grew and were split mechanically every 5-7 days while maintaining their morphology, allowing expansion of the suspension cultures. All these type of medium were found advantages for culturing ESCs and iPS cells in suspension as single cells or small clumps of less than 100 cells.

Alternatively, by using trypsin—EDTA and ROCK inhibitor treatment, suspended cells could be dissociated into single cells and still formed spheroids of the same morphology and features, thus allowing efficient cell expansion. Cells subjected to the suspension culture with the tested culture media showed similar behavior and spheroid morphology and histology. When returned to 2D culture with MEFs or fibronectin after at least 5 passages in suspension, all of the spheroid clumps adhered to the MEFs or fibronectin matrix, respectively, and after 24-48 hours demonstrated typical pluripotent cells colony morphology, exhibiting high nucleus-to-cytoplasm ratio with a notable presence of one to three nucleoli and with typical spacing between the cells.

Maintenance of undifferentiated stem cell phenotype—Several surface markers typical of primate undifferentiated ESCs and iPS cells were examined using immunofluorescent staining essentially as described in Thomson et al, 1998; Bhattacharya, et al. 2004; Kristensen et al, 2005, each of which is fully incorporated herein by reference. Human pluripotent cells cultured in suspension with the tested media for at least 5 passages were found to be still strongly positive for SSEA4, TRA-1-60 and TRA-1-81 and Oct 4. As in other primate ESCs [Thomson et al, 1995 and 1996] and with cells cultured with MEFs, staining for SSEA3 was weak and staining for SSEA1 was negative. Staining for stem cell markers remained high when cells that were cultured in suspension were returned to 2D cultures on MEF feeder cell layers. RT-PCR analyses showed that, similarly to cells cultured with MEFs, pluripotent cells cultured in suspension for at least 5 passages expressed genetic markers of pluripotency [King et al, 2006] including Oct 4, Nanog, Sox2, Rex1, and FGF4. No significant difference in gene expression was detected between cells cultured in suspension. or with cells re-cultured with MEFs after a continuous culture in suspension.

Maintenance of karyotype—Karyotype analysis by Giemsa banding was carried out on cells after at least 7 passages in suspension, and the cells were found to exhibit normal 46,XY or 46,XX karyotype. Thus, the karyotype of the suspension cell culture remained stable.

Pluripotency—Following prolonged expansion in suspension cultures with the tested medium, pluripotent cells conserved their pluripotent differentiation ability. The developmental potential of the cells was first examined in vitro by the formation of EBs. When pluripotent cells cultured in suspension for over 5 passages were transferred to serum-containing medium without the addition of the growth factors, formation of cystic EBs was observed after 7-10 days, similarly to cells cultured with MEFs where cavitated EBs appeared following 10 days in culture [Itskovitz et al, 2000], and cystic EBs after 14-20 days. Within these EBs, there were cell types representative of the three embryonic germ layers typical of pluripotent cells differentiation.

Pluripotency of the suspension pluripotent cells was further demonstrated in vivo by teratoma formation. Cells cultured in suspension for about 10 passages were injected into SCID Beige mice, and 10 weeks later tumors were formed. Within these teratomas, tissues representative of the three germ layers were observed.

Shaking suspension cultures—Pluripotent cells were cultured in suspension in spinner flask for at least a month using the tested medium. An examination after one month showed that morphologically the spheroid clumps formed by the cells remained similar to those observed with cells cultured statically using Petri dishes. When re-cultured on MEFs, the cells in the clumps re-attached, forming again typical colonies of pluripotent cells. The karyotype of the cells cultured for one month in the spinner flask was found to be normal.

Example 2

Two-Dimensional Culture of Pluripotent Stem Cells in the Novel Culture Media of Some Embodiments of the Invention Culturing pluripotent cells in 2D cultures using serum-free, xeno-free and supportive-layers free system—Several possible medium combinations were tested for the ability to support feeder-layer free or animal free (xeno-free, e.g., using foreskin fibroblast as feeders) culture of pluripotent cells. All tested medium (i.e., yFIL25, NCM100F, NCM100Fp, ILCNTF, NILCNTF, cmV5b, cmV5bp, cmTeSR, cmTeSRp, cmTeSR2, cmTeSR2p, cmHA13, CMrb100F, CMrb100Fp, NCMrb100F, or NCMrb100Fp), were found suitable for supporting undifferentiated pluripotent cells cultures. Pluripotent cells were cultured continuously for at least 5 passages while maintaining their stemness features including undifferentiated proliferation, karyotype stability and pluripotency. No morphological differences could be observed between colonies grown in the tested culture systems and those grown on MEF with the basic medium, correspondingly, morphological features remained unchanged on a single-cell level, rendering cells small and round, exhibiting high nucleus-to-cytoplasm ratio, with a notable presence of one to three nucleoli and typical spacing between the cells. Similar to cells grown on MEFs, cells were passaged routinely every five to seven days, at the same ratio of 1/2 or 1/3, indicating a similar population doubling time. The cells were passage at the same seeding efficiency of about 1 million cells per 10 $cm^2$, with the same viability rate of over 90%.

Pluripotent stem cells which are cultured on 2-D culture systems in the presence of the novel culture media of some embodiments of the invention maintain expression pattern of undifferentiated cells—Several surface markers typical of primate undifferentiated ESCs and iPS cells were examined using immunofluorescent staining essentially as described in Thomson et al, 1995, 1996, 1998, each of which is fully incorporated herein by reference. Cells cultured with the tested medium for at least 7 passages (e.g., 10, 15 passages) were found to be strongly positive to surface markers SSEA4, TRA-1-60, TRA-1-81 and Oct 4. As in other primate ESCs, staining with SSEA3 was weak and negative for SSEA1.

Pluripotent stem cells which are cultured on 2-D culture systems in the presence of the novel culture media of some embodiments of the invention are capable of differentiation into cell lineages derived from the three embryonic germ layers in vitro and in vivo—The developmental potential of the cells after prolonged culture in the tested conditions was examined in vitro by the formation of embryoid bodies (EBs). Pluripotent cells cultured in the tested conditions formed EBs similar to those created by ESCs grown on MEFs. Within these EBs, stem cells differentiated into cell types representative of the three embryonic germ layers (data not shown).

In addition, the pluripotent stem cells were shown capable of differentiation in vivo. Thus, following their injection to SCID Beige mice cells cultured under the tested conditions form teratomas containing cell types representative of the three embryonic germ layers i.e., ectoderm, endoderm and mesoderm (data not shown).

Example 3

Culturing of Pluripotent Stem Cells as Single Cells in Suspension without Enzymatic Passaging Experimental Results Culturing single cells in suspension cultures—Pluripotent cells were cultured in suspension in spinner flask or Petri dishes for at least a month using all of the tested medium (yFIL25, NCM100F, NCM100Fp, ILCNTF, NILCNTF, cmV5b, cmV5bp, cmTeSR, cmTeSRp, cmTeSR2, cmTeSR2p, cmHA13, CMrb100F, CMrb100Fp, NCMrb100F, or NCMrb100Fp), as single cells. An examination after one month showed that the cells exhibit pluripotent cells features including stable karyotype, expression on specific markers and differentiation potential. The cells were passage without the use of ROCK inhibitor and without the use of trypsin and were split mechanically using a pipette. This is the first time human ESCs or iPS were shown capable of culturing in a suspension culture as single cells without the need for enzymatic passaging, since the cell adopted a single cell culturing mode. The system can be used for an industrial processes without passage.

Human ESCs which are cultured in a suspension culture as single cells can be replaced on 2-dimensional culture systems, demonstrating typical hESCs morphology—CL1 (13E1) cultured for 17 passages in suspension as single cells were re-plated with inactivated MEFs. During the first passage the colony morphology is not clear. Few weeks after, the cells formed colonies with pluripotent cells morphology of spaces between cells, clear borders and high nucleus to cytoplasm ratio (FIGS. 11A-11B).

Example 4

Human ESCS and IPS Cells can be Shipped while in a Suspension Culture

Shipment of living cells—Cells cultured in suspension as cell clumps using the described method survive shipping at room temperature or at 0-15 Celsius degrees. Using 50 ml tubes with 20-40 ml of culture medium, vented or not vented, 2-10 million cells per tube could be shipped. At least 50% of the cells survived and continued to grow while maintaining all pluripotent features. Other tube size might be use. The medium could be supplemented with anti oxidants and RoCK or other anti apoptotic agents.

Example 5

Expansion of Pluripotent Stem Cells Under Dynamic Culture Conditions in the Presence of the Novel Culture Medium of Some Embodiments of the Invention The present inventors tested the ability of the novel culture media of some embodiments of the invention to support the growth and expansion of pluripotent stem cells such as iPSCs and ESCs under dynamic culture conditions when cultured as single cells (devoid of cell clumps) or in suspension with cell clumps.

Experimental Methods

Cell lines and seeding concentration: The C2 IPS cell line was used at passage 77, of which 37 passages were in suspension before seeding into the dynamic culture conditions. The IPSCs were seeded (inoculated) at a concentration of $3.7 \times 10^4$ cell/ml.

Culture media and conditions: The following culture media were used for the dynamic suspension culture: CM100Fp. The cells were culture in spinner flasks or a controlled bioreactor continuously for 5 days. When cultured in a bioreactor the medium was not changed during the culturing process. When cultured in spinner flasks the medium was changed every day.

Culturing Conditions for Dynamic Growth in Suspension:

Culture in a controlled bioreactor—The cells were cultured in a controlled bioreactor Biostat® Cultibag RM (Sartorius North America, Edgewood, New York, USA) (2 litter bag with 1 litter). The reactor parameters included speed of tilting: 16 rounds per minute (rpm); angle 7°; Temperature: 37° C., PH: 7-7.4, $O_2$ concentration: 50%;

Culture in Spinner flasks—Cell clumps cultured in Petri dish for at least one passage were transferred to a 250 ml spinner flask in the tested medium, shaken continuously at 40-110 rounds per minute (rpm) using magnetic plate, and placed in the incubator. Medium was changed every 1-3 days. Every 5-7 days the clumps were split in a ratio of 1:2-1:4.

Experimental Results

Expansion of pluripotent stem cells in a suspension culture using the culture media according to some embodiments of the invention—The pluripotent stem cells, which were subject to the dynamic culture conditions, were expanded up to about 26-folds in cell number within 11 days of culture in spinner flasks when grown in a suspension culture with cell clumps, or up to about 50-folds in cell number within 11 days of culture in spinner flasks when grown in a suspension culture as single cells devoid of cell clumps. In addition, the pluripotent stem cells were expanded up to about 64-folds in cell number within 5 days of culture in the controlled bioreactor when grown as single cells (FIGS. 5A-5C and data not shown). These results demonstrate that the novel culture media of some embodiments of the invention is capable of supporting pluripotent cell expansion when cultured in suspension under dynamic conditions.

Example 6

Pluripotent Stem Cells Cultured in Suspension Recover Well from Freeze/Thaw Cycles To test the ability of the pluripotent stem cells cultured in suspension in the presence of the novel culture media of some embodiments of the invention to recover from re-freeze/thaw cycles, the cells were frozen in liquid nitrogen by using the following freezing solutions:
(1) 10% DMSO (Sigma), 10% FBS (HyClone), 10% SR (Invitrogen cooperation), 70% DMEM.
(2) 5% DMSO, 10% FBS, 10% SR, 75% DMEM.
(3) 10% DMSO, 90% SR.
(4) 5% DMSO, 95% SR.
(5) Commercial serum free freezing solution (Biological Industries, Beit HaEmek, Israel).

The frozen cells were initially frozen at −80° C. refrigerator, and after 12 hours to three days, were transferred to liquid nitrogen tank for storage.

Experimental Results

The pluripotent stem cells were subject to freezing conditions using the above described freezing solution, and then were thawed, and re-cultured in suspension. FIGS. 6A-6C demonstrate C2 cells cultured for 48 passages in suspension with cmrb100p medium after thawing using three different freezing solutions.

Example 7

Generation of Lineage Specific Cells from the Pluripotent Stem Cells

Differentiation into neuronal cells—Cells from the four tested cell lines (I3, I4, I6 and H9.2) were cultured in suspension with cell clump for at least 25 passages. Then, the factors were removed from the culture medium and $5 \times 10^{-5}$ M Retinoic acid was added for 21 Days. The cells were then transferred to fibronectin coated plates and cultured for additional 5 days before harvesting the cells for analysis. Quantitative RT-PCR, immunostainings (immunofluorescence and FACS) were conducted and the results show expression of genes of the neuronal cell lineage such as PAX6, HNF, nestin, β-tubulin and PSA-NCAM (FIGS. 7A-7C, 8A-8B, 9A-9G).

Differentiation into endodermal cells—Cells cultured in suspension with cell clumps from C2 cell line (iPS cell line derived from foreskin fibroblast) were cultured in suspension for at least 10 passages. Then the factors were removed from the culture medium and the cells were exposed to 10 ng/ml Activin for 48 hours, in medium containing cAMP increasers such as foreskulin, 8-bromocAMP, GABA, IBMX and DBC. Ten days later the cells were analyzed for endodermal markers. Quantitative RT-PCR for Sox17 demonstrate significant increase in Sox17 expression in treated cells in compare to non-treated controls (Data not shown). As shown in FIGS. 10A-10B the differentiated cells express PDX1, a transcription factor indicating differentiation into endoderm lineage, mainly into β-cells.

Differentiation into mesenchymal stem cells (MSCs)—Cells cultured in suspension with cell clumps in suspension were transferred to serum containing medium for 14 days and then plated on ether gelatin or Matrigel. 7-14 days later the resulted MSCs were either frozen or passage while using trypsin.

Example 8

Characterization of the Expression Pattern of Human Pluripotent Embryonic Stem Cells which are Cultured in A Suspension Culture as Single Cells Study Design to Characterize the Novel hESCs which are Cultured in a Suspension Culture as Single Cells Three groups of cultured pluripotent stem cells (PSCs) were tested:
1. hESCs cultured with MEFs in two dimensions standard conditions (2D).
2. hESCs cultured as clump (spheroid, more than 200 cells) in suspension (3D).
3. hESCs cultured as single cells (SC, less than 50 cells, most of them as single cells) in suspension (3D).

The cells were tested for expression of pluripotency markers using flow cytometry after culturing of at least 15 passages in the above conditions.

Experimental Results

Human ESCs which are cultured in a suspension culture as single cells exhibit a unique expression pattern similar to that of the "naïve" mouse ESCs—As shown in FIGS. 12A-12J, FACS analyses of pluripotent stem cells cultured in suspension as single cells demonstrate an altered expression pattern as compared to hESCs cultured in 2-D or in a suspension culture as cell clumps. Thus, while the majority of hESCs which are cultured on 2-D or in a suspension culture as cell clumps express the TRA1-60 (FIGS. 12A, 12C), TRA1-81 (FIGS. 12B, 12D) and SSEA4 (FIG. 12H) markers of pluripotency, the majority of the pluripotent hESCs which are cultured in a suspension culture as single cells do not express the TRA1-60 (FIG. 12E), TRA1-81 (FIG. 12F) and SSEA4 (FIG. 12J) markers. In contrast, while only 11% of the hESCs which are cultured on 2-D or in a suspension culture as cell clumps express SSEA1 (FIG. 12G), the majority of the hESCs which are cultured in a suspension culture as single cells express SSEA1 (FIG. 12I). Thus, hESCs that were cultured in suspension as single cells exhibit a modified expression pattern as compared to hESCs cultured on 2-D or in a suspension culture as cell clumps. Such an expression pattern resembles that of the more "Naïve" mouse ESCs cells, which do not express TRA1-60, TRA1-81 and SSEA4, but which do express SSEA1.

Table 3, hereinbelow summarizes the results of the FACS analyses.

TABLE 3

Expression pattern of human pluripotent stem cells under various culturing conditions

|  | SSEA4 | TRA60 | TRA81 | SSEA1 |
| --- | --- | --- | --- | --- |
| 2D | + | + | + | − |
| Clumps 3D | + | + | + | − |
| Single cells 3D | − | − | − | + |

Table 3. Provided are the expression signatures of the various pluripotent stem cells.

Cells cultured in suspension as single cells exhibit increased levels of OCT-4—Real time RT-PCR analysis was performed on hESCs cultured in 2-D, a suspension culture as cell clumps or in a suspension culture as single cells using the primers listed in Table 2 in "General Materials and Experimental Methods" hereinabove. As shown in FIG. 13A the expression levels of Nanog is slightly decreased in a single cell suspension culture as compared to hESCs grown in 2-D. On the other hand, OCT4 expression was found to be increased by about 8 folds in hESCs cultured in suspension as SC as compared to hESCs cultured in 2D.

Example 9

Characterization of the Cloning Efficiency of Human Pluripotent Embryonic Stem Cells which are Cultured in A Suspension Culture as Single Cells Experimental Results Human ESCs which are cultured in suspension as single cells or hESCs which were cultured in 2-D were tested for their cloning efficiency. Cells which were cultured in 2-D were trypsinized and plated as single cells, each in a single well of a 96-well plate covered with MEFs (as described under "General Materials and Experimental Methods" hereinabove), and cells which were grown as single cells in suspension were plated each in a single well of a low-adhesive 96-well plate (as described under General Materials and Experimental Methods" hereinabove).

Human ESCs which are cultured in suspension as single cells exhibit a significantly higher cloning efficiency as compared to hESCs cultured on 2-D—As shown in Table 4, significantly higher cloning efficiency was observed for hESCs cultured in suspension as single cells (95.63%) compared to hESCs cultured on 2-D (4.33%). In addition, while the addition of the ROCK inhibitor increased the cloning efficiency of hESCs cultured on 2-D, the cloning efficiency of hESCs cultured in suspension as single cells was not increased in the presence of the ROCK inhibitor.

TABLE 4

Cloning efficiency of hESCs under various culture conditions

| Culturing conditions | Cloning efficiency % |
|---|---|
| 2D + trypsin | 4.33 |
| 2D + trypsin + RoCK inhibitor | 17.7 |
| 3D (single cells devoid of cell clumps) without trypsin | 95.63 |
| 3D (single cells devoid of cell clumps) without trypsin but with RoCK inhibitor | 87 |

Table 4. Provided are the percentage of cell cloning obtained under the various culturing conditions.

Human ESCs which are cultured in suspension as single cells exhibit higher survival to freezing and thawing cycles as compared to hESCs cultured on 2-D—In order to test the ability of the pluripotent stem cells to survive freezing and thawing cycles the hESCs (which were cultured in suspension as single cells) were subjected to a freezing cycle using any of the following freezing solutions:
  I. Serum and animal freezing solution (Biological Industries).
  II. DMEM supplemented by 10% DMSO and 20% FBS.
  III. DMEM supplemented by 10% DMSO and 30% SR (serum replacement).

After freezing for about 1-7 days at −80° C. degrees the vials were transferred to liquid nitrogen. The cells were thawed, and the viability was tested by tripan blue staining. The survival of hESCs to the freezing-thawing cycle was about 80% for hESCs cultured in suspension as single cells, which is significantly higher than the survival of hESCs which are cultured on 2-D to a freezing-thawing cycle under identical assay conditions (up to 50%, data not shown). FIG. 15 is a representative image of human ESCs cultured as single cells in a suspension culture after a freezing-thawing cycle.

Human ESCs which are cultured in suspension as single cells exhibit higher survival and efficiency of genetic manipulations as compared to hESCs cultured on 2-D— Cells were transfected using the CMV promoter-GFP nucleic acid construct (based on N1 plasmid) as described under "GENERAL MATERIALS AND EXPERIMENTAL METHODS". Following the genetic manipulation, the survival of the cells was evaluated using phase contrast microscopy. As is shown in FIG. 16A, more than 90% of the suspended single cells survived the procedure. In contrast, from the 2D cells cultured with MEFs, only up to 17 cells (of out of $10^7$ cells) recovered (data not shown). Moreover, while none of the hESCs that were cultured on 2-D were green (data not shown), a few of the hESCs cultured in 3-D as single cells were green, i.e., expressed the transgene CMV-GFP construct (FIG. 16B).

Example 10

Human Pluripotent Embryonic Stem Cells which are Cultured in a Suspension Culture as Single Cells are Capable of Differentiation into Neural Cell Lineage Experimental Results Human ESCs which are cultured in suspension as single cells are capable of differentiating into the neuronal cell linage—To induce neural differentiation, hESCs which are cultured in suspension as single cells were transferred to a neuronal differentiating medium (without bFGF and the IL6RIL6 chimera) which included either retinoic acid ($10^{-3}$ M) or Noggin (10 ngr/ml) as described under "General Materials and Experimental Methods" hereinabove. Differentiation was induced in either 2-D by plating on human plasma fibronectin (HPF)-coated plates (at a concentration of 50 μgr per 10 $cm^2$ HPF) or in a suspension culture. Three weeks after differentiation induction, the cells were plated for staining with fibronectin, O4, GFAP, nestin and β-tubulin. As show in FIGS. 17A-17C, the cells differentiated into neuronal progenitor cells which were positively stained with GFAP (Glial fibrillary acidic protein), a marker of astrocytes, O4, a marker of oligodendrocytes, and β-Tubulin and Nestin, markers of neurons. These results conclusively show that hESCs which are cultured in suspension as single cells are capable of differentiating into the ectoderm embryonic germ layer.

Example 11

A Novel Method for Differentiating Mesenchymal Stem Cells in Suspension

The present inventors have developed a novel method for differentiating pluripotent stem cells into mesenchymal stem cells in suspension, as follows.

To induce differentiation to MSCs, single cells cultured in suspension were transferred gradually to one of the following media:
  (1) Fy enriched; consisting of 80% DMEM/F12 (Biological Industries, Beit Haemek, Israel), containing 10% knockout serum replacement (SR), 10% FBS (HyClone or Biological Industries) 2 mM L-glutamine, 0.1 mM β-mercaptoethanol, 1% non-essential amino acid stock (all from Invitrogen Corporation products, Grand Island NY, USA, unless otherwise indicated).
  (2) MeSus I: consisting of 80% DMEM (Biological Industries, Beit Haemek, Israel), containing 20% FBS (HyClone or Biological Industries) 2 mM L-glutamine, (all from Invitrogen Corporation products, Grand Island NY, USA, unless otherwise indicated).
  (3) MeSus II: consisting of 80% αMEM (Biological Industries, Beit Haemek, Israel), containing 20% FBS (HyClone or Biological Industries) 2 mM L-glutamine, (all from Invitrogen Corporation products, Grand Island NY, USA, unless otherwise indicated).
  (4) MeSus III: consisting of DMEM/F12 (Biological Industries, Beit Haemek, Israel), 1% ITS (Invitrogen) 2 mM L-glutamine, (all from Invitrogen Corporation products, Grand Island NY, USA, unless otherwise indicated).

Human ESCs which were grown in a suspension culture as single cells were transferred to the MSC differentiation medium gradually using any one of the following methods:

I. (i) 25% differentiation medium 75% pCM100F for one passage; (ii) 50% differentiation medium 50% pCM100F for one passage; (iii) 75% differentiation medium 25% pCM100F for one passage; (iv) 100% differentiation medium.

II. (i) 50% differentiation medium 50% pCM100F for one passage; (ii) 75% differentiation medium 25% pCM100F for one passage; (iii) 100% differentiation medium.

III. (i) 50% differentiation medium 50% pCM100F for one passage; (ii) 100% differentiation medium.

All of the above described media and transfer methods resulted in efficient differentiation into MSCs.

The cells were then cultured in suspension (Petri dish, Spinner flasks and/or bio-reactors) and passage every 5-10 days by pipette. After the cells were cultured for at least one passage with the differentiation medium, MSCs features were tested. FIGS. 19A-19B depict images of MSCs which were differentiated from PSCs cultured in suspension as single cells for at least 10 passages. When cells were re-plated on Gelatin they demonstrate typical MSCs morphology. FIG. 19A shows the CL1 cells that were differentiated in the Fy enriched medium, and FIG. 19B shows the CL1 cells that were differentiated in the MeSusII medium.

In order to enrich the MSCs population, magnetic-activated cell sorting (MACS) was employed using an anti-CD73 antibody (Milteniy) according to manufacturer instructions. The CD73-MACS resulted in enrichment of the MSCs from about 40% CD73-positive cells to more than 80% CD73-positive cells.

The MSCs, which were generated by differentiation of hESCs that were cultured in suspension as single cells, exhibit typical MSC expression pattern—As shown in FIGS. 18A-18C, FACS analyses show that when the cells were grown in an animal-free medium, 82.5% of the MSC are CD73-positive and only 4.83% are CD31-positive. In addition, when the MSCs are grown in a serum-containing medium, 99.3% are CD105-positive.

Differentiation of suspension MSCs into an adipogenic cell lineage—The MSCs in suspension were subjected to a differentiation protocol towards the adipogenic lineage on either a 2-D culture system or in a suspension culture, as described in "General Materials and Experimental Methods" hereinabove. Briefly MSC were seeded in density of 20,000 cell/cm$^2$ in 6 well plates or in a concentration of $1 \times 10^6$-$5 \times 10^6$ cells/ml in a suspension culture and grown in the presence of the adipogenic medium for 4 weeks with medium changes twice a week. As shown in FIG. 19D, MSCs (which were generated by differentiation of hESCs that were cultured in suspension as single cells) were capable of differentiation into the adipogenic cell lineage, exhibiting lipid-rich vacuoles within the cells.

Differentiation of suspension MSCs into an osteogenic cell lineage—The MSCs in suspension were subjected to a differentiation protocol towards the osteogenic lineage on either a 2-D culture system or in a suspension culture, as described in "General Materials and Experimental Methods" hereinabove. Briefly MSC were seeded in density of 2000-3000 cell/cm$^2$ in 6 well plate, or in a concentration of $1 \times 10^6$-$5 \times 10^6$/ml in a suspension culture and grown in the presence of the osteogenic medium for 4 weeks with medium changes twice a week. As shown in FIG. 19C, MSCs (which were generated by differentiation of hESCs that were cultured in suspension as single cells) were capable of differentiation into the osteogenic cell lineage, exhibiting mineralized cells, detected by Alizarin red staining.

Differentiation of suspension MSCs into a chondrogenic cell lineage—The MSCs in suspension were subjected to a differentiation protocol towards the chondrogenic lineage on either a 2-D culture system or in a suspension culture, as described in "General Materials and Experimental Methods" hereinabove. Briefly $2 \times 10^5$ MSC were centrifuged at 300 g for 5 minutes in 15 ml polypropylene falcon tubes to form a cell pellet. The cells were grown in chondrogenic medium as a pellet in a tube for 9 weeks with medium changes twice a week without disturbing the cell mass. Cell sections were made after fixing the cell pellets with 4% PFA and embedding it in low melting agarose (1.5%). The cells were stained with Alcian blue, which stains the matrix of chondrocytes of the chondrogenic cell lineage (data not shown), demonstrating the ability of the MSCs to differentiate into the chondrogenic cell lineage.

Example 12

Human Pluripotent Embryonic Stem Cells which are Cultured in a Suspension Culture as Single Cells are Capable of Differentiation into the Endoderm Cell Lineage Experimental Results C2 cells were cultured for more than 10 passages as single cells in suspension in the pCM100F culture medium. For endoderm differentiation, the bFGF and the IL6RIL6 chimera were removed from the culture medium and activin A at concentration of 10 ng/ml was added for 48 hours in a suspension culture. 10 days after exposure to activin A, the cells were plated on Matrigel™ or HFF (human foreskin fibroblast) matrix, or were cultured in a 3-dimensional culture system (in suspension) and were stained to PDX1. When levels of expression of the SOX 17 gene were tested by real time PCR, an increase could be observed during differentiation from day 2 to 10 after exposure to activin A (data not shown). FIGS. 20A-20B show the expression of PDX1 in the cells, demonstrating differentiation into endodermal cells.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

Additional References are Cited in Text

Amit M, Carpenter M K, Inokuma M S, Chiu C P, Harris C P, Waknitz M A, Itskovitz-Eldor J, and Thomson J A. "Clonally derived human embryonic stem cells lines maintain pluripotency and proliferative potential for prolonged periods of culture". Dev Biol 227:271-278, 2000.

Amit, M., Shariki, K., Margulets, V., & Itskovitz-Eldor, J. (2004). Feeder and serum-free culture system for human embryonic stem cells. Biol. Reprod. 70, 837-845.

Aoi T, Yae K, Nakagawa M, Ichisaka T, Okita K, Takahashi K, Chiba T, Yamanaka S. Generation of Pluripotent Stem Cells from Adult Mouse Liver and Stomach Cells. Science. 2008.

Bhattacharya, B. et al. (2004). Gene expression in human embryonic stem cell lines: unique molecular signature. Blood 103, 2956-2964.

Germanguz I, Sedan O, Zeevi-Levin N, Shtrichman R, Barak E, Ziskind A, Eliyahu S, Meiry G, Amit M, Itskovitz-Eldor J, Binah O. Molecular characterization and functional properties of cardiomyocytes derived from human inducible pluripotent stem cells. J Cell Mol Med. 2009 Dec. 11. [Epub ahead of print].

Hanna J, Wernig M, Markoulaki S, Sun C W, Meissner A, Cassady J P, Beard C, Brambrink T, Wu L C, Townes T M, Jaenisch R. Treatment of sickle cell anemia mouse model with iPS cells generated from autologous skin. Science. 2007, 318(5858): 1920-1923.

Hanna J, Markoulaki S, Schorderet P, Carey B W, Beard C, Wernig M, Creyghton M P, Steine E J, Cassady J P, Foreman R, Lengner C J, Dausman J A, Jaenisch R. Direct reprogramming of terminally differentiated mature B lymphocytes to pluripotency. Cell. 2008, 133(2):250-264.

Itskovitz-Eldor, J., Schuldiner, M., Karsenti, D., Eden, A., Yanuka, O., Amit, M., Soreq, H., Benvenisty, N. (2000). Differentiation of human embryonic stem cells into embryoid bodies comprising the three embryonic germ layers. Mol. Med. 6, 88-95.

King, T. D., Gandy, J. C. & Bijur, G. N. (2006). The protein phosphatase-1/inhibitor-2 complex differentially regulates GSK3 dephosphorylation and increases sarcoplasmic/endoplasmic reticulum calcium ATPase 2 levels. Exp. Cell Res. 312, 3693-3700.

Kristensen, D. M., Kalisz, M., & Nielsen, J. H. (2005). Cytokine signalling in embryonic stem cells. APMIS. 113, 756-772.

Lowry W E, Richter L, Yachechko R, Pyle A D, Tchieu J, Sridharan R, Clark A T, Plath K. Generation of human induced pluripotent stem cells from dermal fibroblasts. Proc Natl Acad Sci USA, 2008, 105(8):2883-2888.

Meissner A, Wernig M, Jaenisch R. Direct reprogramming of genetically unmodified fibroblasts into pluripotent stem cells. Nat Biotechnol. 2007, 25(10):1177-1181.

Nakagawa M, Koyanagi M, Tanabe K, Takahashi K, Ichisaka T, Aoi T, Okita K, Mochiduki Y, Takizawa N, Yamanaka S. Generation of induced pluripotent stem cells without Myc from mouse and human fibroblasts. Nat Biotechnol. 2008, 26(1):101-106.

Park I H, Zhao R, West J A, Yabuuchi A, Huo H, Ince T A, Lerou P H, Lensch M W, Daley G Q. Reprogramming of human somatic cells to pluripotency with defined factors. Nature. 2008, 451(7175):141-146.

Takahashi K, Yamanaka S. Induction of pluripotent stem cells from mouse embryonic and adult fibroblast cultures by defined factors. Cell. 2006, 126(4):663-676.

Takahashi K, Tanabe K, Ohnuki M, Narita M, Ichisaka T, Tomoda K, Yamanaka S. Induction of pluripotent stem cells from adult human fibroblasts by defined factors. Cell. 2007, 131(5):861-872.

Thomson, J. A., Itskovitz-Eldor, J., Shapiro, S. S., Waknitz, M. A., Swiergiel, J. J., Marshall, V. S/, Jones, J. M. (1998). Embryonic stem cell lines derived from human blastocysts. Science 282, 1145-1147.

Thomson, J. A., Kalishman, J., Golos, T. G., Durning, M., Harris, C. P., Becker, R. A., Hearn, J. P. (1995). Isolation of a primate embryonic stem cell line. Proc. Natl. Acad. Sci. USA. 92, 7844-7848.

Thomson, J. A., Kalishman, J., Golos, T. G., Durning, M., Harris, C. P., Hearn, J. P. (1995). Pluripotent cell lines derived from common marmoset (*Callithrix jacchus*) blastocysts. Biol. Reprod. 55, 254-259.

Yu J, Hu K, Smuga-Otto K, Tian S, Stewart R, Slukvin I I, Thomson J A. Human induced pluripotent stem cells free of vector and transgene sequences. Science. 2009, 324 (5928):797-801.

---

What is claimed is:

1. A method of expanding and maintaining pluripotent stem cells (PSCs) in an undifferentiated state, the method comprising:
   (a) passaging the PSCs in a suspension culture by mechanical dissociation of PSC clumps to single cells or clusters under conditions devoid of an enzymatic dissociation, each of said clusters comprising no more than 200 PSCs, for at least 2 and no more than 10 passages, to thereby obtain a suspension culture of PSCs devoid of clumps; and (b) passaging without dissociation said suspension culture of PSCs devoid of said clumps and comprising single cells or small clusters, each of the clusters comprising no more than 200 PSCs, thereby expanding and maintaining the PSCs in the undifferentiated state.

2. The method of claim 1, wherein, in step (a), said passaging is for at least 3 and no more than 7 passages.

3. The method of claim 1, wherein each of said clusters comprising no more than 150 PSCs.

4. The method of claim 2, wherein each of said clusters comprising no more than 150 PSCs.

5. The method of claim 1, wherein said culturing conditions being devoid of a Rho-associated kinase (ROCK) inhibitor.

6. The method of claim 2, wherein said culturing conditions being devoid of a Rho-associated kinase (ROCK) inhibitor.

7. The method of claim 3, wherein said culturing conditions being devoid of a Rho-associated kinase (ROCK) inhibitor.

8. The method of claim 1, wherein said pluripotent stem cells are human pluripotent stem cells.

9. The method of claim 1, wherein said suspension culture comprises a culture medium which comprises interleukin 11 (IL11) and Ciliary Neurotrophic Factor (CNTF).

10. The method of claim 1, wherein said suspension culture comprises a culture medium which comprises basic fibroblast growth factor (bFGF) at a concentration of at least 50 ng/ml and an IL6RIL6 chimera.

11. The method of claim 1, wherein said suspension culture comprises a culture medium which comprises an animal contaminant-free serum replacement and an IL6RIL6 chimera.

12. The method of claim 1, wherein said suspension culture comprises a serum-free culture medium which comprises a soluble interleukin 6 receptor (sIL6R) and interleukin 6 (IL6), wherein a concentration of said sIL6R is at least 5 ng/ml, and wherein a concentration of said IL6 is at least 3 ng/ml.

13. The method of claim 1, wherein said suspension culture comprises a culture medium which comprises interleukin 11 (IL11) and oncostatin.

* * * * *